(12) United States Patent
Dai et al.

(10) Patent No.: US 9,932,340 B2
(45) Date of Patent: Apr. 3, 2018

(54) SUBSTITUTED INDOLES

(71) Applicant: AbbVie Inc., North Chicago, IL (US)

(72) Inventors: Yujia Dai, Gurnee, IL (US); William McClellan, Waukegan, IL (US); Mike Michaelides, Libertyville, IL (US); Ramzi Sweis, Lake Bluff, IL (US); Noel Wilson, Kenosha, WI (US); Justin Dietrich, Lindenhurst, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/972,482

(22) Filed: Dec. 17, 2015

(65) Prior Publication Data

US 2017/0174688 A1 Jun. 22, 2017
US 2017/0349589 A9 Dec. 7, 2017

Related U.S. Application Data

(60) Provisional application No. 62/093,523, filed on Dec. 18, 2014.

(51) Int. Cl.
*C07D 473/34* (2006.01)
*C07D 519/00* (2006.01)
*C12Q 1/48* (2006.01)

(52) U.S. Cl.
CPC ......... *C07D 473/34* (2013.01); *C07D 519/00* (2013.01); *C12Q 1/48* (2013.01); *G01N 2333/91017* (2013.01); *G01N 2500/04* (2013.01)

(58) Field of Classification Search
None
See application file for complete search history.

(56) References Cited

FOREIGN PATENT DOCUMENTS

CN WO 2015158283 A1 * 10/2015 ........... C07D 471/04

OTHER PUBLICATIONS

Beck D.B., et al., "The Role of Pr-Set7 in Replication Licensing Depends on Suv4-20h," Genes & Development, 2012, vol. 26, pp. 2580-2589.
Benetti R., et al., "Suv4-20h Deficiency Results in Telomere Elongation and Derepression of Telomere Recombination," Journal of Cell Biology, 2007, vol. 178 (6), pp. 925-936.
Berge S.M., et al., "Pharmaceutical Salts," Journal of Pharmaceutical Sciences, 1977, vol. 66 (1), pp. 1-19.
Chen X., et al., "Rational Design of Human DNA Ligase Inhibitors that Target Cellular DNA Replication and Repair," Cancer Research, 2008, vol. 68 (9), pp. 3169-3177.
Chi P., et al., "Covalent Histone Modifications—Miswritten, Misinterpreted and Mis-Erased in Human Cancers," Nature Reviews Cancer, 2010, vol. 10 (7), pp. 457-469.
Furniss B.S., et al., Vogel's Textbook of Practical Organic Chemistry, 5th Edition, Longman Scientific & Technical, 1989, Table of Contents.
Greene T.W., et al., Protective Groups in Organic Synthesis, 3rd Edition, John Wiley and Sons, Inc., 1999, Preface, Table of Contents, Abbreviations.
IUPAC 1974 Recommendations for Section E, Fundamental Stereochemistry, Pure and Applied Chemistry, 1976, vol. 45, pp. 13-30.
Kuo A.J., et al., "The BAH Domain of Orc1 Links H4k20me2 to DNA Replication Licensing and Meier-Gorlin Syndrome," Nature, 2012, vol. 484 (7392), pp. 115-119.
Lei M, "The MCM Complex: Its Role in DNA Replication and Implications for Cancer Therapy," Current Cancer Drug Targets, 2005, vol. 5 (5), pp. 365-380.
Li Y.H., et al., "Inhibition of Non-Homologous End Joining Repair Impairs Pancreatic Cancer Growth and Enhances Radiation Response," PLOS One, 2012, vol. 7 (6), pp. e39588.
Schotta G., et al., "A Chromatin-Wide Transition to H4k20 Monomethylation Impairs Genome Integrity and Programmed DNA Rearrangements in the Mouse," Genes & Development, 2008, vol. 22 (15), pp. 2048-2061.
Schotta G., et al., "A Silencing Pathway to Induce H3-K9 and H4-K20 Trimethylation at Constitutive Heterochromatin," Genes & Development, 2004, vol. 18 (11), pp. 1251-1262.
Tsang L.W., et al., "Comparative Analyses of Suv420h1 Isoforms and Suv420h2 Reveal Differences in Their Cellular Localization and Effects on Myogenic Differentiation," PLOS One, 2010, vol. 5 (12), pp. e14447.
Tuzon C.T., et al., "Concerted Activities of Distinct H4k20 Methyltransferases at DNA Double-Strand Breaks Regulate 53BP1 Nucleation and NHEJ-Directed Repair," Cell Reports, 2014, vol. 8 (2), pp. 430-438.
Zhao Y., et al., "Preclinical Evaluation of a Potent Novel DNA-Dependent Protein Kinase Inhibitor NU7441," Cancer Research, 2006, vol. 66 (10), pp. 5354-5362.
Zimmerman K.M., et al., "Diminished Origin-Licensing Capacity Specifically Sensitizes Tumor Cells to Replication Stress," Molecular Cancer Research, 2013, vol. 11 (4), pp. 370-380.

* cited by examiner

*Primary Examiner* — Sreeni Padmanabhan
*Assistant Examiner* — Jody Karol
(74) *Attorney, Agent, or Firm* — Changxia Sun

(57) ABSTRACT

The invention provides for compounds of formula (I)

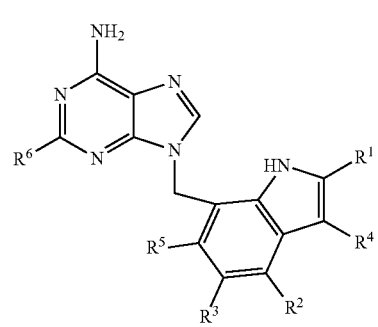

wherein $R^1$, $R^2$, $R^3$, $R^4$, $R^5$, and $R^6$ have any of the values defined in the specification, and pharmaceutically acceptable salts thereof, that are useful as agents in the treatment of diseases and conditions mediated and modulated by SUV420H1. Also provided are pharmaceutical compositions comprised of one or more compounds of formula (I).

27 Claims, No Drawings

SUBSTITUTED INDOLES

CROSS REFERENCE TO RELATED APPLICATIONS

This application claims priority to U.S. Provisional Application No. 62/093,523, filed Dec. 18, 2014, which is incorporated herein by reference for all purposes.

BACKGROUND

Histone methyltransferases (HMTs), a class of enzymatic "writers" of epigenetic marks, have recently emerged as targets of potential therapeutic value. They catalyze the methylation of histone lysines and arginines utilizing S-adenosyl-methionine (SAM) as the cofactor/methyl-source. This process can result in either the activation or repression of transcription. Dysregulation of methylation at specific histone sites (alterations in the "histone code") has been implicated in many cancers such as breast cancers, prostate cancers, renal cell carcinoma, and myeloid and lymphoblastic leukaemia (Chi P. et al. (2010) *Nat. Rev. Cancer* 10, 457-469). Hence, targeting HMT activity has been the subject of much investigation in the field of oncology.

Suppressor of variegation 4-20 homolog 1 (SUV420H1) is a SET domain-containing histone methyltransferase that localizes to heterochromatin (Schotta G. et al. (2004) *Genes & development* 18: 1251-1262). There are two isoforms of SUV420H1, both of which contain the conserved SET domain but differ at their C-termini, as well as a closely related homolog, SUV420H2 (Tsang L. W. et al. (2010) *PloS one* 5: e14447). SUV420H1 binds heterochromatin protein 1 (HP1) and this interaction functions to recruit SUV420H1 to heterochromatin. SUV420H1 catalyzes the di-methylation of histone H4 at lysine 20 (H4K20), which mediates a number of biological processes, including DNA replication, DNA damage-induced stress signaling, and the maintenance of pericentric and telomeric heterochromatin (Schotta G. et al. (2004) *Genes & development* 18: 1251-1262; Benetti R. et al. (2007) *The Journal of cell biology* 178: 925-936; Schotta G. et al. (2008) *Genes & development* 22: 2048-2061; Beck D. B. et al. (2012) *Genes & development* 26: 2580-2589; Kuo A. J. et al. (2012) *Nature* 484: 115-119; Tuzon C. T. et al. (2014) *Cell reports* 8: 430-438).

There is an increasing body of evidence indicating SUV420H1 plays a key role in cell growth and proliferation, and may be associated with proliferative diseases such as cancers. SUV420H1 knockout animals show embryonic and perinatal lethality (Schotta G. et al. (2008) *Genes & development* 22: 2048-2061). Furthermore, SUV420H1-deficient cells show reduced proliferation rates and growth arrest/senescence due to defects in DNA replication during S phase (Schotta G. et al. (2008) *Genes & development* 22: 2048-2061). Mechanistically, these defects in DNA replication arise from the lack of SUV420H1-dependent H4K20 dimethylation and subsequent inhibition of replication origin licensing (Beck D. B. et al. (2012) *Genes & development* 26: 2580-2589; Kuo A. J. et al. (2012) *Nature* 484: 115-119). Indeed, proteins involved in replication origin licensing have been pursued as targets for cancer therapy (Lei M. (2005) *Current cancer drug targets* 5: 365-380; Zimmerman K. M. et al. (2013) *Molecular cancer research: MCR* 11: 370-380). SUV420H1 is also important in regulating non-homologous end joining processes during the DNA damage response to double strand breaks (Schotta G. et al. (2008) *Genes & development* 22: 2048-2061; Tuzon C. T. et al. (2014) *Cell reports* 8: 430-438). In particular, inhibition of non-homologous end joining processes has been shown to sensitize pancreatic, breast, cervical and colon cancer cells to DNA damaging agents (Zhao Y. et al. (2006) *Cancer research* 66: 5354-5362; Chen X. et al. (2008) *Cancer research* 68: 3169-3177; Li Y. H. et al. (2012) *PloS one* 7: e39588).

Currently no small molecule inhibitors of SUV420H1 have been reported. Accordingly, there is a need for novel compounds able to inhibit SUV420H1.

SUMMARY OF THE INVENTION

In one aspect the invention provides for compounds of formula (I)

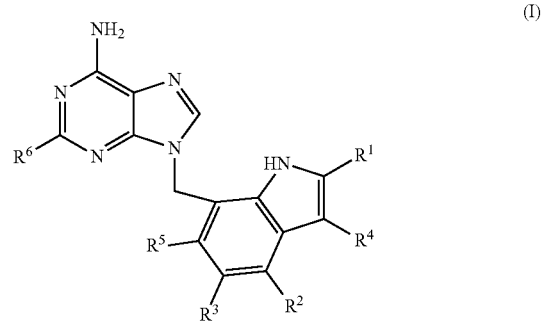

(I)

or a pharmaceutically acceptable salt thereof, wherein:
$R^1$ is hydrogen, —C(O)($C_1$-$C_6$ alkyl), —($C_1$-$C_6$ alkylenyl)-OH, —C(H)(benzyl)-$NH_2$, —C(H)(phenyl)-$NH_2$, —($C_1$-$C_6$ alkylenyl)-$NR^{1A}R^{1B}$, or —($C_1$-$C_6$ alkylenyl)-N($R^J$)C(O)$R^{1C}$;

$R^{1A}$ and $R^{1B}$ are each independently hydrogen, $C_1$-$C_6$ haloalkyl, $C_1$-$C_6$ alkyl, $C_2$-$C_4$ alkenyl, —$(CH_2)_m$-$G^{1A}$, —($C_1$-$C_6$ alkylenyl)-$L^{1A}$-X, or —$(CH_2)_n$-$G^{1A}$-$L^{1B}$-G; or $R^{1A}$ and $R^{1B}$ together with the nitrogen atom to which they are attached, form a $C_5$-$C_6$ heterocycloalkyl which is optionally substituted with 1, 2, or 3 substituents independently selected from the group consisting of $C_1$-$C_6$ haloalkyl, $C_1$-$C_6$ alkyl, and oxo;

$R^{1C}$ is $C_1$-$C_6$ haloalkyl, $C_1$-$C_6$ alkyl, $C_2$-$C_4$ alkenyl, —$(CH_2)_m$-$G^{1A}$, —($C_1$-$C_6$ alkylenyl)-$L^{1A}$-X, or —$(CH_2)_n$-$G^{1A}$-$L^{1B}$-G;

$G^{1A}$ and G, at each occurrence, are each independently phenyl, cycloalkyl, cycloalkenyl, heteroaryl, or heterocycle; wherein each $G^{1A}$ and G is optionally substituted with 1, 2, or 3 independently selected $R^u$;

$L^{1A}$, at each occurrence, is independently O, N(H), or C(O)O;

X, at each occurrence, is independently H, $C_1$-$C_6$ alkyl, or $C_1$-$C_6$ haloalkyl;

$L^{1B}$, at each occurrence, is independently a bond, —$C_1$-$C_3$ alkylenyl, 0, —O—$C_1$-$C_3$ alkylenyl-, C(O), or —N(H)C(O)—;

m is 0, 1, or 2;

n is 0, 1, or 2;

$R^2$ is hydrogen, halogen, $C_1$-$C_6$ alkyl, $C_2$-$C_4$ alkenyl, or $G^{2A}$; wherein $G^{2A}$ is $C_3$-$C_6$ cycloalkyl, $C_5$-$C_6$ cycloalkenyl, phenyl, or $C_5$-$C_6$ heteroaryl; and each $G^{2A}$ is optionally substituted with 1, 2, or 3 independently selected $R^u$ groups;

$R^3$ is hydrogen, halogen, $C_1$-$C_6$ alkyl, $C_2$-$C_4$ alkenyl, $G^{3A}$, -$G^{3A}$-$G^4$, or -$G^{3A}$-$L^3$-Y;

$G^{3A}$, at each occurrence, is independently $C_5$-$C_6$ cycloalkenyl, $C_3$-$C_6$ cycloalkyl, phenyl, $C_5$-$C_6$ heteroaryl, heterocycle; wherein each $G^{3A}$ is optionally substituted with 1, 2, or 3 independently selected $R^u$ groups;

$G^4$ is $C_3$-$C_6$ cycloalkyl or $C_5$-$C_6$ heterocycloalkyl; each of which is optionally substituted with 1, 2, or 3 independently selected $R^u$ groups;

$L^3$ is $C_1$-$C_3$ alkylenyl, C(O), or —C(O)N(H)—;

Y is —(C$_1$-C$_6$ alkylenyl)-N(R$^j$)$_2$, C$_3$-C$_6$ cycloalkyl, or C$_5$-C$_6$ heterocycloalkyl, wherein the C$_3$-C$_6$ cycloalkyl and the C$_5$-C$_6$ heterocycloalkyl are each optionally substituted with 1, 2, or 3 substituents independently selected from the group consisting of C$_1$-C$_3$ alkyl, halogen, and C$_1$-C$_3$ haloalkyl;

R$^4$ is hydrogen, halogen, or —(C$_1$-C$_6$ alkylenyl)-C(O)NR$^{4A}$R$^{4B}$; wherein R$^{4A}$ and R$^{4B}$ are each independently hydrogen or C$_1$-C$_6$ alkyl;

R$^5$ is hydrogen, halogen, C$_2$-C$_4$ alkenyl, C$_1$-C$_6$ alkyl, or phenyl wherein the phenyl is optionally substituted with 1, 2, or 3 independently selected R$^u$ groups;

R$^6$ is hydrogen, halogen, C$_1$-C$_3$ alkyl, or cyclopropyl; wherein the cyclopropyl is optionally substituted with 1, 2, or 3 substituents independently selected from the group consisting of halogen, C$_1$-C$_3$ alkyl, and C$_1$-C$_3$ haloalkyl;

R$^u$, at each occurrence, is independently C$_1$-C$_6$ alkyl, C$_2$-C$_6$ alkenyl, C$_2$-C$_6$ alkynyl, halogen, C$_1$-C$_6$ haloalkyl, —CN, oxo, NO$_2$, —OR$^j$, —OC(O)R$^k$, —OC(O)N(R$^j$)$_2$, —SR$^j$, —S(O)$_2$R$^j$, —S(O)$_2$N(R$^j$)$_2$, —C(O)R$^j$, —C(O)OR$^j$, —C(O)N(R$^j$)$_2$, —N(R$^j$)$_2$, —N(R$^j$)C(O)R$^k$, —N(R$^j$)S(O)$_2$R$^k$, —N(R$^j$)C(O)O(R$^k$), —N(R$^j$)C(O)N(R$^j$)$_2$, —(C$_1$-C$_6$ alkylenyl)-OR$^j$, —(C$_1$-C$_6$ alkylenyl)-OC(O)R$^k$, —(C$_1$-C$_6$ alkylenyl)-OC(O)N(R$^j$)$_2$, —(C$_1$-C$_6$ alkylenyl)-SR$^j$, —(C$_1$-C$_6$ alkylenyl)-S(O)$_2$R$^j$, —(C$_1$-C$_6$ alkylenyl)-S(O)$_2$N(R$^j$)$_2$, —(C$_1$-C$_6$ alkylenyl)-C(O)R$^j$, —(C$_1$-C$_6$ alkylenyl)-C(O)OR$^j$, —(C$_1$-C$_6$ alkylenyl)-C(O)N(R$^j$)$_2$, —(C$_1$-C$_6$ alkylenyl)-N(R$^j$)$_2$, —(C$_1$-C$_6$ alkylenyl)-N(R$^j$)C(O)R$^k$, —(C$_1$-C$_6$ alkylenyl)-N(R$^j$)S(O)$_2$R$^k$, —(C$_1$-C$_6$ alkylenyl)-N(R$^j$)C(O)O(R$^k$), —(C$_1$-C$_6$ alkylenyl)-N(R$^j$)C(O)N(R$^j$)$_2$, or —(C$_1$-C$_6$ alkylenyl)-CN;

R$^j$, at each occurrence, is independently hydrogen, C$_1$-C$_6$ alkyl, or C$_1$-C$_6$ haloalkyl; and R$^k$, at each occurrence, is independently C$_1$-C$_6$ alkyl or C$_1$-C$_6$ haloalkyl.

Another aspect of the invention relates to pharmaceutical compositions comprising compounds of the invention.

The compounds, compositions comprising the compounds, and methods for making the compounds are further described herein.

These and other objects of the invention are described in the following paragraphs. These objects should not be deemed to narrow the scope of the invention.

DETAILED DESCRIPTION OF THE INVENTION

Described herein are compounds of formula (I)

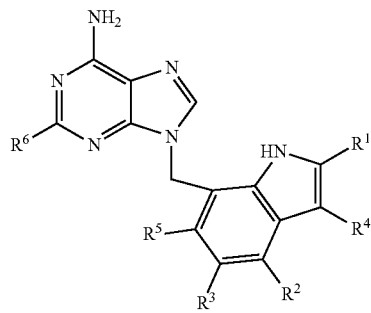

(I)

wherein R$^1$, R$^2$, R$^3$, R$^4$, R$^5$, and R$^6$ are defined above in the Summary of the Invention and below in the Detailed Description. Further, compositions comprising such compounds and methods for making such compounds are also included.

Compounds included herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds, which may be isolated from a reaction mixture.

DEFINITIONS

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "C$_2$-C$_6$ alkenyl" or "C$_2$-C$_4$ alkenyl" means an alkenyl group containing 2-6 carbon atoms or 2-4 carbon atoms respectively. Non-limiting examples of alkenyl include buta-1,3-dienyl, ethenyl, 2-propenyl, 2-methyl-2-propenyl, 3-butenyl, 4-pentenyl, and 5-hexenyl.

The term "alkyl" as used herein, means a saturated, straight or branched hydrocarbon chain radical. In some instances, the number of carbon atoms in an alkyl moiety is indicated by the prefix "C$_x$-C$_y$," wherein x is the minimum and y is the maximum number of carbon atoms in the substituent. Thus, for example, "C$_1$-C$_6$ alkyl" means to an alkyl substituent containing from 1 to 6 carbon atoms and "C$_1$-C$_3$ alkyl" refers to an alkyl substituent containing from 1 to 3 carbon atoms. Representative examples of C$_1$-C$_6$ alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, and 1,2,2-trimethylpropyl.

The term "alkylene" or "alkylenyl" means a divalent radical derived from a straight or branched, saturated hydrocarbon chain, for example, of 1 to 10 carbon atoms or of 1 to 6 carbon atoms (C$_1$-C$_6$ alkylenyl) or of 1 to 4 carbon atoms or of 1 to 3 carbon atoms (C$_1$-C$_3$ alkylenyl) or of 2 to 6 carbon atoms (C$_2$-C$_6$ alkylenyl). Examples of C$_1$-C$_6$ alkylenyl include, but are not limited to, —CH$_2$—, —CH$_2$CH$_2$—, —C((CH$_3$)$_2$)—CH$_2$CH$_2$CH$_2$—, —C((CH$_3$)$_2$)—CH$_2$CH$_2$, —CH$_2$CH$_2$CH$_2$CH$_2$—, and —CH$_2$CH(CH$_3$)CH$_2$—.

The term "C$_2$-C$_6$ alkynyl" as used herein, means a straight or branched chain hydrocarbon radical containing from 2 to 6 carbon atoms and containing at least one carbon-carbon triple bond. Representative examples of C$_2$-C$_6$ alkynyl include, but are not limited, to acetylenyl, 1-propynyl, 2-propynyl, 3-butynyl, 2-pentynyl, and 1-butynyl.

The term "cycloalkyl" as used herein, refers to a radical that is a monocyclic cycloalkyl or a bicyclic cycloalkyl. The monocyclic cycloalkyl is a carbocyclic ring system containing three to eight carbon atoms, zero heteroatoms and zero double bonds. Examples of monocyclic cycloalkyl include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. The monocyclic and the bicyclic cycloalkyl groups may further contain one or two alkylene bridges, each consisting of one, two, three, or four carbon atoms in length, and each bridge links two non-adjacent carbon atoms of the ring system. Non-limiting examples of bicyclic ring systems include bicyclo[3.1.1]heptyl, bicyclo[2.2.1]heptyl, bicyclo[2.2.2]octyl, bicyclo[1.1.1]pentyl, bicyclo[3.2.2]nonyl, bicyclo[3.3.1]nonyl, bicyclo[4.2.1]nonyl, tricyclo[3.3.1.0$^{3,7}$]nonyl (octahydro-2,5-methanopentalene or noradamantyl), and tricyclo[3.3.1.1$^{3,7}$]decane (adamantyl). The monocyclic and the bicyclic cycloalkyls, including exemplary rings, are optionally substituted. The monocyclic cycloalkyl and the bicyclic cycloalkyl are attached to the parent molecular moiety through any substitutable carbon atom contained within the ring systems.

The term "$C_3$-$C_6$ cycloalkyl" as used herein, means cyclopropyl, cyclobutyl, cyclopentyl, and cyclohexyl, each of which is optionally substituted.

The term "cycloalkenyl" as used herein, refers to a monocyclic or a bicyclic hydrocarbon ring radical. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic and bicyclic cycloalkenyl ring may further contain one or two alkylene bridges, each consisting of one, two, or three carbon atoms, and each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and the bicyclic cycloalkenyls, including exemplary rings, are optionally substituted. The monocyclic cycloalkenyl and bicyclic cycloalkenyl are attached to the parent molecular moiety through any substitutable atom contained within the ring systems.

The term "$C_5$-$C_6$ cycloalkenyl" as used herein, means cyclopentenyl and cyclohexenyl; each of which is optionally substituted.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five, or six hydrogen atoms are replaced by halogen. The term "$C_1$-$C_3$ haloalkyl" means a $C_1$-$C_3$ alkyl group, as defined herein, in which one, two, three, four, or five hydrogen atoms are replaced by halogen. Representative examples of $C_1$-$C_6$ haloalkyl include, but are not limited to, chloromethyl, 2-fluoroethyl, 2,2-difluoroethyl, fluoromethyl, 2,2,2-trifluoroethyl, trifluoromethyl, difluoromethyl, pentafluoroethyl, 2-chloro-3-fluoropentyl, trifluorobutyl, and trifluoropropyl.

The term "heterocycle" or "heterocyclic" as used herein, means a radical of a monocyclic heterocycle and a bicyclic heterocycle ring structure that may be saturated (i.e. heterocycloalkyl) or partially saturated (i.e. heterocycloalkenyl). A monocyclic heterocycle is a three-, four-, five-, six-, seven-, or eight-membered carbocyclic ring wherein at least one carbon atom is replaced by heteroatom independently selected from the group consisting of O, N, and S. A three- or four-membered ring contains zero or one double bond, and one heteroatom selected from the group consisting of O, N, and S. A five-membered ring contains zero or one double bond and one, two, or three heteroatoms selected from the group consisting of O, N, and S. Examples of five-membered heterocyclic rings include those containing in the ring: 1 O; 1 S; 1 N; 2 N; 3 N; 1 S and 1 N; 1 S, and 2 N; 1 O and 1 N; or 1 O and 2 N. Non limiting examples of 5-membered heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, isoxazolidinyl, pyrazolidinyl, pyrazolinyl, pyrrolidinyl, 2-pyrrolinyl, 3-pyrrolinyl, thiazolinyl, and thiazolidinyl. A six-membered ring contains zero, one, or two double bonds and one, two, or three heteroatoms selected from the group consisting of O, N, and S. Examples of six-membered heterocyclic rings include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Examples of 6-membered heterocyclic groups include tetrahydropyranyl, dioxanyl, 1,4-dithianyl, hexahydropyrimidine, morpholinyl, piperazinyl, piperidinyl, 1,2,3,4-tetrahydropyridinyl, 1,2,3,6-tetrahydropyridinyl, tetrahydrothiopyranyl, thiomorpholinyl, thioxanyl, and trithianyl. Seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, dihydropyranyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Representative examples of bicyclic heterocycles include, but are not limited to, benzopyranyl, benzothiopyranyl, 2,3-dihydrobenzofuranyl, 2,3-dihydrobenzothienyl, 2,3-dihydro-1H-indolyl, 3,4-dihydroisoquinolin-2(1H)-yl, 2,3,4,6-tetrahydro-1H-pyrido[1,2-a]pyrazin-2-yl, hexahydropyrano[3,4-b][1,4]oxazin-1(5H)-yl. The monocyclic heterocycle and the bicyclic heterocycle may contain one or two alkylene bridges, each consisting of no more than four carbon atoms and each linking two non-adjacent atoms of the ring system. Examples of such bridged heterocycle include, but are not limited to, azabicyclo[2.2.1]heptyl (including 2-azabicyclo [2.2.1]hept-2-yl), 8-azabicyclo[3.2.1]oct-8-yl, octahydro-2, 5-epoxypentalene, hexahydro-2H-2,5-methanocyclopenta [b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The monocyclic and the bicyclic heterocycles, including exemplary rings, are optionally substituted. The monocyclic and the bicyclic heterocycles are connected to the parent molecular moiety through any carbon atom or any nitrogen atom contained within the ring systems. The nitrogen and sulfur heteroatoms in the heterocycle rings may optionally be oxidized (e.g. 1,1-dioxidotetrahydrothienyl, 1,1-dioxido-1, 2-thiazolidinyl, 1,1-dioxidothiomorpholinyl)) and the nitrogen atoms may optionally be quarternized.

The term "$C_4$-$C_6$ heterocycloalkyl" as used herein, means a 4, 5, or 6 membered monocyclic heterocycloalkyl as defined herein above. Examples of $C_4$-$C_6$ heterocycloalkyl include, but are not limited to, azetidinyl, pyrrolidinyl, tetrahydrofuranyl, tetrahydropyranyl, piperazinyl, piperidinyl, thiomorpholinyl, and morpholinyl. The $C_4$-$C_6$ heterocycloalkyl, including exemplary rings, are optionally substituted.

The term "$C_5$-$C_6$ heterocycloalkyl" as used herein, means a 5 or 6 membered monocyclic heterocycloalkyl as defined herein above. Examples of $C_5$-$C_6$ heterocycloalkyl include, but are not limited to, pyrrolidinyl, tetrahydrofuranyl, tetrahydropyranyl, piperazinyl, piperidinyl, thiomorpholinyl, and morpholinyl. The $C_5$-$C_6$ heterocycloalkyl, including exemplary rings, are optionally substituted.

The term "$C_5$-$C_6$ heterocycloalkenyl" as used herein, means a 5 or 6 membered monocyclic heterocycloalkenyl as defined herein above. Examples of $C_5$-$C_6$ heterocycloalkenyl include, but are not limited to, dihydropyranyl, 1,2,3,4-tetrahydropyridinyl, and 1,2,3,6-tetrahydropyridinyl. The $C_5$-$C_6$ heterocycloalkenyl, including exemplary rings, are optionally substituted.

The term "heteroaryl" as used herein, means a monocyclic heteroaryl and a bicyclic heteroaryl. The monocyclic heteroaryl is a five- or six-membered carbocyclic ring wherein at least one carbon atom is replaced by heteroatom independently selected from the group consisting of O, N, and S. The five-membered ring contains two double bonds. The five-membered ring may contain one heteroatom selected from O or S; or one, two, three, or four nitrogen atoms and optionally further contain one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryls include, but are not limited to, benzofuranyl, benzothienyl, benzoxazolyl, benzimidazolyl, benzoxadiazolyl, benzothiazolyl, 1H-benzo[d][1,2,3]triazolyl, furo[3,2-b]pyridinyl, phthalazinyl, benzo[d][1,2,3]thiadiazole, 3H-imidazo[4,5-b]pyridinyl, imidazo[1,2-a]pyridinyl, 1H-pyrrolo[3,2-b]pyridinyl, 1H-pyrrolo[2,3-b]pyridinyl, 1H-pyrazolo[3,4-b]pyridinyl, indazolyl, indolyl, isoindolyl, isoxazolo[5,4-b]pyridinyl, isoquinolinyl, naphthyridinyl, pyridoimidazolyl, quinolinyl, thieno[3,2-b]pyridinyl, thiazolo[5,4-b]pyridin-2-yl, and thiazolo[5,4-d]pyrimidin-2-yl. The monocyclic and bicyclic heteroaryls, including exemplary rings, are optionally substituted unless otherwise indicated. The monocyclic and bicyclic heteroaryls are connected to the parent molecular moiety through any substitutable carbon atom or any substitutable nitrogen atom contained within the ring systems. The nitrogen atom in the heteroaryl rings may optionally be oxidized and may optionally be quaternized.

The term "$C_5$-$C_6$ heteroaryl" as used herein, means a 5- or 6-membered monocyclic heteroaryl as described above. Examples of $C_5$-$C_6$ heteroaryl include furanyl, thienyl, pyrazolyl, imidazolyl, 1,2,4-oxadiazolyl, 1,2,4-triazolyl, 1,3-thiazolyl, pyridinyl, pyrimidinyl, pyridazinyl, and pyrazinyl. The $C_5$-$C_6$ heteroaryls, including exemplary rings, are optionally substituted.

The term "heteroatom" as used herein, means a nitrogen, oxygen, and sulfur.

The term "oxo" as used herein, means a =O group.

The term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3H$ (tritium), $^{14}C$, $^{11}C$, $^{15}O$, $^{18}F$, $^{35}S$, $^{123}I$, and $^{125}I$.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

Unless otherwise indicated, the terms $C_1$-$C_6$ alkyl, $C_1$-$C_3$ alkyl, $C_1$-$C_6$ haloalkyl, and $C_1$-$C_3$ haloalkyl are not further substituted.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent or treatment in a particular subject or subject population. For example in a human or other mammal, a therapeutically effective amount may be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In preferred embodiments, the subject is a human.

Compounds

Compounds of the invention have the general formula (I) as described above.

Particular values of variable groups are as follows. Such values may be used where appropriate with any of the other values, definitions, claims or embodiments defined hereinbefore or hereinafter.

In certain embodiments, $R^1$ is hydrogen, —C(H)(benzyl)-$NH_2$, —C(H)(phenyl)-$NH_2$, —($C_1$-$C_6$ alkylenyl)-$NR^{1A}R^{1B}$, or —($C_1$-$C_6$ alkylenyl)-N($R^J$)C(O)$R^{1C}$.

In certain embodiments, $R^1$ is hydrogen.

In certain embodiments, $R^1$ is —C(O)($C_1$-$C_6$ alkyl), —($C_1$-$C_6$ alkylenyl)-OH, —C(H)(benzyl)-$NH_2$, —C(H)(phenyl)-$NH_2$, —($C_1$-$C_6$ alkylenyl)-$NR^{1A}R^{1B}$, or —($C_1$-$C_6$ alkylenyl)-N($R^J$)C(O)$R^{1C}$.

In certain embodiments, $R^1$ is —($C_1$-$C_6$ alkylenyl)-$NR^{1A}R^{1B}$ or —($C_1$-$C_6$ alkylenyl)-N($R^J$)C(O)$R^{1C}$.

In certain embodiments, $R^1$ is —($C_1$-$C_6$ alkylenyl)-$NR^{1A}R^{1B}$.

In certain embodiments, $R^1$ is —($C_1$-$C_6$ alkylenyl)-N($R^J$)C(O)$R^{1C}$.

In certain embodiments, $R^2$ is hydrogen.

In certain embodiments, $R^2$ is halogen, $C_1$-$C_6$ alkyl, $C_2$-$C_4$ alkenyl, or $G^{2A}$; wherein $G^{2A}$ is $C_3$-$C_6$ cycloalkyl, $C_5$-$C_6$ cycloalkenyl, phenyl, or $C_5$-$C_6$ heteroaryl; and each $G^{2A}$ is optionally substituted. In some such embodiments, $G^{2A}$ is $C_5$-$C_6$ cycloalkenyl, phenyl, or $C_5$-$C_6$ heteroaryl; and each $G^{2A}$ is optionally substituted. In some such embodiments, $G^{2A}$ is phenyl, pyridinyl, pyrazolyl, or cyclopentenyl, each of which is optionally substituted. In some such embodiments, $G^{2A}$ is optionally substituted phenyl. In some such embodiments, $G^{2A}$ is optionally substituted $C_5$-$C_6$ cycloalkenyl. In some such embodiments, $G^{2A}$ is optionally substituted cyclopentenyl. In some such embodiments, $G^{2A}$ is optionally substituted $C_5$-$C_6$ heteroaryl. In some such embodiments, $G^{2A}$ is pyridinyl or pyrazolyl, each of which is optionally substituted.

In certain embodiments, $R^2$ is Cl, $CH_3$, $CH_2CH_3$, ethenyl, prop-1-en-2-yl, or $G^{2A}$; wherein $G^{2A}$ is phenyl, pyridinyl, pyrazolyl, or cyclopentenyl, wherein each $G^{2A}$ is optionally substituted.

In certain embodiments, $R^3$ is hydrogen, halogen, $C_2$-$C_4$ alkenyl, $G^{3A}$, -$G^{3A}$-$G^A$, or -$G^{3A}$-$L^3$-Y.

In certain embodiments, $R^3$ is hydrogen.

In certain embodiments, $R^3$ is halogen, $C_1$-$C_6$ alkyl, $C_2$-$C_4$ alkenyl, $G^{3A}$, -$G^{3A}$-$G^A$, or -$G^{3A}$-$L^3$-Y.

In certain embodiments, $R^3$ is halogen, $C_2$-$C_4$ alkenyl, $G^{3A}$, -$G^{3A}$-$G^A$, or -$G^{3A}$-$L^3$-Y.

In certain embodiments, $R^3$ is halogen. In some such embodiments, $R^3$ is Cl.

In certain embodiments, $R^3$ is $C_2$-$C_4$ alkenyl. In some such embodiments, $R^3$ is ethenyl.

In certain embodiments, $R^3$ is $G^{3A}$.

In certain embodiments, $R^3$ is $G^{3A}$ wherein $G^{3A}$ is cyclopentenyl, cyclohexenyl, cyclohexyl, dihydropyranyl, tetrahydropyridinyl, piperidinyl, dihydrobenzofuranyl, indazolyl, pyridinyl, pyrimidinyl, or phenyl; each of which is optionally substituted.

In certain embodiments, $R^3$ is $G^{3A}$ wherein $G^{3A}$ is optionally substituted cyclohexenyl. In some such embodiments, $G^{3A}$ is cyclohexenyl substituted with 1 or 2 halogen. In some such embodiments, $G^{3A}$ is cyclohexenyl substituted with two halogens wherein the halogens are F.

In certain embodiments, $R^3$ is -$G^{3A}$-$G^A$ or -$G^{3A}$-$L^3$-Y.

In certain embodiments, $R^3$ is -$G^{3A}$-$G^A$ or -$G^{3A}$-$L^3$-Y; wherein $G^{3A}$ is optionally substituted phenyl, and $G^A$ is optionally substituted $C_5$-$C_6$ heterocyloalkyl.

In certain embodiments, $R^3$ is -$G^{3A}$-$G^A$ or -$G^{3A}$-$L^3$-Y; wherein $G^{3A}$ is optionally substituted phenyl, Y is —($C_1$-$C_6$ alkylenyl)-N($R^J$)$_2$, optionally substituted cyclopropyl, optionally substituted morpholinyl, or optionally substituted piperidinyl, and $G^A$ is optionally substituted morpholinyl.

In certain embodiments, $R^3$ is -$G^{3A}$-$G^A$. In some such embodiments, $G^{3A}$ is optionally substituted phenyl and $G^A$ is optionally substituted $C_5$-$C_6$ heterocycloalkyl.

In certain embodiments, $R^3$ is -$G^{3A}$-$L^3$-Y. In some such embodiments, $G^{3A}$ is optionally substituted phenyl; and $L^3$ is —$CH_2$—, C(O), or —C(O)N(H)—.

In certain embodiments, $R^4$ is hydrogen.

In certain embodiments, $R^4$ is halogen or —($C_1$-$C_6$ alkylenyl)-C(O)$NR^{4A}R^{4B}$. In some such embodiments $R^4$ is Br or —($C_1$-$C_2$ alkylenyl)-C(O)$NR^{4A}R^{4B}$ wherein $R^{4A}$ and $R^{4B}$ are each independently hydrogen or $C_1$-$C_3$ alkyl.

In certain embodiments, $R^5$ is hydrogen, halogen, $C_2$-$C_4$ alkenyl, or optionally substituted phenyl.

In certain embodiments, $R^5$ is hydrogen.

In certain embodiments, $R^5$ is halogen, $C_2$-$C_4$ alkenyl, or optionally substituted phenyl.

In some such embodiments, $R^5$ is Cl, ethenyl, prop-1-en-2-yl, or optionally substituted phenyl.

In certain embodiments, $R^6$ is hydrogen.

In certain embodiments, $R^6$ is $C_1$-$C_3$ alkyl or optionally substituted cyclopropyl. In some such embodiments, $R^6$ is $CH_3$ or unsubstituted cyclopropyl.

Various embodiments of substituents $R^1$, $R^2$, $R^3$, $R^4$, $R^5$, and $R^6$ have been discussed above. These substituents embodiments may be combined to form various embodiments of the invention. All embodiments of present compounds, formed by combining the substituent embodiments discussed above are within the scope of Applicant's invention, and some illustrative embodiments of present compounds are provided below.

In one embodiment, the invention is directed to compounds of formula (I) wherein $R^1$, $R^2$, $R^3$, $R^4$, $R^5$, and $R^6$ are hydrogen.

In one embodiment, the invention is directed to compounds of formula (I) wherein $R^1$, $R^2$, $R^3$, $R^4$, and $R^5$ are hydrogen, and $R^6$ is hydrogen, $C_1$-$C_3$ alkyl, or optionally substituted cyclopropyl. In some such embodiments, $R^6$ is hydrogen, $CH_3$, or unsubstituted cyclopropyl.

In one embodiment, the invention is directed to compounds of formula (I) wherein $R^1$, $R^2$, $R^3$, $R^4$, and $R^5$ are hydrogen.

In one embodiment, the invention is directed to compounds of formula (I) wherein $R^1$, $R^2$, $R^3$, $R^4$, and $R^5$ are hydrogen, and $R^6$ is $C_1$-$C_3$ alkyl or optionally substituted cyclopropyl. In some such embodiments, $R^6$ is $CH_3$ or unsubstituted cyclopropyl.

In one embodiment, the invention is directed to compounds of formula (I) wherein $R^4$, $R^5$, and $R^6$ are hydrogen.

In one embodiment, the invention is directed to compounds of formula (I) wherein $R^1$ is hydrogen, —C(H)(benzyl)-$NH_2$, —C(H)(phenyl)-$NH_2$, —($C_1$-$C_6$ alkylenyl)-$NR^{1A}R^{1B}$, or —($C_1$-$C_6$ alkylenyl)-N($R^J$)C(O)$R^{1C}$.

In one embodiment, the invention is directed to compounds of formula (I) wherein $R^1$ is —($C_1$-$C_6$ alkylenyl)-$NR^{1A}R^{1B}$ or —($C_1$-$C_6$ alkylenyl)-N($R^J$)C(O)$R^{1C}$.

In one embodiment, the invention is directed to compounds of formula (I) wherein $R^3$ is hydrogen, halogen, $C_2$-$C_4$ alkenyl, $G^{3A}$, -$G^{3A}$-$G^A$, or -$G^{3A}$-$L^3$-Y.

In one embodiment, the invention is directed to compounds of formula (I) wherein $R^3$ is halogen.

In one embodiment, the invention is directed to compounds of formula (I) wherein
$R^3$ is halogen; and
$R^2$, $R^4$, $R^5$, and $R^6$ are hydrogen.

In one embodiment, the invention is directed to compounds of formula (I) wherein
$R^3$ is halogen;
$R^2$, $R^4$, $R^5$, and $R^6$ are hydrogen; and
$R^1$ is —C(O)($C_1$-$C_6$ alkyl), —($C_1$-$C_6$ alkylenyl)-OH, —C(H)(benzyl)-$NH_2$, —C(H)(phenyl)-$NH_2$, —($C_1$-$C_6$ alkylenyl)-$NR^{1A}R^{1B}$, or —($C_1$-$C_6$ alkylenyl)-N($R^j$)C(O)$R^{1C}$.

In one embodiment, the invention is directed to compounds of formula (I) wherein
$R^3$ is halogen;
$R^2$, $R^4$, $R^5$, and $R^6$ are hydrogen; and
$R^1$ is —($C_1$-$C_6$ alkylenyl)-$NR^{1A}R^{1B}$ or —($C_1$-$C_6$ alkylenyl)-N($R^j$)C(O)$R^{1C}$.

In one embodiment, the invention is directed to compounds of formula (I) wherein $R^3$ is $G^{3A}$.

In one embodiment, the invention is directed to compounds of formula (I) wherein
$R^3$ is $G^{3A}$; and
$R^2$, $R^4$, $R^5$, and $R^6$ are hydrogen.

In one embodiment, the invention is directed to compounds of formula (I) wherein
$R^3$ is $G^{3A}$;
$R^2$, $R^4$, $R^5$, and $R^6$ are hydrogen; and
$R^1$ is —($C_1$-$C_6$ alkylenyl)-$NR^{1A}R^{1B}$ or —($C_1$-$C_6$ alkylenyl)-N($R^j$)C(O)$R^{1C}$.

In one embodiment, the invention is directed to compounds of formula (I) wherein
$R^3$ is $G^{3A}$; wherein $G^{3A}$ is cyclohexenyl optionally substituted with 1, 2, or 3 independently selected $R^u$;
$R^2$, $R^4$, $R^5$, and $R^6$ are hydrogen; and
$R^1$ is —($CH_2$)—N($R^j$)C(O)$R^{1C}$ wherein $R^{1C}$ is —($CH_2$)$_m$-$G^{1A}$ wherein m is 0 or 1.

In one embodiment, the invention is directed to compounds of formula (I) wherein $R^3$ is -$G^{3A}$-$G^4$.

In one embodiment, the invention is directed to compounds of formula (I) wherein
$R^3$ is -$G^{3A}$-$G^4$; and
$R^2$, $R^4$, $R^5$, and $R^6$ are hydrogen.

In one embodiment, the invention is directed to compounds of formula (I) wherein
$R^3$ is -$G^{3A}$-$G^4$;
$R^2$, $R^4$, $R^5$, and $R^6$ are hydrogen; and
$R^1$ is —($C_1$-$C_6$ alkylenyl)-$NR^{1A}R^{1B}$ or —($C_1$-$C_6$ alkylenyl)-N($R^j$)C(O)$R^{1C}$.

In one embodiment, the invention is directed to compounds of formula (I) wherein
$R^3$ is -$G^{3A}$-$G^4$;
$R^2$, $R^4$, $R^5$, and $R^6$ are hydrogen;
$R^1$ is —($C_1$-$C_6$ alkylenyl)-$NR^{1A}R^{1B}$ or —($C_1$-$C_6$ alkylenyl)-N($R^j$)C(O)$R^{1C}$; and
$G^{3A}$ is phenyl optionally substituted with 1, 2, or 3 independently selected $R^u$; and
$G^4$ is $C_5$-$C_6$ heterocycloalkyl optionally substituted with 1, 2, or 3 independently selected $R^u$.

In one embodiment, the invention is directed to compounds of formula (I) wherein $R^3$ is -$G^{3A}$-$L^3$-Y.

In one embodiment, the invention is directed to compounds of formula (I) wherein
$R^3$ is -$G^{3A}$-$L^3$-Y; and
$R^2$, $R^4$, $R^5$, and $R^6$ are hydrogen.

In one embodiment, the invention is directed to compounds of formula (I) wherein
$R^3$ is -$G^{3A}$-$L^3$-Y;
$R^2$, $R^4$, $R^5$, and $R^6$ are hydrogen; and
$R^1$ is —($C_1$-$C_6$ alkylenyl)-$NR^{1A}R^{1B}$ or —($C_1$-$C_6$ alkylenyl)-N($R^j$)C(O)$R^{1C}$.

In one embodiment, the invention is directed to compounds of formula (I) wherein
$R^3$ is -$G^{3A}$-$L^3$-Y;
$R^2$, $R^4$, $R^5$, and $R^6$ are hydrogen;
$R^1$ is —($C_1$-$C_6$ alkylenyl)-$NR^{1A}R^{1B}$ or —($C_1$-$C_6$ alkylenyl)-N($R^j$)C(O)$R^{1C}$.
$G^{3A}$ is phenyl optionally substituted with 1, 2, or 3 independently selected $R^u$ groups; and
$L^3$ is —$CH_2$—, C(O), or —C(O)N(H)—.

In one embodiment, the invention is directed to compounds of formula (I) wherein
$R^2$ is hydrogen, halogen, $C_1$-$C_6$ alkyl, $C_2$-$C_4$ alkenyl, or $G^{2A}$; wherein $G^{2A}$ is $C_5$-$C_6$ cycloalkenyl, phenyl, or $C_5$-$C_6$ heteroaryl; and each $G^{2A}$ is optionally substituted with 1, 2, or 3 independently selected $R^u$ groups.

In one embodiment, the invention is directed to compounds of formula (I) wherein
$R^2$ is hydrogen, halogen, $C_1$-$C_6$ alkyl, $C_2$-$C_4$ alkenyl, or $G^{2A}$; wherein $G^{2A}$ is $C_5$-$C_6$ cycloalkenyl, phenyl, or $C_5$-$C_6$ heteroaryl; and each $G^{2A}$ is optionally substituted with 1, 2, or 3 independently selected $R^u$ groups; and
$R^3$, $R^4$, $R^5$, and $R^6$ are hydrogen.

In one embodiment, the invention is directed to compounds of formula (I) wherein
$R^3$, $R^4$, $R^5$, and $R^6$ are hydrogen;
$R^2$ is hydrogen, halogen, $C_1$-$C_6$ alkyl, $C_2$-$C_4$ alkenyl, or $G^{2A}$; wherein $G^{2A}$ is $C_5$-$C_6$ cycloalkenyl, phenyl, or $C_5$-$C_6$ heteroaryl; and each $G^{2A}$ is optionally substituted with 1, 2, or 3 independently selected $R^u$ groups; and
$R^1$ is —($C_1$-$C_6$ alkylenyl)-$NR^{1A}R^{1B}$ or —($C_1$-$C_6$ alkylenyl)-N($R^j$)C(O)$R^{1C}$.

In one embodiment, the invention is directed to compounds of formula (I) wherein
$R^2$, $R^3$, $R^4$, and $R^6$ are hydrogen; and
$R^5$ is hydrogen, halogen, $C_2$-$C_4$ alkenyl, or phenyl wherein the phenyl is optionally substituted with 1, 2, or 3 independently selected $R^u$ groups.

In one embodiment, the invention is directed to compounds of formula (I) wherein
$R^2$, $R^3$, $R^4$, and $R^6$ are hydrogen;
$R^5$ is hydrogen, halogen, $C_2$-$C_4$ alkenyl, or phenyl wherein the phenyl is optionally substituted with 1, 2, or 3 independently selected $R^u$ groups; and
$R^1$ is —($C_1$-$C_6$ alkylenyl)-$NR^{1A}R^{1B}$.

Exemplary compounds of formula (I) include, but are not limited to:
9-[(3-bromo-1H-indol-7-yl)methyl]-9H-purin-6-amine;
9-(1H-indol-7-ylmethyl)-2-methyl-9H-purin-6-amine;
9-(1H-indol-7-ylmethyl)-9H-purin-6-amine;
2-cyclopropyl-9-(1H-indol-7-ylmethyl)-9H-purin-6-amine;
{7-[(6-amino-9H-purin-9-yl)methyl]-5-chloro-1H-indol-2-yl}methanol;
9-{[2-(aminomethyl)-1H-indol-7-yl]methyl}-9H-purin-6-amine;
9-{[2-(aminomethyl)-5-chloro-1H-indol-7-yl]methyl}-9H-purin-6-amine;
9-{[2-(aminomethyl)-5-ethenyl-1H-indol-7-yl]methyl}-9H-purin-6-amine;
9-{[2-(aminomethyl)-5-(cyclopent-1-en-1-yl)-1H-indol-7-yl]methyl}-9H-purin-6-amine;

9-{[2-(aminomethyl)-5-(3,6-dihydro-2H-pyran-4-yl)-1H-indol-7-yl]methyl}-9H-purin-6-amine;
9-{[2-(aminomethyl)-5-(1,2,3,6-tetrahydropyridin-4-yl)-1H-indol-7-yl]methyl}-9H-purin-6-amine;
9-{[2-(aminomethyl)-5-(4,4-difluorocyclohex-1-en-1-yl)-1H-indol-7-yl]methyl}-9H-purin-6-amine;
1-[4-{2-(aminomethyl)-7-[(6-amino-9H-purin-9-yl)methyl]-1H-indol-5-yl}-3,6-dihydropyridin-1(2H)-yl]ethanone;
1-[5-{2-(aminomethyl)-7-[(6-amino-9H-purin-9-yl)methyl]-1H-indol-5-yl}-3,6-dihydropyridin-1(2H)-yl]ethanone;
1-(4-{2-(aminomethyl)-7-[(6-amino-9H-purin-9-yl)methyl]-1H-indol-5-yl}piperidin-1-yl)ethanone;
9-{[2-(aminomethyl)-5-(1-methyl-1H-pyrazol-4-yl)-1H-indol-7-yl]methyl}-9H-purin-6-amine;
9-{[2-(aminomethyl)-5-(pyrimidin-5-yl)-1H-indol-7-yl]methyl}-9H-purin-6-amine;
9-{[2-(aminomethyl)-5-(pyridin-3-yl)-1H-indol-7-yl]methyl}-9H-purin-6-amine;
9-{[2-(aminomethyl)-5-(pyridin-4-yl)-1H-indol-7-yl]methyl}-9H-purin-6-amine;
9-{[2-(aminomethyl)-5-phenyl-1H-indol-7-yl]methyl}-9H-purin-6-amine;
9-{[2-(aminomethyl)-5-(4-chlorophenyl)-1H-indol-7-yl]methyl}-9H-purin-6-amine;
9-{[2-(aminomethyl)-5-(3-chlorophenyl)-1H-indol-7-yl]methyl}-9H-purin-6-amine;
9-{[2-(aminomethyl)-5-(2-chlorophenyl)-1H-indol-7-yl]methyl}-9H-purin-6-amine;
9-{[2-(aminomethyl)-5-(4-fluorophenyl)-1H-indol-7-yl]methyl}-9H-purin-6-amine;
9-{[2-(aminomethyl)-5-(2-fluorophenyl)-1H-indol-7-yl]methyl}-9H-purin-6-amine;
9-{[2-(aminomethyl)-5-(6-methoxypyridin-3-yl)-1H-indol-7-yl]methyl}-9H-purin-6-amine;
4-{2-(aminomethyl)-7-[(6-amino-9H-purin-9-yl)methyl]-1H-indol-5-yl}benzenesulfonamide;
9-{[2-(aminomethyl)-5-(4-methylphenyl)-1H-indol-7-yl]methyl}-9H-purin-6-amine;
9-{[2-(aminomethyl)-5-(3-methylphenyl)-1H-indol-7-yl]methyl}-9H-purin-6-amine;
9-{[2-(aminomethyl)-5-(2-methylphenyl)-1H-indol-7-yl]methyl}-9H-purin-6-amine;
(4-{2-(aminomethyl)-7-[(6-amino-9H-purin-9-yl)methyl]-1H-indol-5-yl}phenyl)methanol;
9-{[2-(aminomethyl)-5-(4-methoxyphenyl)-1H-indol-7-yl]methyl}-9H-purin-6-amine;
9-{[2-(aminomethyl)-5-(3-methoxyphenyl)-1H-indol-7-yl]methyl}-9H-purin-6-amine;
9-{[2-(aminomethyl)-5-(2-methoxyphenyl)-1H-indol-7-yl]methyl}-9H-purin-6-amine;
9-({2-(aminomethyl)-5-[4-(methylsulfonyl)phenyl]-1H-indol-7-yl}methyl)-9H-purin-6-amine;
4-{2-(aminomethyl)-7-[(6-amino-9H-purin-9-yl)methyl]-1H-indol-5-yl}benzonitrile;
3-{2-(aminomethyl)-7-[(6-amino-9H-purin-9-yl)methyl]-1H-indol-5-yl}benzonitrile;
3-{2-(aminomethyl)-7-[(6-amino-9H-purin-9-yl)methyl]-1H-indol-5-yl}benzamide;
N-(4-{2-(aminomethyl)-7-[(6-amino-9H-purin-9-yl)methyl]-1H-indol-5-yl}phenyl)methanesulfonamide;
N-(3-{2-(aminomethyl)-7-[(6-amino-9H-purin-9-yl)methyl]-1H-indol-5-yl}phenyl)methanesulfonamide;
9-{[2-(aminomethyl)-5-(4-ethylphenyl)-1H-indol-7-yl]methyl}-9H-purin-6-amine;
methyl4-{2-(aminomethyl)-7-[(6-amino-9H-purin-9-yl)methyl]-1H-indol-5-yl}benzoate;
(4-{2-(aminomethyl)-7-[(6-amino-9H-purin-9-yl)methyl]-1H-indol-5-yl}phenyl)acetonitrile;
3-{2-(aminomethyl)-7-[(6-amino-9H-purin-9-yl)methyl]-1H-indol-5-yl}-N-ethylbenzamide;
4-{2-(aminomethyl)-7-[(6-amino-9H-purin-9-yl)methyl]-1H-indol-5-yl}-N,N-dimethylbenzamide;
3-{2-(aminomethyl)-7-[(6-amino-9H-purin-9-yl)methyl]-1H-indol-5-yl}-N,N-dimethylbenzamide;
4-{2-(aminomethyl)-7-[(6-amino-9H-purin-9-yl)methyl]-1H-indol-5-yl}-N-[2-(dimethylamino)ethyl]benzamide;
4-{2-(aminomethyl)-7-[(6-amino-9H-purin-9-yl)methyl]-1H-indol-5-yl}-N-cyclopropylbenzamide;
3-{2-(aminomethyl)-7-[(6-amino-9H-purin-9-yl)methyl]-1H-indol-5-yl}-N-cyclopropylbenzamide;
9-({2-(aminomethyl)-5-[3-(morpholin-4-yl)phenyl]-1H-indol-7-yl}methyl)-9H-purin-6-amine;
(3-{2-(aminomethyl)-7-[(6-amino-9H-purin-9-yl)methyl]-1H-indol-5-yl}phenyl)(morpholin-4-yl)methanone;
9-{[2-(aminomethyl)-5-{4-[(4-methylpiperazin-1-yl)methyl]phenyl}-1H-indol-7-yl]methyl}-9H-purin-6-amine;
9-{[2-(aminomethyl)-5-{3-[(4-methylpiperazin-1-yl)methyl]phenyl})-1H-indol-7-yl]methyl}-9H-purin-6-amine;
(4-{2-(aminomethyl)-7-[(6-amino-9H-purin-9-yl)methyl]-1H-indol-5-yl}phenyl)(4-methylpiperazin-1-yl)methanone;
9-{[2-(aminomethyl)-5-(2,3-dihydro-1-benzofuran-5-yl)-1H-indol-7-yl]methyl}-9H-purin-6-amine;
9-{[2-(aminomethyl)-6-chloro-1H-indol-7-yl]methyl}-9H-purin-6-amine;
9-{[2-(aminomethyl)-6-ethenyl-1H-indol-7-yl]methyl}-9H-purin-6-amine;
9-{[2-(aminomethyl)-6-(prop-1-en-2-yl)-1H-indol-7-yl]methyl}-9H-purin-6-amine;
9-{[2-(aminomethyl)-6-phenyl-1H-indol-7-yl]methyl}-9H-purin-6-amine;
9-{[2-(aminomethyl)-4-chloro-1H-indol-7-yl]methyl}-9H-purin-6-amine;
9-{[2-(aminomethyl)-4-ethenyl-1H-indol-7-yl]methyl}-9H-purin-6-amine;
9-{[2-(aminomethyl)-4-ethyl-1H-indol-7-yl]methyl}-9H-purin-6-amine;
9-{[2-(aminomethyl)-4-(prop-1-en-2-yl)-1H-indol-7-yl]methyl}-9H-purin-6-amine;
9-{[2-(aminomethyl)-4-(propan-2-yl)-1H-indol-7-yl]methyl}-9H-purin-6-amine;
9-{[2-(aminomethyl)-4-(cyclopent-1-en-1-yl)-1H-indol-7-yl]methyl}-9H-purin-6-amine;
9-{[2-(aminomethyl)-4-(1-methyl-1H-pyrazol-4-yl)-1H-indol-7-yl]methyl}-9H-purin-6-amine;
9-{[2-(aminomethyl)-4-(pyridin-3-yl)-1H-indol-7-yl]methyl}-9H-purin-6-amine;
9-{[2-(aminomethyl)-4-phenyl-1H-indol-7-yl]methyl}-9H-purin-6-amine;
9-{[2-(aminomethyl)-4-(3-chlorophenyl)-1H-indol-7-yl]methyl}-9H-purin-6-amine;
9-{[2-(aminomethyl)-4-(2-chlorophenyl)-1H-indol-7-yl]methyl}-9H-purin-6-amine;
9-{[2-(aminomethyl)-4-(4-fluorophenyl)-1H-indol-7-yl]methyl}-9H-purin-6-amine;
9-{[2-(aminomethyl)-4-(2-fluorophenyl)-1H-indol-7-yl]methyl}-9H-purin-6-amine;
9-{[2-(aminomethyl)-4-(4-methylphenyl)-1H-indol-7-yl]methyl}-9H-purin-6-amine;

9-{[2-(aminomethyl)-4-(3-methylphenyl)-1H-indol-7-yl]
methyl}-9H-purin-6-amine;
9-{[2-(aminomethyl)-4-(2-methylphenyl)-1H-indol-7-yl]
methyl}-9H-purin-6-amine;
9-{[2-(aminomethyl)-4-(4-methoxyphenyl)-1H-indol-7-yl]
methyl}-9H-purin-6-amine;
9-{[2-(aminomethyl)-4-(3-methoxyphenyl)-1H-indol-7-yl]
methyl}-9H-purin-6-amine;
9-{[2-(aminomethyl)-4-(2-methoxyphenyl)-1H-indol-7-yl]
methyl}-9H-purin-6-amine;
9-({2-(aminomethyl)-4-[4-(methylsulfonyl)phenyl]-1H-indol-7-yl}methyl)-9H-purin-6-amine;
4-{2-(aminomethyl)-7-[(6-amino-9H-purin-9-yl)methyl]-1H-indol-4-yl}benzonitrile;
3-{2-(aminomethyl)-7-[(6-amino-9H-purin-9-yl)methyl]-1H-indol-4-yl}benzonitrile;
3-{2-(aminomethyl)-7-[(6-amino-9H-purin-9-yl)methyl]-1H-indol-4-yl}benzamide;
N-(4-{2-(aminomethyl)-7-[(6-amino-9H-purin-9-yl)methyl]-1H-indol-4-yl}phenyl)methanesulfonamide;
4-{2-(aminomethyl)-7-[(6-amino-9H-purin-9-yl)methyl]-1H-indol-4-yl}-N,N-dimethylbenzamide;
1-{7-[(6-amino-9H-purin-9-yl)methyl]-5-chloro-1H-indol-2-yl}ethanone;
9-{[2-(1-aminoethyl)-5-chloro-1H-indol-7-yl]methyl}-9H-purin-6-amine;
9-({5-chloro-2-[(methylamino)methyl]-1H-indol-7-yl}methyl)-9H-purin-6-amine;
1-{7-[(6-amino-9H-purin-9-yl)methyl]-5-chloro-1H-indol-2-yl}propan-1-one;
9-{[2-(1-aminopropyl)-5-chloro-1H-indol-7-yl]methyl}-9H-purin-6-amine;
N-({7-[(6-amino-9H-purin-9-yl)methyl]-5-chloro-1H-indol-2-yl}methyl)acetamide;
N-({7-[(6-amino-9H-purin-9-yl)methyl]-5-chloro-1H-indol-2-yl}methyl)prop-2-enamide;
N-({7-[(6-amino-9H-purin-9-yl)methyl]-5-chloro-1H-indol-2-yl}methyl)propanamide;
N-({7-[(6-amino-9H-purin-9-yl)methyl]-5-chloro-1H-indol-2-yl}methyl)-2-methoxyacetamide;
3-[({7-[(6-amino-9H-purin-9-yl)methyl]-5-chloro-1H-indol-2-yl}methyl)amino]propanoic acid;
9-({5-chloro-2-[(diethylamino)methyl]-1H-indol-7-yl}methyl)-9H-purin-6-amine;
N-({7-[(6-amino-9H-purin-9-yl)methyl]-5-chloro-1H-indol-2-yl}methyl)butanamide;
N-({7-[(6-amino-9H-purin-9-yl)methyl]-5-chloro-1H-indol-2-yl}methyl)-2-methylpropanamide;
N-({7-[(6-amino-9H-purin-9-yl)methyl]-5-chloro-1H-indol-2-yl}methyl)-3-methoxypropanamide;
2,2'-[({7-[(6-amino-9H-purin-9-yl)methyl]-5-chloro-1H-indol-2-yl}methyl)imino]diacetic acid;
N-({7-[(6-amino-9H-purin-9-yl)methyl]-5-chloro-1H-indol-2-yl}methyl)-3-methylbutanamide;
N-({7-[(6-amino-9H-purin-9-yl)methyl]-5-chloro-1H-indol-2-yl}methyl)-3-hydroxy-3-methylbutanamide;
N-({7-[(6-amino-9H-purin-9-yl)methyl]-5-chloro-1H-indol-2-yl}methyl)-3,3-dimethylbutanamide;
N-({7-[(6-amino-9H-purin-9-yl)methyl]-5-chloro-1H-indol-2-yl}methyl)-4-methylpentanamide;
tert-butyl [({7-[(6-amino-9H-purin-9-yl)methyl]-5-chloro-1H-indol-2-yl}methyl)amino]acetate;
N-({7-[(6-amino-9H-purin-9-yl)methyl]-5-chloro-1H-indol-2-yl}methyl)cyclopropanecarboxamide;
N-({7-[(6-amino-9H-purin-9-yl)methyl]-5-chloro-1H-indol-2-yl}methyl)-1-methylcyclopropanecarboxamide;
N-({7-[(6-amino-9H-purin-9-yl)methyl]-5-chloro-1H-indol-2-yl}methyl)-2-methylcyclopropanecarboxamide;
N-({7-[(6-amino-9H-purin-9-yl)methyl]-5-chloro-1H-indol-2-yl}methyl)-2-cyclopropylacetamide;
N-({7-[(6-amino-9H-purin-9-yl)methyl]-5-chloro-1H-indol-2-yl}methyl)cyclobutanecarboxamide;
N-({7-[(6-amino-9H-purin-9-yl)methyl]-5-chloro-1H-indol-2-yl}methyl)-1-hydroxycyclobutanecarboxamide;
N-({7-[(6-amino-9H-purin-9-yl)methyl]-5-chloro-1H-indol-2-yl}methyl)tetrahydrofuran-2-carboxamide;
N-({7-[(6-amino-9H-purin-9-yl)methyl]-5-chloro-1H-indol-2-yl}methyl)tetrahydrofuran-3-carboxamide;
(2S)—N-({7-[(6-amino-9H-purin-9-yl)methyl]-5-chloro-1H-indol-2-yl}methyl)pyrrolidine-2-carboxamide;
(2R)—N-({7-[(6-amino-9H-purin-9-yl)methyl]-5-chloro-1H-indol-2-yl}methyl)pyrrolidine-2-carboxamide;
(2S)—N-({7-[(6-amino-9H-purin-9-yl)methyl]-5-chloro-1H-indol-2-yl}methyl)-5-oxopyrrolidine-2-carboxamide;
(2R)—N-({7-[(6-amino-9H-purin-9-yl)methyl]-5-chloro-1H-indol-2-yl}methyl)-5-oxopyrrolidine-2-carboxamide;
N-({7-[(6-amino-9H-purin-9-yl)methyl]-5-chloro-1H-indol-2-yl}methyl)cyclopentanecarboxamide;
N-({7-[(6-amino-9H-purin-9-yl)methyl]-5-chloro-1H-indol-2-yl}methyl)-2-(pyrrolidin-1-yl)acetamide;
N-({7-[(6-amino-9H-purin-9-yl)methyl]-5-chloro-1H-indol-2-yl}methyl)-2-cyclopentylacetamide;
N-({7-[(6-amino-9H-purin-9-yl)methyl]-5-chloro-1H-indol-2-yl}methyl)-3-(pyrrolidin-1-yl)propanamide;
tert-butyl (2S)-2-[({7-[(6-amino-9H-purin-9-yl)methyl]-5-chloro-1H-indol-2-yl}methyl)carbamoyl]pyrrolidine-1-carboxylate;
tert-butyl (2R)-2-[({7-[(6-amino-9H-purin-9-yl)methyl]-5-chloro-1H-indol-2-yl}methyl)carbamoyl]pyrrolidine-1-carboxylate;
9-({5-chloro-2-[(1,1-dioxidothiomorpholin-4-yl)methyl]-1H-indol-7-yl}methyl)-9H-purin-6-amine;
N-({7-[(6-amino-9H-purin-9-yl)methyl]-5-chloro-1H-indol-2-yl}methyl)tetrahydro-2H-pyran-4-carboxamide;
N-({7-[(6-amino-9H-purin-9-yl)methyl]-5-chloro-1H-indol-2-yl}methyl)-2-(morpholin-4-yl)acetamide;
N-({7-[(6-amino-9H-purin-9-yl)methyl]-5-chloro-1H-indol-2-yl}methyl)cyclohexanecarboxamide;
N-({7-[(6-amino-9H-purin-9-yl)methyl]-5-chloro-1H-indol-2-yl}methyl)-1-methylcyclohexanecarboxamide;
N-({7-[(6-amino-9H-purin-9-yl)methyl]-5-chloro-1H-indol-2-yl}methyl)-4-methylcyclohexanecarboxamide;
N-({7-[(6-amino-9H-purin-9-yl)methyl]-5-chloro-1H-indol-2-yl}methyl)-3-methylcyclohexanecarboxamide;
N-({7-[(6-amino-9H-purin-9-yl)methyl]-5-chloro-1H-indol-2-yl}methyl)-2-methylcyclohexanecarboxamide;
N-({7-[(6-amino-9H-purin-9-yl)methyl]-5-chloro-1H-indol-2-yl}methyl)-2-cyclohexylacetamide;
N-({7-[(6-amino-9H-purin-9-yl)methyl]-5-chloro-1H-indol-2-yl}methyl)-4-methoxycyclohexanecarboxamide;
N-({7-[(6-amino-9H-purin-9-yl)methyl]-5-chloro-1H-indol-2-yl}methyl)-3-(piperidin-1-yl)propanamide;
N-({7-[(6-amino-9H-purin-9-yl)methyl]-5-chloro-1H-indol-2-yl}methyl)tricyclo[3.3.1.1$^{3,7}$]decane-1-carboxamide;
N-({7-[(6-amino-9H-purin-9-yl)methyl]-5-chloro-1H-indol-2-yl}methyl)-1,2-thiazole-5-carboxamide;
N-({7-[(6-amino-9H-purin-9-yl)methyl]-5-chloro-1H-indol-2-yl}methyl)-1,3-thiazole-5-carboxamide;
N-({7-[(6-amino-9H-purin-9-yl)methyl]-5-chloro-1H-indol-2-yl}methyl)-1,2-thiazole-4-carboxamide;
N-({7-[(6-amino-9H-purin-9-yl)methyl]methyl]-5-chloro-1H-indol-2-yl}methyl)-1,3-thiazole-4-carboxamide;

N-({7-[(6-amino-9H-purin-9-yl)methyl]-5-chloro-1H-indol-2-yl}methyl)-1,2-oxazole-4-carboxamide;
N-({7-[(6-amino-9H-purin-9-yl)methyl]-5-chloro-1H-indol-2-yl}methyl)-1H-pyrazole-5-carboxamide;
N-({7-[(6-amino-9H-purin-9-yl)methyl]-5-chloro-1H-indol-2-yl}methyl)-1H-pyrazole-4-carboxamide;
N-({7-[(6-amino-9H-purin-9-yl)methyl]-5-chloro-1H-indol-2-yl}methyl)thiophene-2-carboxamide;
N-({7-[(6-amino-9H-purin-9-yl)methyl]-5-chloro-1H-indol-2-yl}methyl)thiophene-3-carboxamide;
N-({7-[(6-amino-9H-purin-9-yl)methyl]-5-chloro-1H-indol-2-yl}methyl)-1H-pyrrole-2-carboxamide;
N-({7-[(6-amino-9H-purin-9-yl)methyl]-5-chloro-1H-indol-2-yl}methyl)-5-methyl-1,3-thiazole-4-carboxamide;
N-({7-[(6-amino-9H-purin-9-yl)methyl]-5-chloro-1H-indol-2-yl}methyl)-4-methyl-1,3-thiazole-5-carboxamide;
N-({7-[(6-amino-9H-purin-9-yl)methyl]-5-chloro-1H-indol-2-yl}methyl)-5-methyl-1,2-oxazole-4-carboxamide;
N-({7-[(6-amino-9H-purin-9-yl)methyl]-5-chloro-1H-indol-2-yl}methyl)-3-methyl-1,2-oxazole-4-carboxamide;
N-({7-[(6-amino-9H-purin-9-yl)methyl]-5-chloro-1H-indol-2-yl}methyl)-1-methyl-1H-pyrazole-3-carboxamide;
N-({7-[(6-amino-9H-purin-9-yl)methyl]-5-chloro-1H-indol-2-yl}methyl)-1-methyl-1H-pyrazole-5-carboxamide;
N-({7-[(6-amino-9H-purin-9-yl)methyl]-5-chloro-1H-indol-2-yl}methyl)-1-methyl-1H-imidazole-5-carboxamide;
N-({7-[(6-amino-9H-purin-9-yl)methyl]-5-chloro-1H-indol-2-yl}methyl)-1-methyl-1H-imidazole-2-carboxamide;
5-amino-N-({7-[(6-amino-9H-purin-9-yl)methyl]-5-chloro-1H-indol-2-yl}methyl)-3-methyl-1,2-oxazole-4-carboxamide;
N-({7-[(6-amino-9H-purin-9-yl)methyl]-5-chloro-1H-indol-2-yl}methyl)-2-methylthiophene-3-carboxamide;
N-({7-[(6-amino-9H-purin-9-yl)methyl]-5-chloro-1H-indol-2-yl}methyl)-3-methylthiophene-2-carboxamide;
N-({7-[(6-amino-9H-purin-9-yl)methyl]-5-chloro-1H-indol-2-yl}methyl)-4-methoxythiophene-3-carboxamide;
N-({7-[(6-amino-9H-purin-9-yl)methyl]-5-chloro-1H-indol-2-yl}methyl)-3-methoxythiophene-2-carboxamide;
N-({7-[(6-amino-9H-purin-9-yl)methyl]-5-chloro-1H-indol-2-yl}methyl)-1-methyl-1H-pyrrole-2-carboxamide;
N-({7-[(6-amino-9H-purin-9-yl)methyl]-5-chloro-1H-indol-2-yl}methyl)-2,4-dimethyl-1,3-thiazole-5-carboxamide;
N-({7-[(6-amino-9H-purin-9-yl)methyl]-5-chloro-1H-indol-2-yl}methyl)-3,5-dimethyl-1,2-oxazole-4-carboxamide;
N-({7-[(6-amino-9H-purin-9-yl)methyl]-5-(1,2,5,6-tetrahydropyridin-3-yl)-1H-indol-2-yl}methyl)-3,5-dimethyl-1,2-oxazole-4-carboxamide;
N-({7-[(6-amino-9H-purin-9-yl)methyl]-5-phenyl-1H-indol-2-yl}methyl)-3,5-dimethyl-1,2-oxazole-4-carboxamide;
N-({7-[(6-amino-9H-purin-9-yl)methyl]-5-(4-fluorophenyl)-1H-indol-2-yl}methyl)-3,5-dimethyl-1,2-oxazole-4-carboxamide;
N-({7-[(6-amino-9H-purin-9-yl)methyl]-5-(4-sulfamoylphenyl)-1H-indol-2-yl}methyl)-3,5-dimethyl-1,2-oxazole-4-carboxamide;
N-({7-[(6-amino-9H-purin-9-yl)methyl]-5-(4-methylphenyl)-1H-indol-2-yl}methyl)-3,5-dimethyl-1,2-oxazole-4-carboxamide;
N-({7-[(6-amino-9H-purin-9-yl)methyl]-5-(4-methoxyphenyl)-1H-indol-2-yl}methyl)-3,5-dimethyl-1,2-oxazole-4-carboxamide;
N-({7-[(6-amino-9H-purin-9-yl)methyl]-5-(3-methoxyphenyl)-1H-indol-2-yl}methyl)-3,5-dimethyl-1,2-oxazole-4-carboxamide;
N-({7-[(6-amino-9H-purin-9-yl)methyl]-5-[4-(methylsulfonyl)phenyl]-1H-indol-2-yl}methyl)-3,5-dimethyl-1,2-oxazole-4-carboxamide;
N-({7-[(6-amino-9H-purin-9-yl)methyl]-5-(4-cyanophenyl)-1H-indol-2-yl}methyl)-3,5-dimethyl-1,2-oxazole-4-carboxamide;
N-({7-[(6-amino-9H-purin-9-yl)methyl]-5-(3-cyanophenyl)-1H-indol-2-yl}methyl)-3,5-dimethyl-1,2-oxazole-4-carboxamide;
N-({7-[(6-amino-9H-purin-9-yl)methyl]-5-(3-carbamoylphenyl)-1H-indol-2-yl}methyl)-3,5-dimethyl-1,2-oxazole-4-carboxamide;
N-[(7-[(6-amino-9H-purin-9-yl)methyl]-5-{4-[(methylsulfonyl)amino]phenyl}-1H-indol-2-yl)methyl]-3,5-dimethyl-1,2-oxazole-4-carboxamide;
N-({7-[(6-amino-9H-purin-9-yl)methyl]-5-[4-(cyanomethyl)phenyl]-1H-indol-2-yl}methyl)-3,5-dimethyl-1,2-oxazole-4-carboxamide;
N-({7-[(6-amino-9H-purin-9-yl)methyl]-5-[4-(dimethylcarbamoyl)phenyl]-1H-indol-2-yl}methyl)-3,5-dimethyl-1,2-oxazole-4-carboxamide;
N-({7-[(6-amino-9H-purin-9-yl)methyl]-5-[3-(dimethylcarbamoyl)phenyl]-1H-indol-2-yl}methyl)-3,5-dimethyl-1,2-oxazole-4-carboxamide;
N-({7-[(6-amino-9H-purin-9-yl)methyl]-5-[3-(cyclopropylcarbamoyl)phenyl]-1H-indol-2-yl}methyl)-3,5-dimethyl-1,2-oxazole-4-carboxamide;
N-({7-[(6-amino-9H-purin-9-yl)methyl]-5-[3-(morpholin-4-yl)phenyl]-1H-indol-2-yl}methyl)-3,5-dimethyl-1,2-oxazole-4-carboxamide;
N-({7-[(6-amino-9H-purin-9-yl)methyl]-5-[3-(morpholin-4-ylcarbonyl)phenyl]-1H-indol-2-yl}methyl)-3,5-dimethyl-1,2-oxazole-4-carboxamide;
N-({7-[(6-amino-9H-purin-9-yl)methyl]-5-chloro-1H-indol-2-yl}methyl)-5-ethyl-1,2-oxazole-4-carboxamide;
N-({7-[(6-amino-9H-purin-9-yl)methyl]-5-chloro-1H-indol-2-yl}methyl)-1,5-dimethyl-1H-pyrazole-3-carboxamide;
N-({7-[(6-amino-9H-purin-9-yl)methyl]-5-chloro-1H-indol-2-yl}methyl)-1,3-dimethyl-1H-pyrazole-5-carboxamide;
N-({7-[(6-amino-9H-purin-9-yl)methyl)methyl]-5-chloro-1H-indol-2-yl}methyl)-1,3-dimethyl-1H-pyrazole-4-carboxamide;
N-({7-[(6-amino-9H-purin-9-yl)methyl]-5-chloro-1H-indol-2-yl}methyl)-5-ethyl-3-methyl-1,2-oxazole-4-carboxamide;
N-({7-[(6-amino-9H-purin-9-yl)methyl]-5-chloro-1H-indol-2-yl}methyl)-3-ethyl-5-methyl-1,2-oxazole-4-carboxamide;
N-({7-[(6-amino-9H-purin-9-yl)methyl]-5-chloro-1H-indol-2-yl}methyl)-5-(propan-2-yl)-1,2-oxazole-4-carboxamide;
N-({7-[(6-amino-9H-purin-9-yl)methyl]-5-chloro-1H-indol-2-yl}methyl)-1-ethyl-3,5-dimethyl-1H-pyrazole-4-carboxamide;
N-({7-[(6-amino-9H-purin-9-yl)methyl]-5-chloro-1H-indol-2-yl}methyl)-5-cyclopropyl-1,2-oxazole-4-carboxamide;
N-({7-[(6-amino-9H-purin-9-yl)methyl]-5-chloro-1H-indol-2-yl}methyl)-5-cyclopropyl-3-methyl-1,2-oxazole-4-carboxamide;

N-({7-[(6-amino-9H-purin-9-yl)methyl]-5-chloro-1H-indol-2-yl}methyl)-1-methyl-1,4,5,6-tetrahydrocyclopenta[c]pyrazole-3-carboxamide;
N-({7-[(6-amino-9H-purin-9-yl)methyl]-5-chloro-1H-indol-2-yl}methyl)-4,5,6,7-tetrahydropyrazolo[1,5-a]pyridine-3-carboxamide;
N-({7-[(6-amino-9H-purin-9-yl)methyl]-5-chloro-1H-indol-2-yl}methyl)pyrazine-2-carboxamide;
9-({2-[amino(phenyl)methyl]-5-chloro-1H-indol-7-yl}methyl)-9H-purin-6-amine;
N-({7-[(6-amino-9H-purin-9-yl)methyl]-5-chloro-1H-indol-2-yl}methyl)pyridine-2-carboxamide;
N-({7-[(6-amino-9H-purin-9-yl)methyl]-5-chloro-1H-indol-2-yl}methyl)pyridine-3-carboxamide;
N-({7-[(6-amino-9H-purin-9-yl)methyl]-5-chloro-1H-indol-2-yl}methyl)-6-hydroxypyridine-2-carboxamide;
N-({7-[(6-amino-9H-purin-9-yl)methyl]-5-chloro-1H-indol-2-yl}methyl)-2-oxo-1,2-dihydropyridine-3-carboxamide;
N-({7-[(6-amino-9H-purin-9-yl)methyl]-5-chloro-1H-indol-2-yl}methyl)-3-methylpyridazine-4-carboxamide;
N-({7-[(6-amino-9H-purin-9-yl)methyl]-5-(1,2,3,6-tetrahydropyridin-4-yl)-1H-indol-2-yl}methyl)-3-methylpyridazine-4-carboxamide;
N-({7-[(6-amino-9H-purin-9-yl)methyl]-5-(4,4-difluorocyclohex-1-en-1-yl)-1H-indol-2-yl}methyl)-3-methylpyridazine-4-carboxamide;
N-({7-[(6-amino-9H-purin-9-yl)methyl]-5-[1-(methylsulfonyl)-1,2,3,6-tetrahydropyridin-4-yl]-1H-indol-2-yl}methyl)-3-methylpyridazine-4-carboxamide;
N-({5-(1-acetyl-1,2,3,6-tetrahydropyridin-4-yl)-7-[(6-amino-9H-purin-9-yl)methyl]-1H-indol-2-yl}methyl)-3-methylpyridazine-4-carboxamide;
tert-butyl4-{7-[(6-amino-9H-purin-9-yl)methyl]-2-({[(3-methylpyridazin-4-yl)carbonyl]amino}methyl)-1H-indol-5-yl]-3,6-dihydropyridine-1(2H)-carboxylate;
N-({7-[(6-amino-9H-purin-9-yl)methyl]-5-chloro-1H-indol-2-yl}methyl)-5-methylpyrazine-2-carboxamide;
9-{[2-(1-amino-2-phenylethyl)-5-chloro-1H-indol-7-yl]methyl}-9H-purin-6-amine;
9-({2-[(benzylamino)methyl]-5-chloro-1H-indol-7-yl}methyl)-9H-purin-6-amine;
9-[(2-{[(2-bromobenzyl)amino]methyl}-5-chloro-1H-indol-7-yl)methyl]-9H-purin-6-amine;
9-[(5-chloro-2-{[(3-chlorobenzyl)amino]methyl}-1H-indol-7-yl)methyl]-9H-purin-6-amine;
9-[(5-chloro-2-{[(2-chlorobenzyl)amino]methyl}-1H-indol-7-yl)methyl]-9H-purin-6-amine;
9-[(5-chloro-2-{[(2,6-dichlorobenzyl)amino]methyl}-1H-indol-7-yl)methyl]-9H-purin-6-amine;
9-[(5-chloro-2-{[(3,5-dichlorobenzyl)amino]methyl}-1H-indol-7-yl)methyl]-9H-purin-6-amine;
9-[(5-chloro-2-{[(3,4-dichlorobenzyl)amino]methyl}-1H-indol-7-yl)methyl]-9H-purin-6-amine;
9-[(5-chloro-2-{[(2-fluorobenzyl)amino]methyl}-1H-indol-7-yl)methyl]-9H-purin-6-amine;
9-[(5-chloro-2-{[(2-chloro-6-fluorobenzyl)amino]methyl}-1H-indol-7-yl)methyl]-9H-purin-6-amine;
9-[(5-chloro-2-{[(3-chloro-5-fluorobenzyl)amino]methyl}-1H-indol-7-yl)methyl]-9H-purin-6-amine;
9-[(5-chloro-2-{[(2-chloro-5-fluorobenzyl)amino]methyl}-1H-indol-7-yl)methyl]-9H-purin-6-amine;
9-[(5-chloro-2-{[(3-chloro-2-fluorobenzyl)amino]methyl}-1H-indol-7-yl)methyl]-9H-purin-6-amine;
9-[(5-chloro-2-{[(2,6-difluorobenzyl)amino]methyl}-1H-indol-7-yl)methyl]-9H-purin-6-amine;
N-({7-[(6-amino-9H-purin-9-yl)methyl]-5-chloro-1H-indol-2-yl}methyl)benzamide;
N-({7-[(6-amino-9H-purin-9-yl)methyl]-5-chloro-1H-indol-2-yl}methyl)-4-chlorobenzamide;
N-({7-[(6-amino-9H-purin-9-yl)methyl]-5-chloro-1H-indol-2-yl}methyl)-3-chlorobenzamide;
N-({7-[(6-amino-9H-purin-9-yl)methyl]-5-chloro-1H-indol-2-yl}methyl)-4-fluorobenzamide;
N-({7-[(6-amino-9H-purin-9-yl)methyl]-5-chloro-1H-indol-2-yl}methyl)-3-fluorobenzamide;
N-({7-[(6-amino-9H-purin-9-yl)methyl]-5-chloro-1H-indol-2-yl}methyl)-2-fluorobenzamide;
N-({7-[(6-amino-9H-purin-9-yl)methyl]-5-chloro-1H-indol-2-yl}methyl)-2-bromo-6-fluorobenzamide;
N-({7-[(6-amino-9H-purin-9-yl)methyl]-5-chloro-1H-indol-2-yl}methyl)-2-chloro-6-fluorobenzamide;
N-({7-[(6-amino-9H-purin-9-yl)methyl]-5-chloro-1H-indol-2-yl}methyl)-2,6-difluorobenzamide;
N-({7-[(6-amino-9H-purin-9-yl)methyl]-5-chloro-1H-indol-2-yl}methyl)-2-fluoro-6-hydroxybenzamide;
N-({7-[(6-amino-9H-purin-9-yl)methyl]-5-chloro-1H-indol-2-yl}methyl)-2-(pyridin-2-yl)acetamide;
N-({7-[(6-amino-9H-purin-9-yl)methyl)methyl]-5-chloro-1H-indol-2-yl}methyl)-2-(pyridin-3-yl)acetamide;
N-({7-[(6-amino-9H-purin-9-yl)methyl]-5-chloro-1H-indol-2-yl}methyl)-2-(pyridin-4-yl)acetamide;
N-({7-[(6-amino-9H-purin-9-yl)methyl]-5-chloro-1H-indol-2-yl}methyl)-2-methylpyridine-3-carboxamide;
N-({7-[(6-amino-9H-purin-9-yl)methyl]-5-chloro-1H-indol-2-yl}methyl)-3,6-dimethylpyridazine-4-carboxamide;
N-({7-[(6-amino-9H-purin-9-yl)methyl]-5-(1,2,3,6-tetrahydropyridin-4-yl)-1H-indol-2-yl}methyl)-3,6-dimethylpyridazine-4-carboxamide;
N-({7-[(6-amino-9H-purin-9-yl)methyl]-5-(4,4-difluorocyclohex-1-en-1-yl)-1H-indol-2-yl}methyl)-3,6-dimethylpyridazine-4-carboxamide;
N-({5-(1-acetyl-1,2,3,6-tetrahydropyridin-4-yl)-7-[(6-amino-9H-purin-9-yl)methyl]-1H-indol-2-yl}methyl)-3,6-dimethylpyridazine-4-carboxamide;
N-({5-(1-acetyl-1,4,5,6-tetrahydropyridin-3-yl)-7-[(6-amino-9H-purin-9-yl)methyl]-1H-indol-2-yl}methyl)-3,6-dimethylpyridazine-4-carboxamide;
N-({7-[(6-amino-9H-purin-9-yl)methyl]-4-chloro-1H-indol-2-yl}methyl)-3,6-dimethylpyridazine-4-carboxamide;
N-({7-[(6-amino-9H-purin-9-yl)methyl]-5-chloro-1H-indol-2-yl}methyl)-6-cyanopyridine-3-carboxamide;
9-[(5-chloro-2-{[(4-methylbenzyl)amino]methyl}-1H-indol-7-yl)methyl]-9H-purin-6-amine;
9-[(5-chloro-2-{[(2-methylbenzyl)amino]methyl})-1H-indol-7-yl)methyl]-9H-purin-6-amine;
9-[(5-chloro-2-{[(2-chloro-6-methylbenzyl)amino]methyl}-1H-indol-7-yl)methyl]-9H-purin-6-amine;
9-[(5-chloro-2-{[(2-fluoro-6-methylbenzyl)amino]methyl}-1H-indol-7-yl)methyl]-9H-purin-6-amine;
9-[(5-chloro-2-{[(2-fluoro-3-methylbenzyl)amino]methyl}-1H-indol-7-yl)methyl]-9H-purin-6-amine;
N-({7-[(6-amino-9H-purin-9-yl)methyl]-5-chloro-1H-indol-2-yl}methyl)-4-methylbenzamide;
N-({7-[(6-amino-9H-purin-9-yl)methyl]-5-chloro-1H-indol-2-yl}methyl)-3-methylbenzamide;
N-({7-[(6-amino-9H-purin-9-yl)methyl]-5-chloro-1H-indol-2-yl}methyl)-2-methylbenzamide;
9-[(5-chloro-2-{[(3-methoxybenzyl)amino]methyl})-1H-indol-7-yl)methyl]-9H-purin-6-amine;
9-[(5-chloro-2-{[(2-methoxybenzyl)amino]methyl}-1H-indol-7-yl)methyl]-9H-purin-6-amine;
N-({7-[(6-amino-9H-purin-9-yl)methyl]-5-chloro-1H-indol-2-yl}methyl)-2-(4-chlorophenyl)acetamide;
N-({7-[(6-amino-9H-purin-9-yl)methyl]-5-chloro-1H-indol-2-yl}methyl)-2-(3-chlorophenyl)acetamide;
N-({7-[(6-amino-9H-purin-9-yl)methyl]-5-chloro-1H-indol-2-yl}methyl)-2-(2-chlorophenyl)acetamide;

N-({7-[(6-amino-9H-purin-9-yl)methyl]-5-chloro-1H-indol-2-yl}methyl)-2-(4-fluorophenyl)acetamide;
N-({7-[(6-amino-9H-purin-9-yl)methyl]-5-chloro-1H-indol-2-yl}methyl)-2-(3-fluorophenyl)acetamide;
N-({7-[(6-amino-9H-purin-9-yl)methyl]-5-chloro-1H-indol-2-yl}methyl)-2-(2-fluorophenyl)acetamide;
N-({7-[(6-amino-9H-purin-9-yl)methyl]-5-chloro-1H-indol-2-yl}methyl)-2-(trifluoromethyl)benzamide;
N-({7-[(6-amino-9H-purin-9-yl)methyl]-5-chloro-1H-indol-2-yl}methyl)-4-methoxybenzamide;
N-({7-[(6-amino-9H-purin-9-yl)methyl]-5-chloro-1H-indol-2-yl}methyl)-3-methoxybenzamide;
N-({7-[(6-amino-9H-purin-9-yl)methyl]-5-chloro-1H-indol-2-yl}methyl)-2-methoxybenzamide;
N-({7-[(6-amino-9H-purin-9-yl)methyl]-5-chloro-1H-indol-2-yl}methyl)-2-(difluoromethoxy)benzamide;
9-{[5-chloro-2-({[3-(methylsulfonyl)benzyl]amino}methyl)-1H-indol-7-yl]methyl}-9H-purin-6-amine;
9-{[5-chloro-2-({[4-fluoro-3-(methylsulfonyl)benzyl]amino}methyl)-1H-indol-7-yl]methyl}-9H-purin-6-amine;
9-{[5-chloro-2-({[3-fluoro-4-(methylsulfonyl)benzyl]amino}methyl)-1H-indol-7-yl]methyl}-9H-purin-6-amine;
N-({7-[(6-amino-9H-purin-9-yl)methyl]-5-chloro-1H-indol-2-yl}methyl)-2-(methylsulfonyl)benzamide;
N-({7-[(6-amino-9H-purin-9-yl)methyl]-5-chloro-1H-indol-2-yl}methyl)-2-chloro-4-(methylsulfonyl)benzamide;
4-{[({7-[(6-amino-9H-purin-9-yl)methyl]-5-chloro-1H-indol-2-yl}methyl)amino]methyl}benzonitrile;
3-{[({7-[(6-amino-9H-purin-9-yl)methyl]-5-chloro-1H-indol-2-yl}methyl)amino]methyl}benzonitrile;
2-{[({7-[(6-amino-9H-purin-9-yl)methyl]-5-chloro-1H-indol-2-yl}methyl)amino]methyl}benzonitrile;
3-{[({7-[(6-amino-9H-purin-9-yl)methyl]-5-chloro-1H-indol-2-yl}methyl)amino]methyl}-4-fluorobenzonitrile;
5-amino-N-({7-[(6-amino-9H-purin-9-yl)methyl]-5-chloro-1H-indol-2-yl}methyl)-2-methylbenzamide;
N-({7-[(6-amino-9H-purin-9-yl)methyl]-5-chloro-1H-indol-2-yl}methyl)-4-cyanobenzamide;
N-({7-[(6-amino-9H-purin-9-yl)methyl]-5-chloro-1H-indol-2-yl}methyl)-3-cyanobenzamide;
N-({7-[(6-amino-9H-purin-9-yl)methyl]-5-chloro-1H-indol-2-yl}methyl)-2-cyanobenzamide;
N-({7-[(6-amino-9H-purin-9-yl)methyl]-5-chloro-1H-indol-2-yl}methyl)-2-(methylamino)benzamide;
N-({7-[(6-amino-9H-purin-9-yl)methyl]-5-chloro-1H-indol-2-yl}methyl)-2-chloro-4-cyanobenzamide;
N-({7-[(6-amino-9H-purin-9-yl)methyl]-5-(1,2,3,6-tetrahydropyridin-4-yl)-1H-indol-2-yl}methyl)-2-chloro-4-cyanobenzamide;
N-({7-[(6-amino-9H-purin-9-yl)methyl]-5-(4,4-difluorocyclohex-1-en-1-yl)-1H-indol-2-yl}methyl)-2-chloro-4-cyanobenzamide;
N-({5-(1-acetyl-1,2,3,6-tetrahydropyridin-4-yl)-7-[(6-amino-9H-purin-9-yl)methyl]-1H-indol-2-yl}methyl)-2-chloro-4-cyanobenzamide;
N-({5-(1-acetyl-1,4,5,6-tetrahydropyridin-3-yl)-7-[(6-amino-9H-purin-9-yl)methyl]-1H-indol-2-yl}methyl)-2-chloro-4-cyanobenzamide;
N-({5-(1-acetylpiperidin-4-yl)-7-[(6-amino-9H-purin-9-yl)methyl]-1H-indol-2-yl}methyl)-2-chloro-4-cyanobenzamide;
N-({7-[(6-amino-9H-purin-9-yl)methyl]-4-chloro-1H-indol-2-yl}methyl)-2-chloro-4-cyanobenzamide;
N-({7-[(6-amino-9H-purin-9-yl)methyl]-5-chloro-1H-indol-2-yl}methyl)-2,6-dichloro-4-cyanobenzamide;
N-({7-[(6-amino-9H-purin-9-yl)methyl]-5-chloro-1H-indol-2-yl}methyl)-4-cyano-2-fluorobenzamide;
N-({7-[(6-amino-9H-purin-9-yl)methyl]-5-(3,6-dihydro-2H-pyran-4-yl)-1H-indol-2-yl}methyl)-4-cyano-2-fluorobenzamide;
N-({7-[(6-amino-9H-purin-9-yl)methyl]-5-(1,2,3,6-tetrahydropyridin-4-yl)-1H-indol-2-yl}methyl)-4-cyano-2-fluorobenzamide;
N-({7-[(6-amino-9H-purin-9-yl)methyl]-5-(4,4-difluorocyclohex-1-en-1-yl)-1H-indol-2-yl}methyl)-4-cyano-2-fluorobenzamide;
N-({5-(1-acetyl-1,2,3,6-tetrahydropyridin-4-yl)-7-[(6-amino-9H-purin-9-yl)methyl]-1H-indol-2-yl}methyl)-4-cyano-2-fluorobenzamide;
tert-butyl 4-(7-[(6-amino-9H-purin-9-yl)methyl]-2-{[(4-cyano-2-fluorobenzoyl)amino]methyl}-1H-indol-5-yl)-3,6-dihydropyridine-1(2H)-carboxylate;
9-[(5-chloro-2-{[(2,6-dimethylbenzyl)amino]methyl}-1H-indol-7-yl)methyl]-9H-purin-6-amine;
N-({7-[(6-amino-9H-purin-9-yl)methyl]-5-chloro-1H-indol-2-yl}methyl)-3-phenylpropanamide;
N-({7-[(6-amino-9H-purin-9-yl)methyl]-5-chloro-1H-indol-2-yl}methyl)-2-(4-methylphenyl)acetamide;
N-({7-[(6-amino-9H-purin-9-yl)methyl]-5-chloro-1H-indol-2-yl}methyl)-2-(3-methylphenyl)acetamide;
N-({7-[(6-amino-9H-purin-9-yl)methyl]-5-chloro-1H-indol-2-yl}methyl)-2-(2-methylphenyl)acetamide;
N-({7-[(6-amino-9H-purin-9-yl)methyl]-5-chloro-1H-indol-2-yl}methyl)-2,6-dimethylbenzamide;
N-({7-[(6-amino-9H-purin-9-yl)methyl]-5-chloro-1H-indol-2-yl}methyl)-2-ethylbenzamide;
N-({7-[(6-amino-9H-purin-9-yl)methyl]-5-chloro-1H-indol-2-yl}methyl)-2-(4-methoxyphenyl)acetamide;
N-({7-[(6-amino-9H-purin-9-yl)methyl]-5-chloro-1H-indol-2-yl}methyl)-2-(2-methoxyphenyl)acetamide;
N-({7-[(6-amino-9H-purin-9-yl)methyl]-5-chloro-1H-indol-2-yl}methyl)-2-methoxy-6-methylbenzamide;
N-({7-[(6-amino-9H-purin-9-yl)methyl]-5-chloro-1H-indol-2-yl}methyl)-3-methoxy-4-methylbenzamide;
4-(aminomethyl)-N-({7-[(6-amino-9H-purin-9-yl)methyl]-5-(4,4-difluorocyclohexyl)-1H-indol-2-yl}methyl)-2-methylbenzamide;
N-({7-[(6-amino-9H-purin-9-yl)methyl]-5-chloro-1H-indol-2-yl}methyl)-4-(dimethylamino)benzamide;
N-({7-[(6-amino-9H-purin-9-yl)methyl]-5-chloro-1H-indol-2-yl}methyl)-4-cyano-2-methylbenzamide;
N-({7-[(6-amino-9H-purin-9-yl)methyl]-5-(3,6-dihydro-2H-pyran-4-yl)-1H-indol-2-yl}methyl)-4-cyano-2-methylbenzamide;
N-({7-[(6-amino-9H-purin-9-yl)methyl]-5-(1,2,3,6-tetrahydropyridin-4-yl)-1H-indol-2-yl}methyl)-4-cyano-2-methylbenzamide;
N-({7-[(6-amino-9H-purin-9-yl)methyl]-5-(4,4-difluorocyclohex-1-en-1-yl)-1H-indol-2-yl}methyl)-4-cyano-2-methylbenzamide;
N-({5-(1-acetyl-1,2,3,6-tetrahydropyridin-4-yl)-7-[(6-amino-9H-purin-9-yl)methyl]-1H-indol-2-yl}methyl)-4-cyano-2-methylbenzamide;
tert-butyl 4-(7-[(6-amino-9H-purin-9-yl)methyl]-2-{[(4-cyano-2-methylbenzoyl)amino]methyl}-1H-indol-5-yl)-3,6-dihydropyridine-1(2H)-carboxylate;
N-({7-[(6-amino-9H-purin-9-yl)methyl]-5-chloro-1H-indol-2-yl}methyl)-3-(dimethylamino)benzamide;
N-({7-[(6-amino-9H-purin-9-yl)methyl]-5-chloro-1H-indol-2-yl}methyl)-2-(ethylamino)benzamide;

4-{[({7-[(6-amino-9H-purin-9-yl)methyl]-5-chloro-1H-indol-2-yl}methyl)amino]methyl}-3-methoxybenzonitrile;
4-(acetylamino)-N-({7-[(6-amino-9H-purin-9-yl)methyl]-5-chloro-1H-indol-2-yl}methyl)benzamide;
N-({7-[(6-amino-9H-purin-9-yl)methyl]-5-chloro-1H-indol-2-yl}methyl)-2-(propan-2-yl)benzamide;
N-({7-[(6-amino-9H-purin-9-yl)methyl]-5-chloro-1H-indol-2-yl}methyl)-3-(4-methoxyphenyl)propanamide;
N-({7-[(6-amino-9H-purin-9-yl)methyl]-5-chloro-1H-indol-2-yl}methyl)-3-(3-methoxyphenyl)propanamide;
N-({7-[(6-amino-9H-purin-9-yl)methyl]-5-chloro-1H-indol-2-yl}methyl)-2-[4-(dimethylamino)phenyl]acetamide;
4-{[({7-[(6-amino-9H-purin-9-yl)methyl]-5-chloro-1H-indol-2-yl}methyl)amino]methyl}-N,N-dimethylbenzamide;
N-({7-[(6-amino-9H-purin-9-yl)methyl]-5-chloro-1H-indol-2-yl}methyl)-3-(2-fluorophenyl)pyrrolidine-1-carboxamide;
N-({7-[(6-amino-9H-purin-9-yl)methyl]-5-chloro-1H-indol-2-yl}methyl)-2-(pyrrolidin-1-ylcarbonyl)benzamide;
N-({7-[(6-amino-9H-purin-9-yl)methyl]-5-chloro-1H-indol-2-yl}methyl)-2-(tetrahydro-2H-pyran-4-yloxy)benzamide;
N-({7-[(6-amino-9H-purin-9-yl)methyl]-5-chloro-1H-indol-2-yl}methyl)-2-(piperidin-1-yl)benzamide;
9-{[5-chloro-2-({[3-(piperidin-1-ylmethyl)benzyl]amino}methyl)-1H-indol-7-yl]methyl}-9H-purin-6-amine;
N-({7-[(6-amino-9H-purin-9-yl)methyl]-5-chloro-1H-indol-2-yl}methyl)-2-(piperidin-1-ylcarbonyl)benzamide;
9-({5-chloro-2-[({3-[2-(piperidin-1-yl)ethoxy]benzyl}amino)methyl]-1H-indol-7-yl}methyl)-9H-purin-6-amine;
N-({7-[(6-amino-9H-purin-9-yl)methyl]-5-chloro-1H-indol-2-yl}methyl)-5-methyl-3-phenyl-1,2-oxazole-4-carboxamide;
N-({7-[(6-amino-9H-purin-9-yl)methyl]-5-chloro-1H-indol-2-yl}methyl)-2-(1-methyl-1H-imidazol-2-yl)benzamide;
N-({7-[(6-amino-9H-purin-9-yl)methyl]-5-chloro-1H-indol-2-yl}methyl)-2-(benzoylamino)benzamide;
N-({7-[(6-amino-9H-purin-9-yl)methyl]-5-chloro-1H-indol-2-yl}methyl)-1,2,3-benzothiadiazole-5-carboxamide;
N-({7-[(6-amino-9H-purin-9-yl)methyl]-5-chloro-1H-indol-2-yl}methyl)-3H-imidazo[4,5-b]pyridine-5-carboxamide;
N-({7-[(6-amino-9H-purin-9-yl)methyl]-5-chloro-1H-indol-2-yl}methyl)-1H-benzotriazole-6-carboxamide;
N-({7-[(6-amino-9H-purin-9-yl)methyl]-5-chloro-1H-indol-2-yl}methyl)-1H-benzotriazole-5-carboxamide;
N-({7-[(6-amino-9H-purin-9-yl)methyl]-5-chloro-1H-indol-2-yl}methyl)-3H-imidazo[4,5-b]pyridine-6-carboxamide;
N-({7-[(6-amino-9H-purin-9-yl)methyl]-5-chloro-1H-indol-2-yl}methyl)-5-fluoro-1H-benzotriazole-6-carboxamide;
N-({7-[(6-amino-9H-purin-9-yl)methyl]-5-chloro-1H-indol-2-yl}methyl)-1,3-benzothiazole-6-carboxamide;
N-({7-[(6-amino-9H-purin-9-yl)methyl]-5-chloro-1H-indol-2-yl}methyl)-1,3-benzothiazole-5-carboxamide;
N-({7-[(6-amino-9H-purin-9-yl)methyl]-5-chloro-1H-indol-2-yl}methyl)thieno[3,2-b]pyridine-6-carboxamide;
N-({7-[(6-amino-9H-purin-9-yl)methyl]-5-chloro-1H-indol-2-yl}methyl)-1,3-benzoxazole-6-carboxamide;
N-({7-[(6-amino-9H-purin-9-yl)methyl]-5-chloro-1H-indol-2-yl}methyl)-1,3-benzoxazole-5-carboxamide;
N-({7-[(6-amino-9H-purin-9-yl)methyl]-5-chloro-1H-indol-2-yl}methyl)furo[3,2-b]pyridine-6-carboxamide;
N-({7-[(6-amino-9H-purin-9-yl)methyl]-5-chloro-1H-indol-2-yl}methyl)-2-hydroxy-1,3-benzothiazole-6-carboxamide;
N-({7-[(6-amino-9H-purin-9-yl)methyl]-5-chloro-1H-indol-2-yl}methyl)-1H-indazole-6-carboxamide;
N-({7-[(6-amino-9H-purin-9-yl)methyl]-5-chloro-1H-indol-2-yl}methyl)-1H-pyrrolo[3,2-b]pyridine-5-carboxamide;
N-({7-[(6-amino-9H-purin-9-yl)methyl]-5-chloro-1H-indol-2-yl}methyl)-1H-benzimidazole-5-carboxamide;
N-({7-[(6-amino-9H-purin-9-yl)methyl]-5-chloro-1H-indol-2-yl}methyl)-1H-benzimidazole-6-carboxamide;
N-({7-[(6-amino-9H-purin-9-yl)methyl]-5-chloro-1H-indol-2-yl}methyl)-1H-indazole-5-carboxamide;
N-({7-[(6-amino-9H-purin-9-yl)methyl]-5-chloro-1H-indol-2-yl}methyl)-1H-pyrrolo[2,3-b]pyridine-5-carboxamide;
N-({7-[(6-amino-9H-purin-9-yl)methyl]-5-chloro-1H-indol-2-yl}methyl)-4-chloro-1H-pyrrolo[2,3-b]pyridine-5-carboxamide;
N-({7-[(6-amino-9H-purin-9-yl)methyl]-5-chloro-1H-indol-2-yl}methyl)-5-chloro-1H-pyrrolo[2,3-b]pyridine-6-carboxamide;
N-({7-[(6-amino-9H-purin-9-yl)methyl]-5-chloro-1H-indol-2-yl}methyl)-4-fluoro-1H-indazole-5-carboxamide;
N-({7-[(6-amino-9H-purin-9-yl)methyl]-5-chloro-1H-indol-2-yl}methyl)-3-methyl[1,2]oxazolo[5,4-b]pyridine-5-carboxamide;
N-({7-[(6-amino-9H-purin-9-yl)methyl]-5-chloro-1H-indol-2-yl}methyl)-1-methyl-1H-benzotriazole-5-carboxamide;
N-({7-[(6-amino-9H-purin-9-yl)methyl]-5-chloro-1H-indol-2-yl}methyl)-3-methyl-1H-pyrazolo[3,4-b]pyridine-5-carboxamide;
N-({7-[(6-amino-9H-purin-9-yl)methyl]-5-chloro-1H-indol-2-yl}methyl)-1-benzothiophene-5-carboxamide;
N-({7-[(6-amino-9H-purin-9-yl)methyl]-5-chloro-1H-indol-2-yl}methyl)-1-benzofuran-5-carboxamide;
N-({7-[(6-amino-9H-purin-9-yl)methyl]-5-chloro-1H-indol-2-yl}methyl)-1H-indole-6-carboxamide;
N-({7-[(6-amino-9H-purin-9-yl)methyl]-5-chloro-1H-indol-2-yl}methyl)-1H-indole-5-carboxamide;
N-({7-[(6-amino-9H-purin-9-yl)methyl]-5-chloro-1H-indol-2-yl}methyl)-2-methyl-1,3-benzothiazole-6-carboxamide;
N-({7-[(6-amino-9H-purin-9-yl)methyl]-5-chloro-1H-indol-2-yl}methyl)-2-methyl-1,3-benzoxazole-6-carboxamide;
N-({7-[(6-amino-9H-purin-9-yl)methyl]-5-chloro-1H-indol-2-yl}methyl)-1-methyl-1H-indazole-6-carboxamide;
N-({7-[(6-amino-9H-purin-9-yl)methyl]-5-chloro-1H-indol-2-yl}methyl)-1-methyl-1H-benzimidazole-5-carboxamide;
N-({7-[(6-amino-9H-purin-9-yl)methyl]-5-chloro-1H-indol-2-yl}methyl)-1-methyl-1H-indazole-5-carboxamide;
N-({7-[(6-amino-9H-purin-9-yl)methyl]-5-chloro-1H-indol-2-yl}methyl)-2-methyl-1H-benzimidazole-5-carboxamide;
N-({7-[(6-amino-9H-purin-9-yl)methyl]-5-chloro-1H-indol-2-yl}methyl)-2-methyl-1-benzofuran-5-carboxamide;
N-({7-[(6-amino-9H-purin-9-yl)methyl]-5-chloro-1H-indol-2-yl}methyl)-1-methyl-1H-indole-6-carboxamide;
N-({7-[(6-amino-9H-purin-9-yl)methyl]-5-chloro-1H-indol-2-yl}methyl)-1-methyl-1H-indole-5-carboxamide;

N-({7-[(6-amino-9H-purin-9-yl)methyl]-5-chloro-1H-indol-2-yl}methyl)-1,2-dimethyl-1H-benzimidazole-5-carboxamide;

N-({7-[(6-amino-9H-purin-9-yl)methyl]-5-chloro-1H-indol-2-yl}methyl)-2-ethyl-1H-benzimidazole-6-carboxamide;

N-({7-[(6-amino-9H-purin-9-yl)methyl]-5-chloro-1H-indol-2-yl}methyl)-3-cyano-1H-indole-5-carboxamide;

N-({7-[(6-amino-9H-purin-9-yl)methyl]-5-chloro-1H-indol-2-yl}methyl)-3-(propan-2-yl)[1,2]oxazolo[5,4-b]pyridine-5-carboxamide;

N-({7-[(6-amino-9H-purin-9-yl)methyl]-5-chloro-1H-indol-2-yl}methyl)-1-(propan-2-yl)-1H-benzotriazole-5-carboxamide;

N-({7-[(6-amino-9H-purin-9-yl)methyl]-5-chloro-1H-indol-2-yl}methyl)-1-(propan-2-yl)-1H-pyrazolo[3,4-b]pyridine-5-carboxamide;

N-({7-[(6-amino-9H-purin-9-yl)methyl]-5-chloro-1H-indol-2-yl}methyl)-4-methoxy-1,3-dimethyl-1H-pyrazolo[3,4-b]pyridine-5-carboxamide;

N-({7-[(6-amino-9H-purin-9-yl)methyl]-5-chloro-1H-indol-2-yl}methyl)-2,3-dimethyl-1H-indole-6-carboxamide;

N-({7-[(6-amino-9H-purin-9-yl)methyl]-5-chloro-1H-indol-2-yl}methyl)-2,3-dimethyl-1H-indole-5-carboxamide;

N-({7-[(6-amino-9H-purin-9-yl)methyl]-5-chloro-1H-indol-2-yl}methyl)-1-(2-hydroxyethyl)-2-methyl-1H-benzimidazole-5-carboxamide;

N-({7-[(6-amino-9H-purin-9-yl)methyl]-5-chloro-1H-indol-2-yl}methyl)-6-methyl-1-(propan-2-yl)-1H-pyrazolo[3,4-b]pyridine-5-carboxamide;

N-({7-[(6-amino-9H-purin-9-yl)methyl]-5-chloro-1H-indol-2-yl}methyl)-1,2,3-trimethyl-1H-indole-5-carboxamide; and N-({7-[(6-amino-9H-purin-9-yl)methyl]-5-chloro-1H-indol-2-yl}methyl)-2-butyl-1,3-benzoxazole-5-carboxamide.

Compound names are assigned by using Name 2012 naming algorithm by Advanced Chemical Development or Struct=Name naming algorithm as part of CHEMDRAW® ULTRA v. 12.0.2.1076.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of formula (I) wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the accompanying Examples using an appropriate isotopically-labeled reagents in place of the non-labeled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Compounds of formula (I) may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of formula (I) may contain either a basic or an acidic functionality, or both, and may be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The invention contemplates compounds of formula (I) formed by synthetic means or formed by in vivo biotransformation of a prodrug.

Compounds described herein may exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

General Synthesis

The compounds described herein in various embodiments, including compounds of general formula (I) and specific examples may be prepared by methodologies known in the art, for example, through the reaction schemes depicted in schemes 1-5. The variables $R^2$, $R^3$, $R^4$, $R^5$, $R^6$, $R^{1A}$, $R^{1B}$, $R^{1C}$, $R^{4A}$, $R^{4B}$, $G^A$, $G^{2A}$, $G^{3A}$, $L^3$, and Y, used in the following schemes have the meanings as set forth in the summary and detailed description sections, unless otherwise noted.

Abbreviations used in the descriptions of the schemes and the specific examples have the following meanings: DBU for 1,8-diazabicyclo[5.4.0]undec-7-ene, DMF for N,N-dimethylformamide, DMSO for dimethyl sulfoxide, HATU for O-(7-azabenzotriazol-1-yl)-N,N,N',N'-tetramethyluronium hexafluorophosphate, HOBT for 1-hydroxybenzotriazole hydrate, HPLC for High Performance Liquid chromatography, LC/MS for liquid chromatography/mass spectrometry, Prep HPLC for Preparative High Performance Liquid chromatography, MeOH for methanol, NMR for nuclear magnetic resonance, SFC for Supercritical Fluid Chromatography, TFA for trifluoroacetic acid, and THF for tetrahydrofuran.

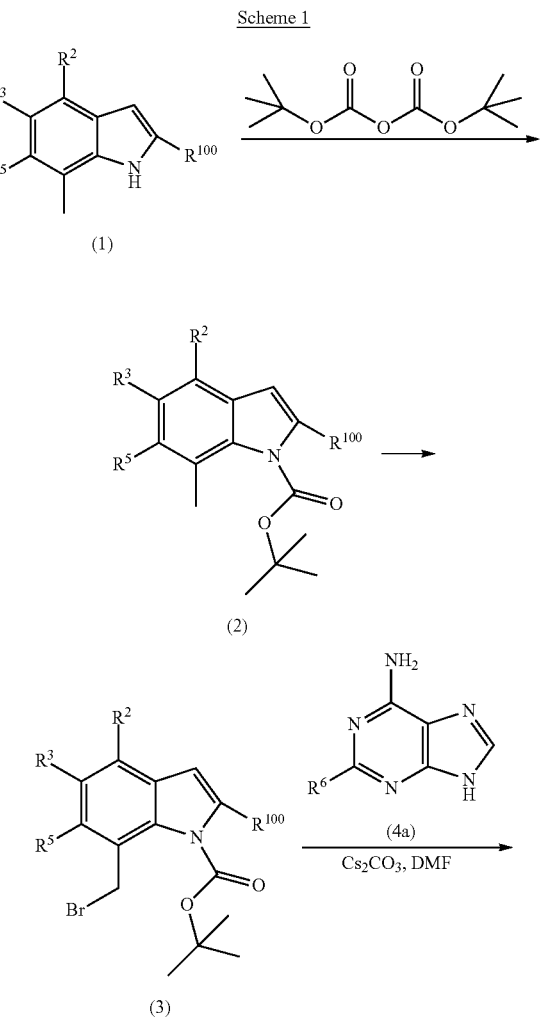

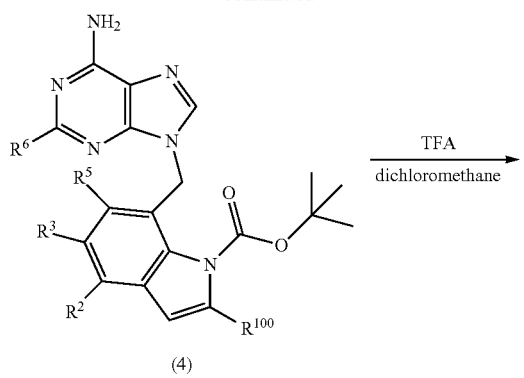

(4)

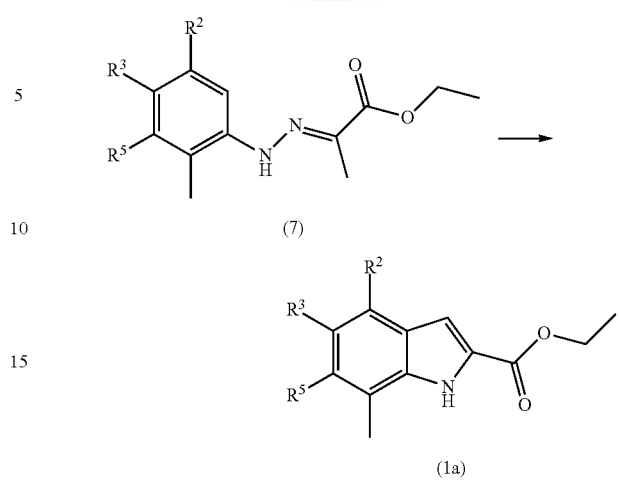

(7)

(1a)

Compounds of formula (1a) wherein $R^2$, $R^3$, and $R^4$ are hydrogen, or one of $R^2$, $R^3$, and $R^4$ is halogen, and the others are hydrogen may be prepared using general procedure as depicted in Scheme 2. Anilines of formula (6) may be treated with an acid such as concentrated hydrochloric acid, and sodium nitrite, followed by treatment with ethyl 2-methyl-3-oxo-butanoate or ethyl pyruvate, to provide intermediates of formula (7). Heating of (7) in the presence of Amberlyst-15 in a solvent such as, but not limited to, toluene, and at a temperature of about 100° C. to about 130° C., provides indoles of formula (1a).

(5)

Compounds of general formula (I) may be prepared utilizing general procedure as described in Scheme 1.

Treatment of substituted indoles of general formula (1) wherein $R^2$, $R^3$, and $R^4$ are hydrogen, or one of $R^2$, $R^3$, and $R^4$ is halogen, and the others are hydrogen, and $R^{100}$ is hydrogen or —C(O)OC$_2$H$_5$, with di-tert-butyl dicarbonate in the presence of N,N-dimethylpyridin-4-amine and a base such as, but not limited to, triethylamine, affords compounds of formula (2). The reaction may generally be conducted in a solvent such as, but not limited to, dichloromethane, and at ambient temperature. Conversion of (2) to (3) may be achieved by treatment with N-bromosuccinimide. Displacement of the bromine atom in compounds (3) with purine-6-amine of formula (4a) in the presence of a base such as, but not limited to, cesium carbonate, and in a solvent such as, but not limited to, N,N-dimethylformamide, provides compounds of formula (4). Removal of the tert-butoxycarbonyl protecting group may be achieved by treatment with an acid such as, but not limited to, trifluoroacetic acid.

Scheme 2

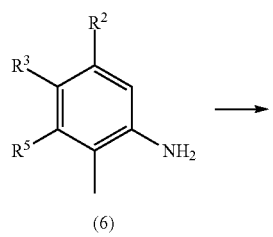

(6)

Scheme 3

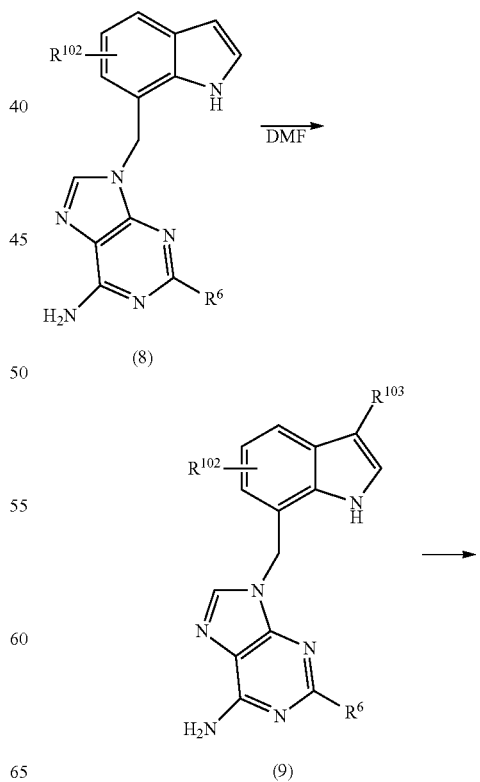

(8)

(9)

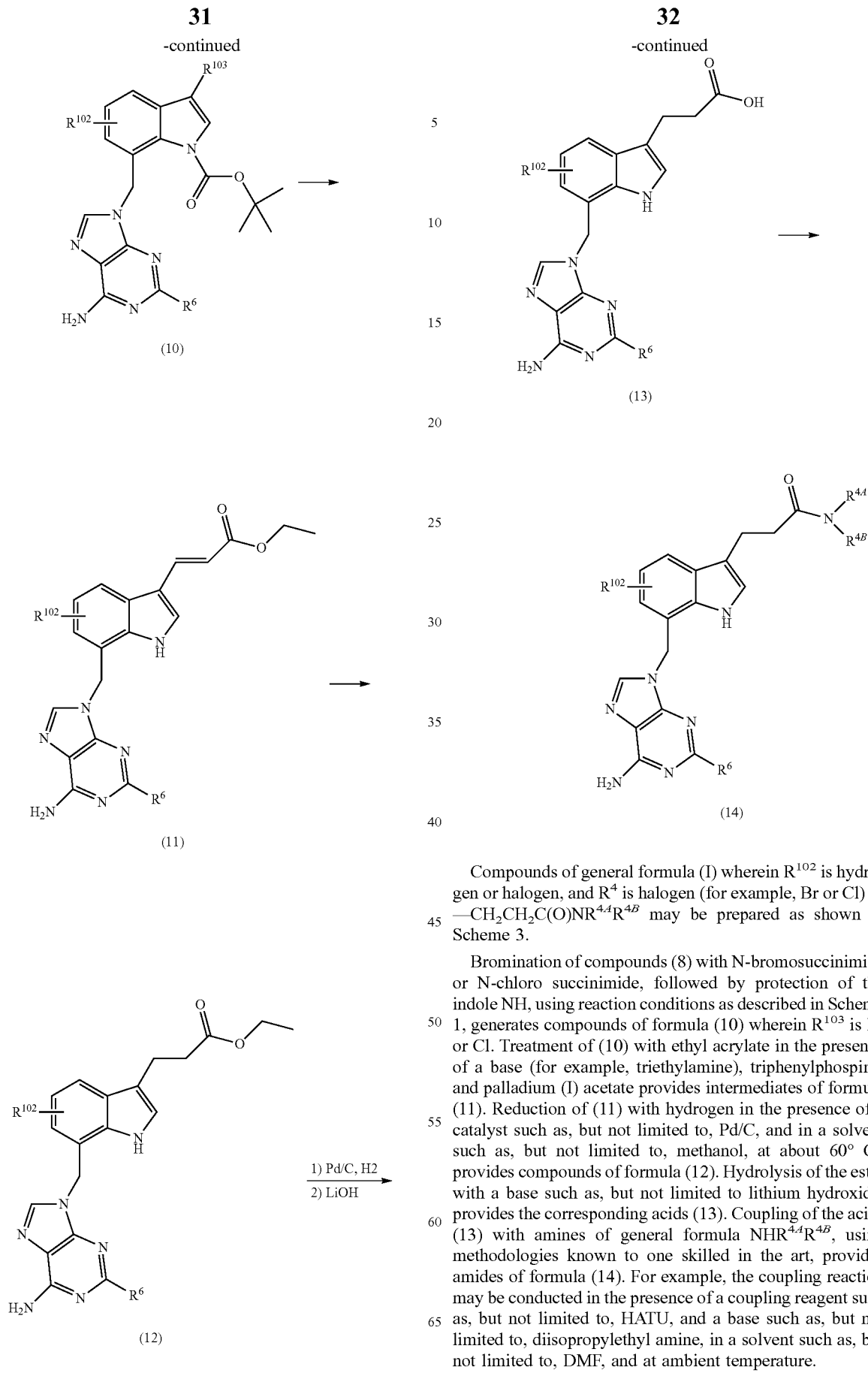

Compounds of general formula (I) wherein $R^{102}$ is hydrogen or halogen, and $R^4$ is halogen (for example, Br or Cl) or —$CH_2CH_2C(O)NR^{4A}R^{4B}$ may be prepared as shown in Scheme 3.

Bromination of compounds (8) with N-bromosuccinimide or N-chloro succinimide, followed by protection of the indole NH, using reaction conditions as described in Scheme 1, generates compounds of formula (10) wherein $R^{103}$ is Br or Cl. Treatment of (10) with ethyl acrylate in the presence of a base (for example, triethylamine), triphenylphospine, and palladium (I) acetate provides intermediates of formula (11). Reduction of (11) with hydrogen in the presence of a catalyst such as, but not limited to, Pd/C, and in a solvent such as, but not limited to, methanol, at about 60° C., provides compounds of formula (12). Hydrolysis of the ester with a base such as, but not limited to lithium hydroxide, provides the corresponding acids (13). Coupling of the acids (13) with amines of general formula $NHR^{4A}R^{4B}$, using methodologies known to one skilled in the art, provides amides of formula (14). For example, the coupling reaction may be conducted in the presence of a coupling reagent such as, but not limited to, HATU, and a base such as, but not limited to, diisopropylethyl amine, in a solvent such as, but not limited to, DMF, and at ambient temperature.

Scheme 4

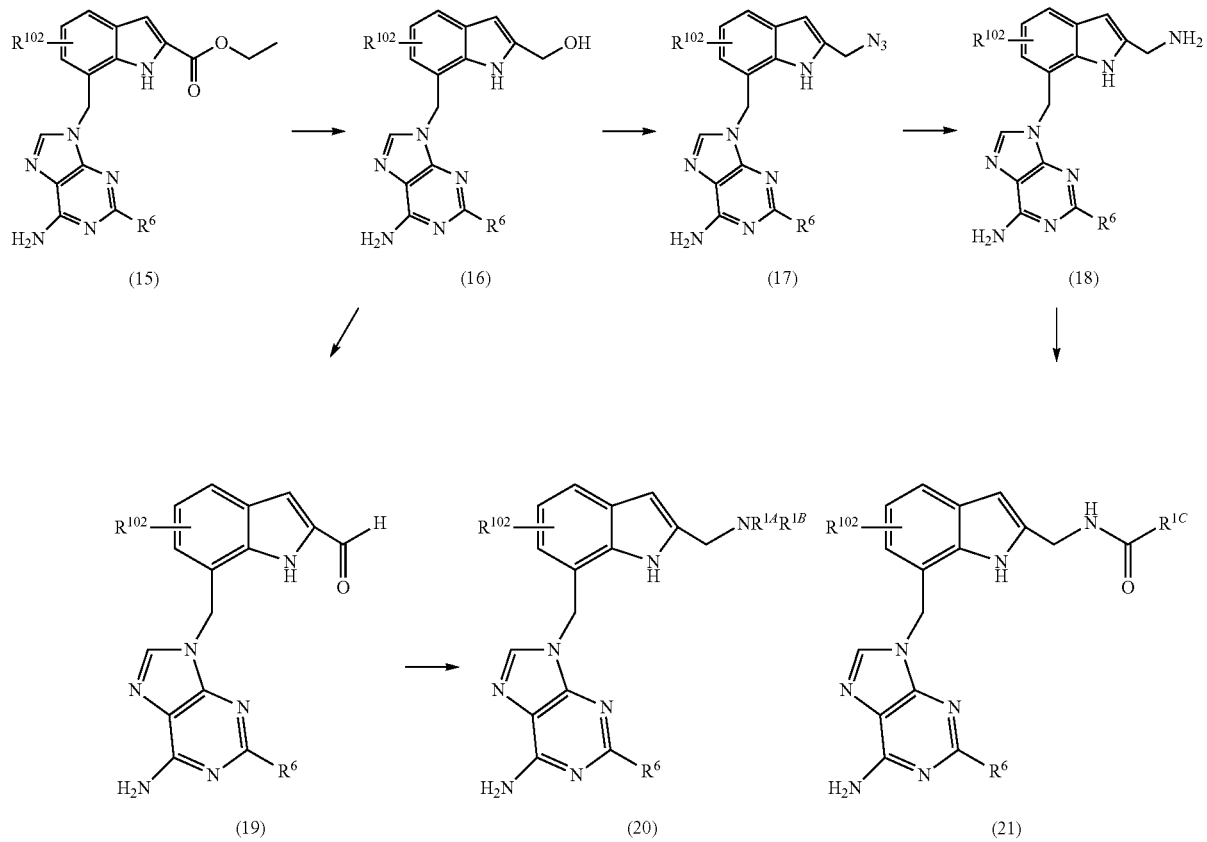

Compounds of general formula (I) wherein $R^1$ is —$CH_2NR^{1A}R^{1B}$ or —$CH_2N(R^J)C(O)R^{1C}$; and $R^{102}$ is halogen, alkenyl, phenyl, $G^{2A}$, $G^{3A}$, -$G^{3A}$-$G^A$, or -$G^{3A}$-$L^3$-Y may be synthesize using general synthetic scheme as shown in Scheme 4.

Reduction of the esters of formula (15) by treatment of a reducing agent such as, but not limited to, lithium aluminum hydride in a solvent such as, but not limited to, tetrahydrofuran, provides alcohols of formula (16). Treatment of the alcohols (16) with diphenyl phosphorazidate in DBU provides azides (17). Upon treatment with triphenylphosphine, the azides may be converted to primary amines of formula (18). Coupling of the amines with acids of formula $R^{1C}C$(O)OH using reaction conditions as described in Scheme (3) provides amides of formula (21). Alternatively, amides (21) may be obtained from the reaction of (18) with acid chlorides of formula $R^{1C}C(O)Cl$ (generated in situ from the corresponding acid) in the presence of a base such as, but not limited, to diisopropylethyl amine.

Treatment of the alcohols with 2-iodoxybenzoic acid and trifluoroacetic acid provides aldehydes of formula (19). Reductive amination of (19) with amines of formula $NHR^{1A}R^{1B}$ affords amines of formula (20).

Scheme 5

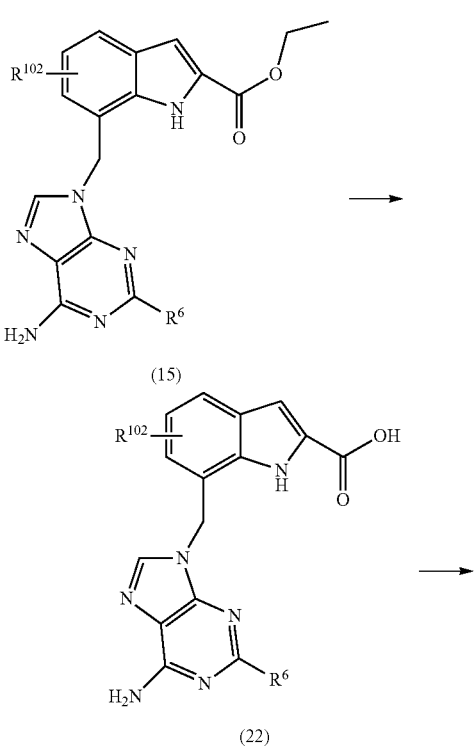

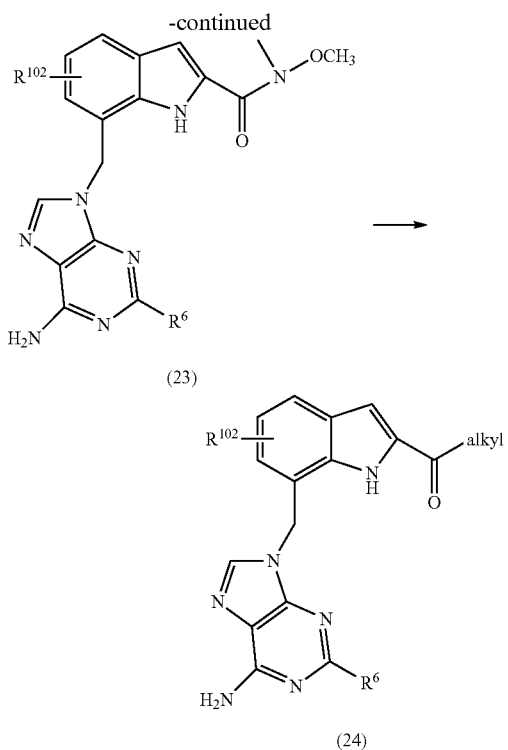

Hydrolysis of ester of formula (15) with lithium hydroxide provides acids of formula (22). Treatment of acids (22) with N,O-dimethylhydroxylamine in the presence of HATU and a base such as, but not limited to, triethylamine provides intermediates of formula (23). Reaction of (23) with an alkyl magnesium bromide such as, but not limited to, methyl magnesium bromide or ethyl magnesium bromide, in tetrahydrofuran provides ketones of formula (24).

Compounds of general formula (20), (21), and (24) wherein $R^{102}$ is Cl may be converted to (20), (21), and (24) wherein $R^{102}$ is alkenyl, phenyl, $G^{2,4}$, $G^{3,4}$, -$G^{3,4}$-$G^4$, or -$G^{3,4}$-$L^3$-Y respectively using methodologies known to one skilled in the art. For example, the chlorides may be treated with an appropriate boronic acids or derivatives thereof (e.g. boronic esters), in the presence of a palladium catalyst and a base, and optionally in the presence of a ligand, and in a suitable solvent at elevated temperature (for example, at a temperature ranging from about 80° C. to about 150° C.). The reaction may be facilitated by microwave irradiation. Examples of the palladium catalyst include, but are not limited to, tetrakis(triphenylphosphine)palladium(0), tris(dibenzylideneacetone)dipalladium(0), and palladium(II)acetate. Examples of suitable bases that may be employed include, but are not limited to, carbonates or phosphates of sodium, potassium, and cesium; and cesium fluoride. Examples of suitable ligands include, but are not limited to, tricyclohexylphosphine, 1,3,5,7-tetramethyl-6-phenyl-2,4,8-trioxa-6-phosphaadamantane, 2-dicyclohexylphosphino-2',4',6'-triisopropylbiphenyl (X-phos), and 1,1'-bis(diphenylphosphanyl) ferrocene. Non-limiting examples of suitable solvent include methanol, n-butanol, dimethoxyethane, N,N-dimethylformamide, dimethylsulfoxide, dioxane, tetrahydrofuran, and water, or a mixture thereof.

Optimal reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be further processed in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that are not compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it may be prepared by carrying out one of the above procedures using a pure geometric isomer as a starting material, or by resolution of a mixture of the geometric isomers of the compound or intermediates using a standard procedure such as chromatographic separation.

Pharmaceutical Compositions

This invention also provides for pharmaceutical compositions comprising a therapeutically effective amount of a compound of formula (I), or a pharmaceutically acceptable salt thereof together with a pharmaceutically acceptable carrier, diluent, or excipient thereof. The phrase "pharmaceutical composition" refers to a composition suitable for administration in medical or veterinary use.

The pharmaceutical compositions that comprise a compound of formula (I), alone or in combination with a second therapeutic agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which may serve as pharmaceutically acceptable carriers are sugars such as, but not limited to, lactose, glucose, and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

Pharmaceutical compositions for parenteral injection comprise pharmaceutically acceptable sterile aqueous or nonaqueous solutions, dispersions, suspensions, or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate), and suitable mixtures thereof. Proper fluidity may be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release may be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations may be sterilized, for example, by filtration through a bacterial-retaining filter or by incorporating sterilizing agents in the form of sterile solid compositions which may be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula (I). In certain embodiments, the compound of formula (I) may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form may be a packaged preparation, the package containing discrete quantities of preparation, such as packeted tablets, capsules, and powders in vials or ampules. Also, the unit dosage form may be a capsule, tablet, cachet, or lozenge itself, or it may be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition may, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician may evaluate factors such as the circulating plasma levels of the compound, compound toxicities, and/or the progression of the disease, etc.

For administration, compounds may be administered at a rate determined by factors that may include, but are not limited to, the $LD_{50}$ of the compound, the pharmacokinetic profile of the compound, contraindicated drugs, and the side-effects of the compound at various concentrations, as applied to the mass and overall health of the subject. Administration may be accomplished via single or divided doses.

The compounds utilized in the pharmaceutical method of the invention may be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules may be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which may be used include polymeric substances and waxes.

The active compounds may also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols, and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which may be prepared by mixing the compounds with suitable non-irritating carriers or carriers such as cocoa butter, polyethylene glycol, or a suppository wax which are solid at room temperature but liquid at body temperature and therefore melt in the rectum or vaginal cavity and release the active compound.

Compounds may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes may be used. The present compositions in liposome form may contain, in addition to a compound of the invention, stabilizers, preservatives, excipients, and the like. Examples of lipids include, but are not limited to, natural and synthetic phospholipids, and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments, and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Methods of Use

The compounds and compositions using any amount and any route of administration may be administered to a subject for the treatment of treating a condition, disease, or disorder implicated by SUV420H1 activity. In certain embodiments, the invention provides a method of treating a condition, disease, or disorder implicated by SUV420H1 activity, the method comprising administering a therapeutically acceptable amount of a compound of formula (I) or a pharmaceutically acceptable salt thereof to a subject in need thereof. In certain embodiments, said subject is a human. In certain embodiments, the compound or salt thereof is administered with a pharmaceutically acceptable carrier.

The term "administering" refers to the method of contacting a compound with a subject. Thus, the compounds may be administered by injection, that is, intravenously, intramuscularly, intracutaneously, subcutaneously, intraduodenally, parentally, or intraperitoneally. Also, the compounds described herein may be administered by inhalation, for example, intranasally. Additionally, the compounds may be administered transdermally, topically, via implantation, transdermally, topically, and via implantation. In certain embodiments, the compounds and compositions thereof may be delivered orally. The compounds may also be delivered rectally, bucally, intravaginally, ocularly, or by insufflation. SUV420H1-modulated disorders and conditions may be treated prophylactically, acutely, and chronically using compounds and compositions thereof, depending on the nature of the disorder or condition. Typically, the host or subject in each of these methods is human, although other mammals may also benefit from the administration of compounds and compositions thereof as set forth hereinabove.

Compounds of the invention are useful as modulators of SUV420H1. Thus, the compounds and compositions are particularly useful for treating or lessening the severity, or progression of a disease, disorder, or a condition where hyperactivity or inactivity of SUV420H1 is involved. Accordingly, the invention provides a method for modulating SUV420H1 in a membrane of a cell, comprising the step of contacting said cell with a compound of formula (I) or a preferred embodiment thereof as set forth above. One embodiment is directed to a method of treating a condition, disease, or disorder in a subject implicated by SUV420H1 activity, comprising the step of administering to said subject a therapeutically effective amount of a compound of formula (I) or a preferred embodiment thereof as set forth above, or a pharmaceutically acceptable salt thereof. In certain embodiments, the subject is a mammal. In certain embodiments, the subject is a human.

One embodiment is directed to a compound according to formula (I) or a pharmaceutically acceptable salt thereof for use in medicine.

One embodiment is directed to a compound according to formula (I) or a pharmaceutically acceptable salt thereof for use in the treatment of condition, disease, or disorder in a subject implicated by SUV420H1 activity.

One embodiment is directed to the use of a compound according to formula (I) or a pharmaceutically acceptable salt thereof in the preparation of a medicament.

One embodiment is directed to the use of a compound according to formula (I) in the preparation of a medicament for use in the treatment of condition, disease, or disorder in a subject implicated by SUV420H1 activity.

The present compounds may be co-administered to a subject. The term "co-administered" means the administration of two or more different therapeutic agents that are administered to a subject by combination in the same pharmaceutical composition or separate pharmaceutical compositions. Thus co-administration involves administration at the same time of a single pharmaceutical composition comprising two or more therapeutic agents or administration of two or more different compositions to the same subject at the same or different times.

The compounds of the invention may be co-administered with a therapeutically effective amount of one or more agents to treat condition, disease, or disorder in a subject implicated by SUV420H1 activity.

This invention also is directed to methods of use of the compounds, salts, compositions, and/or kits of the invention to, for example, modulate SUV420H1 or fragment thereof, and treat a disease treatable by modulating SUV420H1 or a fragment thereof.

This invention also is directed to a use of one or more compounds and/or salts of the invention in the preparation of a medicament. The medicament optionally can comprise one or more additional therapeutic agents. In some embodiments, the medicament is useful for treating a disease, condition, or disorder implicated by SUV420H1 activity.

This invention also is directed to a use of one or more compounds and/or salts of the invention in the manufacture of a medicament for the treatment of a disease, condition, or disorder implicated by SUV420H1 activity. The medicament optionally can comprise one or more additional therapeutic agents.

Another aspect of the invention relates to modulating SUV420H1 activity in a biological sample or a patient (e.g., in vitro or in vivo), which method comprises administering to the patient, or contacting said biological sample with a compound of formula (I) or a composition comprising said compound. The term "biological sample", as use herein, includes, without limitation, cell cultures or extracts thereof, biopsied material obtained from a mammal or extracts thereof, and blood, saliva, urine, feces, semen, tears, or other body fluids of extracts thereof.

Modulation of SUV420H1 activity in a biological sample is useful for a variety of purposes that are known to one of skill in the art. Examples of such purposes include, but are not limited to, the study of SUV420H1 activity in biological and pathological phenomena; and the comparative evaluation of new modulators of SUV420H1.

Further benefits of Applicants' invention will be apparent to one skilled in the art from reading this patent application.

The following Examples may be used for illustrative purposes and should not be deemed to narrow the scope of the invention.

EXAMPLES

Example 1

9-[(3-bromo-1H-indol-7-yl)methyl]-9H-purin-6-amine

Example 5c (100 mg, 0.378 mmol) was dissolved in N,N-dimethylformamide (2.0 mL), stirred, and cooled to about 0° C. for about 10 minutes. N-bromosuccinimide (74.1 mg, 0.416 mmol) was added. The mixture was stirred at room temperature overnight. The reaction mixture was diluted with water. The precipitate was filtered and washed with water, dried in vacuum to give a red solid, which was purified by reverse phase HPLC (C18, 35-70% acetonitrile/water, 0.05% ammonium hydroxide) to afford the title compound (55 mg, 0.160 mmol, 42.4% yield). MS (ESI+): m/z 345 (M+H)$^+$, $^1$H NMR (400 MHz, DMSO-d$_6$): δ 11.82 (s, 1H), 8.25 (s, 1H), 8.16 (s, 1H), 7.69 (s, 1H), 7.36 (d, J=8.0 Hz, 1H), 7.26 (s, 2H), 7.06 (t, J=7.6 Hz, 1H), 6.90 (d, J=6.8 Hz, 1H), 5.64 (s, 2H).

Example 2

3-{7-[(6-amino-9H-purin-9-yl)methyl]-1H-indol-3-yl}-N-methylpropanamide

Example 2a tert-butyl 7-((6-amino-9H-purin-9-yl)methyl)-3-bromo-1H-indole-1-carboxylate A mixture of Example 1 (2.0 g, 5.83 mmol) and di-tert-butyl dicarbonate (2.84 mL, 12.24 mmol) in THF (20 mL) was stirred at about 25° C. for about 10 minutes in a round-bottomed flask to give a red suspension. 4-dimethylpyridine (0.142 g, 1.166 mmol) was added and the reaction mixture was stirred at ambient temperature overnight. The reaction mixture was diluted with saturated sodium bicarbonate solution and dichloromethane. The organic layer was washed with brine, dried over sodium sulfate, filtered, concentrated under reduced pressure, and purified by column chromatography on silica gel (a gradient of 1-4% methanol in dichloromethane:ethyl acetate (1:1)) to give the title compound (2.0 g, 4.51 mmol, 77% yield) as a pale red solid. MS (ESI+): m/z 445 (M+H)+

Example 2b (E)-ethyl 3-(7-((6-amino-9H-purin-9-yl)methyl)-1H-indol-3-yl)acrylate To a mixture of Example 2a (100 mg, 0.226 mmol), ethyl acrylate (27.1 mg, 0.271 mmol) and triethylamine (0.063 mL, 0.451 mmol) in N,N-dimethylformamide (2.0 mL) were added triphenylphosphine (11.83 mg, 0.045 mmol) and palladium(II) acetate (5.06 mg, 0.023 mmol). The mixture was degassed with argon gas and heated at 90° C. for 16 hours. The mixture was concentrated and the residue was purified by reverse phase HPLC (C18, 35-70% acetonitrile/water, 0.05% ammonium hydroxide) to afford the title compound (26 mg, 0.072 mmol, 31.8% yield). MS (ESI+): m/z 363 (M+H)$^+$.

Example 2c ethyl 3-(7-((6-amino-9H-purin-9-yl)methyl)-1H-indol-3-yl)propanoate A mixture of Example 2b (50 mg, 0.138 mmol) and Pd/C (14.68 mg, 0.138 mmol) in methanol (5.0 mL) was stirred at ambient temperature for 12 hours under hydrogen gas atmosphere. The mixture was diluted with methanol (20 mL), stirred at 60° C. for 10 minutes, and filtered through a pad of celite. The filtrate was concentrated and purified by reverse phase HPLC (C18, 35-70% acetonitrile/water, 0.05% ammonium hydroxide) to afford the title compound (20 mg, 0.055 mmol, 39.8% yield). MS (ESI+): m/z 365 $(M+H)^+$.

Example 2d 3-(7-((6-amino-9H-purin-9-yl)methyl)-1H-indol-3-yl)propanoic acid A mixture of Example 2c (55 mg, 0.151 mmol) and lithium hydroxide monohydrate (19.00 mg, 0.453 mmol) in a mixture of water (1.0 mL) and methanol (1.0 mL) was stirred at ambient temperature for 3 hours. Methanol was removed under reduce pressure. The residue was acidified with 1M aqueous HCl solution to about pH 5 and purified by reverse phase HPLC (C18, 35-70% acetonitrile/water, 0.05% ammonium hydroxide) to afford the title compound (14 mg, 0.042 mmol, 27.6% yield) as a white solid. MS (ESI+): m/z 337 $(M+H)^+$.

Example 2e

3-{7-[(6-amino-9H-purin-9-yl)methyl]-1H-indol-3-yl}-N-methylpropanamide

To a mixture of Example 2d (40 mg, 0.119 mmol), diethyl isopropylamine (0.083 mL, 0.476 mmol), HATU (90 mg, 0.238 mmol) in N,N-dimethylformamide (1.0 mL), methanamine (0.089 mL, 0.178 mmol; 2.0M THF solution) were added. The reaction mixture was stirred at ambient temperature for 2 hours. The mixture was purified by reverse phase HPLC (C18, 35-70% acetonitrile/water, 0.05% ammonium hydroxide) to afford the title compound (23 mg, 0.065 mmol, 54.2% yield) as a white solid. MS (ESI+): m/z 350 $(M+H)^+$; $^1$H NMR (400 MHz, DMSO-$d_6$): δ 11.09 (s, 1H), 8.24 (s, 1H), 8.17 (s, 1H), 7.76 (d, J=4.8 Hz, 1H), 7.47 (d, J=7.6 Hz, 1H), 7.26 (s, 2H); 7.20 (s, 1H), 6.92 (t, J=7.6 Hz, 1H), 6.83 (d, J=7.2 Hz, 1H), 5.59 (s, 2H), 2.91 (t, J=7.4 Hz, 2H), 2.55 (d, J=4.8 Hz, 3H), 2.40 (t, J=7.8 Hz, 2H).

Example 3

3-{7-[(6-amino-9H-purin-9-yl)methyl]-1H-indol-3-yl}-N,N-dimethylpropanamide

Example 3 was prepared according to the procedure used for the preparation of Example 2e, substituting dimethylamine for methylamine. MS (ESI+): m/z 364 $(M+H)^+$; $^1$H NMR (400 MHz, DMSO-$d_6$): δ 11.09 (s, 1H), 8.23 (s, 1H), 8.18 (s, 1H), 7.47 (d, J=7.6 Hz, 1H), 7.26 (s, 3H), 6.93 (t, J=7.2 Hz, 1H), 6.85 (d, J=6.8 Hz, 1H), 5.59 (s, 2H), 2.92-2.88 (m, 5H), 2.81 (s, 3H), 2.63 (t, J=7.2 Hz, 2H).

Example 4

9-(1H-indol-7-ylmethyl)-2-methyl-9H-purin-6-amine

Example 4a tert-butyl 7-methyl-1H-indole-1-carboxylate

Di-tert-butyl dicarbonate (3.9 g, 17.87 mmol) was added to a solution of 7-methyl-1H-indole (Aldrich, 2.0 g, 15.25 mmol), triethylamine (2.5 mL, 17.94 mmol), N,N-dimethylpyridin-4-amine (0.187 g, 1.531 mmol) and dichloromethane (25 mL). The reaction mixture was stirred at room temperature for 2 hours. The reaction mixture was diluted with dichloromethane and was washed with water, brine, dried (magnesium sulfate), filtered and concentrated. The crude product was flash chromatographed (Biotage 100 g HP Snap Cartridge, eluting with heptanes containing a gradient with ethyl acetate, 0% to 6%) to provide the title compound. MS DCI 249.1 $(M+NH_4)^+$.

Example 4b tert-butyl 7-(bromomethyl)-1H-indole-1-carboxylate

A solution of Example 4a (2.57 g, 11.11 mmol), 1-bromopyrrolidine-2,5-dione (1.98 g, 11.12 mmol), benzoic peroxyanhydride (0.269 g, 1.111 mmol) and carbon tetrachloride (37 mL) was stirred at 85° C. for 5 hours. The reaction mixture was cooled to room temperature, diluted with dichloromethane and was washed with saturated aqueous sodium bicarbonate solution, water, saturated aqueous sodium chloride solution, dried (magnesium sulfate), filtered and concentrated. The crude product was flash chromatographed (Biotage 340 g KP Snap Cartridge, eluting with heptanes containing a gradient with dichloromethane, 0% to 12%) to afford the title compound. MS DCI 328.9 $(M+NH4)^+$.

Example 4c tert-butyl 7-((6-amino-2-chloro-9H-purin-9-yl)methyl)-1H-indole-1-carboxylate 2-Chloro-9H-purin-6-amine (Aldrich, 0.481 g, 2.84 mmol) was added portion wise to a 0° C. suspension of cesium carbonate (1.09 g, 3.35 mmol) and N,N-dimethylformamide (20 mL). After 10 minutes at 0° C. a solution Example 4b (0.88 g, 2.84 mmol) and N,N-dimethylformamide (10 mL) was added slowly and the reaction mixture was stirred at 0° C. for 3 hours. Water was added and the suspension was stirred at 0° C. for 30 minutes. The solid was filtered, rinsed with water and was dried (in-vacuo) to provide the title compound. MS $ESI^+$ 399.0 $(M+H)^+$.

Example 4d 9-((1H-indol-7-yl)methyl)-2-methyl-9H-purin-6-amine

In a microwave vial, a solution of Example 4c (30 mg, 0.075 mmol), methylboronic acid (14 mg, 0.234 mmol), potassium phosphate (47 mg, 0.221 mmol), {1,3-bis(2,6- diisopropylphenyl)imidazol-2-ylidene}chloro{3-phenylallyl}palladium(II) (15 mg, 0.023 mmol), dioxane (2.5 mL) and water (0.8 mL) was degassed with nitrogen. The reaction mixture was sealed and was heated in a microwave reactor at 150° C. for 1 hour. Another 8 mg of {1,3-bis(2,6-diisopropylphenyl)imidazol-2-ylidene}chloro{3-phenylallyl}palladium(II) was added, the solution was degassed again with nitrogen and was heated in the microwave at 150° C. for another 1 hour. Water and ethyl acetate were added and the layers were separated. The aqueous layer was extracted two more times with ethyl acetate. The combined organic extracts were washed with brine, dried (magnesium sulfate), filtered and concentrated. The crude product was purified by preparative HPLC on *2-coupled C8 5 um 100 Å columns (30 mm×75 mm each) with a gradient of acetonitrile (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11 min linear gradient 100-5% A) to provide the title compound. $^1$H NMR (400 MHz, DMSO-$d_6$) δ 11.39 (s, 1H), 8.43 (s, 1H), 8.34 (s, 2H), 7.52 (dd, J=7.9, 4.7 Hz, 1H), 7.47 (dt, J=5.0, 2.7 Hz, 1H), 6.94 (dd, J=8.7, 6.5 Hz, 1H), 6.75 (d, J=7.2 Hz, 1H), 6.52 (q, J=3.8, 3.1 Hz, 1H), 5.69 (d, J=2.5 Hz, 2H), 2.55 (d, J=5.0 Hz, 3H). MS ESI$^+$ 279.1 (M+H)$^+$.

Example 5

9-(1H-indol-7-ylmethyl)-9H-purin-6-amine

Example 5a tert-butyl 7-(bromomethyl)-1H-indole-1-carboxylate

A mixture of Example 4a (21 g, 91 mmol), benzoic peroxyanhydride (1.100 g, 4.54 mmol) and N-bromosuccinimide (17.13 g, 96 mmol) in carbon tetrachloride (200 mL) was heated to about 80° C. for about 2 hours in a 500 mL round-bottomed flask. The floated succinimide was filtered off and washed with carbon tetrachloride (10 mL). The solvent was removed in vacuum to afford the title compound (25 g, 81 mmol, 89% yield) as orange oil. $^1$H NMR (400 MHz, CDCl$_3$): δ 7.58-7.53 (m, 2H), 7.26 (d, J=2.4 Hz, 1H); 7.19 (d, J=3.6 Hz, 1H), 6.58 (d, J=3.6 Hz, 1H), 5.24 (s, 2H), 1.68 (s, 9H).

Example 5b tert-butyl 7-((6-amino-9H-purin-9-yl)methyl)-1H-indole-1-carboxylate

A mixture of Example 5a (10 g, 32.2 mmol), 9H-purin-6-amine (4.36 g, 32.2 mmol) and cesium carbonate (12.60 g, 38.7 mmol) in N,N-dimethylformamide (60 mL) was heated to about 50° C. for about 2 hours. The reaction solution was cooled to room temperature and poured into water. The precipitate was filtered and washed with water, dried in vacuum, and purified by column chromatography on silica gel (25-75% ethyl acetate in petroleum ether) to afford the title compound (4.5 g, 12.35 mmol, 38.3% yield). MS (ESI+): m/z 365 (M+H)+.

Example 5c 9-(1H-indol-7-ylmethyl)-9H-purin-6-amine

A mixture of Example 5b (4.0 g, 10.98 mmol) and trimethylsilyl chloride (14.03 mL, 110 mmol) in methanol (40 mL) was stirred at about 60° C. for 16 hours. The solvent was removed under reduced pressure. Methanol (2.0 mL) was added. The pH was adjusted to 8-10 with saturated aqueous sodium bicarbonate solution. The precipitate was stirred for about 10 minutes and collected by filtration, washed with water and then ether, dried in vacuum to give a red solid, which was purified by silica gel column chromatography (dichloromethane:ethyl acetate:methanol=25:25:1) to afford the title compound (1.16 g, 4.39 mmol, 40.0% yield) as a white solid. MS (ESI+): m/z 265 (M+H)$^+$; $^1$H NMR (400 MHz, DMSO-$d_6$): δ 11.44 (s, 1H), 8.27 (s, 1H), 8.19 (s, 1H), 7.46-7.51 (m, 2H), 7.28 (s, 2H), 6.93 (t, J=7.2 Hz, 1H), 6.83 (d, J=6.8 Hz, 1H), 6.50 (s, 1H), 5.64 (s, 2H).

Example 6

2-cyclopropyl-9-(1H-indol-7-ylmethyl)-9H-purin-6-amine

Using the procedure described for Example 4d and substituting cyclopropylboronic acid for methylboronic acid provided the title compound. $^1$H NMR (400 MHz, DMSO-$d_6$) δ 11.36 (s, 1H), 8.27 (s, 1H), 7.50 (d, J=7.7 Hz, 1H), 7.44 (t, J=2.7 Hz, 1H), 6.93 (t, J=7.5 Hz, 1H), 6.87 (d, J=7.1 Hz, 1H), 6.52-6.47 (m, 1H), 5.58 (s, 2H), 2.07 (s, 1H), 1.00 (t, J=6.0 Hz, 4H). MS ESI$^+$ 305.1 (M+H)$^+$.

Example 7

{7-[(6-amino-9H-purin-9-yl)methyl]-5-chloro-1H-indol-2-yl}methanol

Example 7a (E)-ethyl 2-(2-(4-chloro-2-methylphenyl)hydrazono)propanoate

A 500 mL round-bottomed flask were charged with 4-chloro-2-methylaniline (15.0 g, 106 mmol) and HCl (37% concentration, 64.4 mL, 773 mmol) and water (100 mL) to give an off-white suspension. The suspension was cooled to about 0° C. in an ice bath and a solution of sodium nitrite (7.31 g, 106 mmol) in water (100 mL) was added slowly under stirring, After the addition, the mixture was stirred for 1 hour. The resulting solution was then added to a mixture of sodium acetate (87 g, 1059 mmol) and ethyl 2-methyl-3-oxo-butanoate (15.27 g, 106 mmol) in ethanol (300 mL) and water (1000 mL) at 0° C. The resulting mixture was stirred at about 0° C. for about 2 hours and then at ambient temperature overnight. The mixture was extracted with ethyl acetate (3×400 mL), washed sequentially with water, saturated sodium bicarbonate solution, and brine. The organic layer was dried with anhydrous sodium sulfate, filtered and concentrated. The residue was triturated in petroleum ether to give the title compound (5.6 g, 21.99 mmol, 20.75% yield) as a yellow solid. MS (ESI+): m/z 255 (M+H)$^+$.

Example 7b ethyl 5-chloro-7-methyl-1H-indole-2-carboxylate

A suspension of Example 7a (3.0 g, 11.78 mmol) and amberlyst 15 (10.0 g, 11.78 mmol) in toluene (50 mL) in a sealed tube was stirred at 120° C. overnight. The reaction mixture was filtered and the filtrate was concentrated. The residue was purified by flash column chromatography on silica gel (ethyl acetate: petroleum ether=1:20) to give the title compound (1.4 g, 5.89 mmol, 50.0% yield) as an off-white solid. MS (ESI+): m/z 238 (M+H)+.

Example 7c ethyl 5-chloro-7-methyl-1H-indole-2-carboxylate

To a solution of Example 7b (9.0 g, 37.9 mmol), triethylamine (6.33 mL, 45.4 mmol), and N,N-dimethylpyridin-4-amine (0.463 g, 3.79 mmol) in dichloromethane (150 mL) was added di-tert-butyl dicarbonate (10.55 mL, 45.4 mmol). The reaction mixture was stirred overnight and then diluted with dichloromethane. The organic layer was washed sequentially with 0.1 M aqueous HCl solution and brine, dried with anhydrous sodium sulfate, filtered and concentrated to give the title compound (12.0 g, 35.5 mmol, 94% yield) as a yellow oil. MS (ESI+): m/z 338 (M+H)+.

Example 7d tert-butyl 2-ethyl 7-(bromomethyl)-5-chloro-1H-indole-1,2-dicarboxylate A mixture of Example 7c (6.0 g, 17.76 mmol), benzoic peroxyanhydride (0.430 g, 1.776 mmol), and N-bromosuccinimide (3.48 g, 19.54 mmol) in carbon tetrachloride (100 mL) was stirred at 80° C. overnight. The mixture was concentrated. The residue was diluted with ethyl acetate, washed sequentially with water and brine, dried with anhydrous sodium sulfate, filtered and concentrated. The residue was purified by flash column chromatography on silica gel (eluent: 1:60 ethyl acetate/petroleum ether) to give the title compound (4.2 g, 10.08 mmol, 56.7% yield).

Example 7e 1-tert-butyl 2-ethyl 7-((6-amino-9H-purin-9-yl) methyl)-5-chloro-1H-indole-1,2-dicarboxylate To a solution of Example 7d (50 g, 120 mmol) and 9H-purin-6-amine (14.59 g, 108 mmol) in N,N-dimethylformamide (500 mL) was added $Cs_2CO_3$ (43.0 g, 132 mmol). The resulting suspension was stirred at ambient temperature overnight. The reaction mixture was diluted with water (1500 mL), extracted with dichloromethane (3×300 mL). The combined organic layers were washed with water (3×500 mL), dried with sodium sulfate, concentrated to about 300 mL volume. The mixture was stirred overnight. The solid formed was collected by filtration and washed with dichloromethane (2×30 mL) to give the first crops of des-BOC product Example 7f (3.0 g, 8.0 mmol, 6.7% yield). The filtrate above was taken into ethyl acetate (300 mL) and washed with water (3×300 mL) to remove residual N,N-dimethylformamide. The organic layer was dried over sodium sulfate, filtered and concentrated. The resulting residue was purified by column chromatography on silica gel (5% methanol in dichloromethane) to give the Example 7e (18 g, 38.2 mmol, 32% yield) (MS (ESI+): m/z 471 (M+H)+) and the second crops of Example 7f (3.5 g, 9.29 mmol, 7.7% yield).

Example 7f ethyl 7-((6-amino-9H-purin-9-yl)methyl)-5-chloro-1H-indole-2-carboxylate Example 7e (15 g, 31.9 mmol) in dichloromethane (200 mL) was treated with trifluoroacetic acid (44.2 mL, 573 mmol) at 0° C. under an atmosphere of nitrogen. The resulting mixture was stirred at ambient temperature overnight. The solvent was removed under reduced pressure. To the dark oil residue was added water (100 mL) under stirring. The pH of the solution was adjusted to about 9 using saturated aqueous sodium carbonate solution. After stirring for 2 hours, the solid was filtered, washed with water (3×30 mL), and lyophilized to provide title compound (12 g, 27.5 mmol, 86% yield). MS (ESI+): m/z 371 (M+H)+.

Example 7g (7-((6-amino-9H-purin-9-yl)methyl)-5-chloro-1H-indol-2-yl)methanol

To a solution of Example 7f (8 g, 21.58 mmol) in anhydrous THF (200 mL) was added lithium aluminum hydride (43.2 mL, 43.2 mmol, 1 M solution in THF) at 0° C. under an atmosphere of nitrogen. The resulting mixture was stirred at ambient temperature overnight. The mixture was quenched with water (4 mL). Magnesium sulfate (20 g) was added to the mixture. The mixture was stirred overnight. The suspension was filtered and the filtering cake was washed with THF (50 mL×3). The filter cake was then stirred in THF (100 mL) for about 1 hour. The suspension was filtered and the filter cake was washed with THF (50 mL×3). All the organic liquid was combined, dried over anhydrous sodium sulfate, filtered, and concentrated to give the title compound (5.3 g, 13.7 mmol, 63.5% yield) a yellow solid. MS (ESI+): m/z 329 (M+H)+. $^1H$ NMR (400 MHz, DMSO-$d_6$): δ 11.63 (s, 1H), 8.29 (s, 1H), 8.19 (s, 1H), 7.47 (d, J=2.0 Hz, 1H), 7.33 (s, 2H), 6.83 (d, J=2.0 Hz, 1H), 6.34 (d, J=2.0 Hz, 1H), 5.61 (s, 2H), 4.65 (s, 2H).

Example 8

9-{[2-(aminomethyl)-1H-indol-7-yl]methyl}-9H-purin-6-amine

A microwave tube was charged with Example 9b (0.05 g, 0.153 mmol), 2-cyclopropyl-4,4,5,5-tetramethyl-1,3,2-dioxaborolane (0.038 g, 0.229 mmol), cesium carbonate (0.149 g, 0.458 mmol) in 1,2-dimethoxyethane (1 mL). The mixture was degassed, tris(dibenzylideneacetone)dipalladium(0) (0.014 g, 0.015 mmol) and 2-(dicyclohexylphosphino)-2',4',6'-triisopropylbiphenyl (7 mg, 0.015 mmol) were added, the vessel sealed, purged with nitrogen for 5 minutes and heated under microwave irradiation at about 140° C. for about 45 minutes. Water and ethyl acetate were added and the solid was filtered. The filtrate was partitioned. The organic layer was washed with brine, dried over magnesium sulfate and filtered. The filtrate was concentrated and purified by preparative HPLC (Waters Sunfire C8, 0-95% methanol/water; 1% TFA) to provide the title compound. $^1H$ NMR (400 MHz, $CD_3OD$) δ 8.37 (s, 1H), 8.21 (s, 1H), 7.63-7.51 (m, 1H), 7.12-6.99 (m, 2H), 6.66 (s, 1H), 5.71 (s, 2H), 4.34 (s, 2H); MS m/z: 277 [M−$NH_2$]+.

Example 9

9-{[2-(aminomethyl)-5-chloro-1H-indol-7-yl] methyl}-9H-purin-6-amine

Example 9a 9-((2-(azidomethyl)-5-chloro-1H-indol-7-yl)methyl)-9H-purin-6-amine

To a solution of Example 7g (8 g, 24.33 mmol) in anhydrous dichloromethane (80 mL) and anhydrous toluene (80 mL) was added diphenyl phosphorazidate (26.8 g, 97 mmol) and DBU (14.67 mL, 97 mmol) dropwise at ambient temperature under an atmosphere of nitrogen gas. The resulting mixture was stirred at ambient temperature overnight. The reaction solution was washed with water (3×75 mL). The organic layer was dried over anhydrous sodium sulfate, filtered and concentrated. The resulting residue was purified by column chromatography on silica gel (5% methanol in dichloromethane) to afford the title compound (4.1 g, 11.59 mmol, 47.6% yield) as a white solid. MS (ESI+): m/z 354 (M+H)$^+$.

Example 9b

9-{[2-(aminomethyl)-5-chloro-1H-indol-7-yl]methyl}-9H-purin-6-amine

To a solution of Example 9a (25 g, 70.7 mmol) in mixture of THF (300 mL) and water (150 mL) were added triphenylphosphine (37.1 g, 141 mmol). The resulting mixture was stirred at ambient temperature overnight. The mixture was concentrated to dryness. The white residue was washed with ethyl acetate/petroleum ether (2:5) three times, and then recrystallized in petroleum ether to give the title compound (20 g, 61.0 mmol, 86% yield). MS (ESI+): m/z 311 (M–NH$_2$)$^+$; $^1$H NMR (400 MHz, DMSO-d$_6$): δ 11.50 (brs, 1H), 8.30 (s, 1H), 8.21 (s, 1H), 7.44 (d, J=2.0 Hz, 1H), 7.34 (s, 2H), 6.77 (s, 1H), 6.31 (s, 1H), 5.60 (s, 2H), 3.90 (s, 2H), 1.95 (brs, 1H).

Example 10

9-{[2-(aminomethyl)-5-ethenyl-1H-indol-7-yl]methyl}-9H-purin-6-amine

In a microwave tube was charged Example 9b (0.08 g, 0.244 mmol), 4,4,5,5-tetramethyl-2-vinyl-1,3,2-dioxaborolane (0.062 mL, 0.366 mmol), potassium phosphate tribasic (0.104 g, 0.488 mmol) in 1,4-dioxane (2 mL) and water (0.11 mL). To the reaction mixture was added Tris(dibenzylideneacetone)dipalladium(0) (0.022 g, 0.024 mmol) and tricyclohexylphosphine (0.014 g, 0.049 mmol) and the vessel was sealed and heated in a microwave (Biotage, Initiator) at about 140° C. for about 45 minutes. The cooled mixture was filtered through Celite®, and concentrated. The residue was purified by preparative HPLC (Waters Sunfire C8, 20-50% acetonitrile/water; 1% TFA) to provide the title compound (0.030 g, 19%). $^1$H NMR (400 MHz, CD$_3$OD) δ 8.41 (s, 1H), 8.28 (s, 1H), 7.60 (d, J=1.5 Hz, 1H), 7.29 (d, J=1.5 Hz, 1H), 6.76 (dd, J=17.6, 10.9 Hz, 1H), 6.65 (s, 1H), 5.73 (s, 2H), 5.65 (dd, J=17.5, 1.0 Hz, 1H), 5.15-5.07 (m, 1H), 4.34 (s, 2H); MS m/z: 303 [M–NH$_2$]$^+$.

Example 11

9-{[2-(aminomethyl)-5-(cyclopent-1-en-1-yl)-1H-indol-7-yl]methyl}-9H-purin-6-amine Example 11 was prepared according to the procedure used for the preparation of Example 10, substituting 2-(cyclopent-1-en-1-yl)-4,4,5,5-tetramethyl-1,3,2-dioxaborolane for 4,4,5,5-tetramethyl-2-vinyl-1,3,2-dioxaborolane. $^1$H NMR (400 MHz, DMSO-d$_6$) δ 11.54 (s, 1H), 8.39-8.09 (m, 6H), 7.54 (s, 1H), 7.20 (s, 1H), 6.59 (s, 1H), 6.02 (s, 1H), 5.64 (s, 2H), 4.25 (q, J=5.7 Hz, 2H), 2.74-2.56 (m, 2H), 2.48-2.37 (m, 2H), 1.93 (p, J=7.5 Hz, 2H); MS m/z: 343 [M–NH$_2$]$^+$.

Example 12

9-{[2-(aminomethyl)-5-(3,6-dihydro-2H-pyran-4-yl)-1H-indol-7-yl]methyl}-9H-purin-6-amine Example 12 was prepared according to the procedure used for the preparation of Example 10, substituting 2-(3,6-dihydro-2H-pyran-4-yl)-4,4,5,5-tetramethyl-1,3,2-dioxaborolane for 4,4,5,5-tetramethyl-2-vinyl-1,3,2-dioxaborolane. 1H NMR (400 MHz, CD$_3$OD) δ 8.42 (s, 1H), 8.29 (s, 1H), 7.62 (d, J=1.5 Hz, 1H), 7.29 (d, J=1.6 Hz, 1H), 6.66 (s, 1H), 6.06 (s, 1H), 5.74 (s, 2H), 4.34 (s, 2H), 4.27 (q, J=2.8 Hz, 2H), 3.91 (t, J=5.5 Hz, 2H), 2.52 (s, 2H); MS m/z: 376 [M+H]$^+$.

Example 13

9-{[2-(aminomethyl)-5-(1,2,3,6-tetrahydropyridin-4-yl)-1H-indol-7-yl]methyl}-9H-purin-6-amine In a microwave tube was added Example 9b (0.100 g, 0.305 mmol), tert-butyl 4-(4,4,5,5-tetramethyl-1,3,2-dioxaborolan-2-yl)-5,6-dihydropyridine-1(2H)-carboxylate (0.142 g, 0.458 mmol, Frontier), potassium phosphate tribasic (0.130 g, 0.610 mmol) and n-butanol (1 mL). Tris(dibenzylideneacetone)dipalladium(0) (0.028 g, 0.031 mmol) and tricyclohexylphosphine (0.017 g, 0.061 mmol) were added, the vessel was sealed, and heated in a microwave (Biotage, Initiator) at about 120° C. for about 30 minutes. The cooled solution was filtered through Celite®, using 1,4-dioxane then methanol as eluent. The filtrate was concentrated under reduced pressure. The crude material was purified using preparative HPLC (Waters Sunfire C8, 30-80% methanol/water; 0.1 M ammonium acetate) to provide crude tert-butyl 4-{7-[(6-amino-9H-purin-9-yl)methyl]-2-(aminomethyl)-1H-indol-5-yl}-5,6-dihydropyridine-1(2H)-carboxylate (0.0526 g). The crude material was treated with 1 mL of 4M HCl in 1,4-dioxane overnight at ambient temperature with stirring. The material was concentrated to dryness and the solid was suspended in ether, filtered, washed with ether, 30% methanol/dichloromethane, and dried under vacuum to provide the title compound (0.019 g, 13%). $^1$H NMR (400 MHz, CD$_3$OD) δ 8.46 (s, 1H), 8.43 (s, 1H), 7.69 (d, J=1.6 Hz, 1H), 7.35 (d, J=1.6 Hz, 1H), 6.70 (s, 1H), 6.11-6.01 (m, 1H), 5.79 (s, 2H), 4.37 (s, 2H), 3.83 (q, J=2.7 Hz, 2H), 3.46 (t, J=6.1 Hz, 2H), 2.84 (dt, J=8.0, 3.9 Hz, 2H); MS m/z: 375 [M+H]$^+$.

Example 14

9-{[2-(aminomethyl)-5-(4,4-difluorocyclohex-1-en-1-yl)-1H-indol-7-yl]methyl}-9H-purin-6-amine Example 14 was prepared according to the procedure used for the preparation of Example 10, substituting 2-(4,4-difluorocyclohex-1-en-1-yl)-4,4,5,5-tetramethyl-1,3,2-dioxaborolane [Frontier] for 4,4,5,5-tetramethyl-2-vinyl-1,3,2-dioxaborolane. $^1$H NMR (400 MHz, CD$_3$OD) δ 8.38 (s, 1H), 8.23 (s, 1H), 7.60 (d, J=1.6 Hz, 1H), 7.24 (d, J=1.6 Hz, 1H), 6.65 (s, 1H), 5.85 (s, 1H), 5.70 (s, 2H), 4.33 (s, 2H), 2.75-2.59 (m, 4H), 2.15 (dq, J=13.7, 7.0 Hz, 2H); MS m/z: 410 [M+H]$^+$.

Example 15

1-[4-{2-(aminomethyl)-7-[(6-amino-9H-purin-9-yl)methyl]-1H-indol-5-yl}-3,6-dihydropyridin-1(2H)-yl]ethanone

Example 15a 1-(4-(4,4,5,5-tetramethyl-1,3,2-dioxaborolan-2-yl)-5,6-dihydropyridin-1(2H)-yl)ethanone To a vial was added 4-(4,4,5,5-tetramethyl-1,3,2-dioxaborolan-2-yl)-1,2,3,6-tetrahydropyridine, hydrochloric acid (0.25 g, 1.018 mmol), dichloromethane (5 mL) and diisopropylethylamine (0.88 mL, 5.09 mmol) followed by acetyl chloride (0.109 mL, 1.527 mmol). The mixture was stirred at room temperature for about 2 hours, diluted with water, and partitioned. The organic phase was washed sequentially with sodium bicarbonate, brine, filtered and concentrated under reduced pressure. The residue was purified using a silica gel column (ethyl acetate/heptanes 0-100%) to give the title compound (0.17 g, 67%). $^1$H NMR (400 MHz, dimethylsulfoxide-d6) δ 6.39 (dt, J=8.7, 2.6 Hz, 1H), 4.01 (q, J=2.8 Hz, 1H), 3.95 (q, J=2.9 Hz, 1H), 3.44 (dd, J=12.1, 5.8 Hz, 2H), 2.16 (dt, J=5.9, 3.0 Hz, 1H), 2.05 (td, J=5.6, 2.6 Hz, 1H), 1.99 (d, J=10.6 Hz, 3H), 1.20 (s, 12H); MS m/z: 293 [M+acetonitrile]$^+$.

Example 15b

1-[4-{2-(aminomethyl)-7-[(6-amino-9H-purin-9-yl)methyl]-1H-indol-5-yl}-3,6-dihydropyridin-1(2H)-yl]ethanone Example 15b was prepared according to the procedure used for the preparation of Example 10, substituting Example 15a for 4,4,5,5-tetramethyl-2-vinyl-1,3,2-dioxaborolane. $^1$H NMR (400 MHz, CD$_3$OD) δ 8.40 (s, 1H), 8.28 (s, 1H), 7.62 (t, J=2.1 Hz, 1H), 7.26 (s, 1H), 6.66 (s, 1H), 6.01 (s, 1H), 5.73 (s, 2H), 4.34 (s, 2H), 4.17 (dd, J=8.4, 3.0 Hz, 2H), 3.79-3.70 (m, 2H), 2.68-2.51 (m, 2H), 2.15 (d, J=15.6 Hz, 3H); MS m/z: 417 [M+H]$^+$.

Example 16

1-[5-{2-(aminomethyl)-7-[(6-amino-9H-purin-9-yl)methyl]-1H-indol-5-yl}-3,6-dihydropyridin-1(2H)-yl]ethanone

Example 16a

Mixture of 1-(3-(4,4,5,5-tetramethyl-1,3,2-dioxaborolan-2-yl)-5,6-dihydropyridin-1(2H)-yl)ethanone and 1-(5-(4,4,5,5-tetramethyl-1,3,2-dioxaborolan-2-yl)-3,4-dihydropyridin-1(2H)-yl)ethanone (1:1)

Example 16a was prepared according to the procedure used for the preparation of Example 15a, substituting 5-(4,4,5,5-tetramethyl-1,3,2-dioxaborolan-2-yl)-1,2,3,6-tetrahydropyridine, hydrochloric acid [Frontier] for 4-(4,4,5,5-tetramethyl-1,3,2-dioxaborolan-2-yl)-1,2,3,6-tetramethyl-1,3,2-dioxaborolan-2-yl)-1,2,3,6-tetrahydropyridine, hydrochloric acid. MS m/z: 252 [M+H]$^+$.

Example 16b

1-[5-{2-(aminomethyl)-7-[(6-amino-9H-purin-9-yl)methyl]-1H-indol-5-yl}-3,6-dihydropyridin-1(2H)-yl]ethanone Example 16b was prepared according to the procedure used for the preparation of Example 10, substituting Example 16a for 4,4,5,5-tetramethyl-2-vinyl-1,3,2-dioxaborolane. $^1$H NMR (500 MHz, CD$_3$OD) δ 8.50-8.39 (m, 1H), 8.39-8.30 (m, 1H), 7.62-7.58 (m, 1H), 7.29 (d, J=1.6 Hz, 1H), 6.70-6.65 (m, 1H), 6.27-6.07 (m, 1H), 5.79-5.71 (m, 2H), 4.42-4.37 (m, 2H), 3.72-3.61 (m, 2H), 2.42-2.34 (m, 1H), 2.31-2.24 (m, 1H), 2.17 (s, 3H); MS m/z: 417 [M+H]$^+$.

Example 17

1-(4-{2-(aminomethyl)-7-[(6-amino-9H-purin-9-yl)methyl]-1H-indol-5-yl}piperidin-1-yl)ethanone Example 15b (0.32 g, 0.768 mmol) and 2,2,2-trifluoroethanol (20 mL) were added to 20% Pd(OH)$_2$/C, wet (0.1 g, 0.073 mmol) in a 50 mL pressure bottle and stirred or shaken for 16 hours at 50° C. under hydrogen gas (30 psi pressure) and 16 hours at room temperature. The solvent was removed in vacuo. The residue was dissolved in 1:1 methanol/dichloromethane and concentrated onto silica. The crude product was added to a silica gel column and was eluted with 0.5 M ammonia in methanol/dichloromethane (0-20%). Collected fractions containing the product were combined and concentrated to give the crude product which was further purified using normal phase SFC (ChiralCel IB, 5-50% methanol/CO$_2$, 0.1% diethyl amine) to give the title compound (0.052 g, 16%). $^1$H NMR (400 MHz, CD$_3$OD) δ 8.30 (s, 1H), 8.05 (s, 1H), 7.34 (d, J=1.5 Hz, 1H), 6.39 (s, 1H), 5.59 (s, 2H), 4.64-4.53 (m, 1H), 4.02 (s, 2H), 3.99-3.91 (m, 1H), 3.16 (td, J=13.2, 2.7 Hz, 1H), 2.77 (tt, J=12.2, 3.7 Hz, 1H), 2.64 (td, J=13.0, 2.8 Hz, 1H), 2.11 (s, 3H), 1.90-1.74 (m, 2H), 1.59 (dqd, J=35.3, 12.7, 4.3 Hz, 2H); MS m/z: 419 [M+H]$^+$.

Example 18

9-{[2-(aminomethyl)-5-(1-methyl-1H-pyrazol-4-yl)-1H-indol-7-yl]methyl}-9H-purin-6-amine Example 18 was prepared according to the procedure used for the preparation of Example 55, substituting 1-methyl-4-(4,4,5,5-tetramethyl-1,3,2-dioxaborolan-2-yl)-1H-pyrazole for 1-methyl-4-(3-(4,4,5,5-tetramethyl-1,3,2-dioxaborolan-2-yl)benzyl)piperazine. $^1$H NMR (400 MHz, DMSO-d$_6$) δ 8.44 (s, 1H), 8.39 (s, 1H), 7.95 (s, 1H), 7.73 (d, J=0.8 Hz, 1H), 7.72 (d, J=1.6 Hz, 1H), 7.22 (d, J=1.6 Hz, 1H), 6.61 (s, 1H), 5.67 (s, 2H), 4.25 (s, 2H), 3.84 (s, 3H). MS (APCI) m/z: 357 (M+H–NH$_3$)$^+$.

Example 19

9-{[2-(aminomethyl)-5-(pyrimidin-5-yl)-1H-indol-7-yl]methyl}-9H-purin-6-amine

Example 19 was prepared according to the procedure used for the preparation of Example 55, substituting pyrimidin-5-ylboronic acid for 1-methyl-4-(3-(4,4,5,5-tetramethyl-1,3,2-dioxaborolan-2-yl)benzyl)piperazine. $^1$H NMR (400 MHz, DMSO-d$_6$) δ 8.35 (s, 1H), 8.31 (s, 1H), 8.26 (s, 1H), 7.76 (s, 1H), 7.24 (s, 2H), 7.15 (s, 1H), 5.71 (s, 2H), 4.40 (q, J=6.9 Hz, 2H). MS (APCI) m/z 372 (M+H)$^+$.

Example 20

9-{[2-(aminomethyl)-5-(pyridin-3-yl)-1H-indol-7-yl]methyl}-9H-purin-6-amine

Example 20 was prepared according to the procedure used for the preparation of Example 55, substituting pyridin-3-ylboronic acid for 1-methyl-4-(3-(4,4,5,5-tetramethyl-1,3,2-dioxaborolan-2-yl)benzyl)piperazine. $^1$H NMR (DMSO-d$_6$) δ 4.30 (s, 2H), 5.76 (s, 2H), 6.76 (s, 1H), 7.44 (d, J=1.7 Hz, 1H), 7.77-7.89 (m, 1H), 8.02 (d, J=1.6 Hz, 1H), 8.39 (s, 1H), 8.45-8.48 (m, 1H), 8.49 (s, 1H), 8.66 (d, J=5.1, 1.5 Hz, 1H), 8.98 (d, J=2.2 Hz, 1H). MS (APCI) m/z 354 (M+H−NH$_3$)$^+$.

Example 21

9-{[2-(aminomethyl)-5-(pyridin-4-yl)-1H-indol-7-yl]methyl}-9H-purin-6-amine

Example 21 was prepared according to the procedure used for the preparation of Example 55, substituting pyridin-4-ylboronic acid for 1-methyl-4-(3-(4,4,5,5-tetramethyl-1,3,2-dioxaborolan-2-yl)benzyl)piperazine. $^1$H NMR (DMSO-d$_6$) δ 4.31 (s, 2H), 5.76 (s, 2H), 6.82 (s, 1H), 7.66 (d, J=1.7 Hz, 1H), 8.21 (d, 2H), 8.30 (d, J=1.7 Hz, 1H), 8.35 (s, 1H), 8.45 (s, 1H), 8.77 (d, 2H). MS (APCI) m/z 371 (M+H)$^+$.

Example 22

9-{[2-(aminomethyl)-5-phenyl-1H-indol-7-yl]methyl}-9H-purin-6-amine

Example 9b (0.05 g, 0.153 mmol), phenylboronic acid (0.028 g, 0.229 mmol), cesium carbonate (0.149 g, 0.458 mmol) in 1,2-dimethoxyethane (1 mL) were added to a microwave tube. The reaction was degassed, tris(dibenzylideneacetone)dipalladium(0) (0.014 g, 0.015 mmol) and 2-(dicyclohexylphosphino)-2',4',6'-triisopropylbiphenyl (0.007 g, 0.015 mmol) were added, the vessel was sealed, purged with nitrogen for 5 minutes and heated in a microwave (Biotage, Initiator) at about 140° C. for about 45 minutes. Water and ethyl acetate were added and the solid was filtered. The filtrate was partitioned and the organic layer was washed with brine, dried over magnesium sulfate and filtered. The filtrate was concentrated and purified by preparative HPLC (Waters Sunfire C8, 0-80% methanol/water; 1% TFA) followed by trituration 2× with ethyl acetate to give the title compound (0.01 g, 14%). $^1$H NMR (400 MHz, CD$_3$OD) δ 8.41 (s, 1H), 8.32 (s, 1H), 7.81 (d, J=1.6 Hz, 1H), 7.56 (dd, J=7.5, 1.6 Hz, 2H), 7.46-7.33 (m, 3H), 7.28 (t, J=7.4 Hz, 1H), 6.72 (s, 1H), 5.79 (s, 2H), 4.36 (s, 2H); MS m/z: 353 [M−NH2]$^+$.

Example 23

9-{[2-(aminomethyl)-5-(4-chlorophenyl)-1H-indol-7-yl]methyl}-9H-purin-6-amine

Example 23 was prepared according to the procedure used for the preparation of Example 55, substituting (4-chlorophenyl)boronic acid for 1-methyl-4-(3-(4,4,5,5-tetramethyl-1,3,2-dioxaborolan-2-yl)benzyl)piperazine. $^1$H NMR (400 MHz, DMSO-d$_6$) δ 8.34 (s, 1H), 8.23 (s, 1H), 8.01 (d, J=8.1 Hz, 2H), 7.87 (d, J=8.8 Hz, 3H), 7.84 (s, 1H), 7.48 (s, 1H), 7.12 (s, 1H), 5.71 (s, 2H), 4.28 (s, 2H). MS (APCI) m/z: 404 (M+H)$^+$.

Example 24

9-{[2-(aminomethyl)-5-(3-chlorophenyl)-1H-indol-7-yl]methyl}-9H-purin-6-amine

Example 24 was prepared according to the procedure used for the preparation of Example 55, substituting (3-chlorophenyl)boronic acid for 1-methyl-4-(3-(4,4,5,5-tetramethyl-1,3,2-dioxaborolan-2-yl)benzyl)piperazine. $^1$H NMR (400 MHz, DMSO-d$_6$) δ 8.57 (s, 1H), 8.46 (s, 1H), 8.10 (t, J=1.8 Hz, 1H), 7.92 (d, J=1.5 Hz, 1H), 7.80 (dt, J=7.6, 1.3 Hz, 1H), 7.75 (dt, J=8.1, 1.3 Hz, 1H), 7.53 (t, J=7.8 Hz, 1H), 7.40 (d, J=1.7 Hz, 1H), 6.73 (s, 1H), 5.78 (s, 2H), 4.29 (s, 2H). MS (APCI) m/z 387 (M+H−NH$_3$)$^+$.

Example 25

9-{[2-(aminomethyl)-5-(2-chlorophenyl)-1H-indol-7-yl]methyl}-9H-purin-6-amine

Example 25 was prepared according to the procedure used for the preparation of Example 55, substituting (2-chlorophenyl)boronic acid for 1-methyl-4-(3-(4,4,5,5-tetramethyl-1,3,2-dioxaborolan-2-yl)benzyl)piperazine. $^1$H NMR (400 MHz, DMSO-d$_6$) δ 8.35 (s, 1H), 8.25 (s, 1H), 7.58 (d, J=1.7 Hz, 1H), 7.50 (d, J=7.6 Hz, 1H), 7.28-7.40 (m, 3H), 7.37 (d, J=1.6 hz, 1H), 6.69 (s, 1H), 5.69 (s, 2H), 4.28 (s, 2H). MS (APCI) m/z: 387 (M+H−NH$_3$)$^+$.

Example 26

9-{[2-(aminomethyl)-5-(4-fluorophenyl)-1H-indol-7-yl]methyl}-9H-purin-6-amine

Example 26 was prepared according to the procedure used for the preparation of Example 55, substituting (4-fluorophenyl)boronic acid for 1-methyl-4-(3-(4,4,5,5-tetramethyl-1,3,2-dioxaborolan-2-yl)benzyl)piperazine. $^1$H NMR (DMSO-d$_6$) δ 4.28 (s, 2H), 5.74 (s, 2H), 6.70 (s, 1H), 7.22-7.31 (m, 3H), 7.57-7.63 (m, 2H), 7.81 (d, J=1.6 Hz, 1H), 8.40 (s, 1H), 8.51 (s, 1H). MS (APCI) m/z 371 (M+H−NH$_3$)$^+$.

Example 27

9-{[2-(aminomethyl)-5-(2-fluorophenyl)-1H-indol-7-yl]methyl}-9H-purin-6-amine

Example 27 was prepared according to the procedure used for the preparation of Example 55, substituting (2-fluorophenyl)boronic acid for 1-methyl-4-(3-(4,4,5,5-tetramethyl-1,3,2-dioxaborolan-2-yl)benzyl)piperazine. $^1$H NMR (DMSO-d$_6$) δ 4.29 (s, 2H), 5.75 (s, 2H), 6.71 (s, 1H), 7.07-7.15 (m, 1H), 7.21-7.31 (m, 2H), 7.33-7.41 (m, 1H), 7.46 (td, J=8.1, 2.0 Hz, 1H), 7.69-7.77 (m, 1H), 8.40 (s, 1H), 8.53 (s, 1H). MS (APCI) m/z: 371 (M+H−NH$_3$)$^+$.

Example 28

9-{[2-(aminomethyl)-5-(6-methoxypyridin-3-yl)-1H-indol-7-yl]methyl}-9H-purin-6-amine Example 28 was prepared according to the procedure used for the preparation of Example 55, substituting (6-methoxypyridin-3-yl)boronic acid for 1-methyl-4-(3-(4,4,5,5-tetramethyl-1,3,2-dioxaborolan-2-yl)benzyl)piperazine. $^1$H NMR (DMSO-d$_6$) δ 3.88 (s, 3H), 4.28 (s, 2H), 5.76 (s, 2H), 6.70 (s, 1H), 6.90 (d, J=8.6 Hz, 1H), 7.25 (d, J=1.7 Hz, 1H), 7.82 (d, J=1.6 Hz, 1H), 7.94 (dd, J=8.6, 2.6 Hz, 1H), 8.36 (d, J=2.5 Hz, 1H), 8.45 (s, 1H), 8.57 (s, 1H). MS (APCI) m/z 384 (M+H−NH$_3$)$^+$.

Example 29

4-{2-(aminomethyl)-7-[(6-amino-9H-purin-9-yl)methyl]-1H-indol-5-yl}benzenesulfonamide Example 29 was prepared according to the procedure used for the preparation of Example 55, substituting 4-(4,4,5,5-tetramethyl-1,3,2-dioxaborolan-2-yl)benzenesulfonamide for 1-methyl-4-(3-(4,4,5,5-tetramethyl-1,3,2-dioxaborolan-2-yl)benzyl)piperazine. $^1$H NMR (DMSO-d$_6$) δ 1.08 (s, 3H), 4.29 (s, 2H), 5.75 (s, 2H), 6.74 (s, 1H), 7.39 (d, J=1.7 Hz, 1H), 7.77-7.80 (m, 2H), 7.84-7.89 (m, 2H), 7.94 (d, J=1.7 Hz, 1H), 8.40 (s, 1H), 8.51 (s, 1H). MS (APCI) m/z 432 (M+H−NH$_3$)$^+$.

Example 30

9-{[2-(aminomethyl)-5-(4-methylphenyl)-1H-indol-7-yl]methyl}-9H-purin-6-amine

Example 30 was prepared according to the procedure used for the preparation of Example 55, substituting p-tolylboronic acid for 1-methyl-4-(3-(4,4,5,5-tetramethyl-1,3,2-dioxaborolan-2-yl)benzyl)piperazine. $^1$H NMR (DMSO-d$_6$) δ 2.32 (s, 3H), 4.27 (s, 2H), 5.73 (s, 2H), 6.69 (s, 1H), 7.23 (s, 1H), 7.24-7.29 (m, 2H), 7.44-7.49 (m, 2H), 7.79 (d, J=1.6 Hz, 1H), 8.39 (s, 1H), 8.51 (s, 1H). MS (APCI) m/z 367 (M+H−NH$_3$)$^+$.

Example 31

9-{[2-(aminomethyl)-5-(3-methylphenyl)-1H-indol-7-yl]methyl}-9H-purin-6-amine

Example 31 was prepared according to the procedure used for the preparation of Example 55, substituting m-tolylboronic acid for 1-methyl-4-(3-(4,4,5,5-tetramethyl-1,3,2-dioxaborolan-2-yl)benzyl)piperazine. $^1$H NMR (DMSO-d$_6$) δ 2.36 (s, 3H), 4.28 (s, 2H), 5.74 (s, 2H), 6.70 (s, 1H), 7.13 (d, J=7.1 Hz, 1H), 7.28-7.37 (m, 3H), 7.38-7.44 (m, 1H), 7.82 (d, J=1.6 Hz, 1H), 8.41 (s, 1H), 8.53 (s, 1H). MS (APCI) m/z 367 (M+H−NH$_3$)$^+$.

Example 32

9-{[2-(aminomethyl)-5-(2-methylphenyl)-1H-indol-7-yl]methyl}-9H-purin-6-amine

Example 32 was prepared according to the procedure used for the preparation of Example 55, substituting o-tolylboronic acid for 1-methyl-4-(3-(4,4,5,5-tetramethyl-1,3,2-dioxaborolan-2-yl)benzyl)piperazine. $^1$H NMR (DMSO-d$_6$) δ 2.09 (s, 3H), 4.29 (s, 2H), 5.73 (s, 2H), 6.67 (s, 1H), 6.83 (d, J=1.5 Hz, 1H), 7.09-7.27 (m, 4H), 7.48 (d, J=1.5 Hz, 1H), 8.37 (s, 1H), 8.51 (s, 1H). MS (APCI) m/z 367 (M+H−NH$_3$)$^+$.

Example 33

(4-{2-(aminomethyl)-7-[(6-amino-9H-purin-9-yl)methyl]-1H-indol-5-yl}phenyl)methanol Example 33 was prepared according to the procedure used for the preparation of Example 55, substituting (4-(hydroxymethyl)phenyl)boronic acid for 1-methyl-4-(3-(4,4,5,5-tetramethyl-1,3,2-dioxaborolan-2-yl)benzyl)piperazine. $^1$H NMR (DMSO-d$_6$) δ 4.28 (s, 2H), 4.52 (s, 2H), 5.74 (s, 2H), 6.70 (s, 1H), 7.29 (d, J=1.7 Hz, 1H), 7.37 (d, 2H), 7.54 (d, 2H), 7.82 (d, J=1.6 Hz, 1H), 8.39 (s, 1H), 8.52 (s, 1H). MS (APCI) m/z 383 (M+H−NH$_3$)$^+$.

Example 34

9-{[2-(aminomethyl)-5-(4-methoxyphenyl)-1H-indol-7-yl]methyl}-9H-purin-6-amine

Example 34 was prepared according to the procedure used for the preparation of Example 55, substituting (4-methoxyphenyl)boronic acid for 1-methyl-4-(3-(4,4,5,5-tetramethyl-1,3,2-dioxaborolan-2-yl)benzyl)piperazine. $^1$H NMR (DMSO-d$_6$) δ 3.78 (s, 3H), 4.27 (s, 2H), 5.73 (s, 2H), 6.68 (s, 1H), 6.96-7.01 (m, 2H), 7.23 (d, J=1.7 Hz, 1H), 7.47-7.53 (m, 2H), 7.76 (d, J=1.6 Hz, 1H), 8.40 (s, 1H), 8.52 (s, 1H). MS (APCI) m/z: 383 (M+H−NH$_3$)$^+$.

Example 35

9-{[2-(aminomethyl)-5-(3-methoxyphenyl)-1H-indol-7-yl]methyl}-9H-purin-6-amine

Example 35 was prepared according to the procedure used for the preparation of Example 10, substituting (3-methoxyphenyl)boronic acid for 4,4,5,5-tetramethyl-2-vinyl-1,3,2-dioxaborolane. $^1$H NMR (400 MHz, CD$_3$OD) δ 8.41 (s, 1H), 8.33 (s, 1H), 7.81 (d, J=1.6 Hz, 1H), 7.41 (d, J=1.6 Hz, 1H), 7.31 (t, J=7.9 Hz, 1H), 7.19-7.00 (m, 2H), 6.86 (dd, J=8.2, 2.5 Hz, 1H), 6.72 (s, 1H), 5.79 (s, 2H), 4.36 (s, 2H), 3.83 (s, 3H); MS m/z: 266 [M-adenine]$^+$.

Example 36

9-{[2-(aminomethyl)-5-(2-methoxyphenyl)-1H-indol-7-yl]methyl}-9H-purin-6-amine

Example 36 was prepared according to the procedure used for the preparation of Example 55, substituting (2-methoxyphenyl)boronic acid for 1-methyl-4-(3-(4,4,5,5-tetramethyl-1,3,2-dioxaborolan-2-yl)benzyl)piperazine. $^1$H NMR (DMSO-d$_6$) δ 3.63 (s, 3H), 4.28 (s, 2H), 5.72 (s, 2H), 6.66 (s, 1H), 6.97-7.03 (m, 2H), 7.05 (d, J=8.2, 1.1 Hz, 1H), 7.23 (dd, J=7.5, 1.7 Hz, 1H), 7.27-7.35 (m, 1H), 7.61 (d, J=1.5 Hz, 1H), 8.39 (s, 1H), 8.51 (s, 1H). MS (APCI) m/z: 383 (M+H−NH$_3$)$^+$.

Example 37

9-({2-(aminomethyl)-5-[4-(methylsulfonyl)phenyl]-1H-indol-7-yl}methyl)-9H-purin-6-amine Example 37 was prepared according to the procedure used for the preparation of Example 55, substituting (4-(methylsulfonyl)phenyl)boronic acid for 1-methyl-4-(3-(4,4,5,5-tetramethyl-1,3,2-dioxaborolan-2-yl)benzyl)piperazine. $^1$H NMR (400 MHz, DMSO-d$_6$) δ 8.52 (s, 1H), 8.40 (s, 1H), 8.01 (d, J=8.1 Hz, 2H), 7.98 (d, J=1.9 Hz, 1H), 7.87 (d, J=8.8 Hz, 3H), 7.40 (d, J=1.6 Hz, 1H), 6.75 (s, 1H), 5.76 (s, 2H), 3.22 (s, 3H). MS (APCI) m/z: 448 (M+H)$^+$.

Example 38

4-{2-(aminomethyl)-7-[(6-amino-9H-purin-9-yl)methyl]-1H-indol-5-yl}benzonitrile

Example 38 was prepared according to the procedure used for the preparation of Example 55, substituting (4-cyanophenyl)boronic acid for 1-methyl-4-(3-(4,4,5,5-tetramethyl-1,3,2-dioxaborolan-2-yl)benzyl)piperazine. $^1$H NMR (DMSO-d$_6$) δ 4.29 (s, 2H), 5.75 (s, 2H), 6.74 (s, 1H), 7.40 (d, J=1.7 Hz, 1H), 7.77-7.85 (m, 2H), 7.84-7.92 (m, 2H), 7.97 (d, J=1.6 Hz, 1H), 8.40 (s, 1H), 8.52 (s, 1H). MS (APCI) m/z: 378 (M+H−NH$_3$)$^+$.

Example 39

3-{2-(aminomethyl)-7-[(6-amino-9H-purin-9-yl)methyl]-1H-indol-5-yl}benzonitrile

Example 39 was prepared according to the procedure used for the preparation of Example 55, substituting (3-cyanophenyl)boronic acid for 1-methyl-4-(3-(4,4,5,5-tetramethyl-1,3,2-dioxaborolan-2-yl)benzyl)piperazine. $^1$H NMR (DMSO-d$_6$) δ 4.29 (s, 2H), 5.75 (s, 2H), 6.73 (s, 1H), 7.42 (d, J=1.7 Hz, 1H), 7.65 (t, J=7.8 Hz, 1H), 7.76 (dt, J=7.8, 1.3 Hz, 1H), 7.93-7.97 (m, 2H), 8.06 (t, J=1.7 Hz, 1H), 8.41 (s, 1H), 8.52 (s, 1H). MS (APCI) m/z: 378 (M+H−NH$_3$)$^+$.

Example 40

3-{2-(aminomethyl)-7-[(6-amino-9H-purin-9-yl)methyl]-1H-indol-5-yl}benzamide

Example 40 was prepared according to the procedure used for the preparation of Example 55, substituting (3-carbamoylphenyl)boronic acid for 1-methyl-4-(3-(4,4,5,5-tetramethyl-1,3,2-dioxaborolan-2-yl)benzyl)piperazine. $^1$H NMR (400 MHz, DMSO-d$_6$) δ 8.57 (s, 1H), 8.46 (s, 1H), 8.10 (t, J=1.8 Hz, 1H), 7.92 (d, J=1.5 Hz, 1H), 7.80 (dt, J=7.6, 1.3 Hz, 1H), 7.75 (dt, J=8.1, 1.3 Hz, 1H), 7.53 (t, J=7.8 Hz, 1H), 7.40 (d, J=1.7 Hz, 1H), 6.73 (s, 1H), 5.78 (s, 2H), 4.29 (s, 2H). MS (APCI) m/z: 413 (M+H)$^+$.

Example 41

N-(4-{2-(aminomethyl)-7-[(6-amino-9H-purin-9-yl)methyl]-1H-indol-5-yl}phenyl)methanesulfonamide Example 41 was prepared according to the procedure used for the preparation of Example 55, substituting N-(4-(4,4,5,5-tetramethyl-1,3,2-dioxaborolan-2-yl)phenyl)methanesulfonamide for 1-methyl-4-(3-(4,4,5,5-tetramethyl-1,3,2-dioxaborolan-2-yl)benzyl)piperazine. $^1$H NMR (DMSO-d$_6$) δ 3.00 (s, 3H), 4.28 (s, 2H), 5.75 (s, 2H), 6.70 (s, 1H), 7.24-7.31 (m, 3H), 7.57 (d, 2H), 7.81 (d, J=1.6 Hz, 1H), 8.43 (s, 1H), 8.54 (s, 1H). MS (APCI) m/z: 446 (M+H−NH$_3$)$^+$.

Example 42

N-(3-{2-(aminomethyl)-7-[(6-amino-9H-purin-9-yl)methyl]-1H-indol-5-yl}phenyl)methanesulfonamide Example 42 was prepared according to the procedure used for the preparation of Example 55, substituting N-(3-(4,4,5,5-tetramethyl-1,3,2-dioxaborolan-2-yl)phenyl)methanesulfonamide for 1-methyl-4-(3-(4,4,5,5-tetramethyl-1,3,2-dioxaborolan-2-yl)benzyl)piperazine. $^1$H NMR (DMSO-d$_6$) δ 3.00 (s, 3H), 4.29 (s, 2H), 5.76 (s, 2H), 6.72 (s, 1H), 7.11-7.16 (m, 1H), 7.20 (d, J=1.7 Hz, 1H), 7.24-7.36 (m, 2H), 7.36-7.43 (m, 2H), 7.52-7.61 (m, 1H), 7.79 (d, J=1.6 Hz, 1H), 8.40 (s, 1H), 8.53 (s, 1H). MS (APCI) m/z: 463 (M+H)$^+$.

Example 43

9-{[2-(aminomethyl)-5-(4-ethylphenyl)-1H-indol-7-yl]methyl}-9H-purin-6-amine

Example 43 was prepared according to the procedure used for the preparation of Example 55, substituting (4-ethylphenyl)boronic acid for 1-methyl-4-(3-(4,4,5,5-tetramethyl-1,3,2-dioxaborolan-2-yl)benzyl)piperazine. $^1$H NMR (DMSO-d$_6$) δ 1.19 (t, J=7.6 Hz, 3H), 2.62 (q, J=7.6 Hz, 2H), 4.27 (s, 2H), 5.68 (s, 2H), 6.68 (s, 1H), 7.21-7.32 (m, 3H), 7.48 (d, J=8.0 Hz, 2H), 7.78 (d, J=1.6 Hz, 1H), 8.27 (s, 1H), 8.37 (s, 1H). MS (APCI) m/z 381 (M+H−NH$_3$)$^+$.

Example 44 methyl 4-{2-(aminomethyl)-7-[(6-amino-9H-purin-9-yl)methyl]-1H-indol-5-yl}benzoate Example 44 was prepared according to the procedure used for the preparation of Example 55, substituting (4-(methoxycarbonyl)phenyl)boronic acid for 1-methyl-4-(3-(4,4,5,5-tetramethyl-1,3,2-dioxaborolan-2-yl)benzyl)piperazine. $^1$H NMR (DMSO-d$_6$) δ 3.87 (s, 3H), 4.29 (s, 2H), 5.75 (s, 2H), 6.74 (s, 1H), 7.43 (d, J=1.7 Hz, 1H), 7.77 (d, 2H), 7.96 (d, J=1.7 Hz, 1H), 7.98-8.08 (m, 2H), 8.39 (s, 1H), 8.50 (s, 1H); MS (APCI) m/z: 411 (M+H−NH$_3$)$^+$.

Example 45

(4-{2-(aminomethyl)-7-[(6-amino-9H-purin-9-yl)methyl]-1H-indol-5-yl}phenyl)acetonitrile Example 45 was prepared according to the procedure used for the preparation of Example 55, substituting (4-(cyanomethyl)phenyl)boronic acid for 1-methyl-4-(3-(4,4,5,5-tetramethyl-1,3,2-dioxaborolan-2-yl)benzyl)piperazine. $^1$H NMR (DMSO-d$_6$) δ 4.02 (s, 2H), 4.28 (s, 2H), 5.74 (s, 2H), 6.71 (s, 1H), 7.31 (d, J=1.7 Hz, 1H), 7.42 (d, 2H), 7.61 (d, 2H), 7.85 (d, J=1.6 Hz, 1H), 8.39 (s, 1H), 8.50 (s, 1H). MS (APCI) m/z: 409 (M+H)$^+$.

Example 46

3-{2-(aminomethyl)-7-[(6-amino-9H-purin-9-yl)methyl]-1H-indol-5-yl}-N-ethylbenzamide Example 46 was prepared according to the procedure used for the preparation of Example 55, substituting (3-(ethylcarbamoyl)phenyl)boronic acid for 1-methyl-4-(3-(4,4,5,5-tetramethyl-1,3,2-dioxaborolan-2-yl)benzyl)piperazine. $^1$H NMR (400 MHz, DMSO-d$_6$) δ 8.53 (s, 1H), 8.42 (s, 1H), 8.04 (t, J=1.8 Hz, 1H), 7.91 (d, J=1.7 Hz, 1H), 7.74 (ddt, J=8.1, 6.6, 1.3 Hz, 2H), 6.73 (s, 1H), 5.76 (s, 2H), 4.29 (s, 2H), 3.32 (q, J=7.2 Hz, 2H), 1.15 (t, J=7.5 Hz, 3H). MS (APCI) m/z: 441 (M+H)$^+$.

Example 47

4-{2-(aminomethyl)-7-[(6-amino-9H-purin-9-yl)methyl]-1H-indol-5-yl}-N,N-dimethylbenzamide Example 47 was prepared according to the procedure used for the preparation of Example 55, substituting (4-(dimethylcarbamoyl)phenyl)boronic acid for 1-methyl-4-(3-(4,4,5,5-tetramethyl-1,3,2-dioxaborolan-2-yl)benzyl)piperazine. $^1$H NMR (400 MHz, DMSO-d$_6$) δ 8.60 (s, 1H), 8.47 (s, 1H), 7.90 (d, J=1.6 Hz, 1H), 7.83 (d, J=7.9 Hz, 2H), 7.36 (d, J=7.8 Hz, 2H), 7.34 (d, J=1.7 Hz, 1H), 6.73 (s, 1H), 5.78 (s, 2H), 4.30, (s, 2H), 3.00 (s, 6H). MS (APCI) m/z: 441 (M+H)$^+$.

Example 48

3-{2-(aminomethyl)-7-[(6-amino-9H-purin-9-yl)methyl]-1H-indol-5-yl}-N,N-dimethylbenzamide A microwave vial was charged with tris(dibenzylideneacetone)dipalladium(0) (25 mg, 0.027 mmol), of potassium phosphate (70 mg, 0.33 mmol) and tricyclohexylphosphine (20 mg, 0.071 mmol), followed by addition of a solution of Example 9b (25 mg, 0.08 mmol) in dioxane (1.0 mL) and N,N-dimethyl-3-(4,4,5,5-tetramethyl-1,3,2-dioxaborolan-2-yl)benzamide (0.15 mmol) in dioxane (0.5 mL) and water (200 μL). The resulting mixture was heated in the microwave oven (Biotage Initiator, Power range 0-400 W from magnetron at 2.45 GHz) for 20 minutes at 140° C. The reaction mixture was filtered, and purified by reverse phase preparative HPLC on a Phenomenex Luna C8 (2) 5 um 100 Å AXIA column (30 mm×150 mm). A gradient of acetonitrile (A) and 0.1% trifluoroacetic acid in water (B) was used, at a flow rate of 50 mL/min (0-0.5 minutes 10% A, 0.5-6.0 minutes linear gradient 10-100% A, 6.0-7.0 minutes 100% A, 7.0-8.0 minutes linear gradient 100-10% A). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/min. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export. $^1$H NMR (DMSO-d$_6$) δ 2.98 (s, 6H), 3.93 (s, 2H), 5.67 (s, 2H), 6.40 (s, 1H), 7.22-7.33 (m, 2H), 7.40-7.58 (m, 2H), 7.58-7.66 (m, 1H), 7.66-7.76 (m, 1H), 8.25 (d, J=9.3 Hz, 2H); (ESI) m/z 441 (M+H)$^+$.

Example 49

4-{2-(aminomethyl)-7-[(6-amino-9H-purin-9-yl)methyl]-1H-indol-5-yl}-N-[2-(dimethylamino)ethyl]benzamide Example 49 was prepared according to the procedure used for the preparation of Example 55, substituting N-(2-(dimethylamino)ethyl)-4-(4,4,5,5-tetramethyl-1,3,2-dioxaborolan-2-yl)benzamide for 1-methyl-4-(3-(4,4,5,5-tetramethyl-1,3,2-dioxaborolan-2-yl)benzyl)piperazine. $^1$H NMR (DMSO-d$_6$) δ 2.87 (s, 6H), 3.26-3.30 (m, 2H), 3.61-3.65 (m, 2H), 4.29 (s, 2H), 5.75 (s, 2H), 6.72 (s, 1H), 7.36 (d, J=1.6 Hz, 1H), 7.69-7.75 (m, 2H), 7.88-7.95 (m, 3H), 8.38 (s, 1H), 8.49 (s, 1H). MS (APCI) m/z 484 (M+H)$^+$.

Example 50

4-{2-(aminomethyl)-7-[(6-amino-9H-purin-9-yl)methyl]-1H-indol-5-yl}-N-cyclopropylbenzamide Example 50 was prepared according to the procedure used for the preparation of Example 55, substituting N-cyclopropyl-4-(4,4,5,5-tetramethyl-1,3,2-dioxaborolan-2-yl)benzamide for 1-methyl-4-(3-(4,4,5,5-tetramethyl-1,3,2-dioxaborolan-2-yl)benzyl)piperazine. $^1$H NMR (400 MHz, DMSO-d$_6$) δ 8.51 (s, 1H), 8.39 (s, 1H), 7.91 (d, J=1.6 Hz, 1H), 7.89-7.85 (m, 2H), 7.70-7.63 (m, 2H), 7.36 (d, J=1.7 Hz, 1H), 6.72 (s, 1H), 5.75 (s, 2H), 4.28 (s, 2H), 2.85 (tt, J=7.3, 3.9 Hz, 1H), 0.83-0.49 (m, 6H). MS (APCI) m/z: 453 (M+H)$^+$.

Example 51

3-{2-(aminomethyl)-7-[(6-amino-9H-purin-9-yl)methyl]-1H-indol-5-yl}-N-cyclopropylbenzamide Example 51 was prepared according to the procedure used for the preparation of Example 48, substituting N,N-dimethyl-3-(4,4,5,5-tetramethyl-1,3,2-dioxaborolan-2-yl)benzamide for (3-(cyclopropylcarbamoyl)phenyl) boronic acid. $^1$H NMR (DMSO-d$_6$) δ 0.55-0.67 (m, 2H), 0.67-0.79 (m, 2H), 2.80-2.95 (m, 1H), 3.94 (s, 2H), 5.67 (s, 2H), 6.41 (s, 1H), 7.30-7.39 (m, 1H), 7.46 (t, J=7.7 Hz, 1H), 7.66-7.70 (m, 2H), 7.72-7.79 (m, 1H), 7.94-8.03 (m, 1H), 8.24 (d, J=17.9 Hz, 2H); (ESI) m/z 453 (M+H)$^+$ and 436 (M−16).

Example 52

9-({2-(aminomethyl)-5-[3-(morpholin-4-yl)phenyl]-1H-indol-7-yl}methyl)-9H-purin-6-amine Example 52 was prepared according to the procedure used for the preparation of Example 48, substituting (3-morpholinophenyl)boronic acid hydrochloride for N,N-dimethyl-3-(4,4,5,5-tetramethyl-1,3,2-dioxaborolan-2-yl)benzamide. $^1$H NMR (DMSO-d$_6$) δ 3.12-3.15 (m, 4H), 3.74-3.80 (m, 4H), 3.94 (s, 2H), 5.66 (s, 2H), 6.39 (s, 1H), 6.95-7.05 (m, 2H), 7.16-7.21 (m, 1H), 7.21-7.31 (m, 1H), 7.61-7.70 (m, 1H), 8.18-8.29 (m, 2H); (ESI) m/z 455 (M+H)$^+$ and 438 (M−16).

Example 53

(3-{2-(aminomethyl)-7-[(6-amino-9H-purin-9-yl)methyl]-1H-indol-5-yl}phenyl)(morpholin-4-yl)methanone Example 53 was prepared according to the procedure used for the preparation of Example 48, substituting (3-(morpholine-4-carbonyl)phenyl)boronic acid for N,N-dimethyl-3-(4,4,5,5-tetramethyl-1,3,2-dioxaborolan-2-yl)benzamide. $^1$H NMR (DMSO-d$_6$) δ 3.47-3.56 (m, 4H), 3.56-3.67 (m, 4H), 3.94 (s, 2H), 5.67 (s, 2H), 6.41 (s, 1H), 7.23-7.34 (m, 2H), 7.48 (t, J=7.7 Hz, 1H), 7.52-7.56 (m, 1H), 7.61-7.67 (m, 1H), 7.70-7.76 (m, 1H), 8.19-8.30 (m, 2H); (ESI) m/z 483 (M+H)$^+$.

Example 54

9-{[2-(aminomethyl)-5-{4-[(4-methylpiperazin-1-yl) methyl]phenyl}-1H-indol-7-yl]methyl}-9H-purin-6-amine Example 54 was prepared according to the procedure used for the preparation of Example 55, substituting 1-methyl-4-(4-(4,4,5,5-tetramethyl-1,3,2-dioxaborolan-2-yl)benzyl)piperazine for 1-methyl-4-(3-(4,4,5,5-tetramethyl-1,3,2-dioxaborolan-2-yl)benzyl)piperazine. $^1$H NMR (400 MHz, DMSO-$d_6$) δ 8.51 (s, 1H), 8.38 (s, 1H), 7.85 (d, J=1.6 Hz, 1H), 7.62 (d, J=8.2 Hz, 2H), 7.46 (d, J=8.2 Hz, 2H), 7.25 (d, J=1.7 Hz, 1H), 6.71 (s, 1H), 5.75 (s, 2H), 4.28 (s, 2H), 3.98 (s, 2H), 2.80-3.63 (br m, 8H), 2.81 (d, 3H). MS (APCI) m/z: 482 (M+H)$^+$.

Example 55

9-{[2-(aminomethyl)-5-{3-[(4-methylpiperazin-1-yl) methyl]phenyl}-1H-indol-7-yl]methyl}-9H-purin-6-amine In a microwave vial was added Example 9b (25 mg, 0.076 mmol), 1-methyl-4-(3-(4,4,5,5-tetramethyl-1,3,2-dioxaborolan-2-yl)benzyl)piperazine (48 mg, 0.15 mmol), potassium phosphate tribasic (32 mg, 0.15 mmol), tris(dibenzylideneacetone)dipalladium (0) (14 mg, 0.014 mmol) and tricyclohexylphosphine (9 mg, 0.032 mmol), followed by the addition of dry, degassed dioxane (2 mL) and water (0.111 mL). The vessel was sealed and heated under microwave irradiation using a Biotage Initiator 60 at 140° C. for 15 minutes. The cooled solution was then filtered through Celite®, concentrated, and purified by reverse phase preparative HPLC to provide the title compound. Preparative HPLC condition: Sample was purified by preparative HPLC on a Phenomenex Luna C8 (2) 5 μm 100 Å AXIA column (30 mm×150 mm). A gradient of acetonitrile (A) and 0.1% trifluoroacetic acid in water (B) was used, at a flow rate of 50 mL/min (0-0.5 minutes 10% A, 0.5-6.0 minutes linear gradient 10-100% A, 6.0-7.0 minutes 100% A, 7.0-8.0 minutes linear gradient 100-10% A). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/min. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export. $^1$H NMR (400 MHz, DMSO-$d_6$) δ 8.46 (s, 1H), 8.36 (s, 1H), 7.84 (d, J=1.6 Hz, 1H), 7.71-7.64 (m, 1H), 7.64-7.38 (m, 4H), 7.32 (d, J=7.4 Hz, 1H), 7.29 (d, J=1.6 Hz, 1H), 6.70 (s, 1H), 5.73 (s, 2H), 4.28 (s, 2H), 3.92 (s, 2H), 2.80 (d, J=1.7 Hz, 3H), 2.7-3.6 (br m, 8H). MS (APCI) m/z: 482 (M+H)$^+$.

Example 56

(4-{2-(aminomethyl)-7-[(6-amino-9H-purin-9-yl) methyl]-1H-indol-5-yl}phenyl)(4-methylpiperazin-1-yl)methanone Example 56 was prepared according to the procedure used for the preparation of Example 55, substituting (4-methylpiperazin-1-yl)(4-(4,4,5,5-tetramethyl-1,3,2-dioxaborolan-2-yl)phenyl)methanone for 1-methyl-4-(3-(4,4,5,5-tetramethyl-1,3,2-dioxaborolan-2-yl)benzyl)piperazine. $^1$H NMR (400 MHz, DMSO-$d_6$) δ 8.53 (s, 1H), 8.40 (s, 1H), 7.90 (d, J=1.6 Hz, 1H), 7.73-7.65 (m, 2H), 7.56-7.49 (m, 2H), 7.32 (d, J=1.6 Hz, 1H), 6.72 (s, 1H), 5.76 (s, 2H), 4.29 (s, 2H), 3.0-3.6 (br m, 8H), 2.85 (s, 3H). MS (APCI) m/z: 496 (M+H)$^+$.

Example 57

9-{[2-(aminomethyl)-5-(2,3-dihydro-1-benzofuran-5-yl)-1H-indol-7-yl]methyl}-9H-purin-6-amine Example 57 was prepared according to the procedure used for the preparation of Example 55, substituting (2,3-dihydrobenzofuran-5-yl)boronic acid for 1-methyl-4-(3-(4,4,5,5-tetramethyl-1,3,2-dioxaborolan-2-yl)benzyl)piperazine. $^1$H NMR (DMSO-$d_6$) δ 3.22 (t, J=8.6 Hz, 2H), 4.27 (s, 2H), 4.55 (t, J=8.7 Hz, 2H), 5.72 (s, 2H), 6.66 (s, 1H), 6.81 (d, J=8.3 Hz, 1H), 7.23 (d, J=1.7 Hz, 1H), 7.28 (dd, J=8.3, 2.0 Hz, 1H), 7.44 (d, J=1.9 Hz, 1H), 7.73 (d, J=1.6 Hz, 1H), 8.39 (s, 1H), 8.50 (s, 1H). MS (APCI) m/z: 395 (M+H−NH$_3$)$^+$.

Example 58

9-{[2-(aminomethyl)-6-chloro-1H-indol-7-yl] methyl}-9H-purin-6-amine

Example 58a (3-chloro-2-methylphenyl)hydrazine 3-chloro-2-methylaniline (30 g, 212 mmol) was treated with trifluoroacetic acid (65 mL) and concentrated hydrochloric acid (300 mL, 9874 mmol) in a 250 mL round-bottomed flask and then stirred at ambient temperature for 10 minutes. The suspension was cooled to about 0° C. in an ice bath. A solution of sodium nitrite (17.98 g, 261 mmol) in water (150 mL) was added dropwise via syringe. After the completion of addition, the mixture was stirred at 0° C. for 1 hour. A cold solution of tin(II) chloride (88 g, 466 mmol) in water (50 mL) and concentrated hydrochloric acid (100 mL, 3291 mmol) were added drop wise via dropping funnel to the reaction mixture. The mixture was stirred at ambient temperature, filtered through Büchner funnel to afford the title compound (40 g, 207 mmol, 98% yield). MS (ESI+): m/z 157 (M+H)$^+$.

Example 58b (E)-ethyl 2-(2-(3-chloro-2-methylphenyl)hydrazono) propanoate

Example 58a (39 g, 202 mmol) was dissolved in acetic acid (20 mL) in a 100 mL round-bottomed flask. Ethyl pyruvate (22.55 mL, 202 mmol) was added slowly. The resulting suspension was stirred at 35° C. for 2 hours, filtered through Büchner funnel to afford the title compound (40 g, 176 mmol, 87% yield). MS (ESI+): m/z 255 (M+H)$^+$.

Example 58c ethyl 6-chloro-7-methyl-1H-indole-2-carboxylate

To a solution of Example 58b (20 g, 79 mmol) in toluene (300 mL) was added 30 g of Amberlyst-15. The resulting suspension was stirred at 120° C. for 16 hours. The reaction mixture was filtered to remove solid material and the filtrate was concentrated under reduced pressure to afford the title compound (16 g, 67.3 mmol, 86% yield) as a brown solid. MS (ESI+): m/z 238 (M+H)+.

Example 58d 1-tert-butyl 2-ethyl 6-chloro-7-methyl-1H-indole-1,2-dicarboxylate

To a solution of Example 58c (41 g, 172 mmol) in dichloromethane (150 mL) was added N,N-dimethylpyridin-4-amine (2.107 g, 17.25 mmol), triethylamine (28.9 mL, 207 mmol) and di-tert-butyl dicarbonate (48.1 mL, 207 mmol) at 0° C. The resulting solution was stirred at 25° C. for 16 hours and then washed sequentially with water, saturated sodium bicarbonate solution, and brine. The organic layer was dried with sodium sulfate, filtered and concentrated under reduced pressure. The residue was purified by column chromatography using petroleum ether/ethyl acetate with a gradient from 15/1 to 5/1 to afford the title compound (49.8 g, 147 mmol, 85% yield). MS (ESI+): m/z 338 (M+H)+.

Example 58e 1-tert-butyl 2-ethyl 7-(bromomethyl)-6-chloro-1H-indole-1,2-dicarboxylate To a solution of Example 58d (10 g, 29.6 mmol) in carbon tetrachloride (50 mL) was added benzoic peroxyanhydride (0.717 g, 2.96 mmol) and N-bromosuccinimide (5.27 g, 29.6 mmol). After stirring at 85° C. for 16 hours, the mixture was cooled to 0° C. and filtered to remove solid material. The filtrate was concentrated under reduced pressure. The residue was taken into ethyl acetate (200 mL), and washed sequentially with water and brine. The organic layer was dried with anhydrous sodium sulfate, filtered, and concentrated under reduced pressure to afford the title compound (12 g, 25.9 mmol, 88% yield). MS (ESI+): m/z 418 (M+H)+.

Example 58f ethyl 7-((6-amino-9H-purin-9-yl)methyl)-6-chloro-1H-indole-2-carboxylate In a 250 mL round-bottomed flask, a mixture of Example 58e (12 g, 25.9 mmol), 9H-purin-6-amine (3.50 g, 25.9 mmol) and cesium carbonate (12.67 g, 38.9 mmol) in N,N-dimethylformamide (100 mL) was stirred at ambient temperature for 16 hours. The reaction mixture was then diluted with ethyl acetate (300 mL) and washed sequentially with water (50 mL×3), and brine. The organic layer was dried with sodium sulfate, filtered, and concentrated under reduced pressure. The residue was re-dissolved in ethyl acetate (20 mL). Petroleum ether (20 mL) was added. The solid formed was collected to give a mixture of the tile compound and its BOC-protected analog. The solid material above was suspended in dichloromethane (5 mL) and treated with trifluoroacetic acid (5 mL). The mixture was stirred at room temperature for 2 hours and then concentrated under reduced pressure. The residue was treated with saturated sodium bicarbonate solution. The solid was collected by filtration, washed with water, and dried to afford the title compound (5.5 g, 12.90 mmol, 101% yield) as white solid. MS (ESI+): m/z 371 (M+H)+.

Example 58g (7-((6-amino-9H-purin-9-yl)methyl)-6-chloro-1H-indol-2-yl)methanol

To a suspension of Example 58f (6 g, 14.08 mmol) in THF (100 mL) was added lithium aluminum hydride (56.3 mL, 56.3 mmol, 1.0 M THF solution) at 0° C. drop wise. The mixture was stirred at ambient temperature for 5 hours. The reaction mixture was quenched with water (150 mL) carefully, followed by the addition of ethyl acetate (400 mL). The mixture was filtered to remove solid material. The filtrate was extracted with ethyl acetate (2×). The combined organic phases were washed with brine, dried over anhydrous sodium sulfate, filtered and concentrated under reduce pressure. The residue was triturated in petroleum ether/ethyl acetate (10/1, 30 mL) to give the title compound (3.0 g, 64% yield). MS (ESI+): m/z 329 (M+H)+.

Example 58h 9-((2-(azidomethyl)-6-chloro-1H-indol-7-yl)methyl)-9H-purin-6-amine

To a suspension of Example 58g (3.6 g, 10.40 mmol) in dichloromethane (30 mL) and toluene (30 mL) was added diphenyl phosphorazidate (11.45 g, 41.6 mmol) drop wise and DBU (6.27 mL, 41.6 mmol) at ambient temperature under nitrogen atmosphere. The resulting mixture was stirred at ambient temperature overnight. The mixture was poured into ice-water (40 mL) and extracted with dichloromethane (60 mL×2). The combined organic phases were washed with brine, dried over anhydrous magnesium sulfate, filtered, and concentrated under reduced pressure. The residue was purified by column chromatography on silica gel with a gradient of 1-2% methanol in dichloromethane to yield the title compound (1.5 g, 4.24 mmol, 40.8% yield). MS (ESI+): m/z 354 (M+H)+.

Example 58i 9-((2-(aminomethyl)-6-chloro-1H-indol-7-yl) methyl)-9H-purin-6-amine To a solution of Example 58h (1.4 g, 3.96 mmol) in THF (10 mL) and water (5 mL) was added triphenylphosphine (2.076 g, 7.91 mmol). The resulting mixture was stirred at ambient temperature overnight and then concentrated under reduced pressure. The residue was triturated in petroleum ether/ethyl acetate (5/1, 20 mL) and then recrystallized in ethyl acetate to give the title compound (400 mg, 1.159 mmol, 29.3% yield). MS (ESI+): m/z 328 (M+H)+; $^1$H NMR: (400 MHz, DMSO-$d_6$): δ 8.24 (s, 1H), 7.80 (s, 1H), 7.38 (d, J=8.4 Hz, 1H), 7.00 (d, J=8.4 Hz, 1H), 6.31 (s, 1H), 5.64 (s, 2H), 3.88 (s, 2H).

Example 59

9-{[2-(aminomethyl)-6-ethenyl-1H-indol-7-yl] methyl}-9H-purin-6-amine

A nitrogen degassed suspension Example 58i (50 mg, 0.153 mmol), 4,4,5,5-tetramethyl-2-vinyl-1,3,2-dioxaborolane (0.039 mL, 0.230 mmol), potassium phosphate (65 mg, 0.306 mmol), tricyclohexylphosphine (8.3 mg, 0.030 mmol), tris(dibenzylideneacetone)dipalladium(0) (14 mg, 0.015 mmol), dioxane (1.0 mL) and water (0.05 mL) was heated in the microwave (Biotage, Initiator, 200 W) at 140° C. for 1 hour. Water and ethyl acetate were added and the layers were separated. The aqueous layer was extracted 2 more times with ethyl acetate and the combined extracts were washed sequentially with water and brine, dried (magnesium sulfate), filtered, and concentrated. The crude product was absorbed onto silica gel and was flash chromatographed (Biotage 10 g HP Snap Cartridge, eluting with dichloromethane containing a gradient (2% to 15%) with methanol which contained 1% NH$_4$OH) to provide the title compound. $^1$H NMR (400 MHz, DMSO-d$_6$) δ 11.43 (s, 1H), 8.27 (s, 1H), 7.68 (s, 1H), 7.48 (d, J=8.2 Hz, 1H), 7.36-7.23 (m, 4H), 6.37 (s, 1H), 5.79-5.58 (m, 3H), 5.29-5.08 (m, 1H), 3.95 (s, 2H). MS ESI$^+$ 320.1 (M+H)$^+$.

Example 60

9-{[2-(aminomethyl)-6-(prop-1-en-2-yl)-1H-indol-7-yl]methyl}-9H-purin-6-amine

Using the procedure described for Example 59 and substituting 4,4,5,5-tetramethyl-2-(prop-1-en-2-yl)-1,3,2-dioxaborolane for 4,4,5,5-tetramethyl-2-vinyl-1,3,2-dioxaborolane provided the title compound. $^1$H NMR (500 MHz, DMSO-d$_6$) δ 11.27 (s, 1H), 8.24 (s, 1H), 7.46 (d, J=8.1 Hz, 1H), 7.44 (s, 1H), 7.25 (s, 2H), 6.87 (d, J=8.0 Hz, 1H), 6.31 (s, 1H), 5.53 (s, 2H), 5.16 (t, J=1.9 Hz, 1H), 4.68-4.47 (m, 1H), 3.86 (s, 2H), 1.94 (s, 3H). MS ESI$^+$ 334.1 (M+H)$^+$.

Example 61

9-{[2-(aminomethyl)-6-phenyl-1H-indol-7-yl]methyl}-9H-purin-6-amine

Using the procedure described for Example 59 and substituting phenylboronic acid for 4,4,5,5-tetramethyl-2-vinyl-1,3,2-dioxaborolane provided the title compound. $^1$H NMR (400 MHz, DMSO-d$_6$) δ 11.28 (s, 1H), 8.14 (s, 1H), 7.55 (d, J=8.0 Hz, 1H), 7.43-7.26 (m, 3H), 7.20 (d, J=6.3 Hz, 4H), 7.11 (s, 1H), 6.93 (d, J=7.9 Hz, 1H), 6.38 (s, 1H), 5.44 (s, 2H), 3.89 (s, 2H). MS ESI$^+$ 370.1 (M+H)$^+$.

Example 62

9-{[2-(aminomethyl)-4-chloro-1H-indol-7-yl]methyl}-9H-purin-6-amine

Example 62a (E)-ethyl 2-((5-chloro-2-methylphenyl)diazenyl)-2-methyl-3-oxobutanoate A solution of NaNO$_2$ (43.9 g, 636 mmol) in H$_2$O (60 mL) was dropped on to an ice-cooled mixture of 5-chloro-2-methylaniline (90 g, 636 mmol) in concentrated hydrochloric acid (160 mL) and water (160 mL). After stirring for 20 minutes, a solution of sodium acetate (71.4 g, 871 mmol) in water (160 mL) was added drop wise via dropping funnel at 0° C. After stirring for additional 30 minutes, the mixture was added to an ice-cooled and well-stirred mixture of ethyl 2-methyl-3-oxobutanoate (93 g, 642 mmol) and potassium carbonate (125 g, 1271 mmol) in methanol (500 mL). The mixture was stirred at 0° C. for 3 hours and then at ambient temperature for 16 hours. Water (700 mL) was added. The aqueous layer was extracted with ethyl acetate (2×500 mL). The combined organic phases were dried over sodium sulfate, filtered, and concentrated under reduced pressure to give the title compound (120 g, 404 mmol, 63.6% yield).

Example 62b (E)-ethyl 2-(2-(5-chloro-2-methylphenyl)hydrazono)propanoate

A mixture of Example 62a (60 g, 202 mmol) and concentrated hydrochloric acid (20 mL) in ethanol (200 mL) was stirred at 100° C. for 1 hour. The solid was collected via filtration through Büchner funnel and washed with ethanol (30 mL×2) to give the title compound (35 g, 137 mmol, 68% yield). MS (ESI+): m/z 255 (M+H)$^+$.

Example 62c ethyl 4-chloro-7-methyl-1H-indole-2-carboxylate

Example 62c was prepared according to the procedure used for the preparation of Example 58c, substituting Example 62b for Example 58b. MS (ESI+): m/z 238 (M+H)$^+$.

Example 62d 1-tert-butyl 2-ethyl 4-chloro-7-methyl-1H-indole-1,2-dicarboxylate

Example 62d was prepared according to the procedure used for the preparation of Example 58d, substituting Example 62c for Example 58c. MS (ESI+): m/z 360 (M+Na)$^+$.

Example 62e 1-tert-butyl 2-ethyl 7-(bromomethyl)-4-chloro-1H-indole-1,2-dicarboxylate Example 62e was prepared according to the procedure used for the preparation of Example 58e, substituting Example 62d for Example 58d. MS (ESI+): m/z 440 (M+Na)$^+$.

Example 62f 1-tert-butyl 2-ethyl 7-((6-amino-9H-purin-9-yl)methyl)-4-chloro-1H-indole-1,2-dicarboxylate A mixture of Example 62e (35 g, 84 mmol), 9H-purin-6-amine (10.21 g, 76 mmol) and cesium carbonate (32.8 g, 101 mmol) in N,N-dimethylformamide (200 mL) was stirred at room temperature for 16 hours. The reaction mixture was diluted with water and ethyl acetate. The aqueous layer was extracted with ethyl acetate (3×150 mL). The combined organic phases were washed with brine, dried with anhydrous sodium sulfate, filtered, and concentrated. The residue was purified by column chromatography on silica gel (3% methanol in dichloromethane) to afford the title compound (16 g, 40.5 mmol, 40.5% yield). MS (ESI+): m/z 471 (M+H)$^+$.

Example 62g ethyl 7-((6-amino-9H-purin-9-yl)methyl)-4-chloro-1H-indole-2-carboxylate Trifluoroacetic acid (45.6 mL, 592 mmol) was added slowly to a mixture of Example 62f (15.5 g, 32.9 mmol) in dichloromethane (200 mL) at 0° C. under nitrogen atmosphere. The resulting mixture was stirred at ambient temperature overnight. After the removal of solvent under reduced pressure, the residue was treated with saturated sodium carbonate solution to adjust pH to about 8. The mixture was stirred at ambient temperature for 2 hours and the solid material was collected via filtration to afford the title compound (10.8 g, 28.5 mmol, 87% yield). MS (ESI+): m/z 371 (M+H)$^+$.

Example 62h (7-((6-amino-9H-purin-9-yl)methyl)-4-chloro-1H-indol-2-yl)methanol Example 62h was prepared according to the procedure used for the preparation of Example 58g, substituting Example 62g for Example 58f. MS (ESI+): m/z 329 (M+H)$^+$.

Example 62i 9-((2-(azidomethyl)-4-chloro-1H-indol-7-yl)methyl)-9H-purin-6-amine Example 62i was prepared according to the procedure used for the preparation of Example 58h, substituting Example 62h for Example 58g. MS (ESI+): m/z 354 (M+H)$^+$.

Example 62j 9-((2-(aminomethyl)-4-chloro-1H-indol-7-yl)methyl)-9H-purin-6-amine Example 62j was prepared according to the procedure used for the preparation of Example 58i, substituting Example 62i for Example 58h. MS (ESI+): m/z 311 (M−NH$_2$)$^+$; $^1$H NMR (400 MHz, DMSO-d$_6$): δ 11.68 (brs, 1H), 8.26 (s, 1H), 8.20 (s, 1H), 7.30 (s, 2H), 6.97 (d, J=7.6 Hz, 1H), 6.80 (d, J=7.6 Hz, 1H), 6.39 (s, 1H), 5.61 (s, 2H), 3.94 (s, 2H), 2.30 (brs, 2H).

Example 63

9-{[2-(aminomethyl)-4-ethenyl-1H-indol-7-yl]methyl}-9H-purin-6-amine

Example 63 was prepared according to the procedure used for the preparation of Example 9b. $^1$H NMR (400 MHz, CD$_3$OD) δ 8.40 (s, 1H), 8.26 (s, 1H), 7.21 (d, J=7.6 Hz, 1H), 7.14-7.01 (m, 2H), 6.90 (s, 1H), 5.89 (dd, J=17.7, 1.3 Hz, 1H), 5.73 (s, 2H), 5.37 (dd, J=11.0, 1.3 Hz, 1H), 4.37 (s, 2H); MS m/z: 303 [M−NH$_2$]$^+$.

Example 64

9-{[2-(aminomethyl)-4-ethyl-1H-indol-7-yl]methyl}-9H-purin-6-amine

Example 63 (0.039 g, 0.071 mmol) and tetrahydrofuran (20 mL) were added to 5% Pd/C (0.008 g, 0.033 mmol) in a 50 mL pressure bottle and stirred or shaken for 8 hours under hydrogen gas (30 psi pressure) at room temperature. The solvent was removed in vacuo and the residue was purified by preparative HPLC (Waters Sunfire C8, 5-100% methanol/water; 1% TFA) to give the title compound (0.012 g, 31%). $^1$H NMR (500 MHz, CD$_3$OD) δ 8.40 (s, 1H), 8.21 (s, 1H), 7.04 (d, J=7.4 Hz, 1H), 6.88 (d, J=7.3 Hz, 1H), 6.72 (s, 1H), 5.69 (s, 2H), 4.35 (s, 2H), 2.88 (q, J=7.6 Hz, 2H), 1.29 (t, J=7.6 Hz, 3H); MS m/z: 305 [M−NH$_2$]$^+$.

Example 65

9-{[2-(aminomethyl)-4-(prop-1-en-2-yl)-1H-indol-7-yl]methyl}-9H-purin-6-amine

Example 65 was prepared according to the procedure used for the preparation of Example 10, substituting Example 62j for Example 9b, and 4,4,5,5-tetramethyl-2-(prop-1-en-2-yl)-1,3,2-dioxaborolane for 4,4,5,5-tetramethyl-2-vinyl-1,3,2-dioxaborolane. 1H NMR (400 MHz, CD$_3$OD) δ 8.40 (s, 1H), 8.26 (s, 1H), 7.07 (d, J=7.6 Hz, 1H), 7.02 (d, J=7.6 Hz, 1H), 6.84 (s, 1H), 5.74 (s, 2H), 5.30 (s, 2H), 4.36 (s, 2H), 2.20 (t, J=1.1 Hz, 3H); MS m/z: 317 [M−NH$_2$]$^+$.

Example 66

9-{[2-(aminomethyl)-4-(propan-2-yl)-1H-indol-7-yl]methyl}-9H-purin-6-amine

Example 66 was prepared according to the procedure used for the preparation of Example 64, substituting Example 65 for Example 63. $^1$H NMR (500 MHz, CD$_3$OD) δ 8.41 (s, 1H), 8.23 (s, 1H), 7.06 (d, J=7.5 Hz, 1H), 6.93 (d, J=7.6 Hz, 1H), 6.76 (s, 1H), 5.70 (s, 2H), 4.35 (s, 2H), 3.33 (sep, J=6.8 Hz, 1H), 1.33 (d, J=6.8 Hz, 6H); MS m/z: 319 [M−NH$_2$]$^+$.

Example 67

9-{[2-(aminomethyl)-4-(cyclopent-1-en-1-yl)-1H-indol-7-yl]methyl}-9H-purin-6-amine Example 67 was prepared according to the procedure used for the preparation of Example 10, substituting Example 62j for Example 9b, and substituting 2-(cyclopent-1-en-1-yl)-4,4,5,5-tetramethyl-1,3,2-dioxaborolane for 4,4,5,5-tetramethyl-2-vinyl-1,3,2-dioxaborolane. $^1$H NMR (400 MHz, DMSO-d$_6$) δ 11.62 (s, 1H), 8.39-8.30 (m, 4H), 8.09 (s, 2H), 6.95 (d, J=7.6 Hz, 1H), 6.92 (s, 1H), 6.85 (d, J=7.6 Hz, 1H), 6.31 (t, J=2.4 Hz, 1H), 5.64 (s, 2H), 4.36-4.21 (m, 2H), 2.76 (dt, J=7.6, 3.8 Hz, 2H), 2.60-2.53 (m, 2H), 1.95 (q, J=7.5 Hz, 2H); MS m/z: 343 [M−NH$_2$]$^+$.

Example 68

9-{[2-(aminomethyl)-4-(1-methyl-1H-pyrazol-4-yl)-1H-indol-7-yl]methyl}-9H-purin-6-amine Example 68 was prepared according to the procedure used for the preparation of Example 85, substituting 1-methyl-4-(4,4,5,5-tetramethyl-1,3,2-dioxaborolan-2-yl)-1H-pyrazole for (4-(methylsulfonamido)phenyl)boronic acid. $^1$H NMR (DMSO-d$_6$) δ 3.92 (s, 3H), 4.30 (s, 2H), 5.73 (s, 2H), 6.92-6.96 (m, 2H), 7.17 (d, J=7.6 Hz, 1H), 7.89 (s, 1H), 8.13 (s, 1H), 8.49 (s, 1H), 8.56 (s, 1H); (ESI) m/z 357 (M−NH$_2$)$^+$.

Example 69

9-{[2-(aminomethyl)-4-(pyridin-3-yl)-1H-indol-7-yl]methyl}-9H-purin-6-amine

Example 69 was prepared according to the procedure used for the preparation of Example 85, substituting pyridin-3-ylboronic acid for (4-(methylsulfonamido)phenyl)boronic acid. MS (ESI) m/z 371 (M+H)$^+$.

Example 70

9-{[2-(aminomethyl)-4-phenyl-1H-indol-7-yl]methyl}-9H-purin-6-amine

Example 70 was prepared according to the procedure used for the preparation of Example 10, substituting Example 62j for Example 9b, and substituting phenylboronic acid for 4,4,5,5-tetramethyl-2-vinyl-1,3,2-dioxaborolane. $^1$H NMR (400 MHz, DMSO-d$_6$) δ 11.75 (s, 1H), 8.45 (s, 1H), 8.42-8.27 (m, 3H), 8.24-7.99 (m, 2H), 7.67-7.54 (m, 2H), 7.50 (t, J=7.6 Hz, 2H), 7.44-7.34 (m, 1H), 7.07 (d, J=7.4 Hz, 1H), 6.97 (d, J=7.6 Hz, 1H), 6.77 (s, 1H), 5.71 (s, 2H), 4.30 (q, J=5.7 Hz, 2H); MS m/z: 353 [M−NH$_2$]$^+$.

Example 71

9-{[2-(aminomethyl)-4-(3-chlorophenyl)-1H-indol-7-yl]methyl}-9H-purin-6-amine

Example 71 was prepared according to the procedure used for the preparation of Example 85, substituting (3-chlorophenyl)boronic acid for (4-(methylsulfonamido)phenyl)boronic acid. $^1$H NMR (DMSO/D$_2$O-d$_6$) δ 4.29 (s, 2H), 5.68 (s, 2H), 6.77 (s, 1H), 6.98 (d, J=7.6 Hz, 1H), 7.12 (d, J=7.5 Hz, 1H), 7.47 (d, J=7.7 Hz, 1H), 7.51-7.60 (m, 2H), 7.62 (s, 1H), 8.25 (s, 1H), 8.34 (s, 1H); (ESI) m/z (M+H)$^+$.

Example 72

9-{[2-(aminomethyl)-4-(2-chlorophenyl)-1H-indol-7-yl]methyl}-9H-purin-6-amine

Example 72 was prepared according to the procedure used for the preparation of Example 85, substituting (2-chlorophenyl)boronic acid for (4-(methylsulfonamido)phenyl)boronic acid. $^1$H NMR (DMSO/D$_2$O-d$_6$) δ 4.25 (s, 2H), 5.77 (s, 2H), 6.34 (s, 1H), 6.94 (q, J=7.5 Hz, 2H), 7.35-7.42 (m, 1H), 7.42-7.49 (m, 2H), 7.55-7.63 (m, 1H), 8.45 (s, 1H), 8.60 (s, 1H); (ESI) m/z 387 (M−NH$_2$)$^+$.

Example 73

9-{[2-(aminomethyl)-4-(4-fluorophenyl)-1H-indol-7-yl]methyl}-9H-purin-6-amine

Example 73 was prepared according to the procedure used for the preparation of Example 85, substituting (4-fluorophenyl)boronic acid for (4-(methylsulfonamido)phenyl)boronic acid. $^1$H NMR (DMSO/D$_2$O-d$_6$) δ 4.29 (s, 2H), 5.75 (s, 2H), 6.76 (s, 1H), 6.96 (d, J=7.6 Hz, 1H), 7.07 (d, J=7.5 Hz, 1H), 7.28-7.38 (m, 2H), 7.59-7.69 (m, 2H), 8.44 (s, 1H), 8.56 (s, 1H); (ESI) m/z 371 (M−NH$_2$)$^+$.

Example 74

9-{[2-(aminomethyl)-4-(2-fluorophenyl)-1H-indol-7-yl]methyl}-9H-purin-6-amine

Example 74 was prepared according to the procedure used for the preparation of Example 85, substituting (2-fluorophenyl)boronic acid for (4-(methylsulfonamido)phenyl)boronic acid. $^1$H NMR (DMSO/D$_2$O-d$_6$) δ 4.28 (s, 2H), 5.79 (s, 2H), 6.51 (d, J=2.0 Hz, 1H), 6.96 (d, J=7.6 Hz, 1H), 7.04 (d, J=7.6 Hz, 1H), 7.31-7.38 (m, 2H), 7.44-7.52 (m, 2H), 8.48 (s, 1H), 8.62 (s, 1H); (ESI) m/z 371 (M−NH$_2$)$^+$.

Example 75

9-{[2-(aminomethyl)-4-(4-methylphenyl)-1H-indol-7-yl]methyl}-9H-purin-6-amine

Example 75 was prepared according to the procedure used for the preparation of Example 85, substituting p-tolylboronic acid for (4-(methylsulfonamido)phenyl)boronic acid. $^1$H NMR (DMSO/D$_2$O-d$_6$) δ 2.37 (s, 3H), 4.28 (s, 2H), 5.71 (s, 2H), 6.77 (s, 1H), 6.96 (d, J=7.6 Hz, 1H), 7.06 (d, J=7.6 Hz, 1H), 7.32 (d, J=7.9 Hz, 2H), 7.50 (d, 2H), 8.35 (s, 1H), 8.45 (s, 1H); (ESI) m/z 367 (M−NH$_2$)$^+$

Example 76

9-{[2-(aminomethyl)-4-(3-methylphenyl)-1H-indol-7-yl]methyl}-9H-purin-6-amine

Example 76 was prepared according to the procedure used for the preparation of Example 85, substituting m-tolylboronic acid for (4-(methylsulfonamido)phenyl)boronic acid. $^1$H NMR (DMSO/D$_2$O-d$_6$) δ 2.39 (s, 3H), 4.29 (s, 2H), 5.75 (s, 2H), 6.78 (s, 1H), 6.96 (d, J=7.6 Hz, 1H), 7.07 (d, J=7.6 Hz, 1H), 7.19-7.25 (m, 1H), 7.35-7.44 (m, 3H), 8.45 (s, 1H), 8.56 (s, 1H); (ESI) m/z 367 (M−NH$_2$)$^+$.

Example 77

9-{[2-(aminomethyl)-4-(2-methylphenyl)-1H-indol-7-yl]methyl}-9H-purin-6-amine

Example 77 was prepared according to the procedure used for the preparation of Example 85, substituting o-tolylboronic acid for (4-(methylsulfonamido)phenyl)boronic acid. $^1$H NMR (DMSO/D$_2$O-d$_6$) δ 2.09 (s, 3H), 4.24 (s, 2H), 5.75 (s, 2H), 6.28 (s, 1H), 6.87 (d, J=7.4 Hz, 1H), 6.92 (d, J=7.6 Hz, 1H), 7.18 (dd, J=7.4, 1.5 Hz, 1H), 7.24-7.31 (m, 1H), 7.31-7.38 (m, 2H), 8.44 (s, 1H), 8.56 (s, 1H); (ESI) m/z 367 (M−NH$_2$)$^+$.

Example 78

9-{[2-(aminomethyl)-4-(4-methoxyphenyl)-1H-indol-7-yl]methyl}-9H-purin-6-amine

Example 78 was prepared according to the procedure used for the preparation of Example 85, substituting (4-methoxyphenyl)boronic acid for (4-(methylsulfonamido)phenyl)boronic acid. $^1$H NMR (DMSO/D$_2$O-d$_6$) δ 3.81 (s, 3H), 4.28 (s, 2H), 5.73 (s, 2H), 6.67-6.71 (m, 1H), 6.73-6.80 (m, 2H), 6.96 (d, J=7.6 Hz, 1H), 7.04 (d, J=7.5 Hz, 1H), 7.05-7.11 (m, 2H), 7.52-7.59 (m, 2H), 8.43 (s, 1H), 8.53 (s, 1H); (ESI) m/z 383 (M–NH$_2$)$^+$.

Example 79

9-{[2-(aminomethyl)-4-(3-methoxyphenyl)-1H-indol-7-yl]methyl}-9H-purin-6-amine

Example 79 was prepared according to the procedure used for the preparation of Example 85, substituting (3-methoxyphenyl)boronic acid for (4-(methylsulfonamido)phenyl)boronic acid. $^1$H NMR (DMSO/D$_2$O-d$_6$) δ 3.82 (s, 3H), 4.29 (s, 2H), 5.77 (s, 2H), 6.81 (s, 1H), 6.94-7.01 (m, 2H), 7.10 (d, J=7.5 Hz, 1H), 7.13 (t, J=2.0 Hz, 1H), 7.16-7.22 (m, 1H), 7.43 (t, J=7.9 Hz, 1H), 8.48 (s, 1H), 8.60 (s, 1H); (ESI) m/z 383 (M–NH$_2$)$^+$.

Example 80

9-{[2-(aminomethyl)-4-(2-methoxyphenyl)-1H-indol-7-yl]methyl}-9H-purin-6-amine

Example 80 was prepared according to the procedure used for the preparation of Example 85, substituting (2-methoxyphenyl)boronic acid for (4-(methylsulfonamido)phenyl)boronic acid. $^1$H NMR (DMSO/D$_2$O-d$_6$) δ 3.68 (s, 3H), 4.25 (s, 2H), 5.76 (s, 2H), 6.37 (s, 1H), 6.90-6.97 (m, 2H), 7.05 (td, J=7.4, 1.0 Hz, 1H), 7.15 (d, J=8.2 Hz, 1H), 7.25 (dd, J=7.5, 1.7 Hz, 1H), 7.40 (ddd, J=8.8, 7.5, 1.8 Hz, 1H), 8.49 (s, 1H), 8.63 (s, 1H); (ESI) m/z 383 (M–NH$_2$)$^+$.

Example 81

9-({2-(aminomethyl)-4-[4-(methylsulfonyl)phenyl]-1H-indol-7-yl}methyl)-9H-purin-6-amine Example 81 was prepared according to the procedure used for the preparation of Example 85, substituting (4-(methylsulfonyl)phenyl)boronic acid for (4-(methylsulfonamido)phenyl)boronic acid. $^1$H NMR (DMSO/D$_2$O-d$_6$) δ 3.11 (s, 2H), 3.27 (s, 3H), 4.32 (s, 2H), 5.80 (s, 2H), 6.83 (s, 1H), 6.99 (t, J=8.0 Hz, 2H), 7.19 (d, J=7.5 Hz, 1H), 7.65-7.79 (m, 1H), 7.85-7.95 (m, 2H), 8.00-8.10 (m, 2H), 8.48 (s, 1H), 8.62 (s, 1H); (ESI) m/z 431 (M–NH$_2$)$^+$.

Example 82

4-{2-(aminomethyl)-7-[(6-amino-9H-purin-9-yl)methyl]-1H-indol-4-yl}benzonitrile

Example 82 was prepared according to the procedure used for the preparation of Example 85, substituting (4-cyanophenyl)boronic acid for (4-(methylsulfonamido)phenyl)boronic acid. $^1$H NMR (DMSO/D$_2$O-d$_6$) δ 4.29 (s, 2H), 5.74 (s, 2H), 6.79 (s, 1H), 6.98 (d, J=7.6 Hz, 1H), 7.17 (d, J=7.5 Hz, 1H), 7.79-7.86 (m, 2H), 7.94-7.99 (m, 2H), 8.35 (s, 1H), 8.47 (s, 1H); (ESI) m/z 378 (M–NH$_2$)$^+$.

Example 83

3-{2-(aminomethyl)-7-[(6-amino-9H-purin-9-yl)methyl]-1H-indol-4-yl}benzonitrile

Example 83 was prepared according to the procedure used for the preparation of Example 85, substituting (3-cyanophenyl)boronic acid for (4-(methylsulfonamido)phenyl)boronic acid. 1H NMR (DMSO/D$_2$O-d$_6$) δ 4.31 (s, 2H), 5.78 (s, 2H), 6.80 (s, 1H), 6.98 (d, J=7.6 Hz, 1H), 7.17 (d, J=7.5 Hz, 1H), 7.74 (t, J=7.8 Hz, 1H), 7.87 (dt, J=7.8, 1.3 Hz, 1H), 7.96 (dt, J=7.9, 1.4 Hz, 1H), 8.01 (t, J=1.7 Hz, 1H), 8.46 (s, 1H), 8.59 (s, 1H); (ESI) m/z 378 (M–NH$_2$)$^+$.

Example 84

3-{2-(aminomethyl)-7-[(6-amino-9H-purin-9-yl)methyl]-1H-indol-4-yl}benzamide

Example 84 was prepared according to the procedure used for the preparation of Example 85, substituting (3-carbamoylphenyl)boronic acid for (4-(methylsulfonamido)phenyl)boronic acid. $^1$H NMR (DMSO/D$_2$O-d$_6$) δ 4.30 (s, 2H), 5.76 (s, 2H), 6.78 (s, 1H), 7.00 (d, J=7.6 Hz, 1H), 7.15 (d, J=7.5 Hz, 1H), 7.43-7.56 (m, 1H), 7.60 (t, J=7.8 Hz, 1H), 7.77 (dt, J=7.6, 1.4 Hz, 1H), 7.84-7.92 (m, 2H), 8.09 (t, J=1.8 Hz, 1H), 8.43 (s, 1H), 8.55 (s, 1H); (ESI) m/z 396 (M–NH$_2$)$^+$.

Example 85

N-(4-{2-(aminomethyl)-7-[(6-amino-9H-purin-9-yl)methyl]-1H-indol-4-yl}phenyl)methanesulfonamide A microwave vial was charged with tris(dibenzylideneacetone)dipalladium(0) (25 mg, 0.027 mmol), potassium phosphate (70 mg, 0.33 mmol) and tricyclohexylphosphine (20 mg, 0.071 mmol). Then a solution of Example 62j (27 mg, 0.08 mmol) in dioxane (1.0 mL) was added, followed by (4-(methylsulfonamido)phenyl)boronic acid (0.16 mmol) in dioxane (0.4 mL) and water (200 μL). The resulting mixture was heated in the microwave oven (Biotage Initiator, Power range 0-400 W from magnetron at 2.45 GHz) for 20 minutes at 140° C. The reaction was filtered, and purified by reverse phase HPLC on a Phenomenex Luna C8 (2) 5 μm 100 Å AXIA column (30 mm×150 mm): A gradient of acetonitrile (A) and 0.1% trifluoroacetic acid in water (B) was used, at a flow rate of 50 mL/min (0-0.5 minutes 10% A, 0.5-6.0 minutes linear gradient 10-100% A, 6.0-7.0 minutes 100% A, 7.0-8.0 minutes linear gradient 100-10% A). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/min. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export. $^1$H NMR (DMSO/D$_2$O-d$_6$) δ 3.05 (s, 3H), 4.31 (s, 2H), 5.77 (s, 2H), 6.73-6.80 (m, 1H), 6.81 (s, 1H), 6.98 (d, J=7.5 Hz, 1H), 7.07 (t, J=8.6 Hz, 2H), 7.32-7.39 (m, 2H), 7.58-7.65 (m, 2H), 8.49 (s, 1H), 8.60 (s, 1H); (ESI) m/z 446 (M–NH$_2$)$^+$.

Example 86

4-{2-(aminomethyl)-7-[(6-amino-9H-purin-9-yl)methyl]-1H-indol-4-yl}-N,N-dimethylbenzamide Example 86 was prepared according to the procedure used for the preparation of Example 85, substituting (4-(dimethylcarbamoyl)phenyl)boronic acid for (4-(methylsulfonamido)phenyl)boronic acid. $^1$H NMR (DMSO/D$_2$O-d$_6$) δ 2.97-3.09 (m, 6H), 4.31 (s, 2H), 5.79 (s, 2H), 6.83 (s, 1H), 6.98 (d, J=7.6 Hz, 1H), 7.15 (d, J=7.5 Hz, 1H), 7.50-7.61 (m, 2H), 7.65-7.74 (m, 2H), 8.49 (s, 1H), 8.62 (s, 1H); (ESI) m/z 424 (M−NH$_2$)$^+$.

Example 87

1-{7-[(6-amino-9H-purin-9-yl)methyl]-5-chloro-1H-indol-2-yl}ethanone

Example 87a 7-((6-amino-9H-purin-9-yl)methyl)-5-chloro-1H-indole-2-carboxylic acid Example 7e (2.31 g, 4.91 mmol) was suspended in ethanol (25 mL) and treated with aqueous sodium hydroxide (15 mL, 30.0 mmol). The mixture was stirred for about 16 hours at 85° C. The reaction was cooled to ambient temperature and acidified using 1N HCl. The precipitate was collected by filtration, washed with water, and dried under vacuum to give the crude title compound (1.8 g, 107%), which was used in the next step without further purification. MS m/z: 207 [M-adenine and —H]$^+$.

Example 87b 7-((6-amino-9H-purin-9-yl)methyl)-5-chloro-N-methoxy-N-methyl-1H-indole-2-carboxamide To a mixture of Example 87a (1 g, 2.92 mmol), 2-(3H-[1,2,3]triazolo[4,5-b]pyridin-3-yl)-1,1,3,3-tetramethyl-isouronium hexafluorophosphate(V) (1.22 g, 3.21 mmol), and triethylamine (3.25 mL, 23.34 mmol) in N,N-dimethylacetamide (50 mL) was added N,O-dimethylhydroxylamine hydrochloride (1.138 g, 11.67 mmol). The mixture was stirred for 6 hours at room temperature, diluted with ethyl acetate, washed sequentially with water (3 times) and brine, and dried over magnesium sulfate to give the title compound (0.82 g, 2.125 mmol, 72.8% yield). $^1$H NMR (400 MHz, DMSO-d$_6$) δ 12.23 (s, 1H), 8.32 (s, 1H), 8.24 (s, 1H), 7.72 (d, J=1.9 Hz, 1H), 7.37 (s, 2H), 7.18 (dd, J=4.6, 1.9 Hz, 2H), 5.68 (s, 2H), 3.78 (s, 3H), 1.08 (t, J=7.0 Hz, 3H); MS m/z: 251 [M-adenine]$^+$.

Example 87c

1-{7-[(6-amino-9H-purin-9-yl)methyl]-5-chloro-1H-indol-2-yl}ethanone

To a chilled (0° C.) suspension of Example 87b (0.1 g, 0.259 mmol) in tetrahydrofuran (3 mL) was slowly added methylmagnesium bromide (0.926 mL, 1.296 mmol) under nitrogen atmosphere. The reaction was slowly warmed to room temperature and stirred for about 16 hours. The reaction was quenched with 0.5 M HCl. Ethyl acetate was added and the suspension was collected by filtration, washed with 0.5 M HCl and ethyl acetate, and dried under vacuum to give the title compound (0.0855 g, 97%). $^1$H NMR (400 MHz, CD$_3$OD) δ 8.46 (d, J=17.9 Hz, 2H), 7.73 (d, J=1.9 Hz, 1H), 7.34 (s, 1H), 7.28 (d, J=1.9 Hz, 1H), 5.79 (s, 2H), 2.60 (s, 3H); MS m/z: 341 [M+H]$^+$.

Example 88

9-{[2-(1-aminoethyl)-5-chloro-1H-indol-7-yl]methyl}-9H-purin-6-amine

A suspension of Example 87c (0.075 g, 0.220 mmol,) and ammonium acetate (0.170 g, 2.201 mmol) in methanol (3 mL) was treated with sodium cyanotrihydroborate (0.042 g, 0.668 mmol) and heated for 30 minutes at 125° C. in the microwave (Biotage, Initiator). The cooled mixture was concentrated to dryness. The residue was suspended in water and sonicated for about 5 minutes, filtered, washed with water and dried under vacuum. The filter cake was purified by preparative HPLC (Waters Sunfire C8, 10-40% acetonitrile/water; 1% TFA) to give the title compound (0.043 g, 42.9%). $^1$H NMR (400 MHz, CD$_3$OD) δ 8.35 (s, 1H), 8.27 (s, 1H), 7.56 (d, J=1.9 Hz, 1H), 7.05 (s, 1H), 6.60 (s, 1H), 5.69 (s, 2H), 1.77 (d, J=6.9 Hz, 3H); MS m/z: 325 [M−NH$_2$]$^+$.

Example 89

9-({5-chloro-2-[(methylamino)methyl]-1H-indol-7-yl}methyl)-9H-purin-6-amine

Example 89a 7-((6-amino-9H-purin-9-yl)methyl)-5-chloro-1H-indole-2-carbaldehyde

Example 7g (0.22 g, 0.669 mmol) was added to a solution of 2-iodoxybenzoic acid (0.375 g, 1.338 mmol) and 2,2,2-trifluoroacetic acid (0.103 mL, 1.338 mmol) in dimethylsulfoxide (6 mL). The solution was stirred overnight at room temperature. The solution was diluted with aqueous sodium bicarbonate (2.5%), and extracted with ethyl acetate. The combined organic layers were washed with water, dried over sodium sulfate, and concentrated to dryness under vacuum to give the crude title compound (0.13 g, 59.5%). $^1$H NMR (400 MHz, DMSO-d$_6$) δ 12.54 (s, 1H), 9.93 (s, 1H), 8.31 (s, 1H), 8.21 (s, 1H), 7.82 (s, 1H), 7.45 (s, 1H), 7.34 (s, 2H), 7.10 (s, 1H), 5.71 (s, 2H); MS m/z: 327 [M+H]$^+$.

Example 89b 9-({5-chloro-2-[(methylamino)methyl]-1H-indol-7-yl}methyl)-9H-purin-6-amine To a stirring suspension of Example 89a (0.12 g, 0.367 mmol) and methanamine in methanol (0.735 mL, 1.469 mmol) was added N,N,N-trimethyl-1-(p-tolyl)methanaminium cyanotrihydroborate (0.671 g, 1.469 mmol) and acetic acid (0.084 mL, 1.469 mmol). The mixture was stirred overnight at 50° C. The reaction was cooled to room temperature, filtered and the resin washed with methanol and dichloromethane. The filtrate was concentrated and the residue purified by preparative HPLC (Waters Sunfire C8, 0-100% methanol/water; 0.1 M ammonium acetate) to give the title compound (0.03 g, 20.33%). $^1$H NMR (501 MHz, DMSO-d$_6$) δ 11.73 (s, 1H), 8.36 (s, 1H), 8.26 (s, 1H), 7.51 (s, 1H), 7.35 (s, 2H), 6.86 (d, J=2.0 Hz, 1H), 6.40 (s, 1H), 5.67 (s, 2H), 3.91 (s, 2H), 2.37 (s, 3H), 1.95 (s, 3H); MS m/z: 311 [M−NHCH$_3$]$^+$.

Example 90

1-{7-[(6-amino-9H-purin-9-yl)methyl]-5-chloro-1H-indol-2-yl}propan-1-one

Example 90 was prepared according to the procedure used for the preparation of Example 87c, substituting ethylmagnesium bromide for methylmagnesium bromide. 1H NMR (400 MHz, CD$_3$OD) δ 8.46 (s, 1H), 8.33 (s, 1H), 7.71 (d, J=1.9 Hz, 1H), 7.32 (s, 2H), 5.73 (s, 2H), 3.03 (q, J=7.4 Hz, 2H), 1.23 (t, J=7.3 Hz, 3H); MS m/z: 220 [M-adenine]$^+$.

Example 91

9-{[2-(1-aminopropyl)-5-chloro-1H-indol-7-yl]methyl}-9H-purin-6-amine

A suspension of Example 90 (0.055 g, 0.155 mmol) and ammonium acetate (0.119 g, 1.550 mmol) in methanol (5 mL) was treated with sodium cyanotrihydroborate (0.029 g, 0.465 mmol). The mixture was stirred at room temperature for 3 hours. The mixture was transferred equally between two microwave vials. The first vial was heated in the microwave for 15 minutes at 125° C. then again at 110° C. for 30 minutes. Vial two was heated in the microwave for 30 minutes at 110° C. The contents were combined and concentrated to dryness. The crude material was suspended in water and sonicated for about 5 minutes, filtered, washed with water and dried overnight. The solid was purified by preparative HPLC (Waters Sunfire C8, 0-80% methanol/water; 1% TFA) to give the title compound (0.017 g, 23.3%). $^1$H NMR (400 MHz, CD$_3$OD) δ 8.37 (s, 1H), 8.32 (s, 1H), 7.57 (d, J=1.8 Hz, 1H), 7.06 (d, J=1.8 Hz, 1H), 6.63 (s, 1H), 5.73 (s, 2H), 4.47 (t, J=7.4 Hz, 1H), 2.14 (p, J=7.2 Hz, 2H), 0.96 (t, J=7.4 Hz, 3H); MS m/z: 204 [M-adenine and NH$_2$]$^+$.

Example 92

N-({7-[(6-amino-9H-purin-9-yl)methyl]-5-chloro-1H-indol-2-yl}methyl)acetamide

To a suspension of Example 9b (0.05 g, 0.153 mmol) and triethylamine (0.064 mL, 0.458 mmol) in THF (5 mL) was added acetyl chloride (10.85 μL, 0.153 mmol). The resulting mixture was stirred at ambient temperature for 2 hours. The mixture was concentrated and the residue was purified by reverse phase HPLC (C18, 35-70% acetonitrile/water, 0.05% ammonium hydroxide) to give the title compound (0.02 g, 0.054 mmol, 35.5% yield). MS (ESI+): m/z 370 (M+H)+; $^1$H NMR (400 MHz, DMSO-d$_6$): δ 11.49 (s, 1H), 8.39 (s, 1H), 8.29 (s, 1H), 8.22 (s, 1H), 7.48 (d, J=1.6 Hz, 1H), 7.32 (s, 1H), 6.83 (d, J=2.0 Hz, 1H), 6.34 (s, 1H), 5.59 (s, 1H), 4.46 (d, J=6.4 Hz, 2H), 1.90 (s, 3H).

Example 93

N-({7-[(6-amino-9H-purin-9-yl)methyl]-5-chloro-1H-indol-2-yl}methyl)prop-2-enamide Acryloyl chloride (12.39 μL, 0.153 mmol) was added to a suspension of Example 9b (50 mg, 0.153 mmol) in triethylamine (45 μL, 0.323 mmol) and dichloromethane (1.5 mL) at 0° C. The reaction mixture was stirred at 0° C. for 1.5 hours and at room temperature for 2 hours. Water was added to the reaction mixture to afford a solid which was collected by filtration, rinsed with water, and dried (in-vacuo). The solid was absorbed onto silica gel and was flash chromatographed (Biotage 10 g HP Snap Cartridge, eluting with heptane containing a gradient (20% to 90%) with a solution of 3:1 ethyl acetate:ethanol) to provide the title compound. $^1$H NMR (500 MHz, DMSO-d$_6$) δ 11.67-11.47 (m, 1H), 8.67 (t, J=5.6 Hz, 1H), 8.30 (s, 1H), 8.20 (s, 1H), 7.49 (d, J=2.0 Hz, 1H), 7.32 (s, 2H), 6.84 (d, J=1.9 Hz, 1H), 6.36 (d, J=1.9 Hz, 1H), 6.32 (dd, J=17.1, 10.2 Hz, 1H), 6.18 (dd, J=17.1, 2.2 Hz, 1H), 5.67 (dd, J=10.2, 2.2 Hz, 1H), 5.59 (s, 2H), 4.56 (d, J=5.5 Hz, 2H). MS ESI$^+$ 382.0 (M+H)$^+$.

Example 94

N-({7-[(6-amino-9H-purin-9-yl)methyl]-5-chloro-1H-indol-2-yl}methyl)propanamide

Example 94 was prepared according to the procedure used for the preparation of Example 92, substituting propionyl chloride for acetyl chloride. MS (ESI+): m/z 384 (M+H)$^+$; $^1$H NMR (400 MHz, DMSO-d$_6$): δ 11.50 (s, 1H), 8.33 (s, 1H), 8.29 (s, 1H), 8.21 (s, 1H), 7.48 (d, J=1.6 Hz, 1H), 7.33 (s, 1H), 6.83 (d J=2.0 Hz, 1H), 6.33 (d J=1.6 Hz, 1H), 5.59 (s, 2H), 4.46 (d, J=6.4 Hz, 2H), 2.15-2.21 (q, J=7.6 Hz, 2H), 1.05 (t, J=7.6 Hz, 3H).

Example 95

N-({7-[(6-amino-9H-purin-9-yl)methyl]-5-chloro-1H-indol-2-yl}methyl)-2-methoxyacetamide Example 95 was prepared according to the procedure used for the preparation of Example 232, substituting 2-methoxyacetic acid for 2-(pyridin-4-yl)acetic acid. $^1$H NMR (400 MHz, DMSO-d$_6$) δ 3.35 (s, 3H), 3.90 (s, 3H), 4.51 (d, J=6.0 Hz, 2H), 5.66 (s, 2H), 6.32 (d, J=1.9 Hz, 1H), 6.82 (d, J=2.0 Hz, 1H), 7.49 (d, J=2.0 Hz, 1H), 8.37 (d, J=7.6 Hz, 3H), 8.47 (s, 1H), 11.42 (d, J=2.2 Hz, 1H). MS (APCI) m/z 400.1 [M+H]$^+$.

Example 96

3-[({7-[(6-amino-9H-purin-9-yl)methyl]-5-chloro-1H-indol-2-yl}methyl)amino]propanoic acid Acrylic acid (0.023 mL, 0.336 mmol) was added to Example 9b (0.1 g, 0.305 mmol) in pyridine (1 mL) and the mixture stirred overnight at room temperature. The solvent was removed and the residue was purified by preparative HPLC (Waters Sunfire C8, 0-80% methanol/water; 1% TFA) to give the title compound (0.07 g, 44.7%). $^1$H NMR (400 MHz, CD$_3$OD) δ 8.32 (s, 1H), 8.21 (s, 1H), 7.58 (s, 1H), 7.06 (s, 1H), 6.71 (s, 1H), 5.66 (s, 2H), 4.47 (s, 2H), 3.37-3.32 (m, 2H), 2.76 (t, J=6.5 Hz, 2H); MS m/z: 400 [M+H]$^+$.

Example 97

9-({5-chloro-2-[(diethylamino)methyl]-1H-indol-7-yl}methyl)-9H-purin-6-amine

To a stirring solution of Example 9b (0.05 g, 0.153 mmol) and acetaldehyde (10 μL, 0.178 mmol) was added MP-cyanoborohydride (0.271 g, 0.610 mmol) and acetic acid (35 μL, 0.611 mmol). The slurry was stirred at room temperature for about 64 hours. The mixture was filtered and the resin washed sequentially with methanol (2×25 mL) and dichloromethane (25 mL). The filtrate was concentrated in vacuo and the residue purified by preparative HPLC (Waters Sunfire C8, 20-80% methanol/water; 1% TFA). The product was dissolved in dicholormethane and washed with saturated sodium bicarbonate, filter through a phase separator, and concentrated to give the title compound (0.0299 g, 51.1%). 1H NMR (500 MHz, CD$_3$OD/trace trifluoroacetic acid) δ 8.41 (d, J=4.0 Hz, 2H), 7.60 (d, J=2.0 Hz, 1H), 7.10 (d, J=1.9 Hz, 1H), 6.78 (s, 1H), 5.78 (s, 2H), 4.57 (s, 2H), 3.26 (dt, J=11.5, 7.2 Hz, 2H), 1.37 (t, J=7.3 Hz, 3H); MS m/z: 311 [M-diethylamine]$^+$.

Example 98

N-({7-[(6-amino-9H-purin-9-yl)methyl]-5-chloro-1H-indol-2-yl}methyl)butanamide

Example 98 was prepared according to the procedure used for the preparation of Example 232, substituting butyric acid for 2-(pyridin-4-yl)acetic acid. $^1$H NMR (400 MHz, DMSO-d$_6$) δ 0.89 (t, J=7.4 Hz, 3H), 1.57 (h, J=7.4 Hz, 2H), 2.15 (t, J=7.3 Hz, 2H), 4.46 (d, J=5.6 Hz, 2H), 5.65 (s, 2H), 6.33 (d, J=1.9 Hz, 1H), 6.83 (d, J=2.0 Hz, 1H), 7.49 (d, J=2.0 Hz, 1H), 7.97-8.41 (m, 4H), 8.45 (s, 1H), 11.45 (d, J=2.2 Hz, 1H). MS (APCI) m/z 398.1 [M+H]$^+$.

Example 99

N-({7-[(6-amino-9H-purin-9-yl)methyl]-5-chloro-1H-indol-2-yl}methyl)-2-methylpropanamide Example 99 was prepared according to the procedure used for the preparation of Example 232, substituting isobutyric acid for 2-(pyridin-4-yl)acetic acid. $^1$H NMR (400 MHz, DMSO-d$_6$) δ 1.06 (d, J=6.8 Hz, 6H), 4.45 (d, J=5.5 Hz, 2H), 5.67 (s, 2H), 6.32 (d, J=1.8 Hz, 1H), 6.83 (d, J=2.0 Hz, 1H), 7.50 (d, J=2.0 Hz, 1H), 8.26-8.61 (m, 4H), 11.45 (d, J=2.3 Hz, 1H). MS (APCI) m/z 398.1 [M+H]$^+$.

Example 100

N-({7-[(6-amino-9H-purin-9-yl)methyl]-5-chloro-1H-indol-2-yl}methyl)-3-methoxypropanamide To a solution of 3-methoxypropanoic acid (0.016 mL, 0.168 mmol) in N,N-dimethylacetamide (1.525 mL) and N-ethyl-N-isopropylpropan-2-amine (0.030 mL, 0.183 mmol) was added 2-(3H-[1,2,3]triazolo[4,5-b]pyridin-3-yl)-1,1,3,3-tetramethylisouronium hexafluorophosphate(V) (0.070 g, 0.183 mmol). The mixture was stirred at room temperature for 5 minutes followed by the addition of Example 9b (0.05 g, 0.153 mmol) and the mixture was stirred at room temperature for 4 hours. Water and ethyl acetate were added to the reaction and the organics were separated, concentrated, and purified by preparative HPLC (Waters Sunfire C8, 20-80% methanol/water; 1% TFA) to give the title compound (0.029 g, 45.9%). $^1$H NMR (400 MHz, CD$_3$OD) δ 8.46 (s, 1H), 8.32 (s, 1H), 7.47 (d, J=1.9 Hz, 1H), 7.05 (d, J=1.9 Hz, 1H), 6.38 (s, 1H), 5.69 (s, 2H), 4.54 (s, 2H), 3.68 (t, J=6.0 Hz, 2H), 3.33 (s, 3H), 2.50 (t, J=6.0 Hz, 2H); MS m/z: 279 [M-adenine]$^+$.

Example 101

2,2'-[({7-[(6-amino-9H-purin-9-yl)methyl]-5-chloro-1H-indol-2-yl}methyl)imino]diacetic acid Example 101a tert-butyl 2-(((7-((6-amino-9H-purin-9-yl)methyl)-5-chloro-1H-indol-2-yl)methyl)(tert-butoxycarbonyl)amino)acetate tert-butyl 2-bromoacetate (0.030 mL, 0.201 mmol) was added to Example 9b (0.06 g, 0.183 mmol) in N,N-dimethylformamide (1 mL). The reaction was stirred at room temperature for about 1 hour. The reaction was diluted with water and extracted 2 times with dichloromethane; the organics were combined, passed through a phase separator, and concentrated. The residue was purified by preparative HPLC (Waters Sunfire C8, 45-95% methanol/water; 0.1 M ammonium acetate) to afford the title compound (0.021 g, 21.16%) and Example 106. $^1$H NMR (400 MHz, CD$_3$OD) δ 8.37 (s, 1H), 8.18 (s, 1H), 7.45 (d, J=1.8 Hz, 1H), 7.05 (d, J=1.8 Hz, 1H), 6.32 (s, 1H), 5.63 (s, 2H), 4.60 (s, 2H), 4.04 (s, 2H), 1.95 (d, J=3.9 Hz, 1H), 1.43 (s, 18H); MS (APCI+): m/z 556 [M+H]$^+$.

Example 101b 2,2'-[({7-[(6-amino-9H-purin-9-yl)methyl]-5-chloro-1H-indol-2-yl}methyl)imino]diacetic acid A round bottom flask was charged with Example 101a (0.037 g, 0.067 mmol) and 0.5 mL of 1M HCl in diethyl ether. The reaction mixture was stirred for 4 hours at room temperature. The solvent was removed under reduced pressure and the residue was precipitated from methanol to give the title compound (0.0057 g, 19.3%). $^1$H NMR (400 MHz, DMSO-d$_6$) δ 11.63 (s, 1H), 8.59 (s, 1H), 8.45 (s, 1H), 7.54 (d, J=1.9 Hz, 1H), 6.88 (d, J=1.9 Hz, 1H), 6.47 (s, 1H), 5.72 (s, 2H), 4.20 (s, 2H), 3.64 (s, 2H); MS m/z: 444 [M+H]$^+$.

Example 102

N-({7-[(6-amino-9H-purin-9-yl)methyl]-5-chloro-1H-indol-2-yl}methyl)-3-methylbutanamide Example 102 was prepared according to the procedure used for the preparation of Example 232, substituting 3-methylbutanoic acid for 2-(pyridin-4-yl)acetic acid. $^1$H NMR (400 MHz, DMSO-d$_6$) δ 0.85-0.97 (m, 6H), 1.99-2.06 (m, 3H), 4.46 (d, J=5.7 Hz, 2H), 5.64 (s, 2H), 6.32 (d, J=1.9 Hz, 1H), 6.83 (d, J=2.0 Hz, 1H), 7.49 (d, J=2.0 Hz, 1H), 8.09 (s, 2H), 8.35 (d, J=3.3 Hz, 2H), 8.43 (s, 1H), 11.46 (d, J=2.2 Hz, 1H). MS (APCI) m/z 412.1 [M+H]$^+$.

Example 103

N-({7-[(6-amino-9H-purin-9-yl)methyl]-5-chloro-1H-indol-2-yl}methyl)-3-hydroxy-3-methylbutanamide A mixture of 3-hydroxy-3-methylbutanoic acid (13.11 µL, 0.122 mmol), HATU (46.4 mg, 0.122 mmol) and N-ethyl-N-isopropylpropan-2-amine (63.9 µL, 0.366 mmol) in N,N-dimethylformamide (0.5 mL) was stirred at ambient temperature for 5 minutes and then treated with Example 9b (40 mg, 0.122 mmol) and stirred at ambient temperature overnight. The mixture was diluted with ethyl acetate (30 mL), washed sequentially with water (2×) and brine, dried over MgSO$_4$, and filtered. The filtrate was concentrated and the residue was purified by column chromatography on silica gel (1-10% methanol in dichloromethane) to give the title compound (37 mg, 0.086 mmol, 70.9% yield). $^1$H NMR (400 MHz, DMSO-d$_6$) δ 11.51 (s, 1H), 8.38 (t, J=5.6 Hz, 1H), 8.29 (s, 1H), 8.22 (s, 1H), 7.48 (d, J=1.8 Hz, 1H), 7.30 (s, 2H), 6.82 (d, J=1.9 Hz, 1H), 6.35 (d, J=1.5 Hz, 1H), 5.59 (s, 2H), 4.83 (s, 1H), 4.49 (d, J=5.6 Hz, 2H), 2.31 (s, 2H), 1.19 (s, 6H). MS (ESI+) m/z 428.0 (M+H)$^+$.

Example 104

N-({7-[(6-amino-9H-purin-9-yl)methyl]-5-chloro-1H-indol-2-yl}methyl)-3,3-dimethylbutanamide Example 104 was prepared according to the procedure used for the preparation of Example 103, substituting 3,3-dimethylbutanoic acid for 3-hydroxy-3-methylbutanoic acid. $^1$H NMR (400 MHz, DMSO-d$_6$) δ 11.54 (s, 1H), 8.35-8.29 (m, 2H), 8.26 (s, 1H), 7.52 (d, J=1.9 Hz, 1H), 7.34 (s, 2H), 6.87 (d, J=1.9 Hz, 1H), 6.36 (d, J=1.6 Hz, 1H), 5.62 (s, 2H), 4.49 (d, J=5.6 Hz, 2H), 2.11 (d, J=7.3 Hz, 2H), 1.03 (s, 9H). MS (ESI+) m/z 426.0 (M+H)$^+$.

Example 105

N-({7-[(6-amino-9H-purin-9-yl)methyl]-5-chloro-1H-indol-2-yl}methyl)-4-methylpentanamide A stock solution of Example 9b (0.18 M in N,N-dimethylacetamide, 297 μL, 0.055 mmol), diisopropylethyl amine (0.21 M in N,N-dimethylacetamide, 0.066 mmol), HATU (0.20 M in N,N-dimethylacetamide, 297 μL, 0.060 mmol), and 4-methy-pentanoic acid (0.40 M in N,N-dimethylacetamide, 151 μL, 0.06 mmol) were aspirated from their respective source vials, mixed through a perfluoroalkoxy mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 μL min$^{-1}$ (10 minute residence time). Upon exiting the reactor, the reaction was loaded directly into an injection loop and purified by preparative HPLC on a Phenomenex Luna C8 (2) 5 μm 100 Å AXIA column (50 mm×21.2 mm). A gradient of acetonitrile (A) and 0.1% trifluoroacetic acid in water (B) was used, at a flow rate of 30 mL/min (0-0.5 minutes 5% A, 0.5-6.5 minutes linear gradient 5-60% A, 6.5-7.0 minutes 60-100% A, 7.0-8.9 minutes 100% A, 8.9-9.0 minutes linear gradient 100-5% A, 9.0-10 minutes 5% A). A sample volume of 1.0 mL was injected directly from the flow reactor stream to the HPLC system. A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0. $^1$H NMR (400 MHz, DMSO-d$_6$) δ 11.45 (s, 1H), 8.45 (s, 1H), 8.37 (s, 2H), 8.24 (s, 2H), 7.49 (d, J=2.2 Hz, 1H), 6.82 (d, J=2.0 Hz, 1H), 6.32 (d, J=1.9 Hz, 1H), 5.65 (s, 2H), 4.45 (d, J=5.6 Hz, 2H), 2.22-2.13 (m, 2H), 1.61-1.48 (m, 1H), 1.48-1.40 (m, 2H), 0.88 (d, J=6.6 Hz, 6H). MS (APCI+) m/z 426.1 (M+H)$^+$.

Example 106 tert-butyl [({7-[(6-amino-9H-purin-9-yl)methyl]-5-chloro-1H-indol-2-yl}methyl)amino]acetate tert-butyl 2-bromoacetate (0.030 mL, 0.201 mmol) was added to Example 9b (0.06 g, 0.183 mmol) in N,N-dimethylformamide (1 mL). The reaction was stirred at room temperature for about 1 hour. The reaction was diluted with water and extracted 2 times with dichloromethane; the organics were combined, passed through a phase separator, and concentrated. The residue was purified by preparative HPLC (Waters Sunfire C8, 45-95% methanol/water; 0.1 M ammonium acetate) to afford the title compound (0.042 g, 48.6%) and Example 101a. $^1$H NMR (400 MHz, DMSO-d$_6$) δ 11.55 (s, 1H), 8.30 (s, 1H), 8.20 (s, 1H), 7.46 (d, J=2.0 Hz, 1H), 7.32 (s, 2H), 6.80 (d, J=2.0 Hz, 1H), 6.32 (d, J=1.6 Hz, 1H), 5.60 (s, 2H), 4.05 (s, 1H), 3.91 (s, 2H), 3.24 (s, 2H), 1.42 (s, 9H)); MS m/z: 442 [M+H]$^+$.

Example 107

N-({7-[(6-amino-9H-purin-9-yl)methyl]-5-chloro-1H-indol-2-yl}methyl)cyclopropanecarboxamide Example 107 was prepared according to the procedure used for the preparation of Example 92, substituting cyclopropanecarbonyl chloride for acetyl chloride. MS (ESI+): m/z 396 (M+H)+; $^1$H NMR (400 MHz, DMSO-d$_6$): δ 11.52 (s, 1H), 8.61 (s, 1H), 8.32 (s, 1H), 8.24 (s, 1H), 7.50-7.48 (m, 3H), 6.84 (d, J=2.0 Hz, 1H), 6.35 (s, 1H), 5.60 (s, 2H), 4.49 (d, J=5.2 Hz, 2H), 1.60-1.68 (m, 1H), 0.75-0.68 (m, 4H).

Example 108

N-({7-[(6-amino-9H-purin-9-yl)methyl]-5-chloro-1H-indol-2-yl}methyl)-1-methylcyclopropanecarboxamide Example 108 was prepared according to the procedure used for the preparation of Example 105, substituting 1-methyl-cyclopropanecarboxylic acid for 4-methyl-pentanoic acid. $^1$H NMR (400 MHz, DMSO-d$_6$) δ 11.35 (s, 1H), 8.72 (s, 2H), 8.55 (s, 1H), 8.44 (s, 1H), 8.10 (t, J=5.8 Hz, 1H), 7.50 (d, J=2.0 Hz, 1H), 6.84 (d, J=2.0 Hz, 1H), 6.29 (d, J=1.8 Hz, 1H), 5.69 (s, 2H), 4.46 (d, J=5.7 Hz, 2H), 1.31 (s, 3H), 1.01 (q, J=3.5 Hz, 2H), 0.56 (q, J=3.6 Hz, 2H). MS (APCI+) m/z 410.0 (M+H)$^+$.

Example 109

N-({7-[(6-amino-9H-purin-9-yl)methyl]-5-chloro-1H-indol-2-yl}methyl)-2-methylcyclopropanecarboxamide Example 109 was prepared according to the procedure used for the preparation of Example 105, substituting 2-methyl-cyclopropanecarboxylic acid for 4-methyl-pentanoic acid. $^1$H NMR (400 MHz, DMSO-d$_6$) δ 11.47 (d, J=2.0 Hz, 1H), 8.54 (t, J=5.6 Hz, 1H), 8.44 (s, 1H), 8.35 (s, 1H), 8.16 (s, 2H), 7.50 (d, J=2.0 Hz, 1H), 6.84 (d, J=2.1 Hz, 1H), 6.34 (dd, J=5.2, 2.0 Hz, 1H), 5.65 (s, 2H), 4.58-4.39 (m, 2H), 1.39 (dt, J=8.2, 4.3 Hz, 1H), 1.22-1.03 (m, 4H), 0.98-0.83 (m, 1H), 0.54 (ddd, J=9.0, 5.9, 3.4 Hz, 1H). MS (APCI+) m/z 410.1 (M+H)$^+$.

Example 110

N-({7-[(6-amino-9H-purin-9-yl)methyl]-5-chloro-1H-indol-2-yl}methyl)-2-cyclopropylacetamide Example 110 was prepared according to the procedure used for the preparation of Example 232, substituting 2-cyclopropylacetic acid for 2-(pyridin-4-yl)acetic acid. $^1$H NMR (400 MHz, DMSO-d$_6$) δ 0.10-0.35 (m, 2H), 0.36-0.57 (m, 2H), 1.01 (dddd, J=12.2, 7.2, 5.2, 2.5 Hz, 2H), 2.08 (d, J=7.0 Hz, 2H), 4.47 (d, J=5.6 Hz, 2H), 5.66 (s, 2H), 6.34 (d, J=1.9 Hz, 1H), 6.83 (d, J=2.0 Hz, 1H), 7.50 (d, J=2.0 Hz, 1H), 8.33 (d, J=28.2 Hz, 4H), 8.46 (s, 1H), 11.46 (d, J=2.3 Hz, 1H). MS (APCI) m/z 410.1.1 [M+H]$^+$.

Example 111

N-({7-[(6-amino-9H-purin-9-yl)methyl]-5-chloro-1H-indol-2-yl}methyl)cyclobutanecarboxamide Example 111 was prepared according to the procedure used for the preparation of Example 105, substituting cyclobutanecarboxylic acid for 4-methyl-pentanoic acid. $^1$H NMR (400 MHz, DMSO-d$_6$) δ 11.42 (d, J=2.0 Hz, 1H), 8.47 (s, 1H), 8.38 (s, 3H), 8.21 (t, J=5.6 Hz, 1H), 7.48 (d, J=2.0 Hz, 1H), 6.82 (d, J=2.1 Hz, 1H), 6.30 (d, J=1.8 Hz, 1H), 5.65 (s, 2H), 4.44 (d, J=5.5 Hz, 2H), 3.08 (p, J=8.6 Hz, 1H), 2.17 (dq, J=11.2, 9.0 Hz, 2H), 2.04 (dtt, J=11.8, 8.6, 2.6 Hz, 2H), 1.94-1.83 (m, 1H), 1.82-1.71 (m, 1H). MS (APCI+) m/z 410.0 (M+H)$^+$.

Example 112

N-({7-[(6-amino-9H-purin-9-yl)methyl]-5-chloro-1H-indol-2-yl}methyl)-1-hydroxycyclobutanecarboxamide Example 112 was prepared according to the procedure used for the preparation of Example 100, substituting 1-hydroxycyclobutanecarboxylic acid for 3-methoxypropanoic acid. $^1$H NMR (400 MHz, CD$_3$OD) δ 8.49 (s, 1H), 8.32 (s, 1H), 7.46 (d, J=1.9 Hz, 1H), 7.05 (d, J=1.9 Hz, 1H), 6.35 (s, 1H), 5.68 (s, 2H), 4.55 (s, 2H), 2.63-2.47 (m, 2H), 2.23-2.07 (m, 2H), 1.93 (h, J=9.3, 8.8 Hz, 2H). MS m/z: 291 [M-adenine]$^+$.

Example 113

N-({7-[(6-amino-9H-purin-9-yl)methyl]-5-chloro-1H-indol-2-yl}methyl)tetrahydrofuran-2-carboxamide Example 113 was prepared according to the procedure used for the preparation of Example 232, substituting tetrahydrofuran-2-carboxylic acid for 2-(pyridin-4-yl)acetic acid. $^1$H NMR (400 MHz, DMSO-d$_6$) δ 1.74-1.96 (m, 4H), 2.16 (dq, J=11.6, 7.5 Hz, 1H), 3.79 (dt, J=8.0, 6.7 Hz, 1H), 3.93 (dt, J=7.9, 6.5 Hz, 1H), 4.29 (dd, J=8.2, 5.3 Hz, 1H), 4.38-4.57 (m, 2H), 5.66 (s, 2H), 6.29 (d, J=1.8 Hz, 1H), 6.83 (d, J=2.0 Hz, 1H), 7.50 (d, J=2.0 Hz, 1H), 8.23-8.53 (m, 4H), 11.42 (d, J=2.1 Hz, 1H). MS (APCI) m/z 426.1 [M+H]$^+$.

Example 114

N-({7-[(6-amino-9H-purin-9-yl)methyl]-5-chloro-1H-indol-2-yl}methyl)tetrahydrofuran-3-carboxamide Example 114 was prepared according to the procedure used for the preparation of Example 232, substituting tetrahydrofuran-3-carboxylic acid for 2-(pyridin-4-yl)acetic acid. $^1$H NMR (400 MHz, DMSO-d$_6$) δ 1.98-2.13 (m, 2H), 2.93-3.08 (m, 1H), 3.70-3.82 (m, 2H), 3.88 (t, J=8.2 Hz, 2H), 4.48 (d, J=5.5 Hz, 2H), 5.66 (s, 2H), 6.34 (d, J=1.9 Hz, 1H), 6.82 (d, J=2.0 Hz, 1H), 7.50 (d, J=1.9 Hz, 1H), 8.16-8.57 (m, 5H), 11.49 (d, J=2.1 Hz, 1H). MS (APCI) m/z 426.1 [M+H]$^+$.

Example 115

(2S)—N-({7-[(6-amino-9H-purin-9-yl)methyl]-5-chloro-1H-indol-2-yl}methyl)pyrrolidine-2-carboxamide Example 123 (72 mg, 0.137 mmol) was treated with dichloromethane (2 mL) and trifluoroacetic acid (1 mL) and stirred at ambient temperature for 2.5 hours. The solvent was removed and the residue was triturated in diethyl ether to give the title compound as a trifluoroacetic acid salt (74 mg, 0.113 mmol, 83% yield). 1H NMR (400 MHz, DMSO-d$_6$, 90° C.) δ 11.33 (bs, 1H), 8.82 (bs, 1H), 8.28 (s, 1H), 8.24 (s, 1H), 7.47 (d, J=2.0 Hz, 1H), 7.26 (bs, 1H), 6.92 (d, J=1.9 Hz, 1H), 6.38 (d, J=2.1 Hz, 1H), 5.61 (s, 2H), 4.56 (dd, J=5.5, 2.8 Hz, 2H), 4.27-4.19 (m, 1H), 3.43-3.28 (m, 1H), 3.24 (dt, J=11.2, 6.8 Hz, 1H), 2.42-2.26 (m, 1H), 2.00-1.87 (m, 3H). ms (ESI+) m/z 425.1 (M+H)$^+$.

Example 116

(2R)—N-({7-[(6-amino-9H-purin-9-yl)methyl]-5-chloro-1H-indol-2-yl}methyl)pyrrolidine-2-carboxamide Example 116 was prepared according to the procedure used for the preparation of Example 115, substituting Example 124 for Example 123. 1H NMR (400 MHz, DMSO-d$_6$) δ 11.53 (s, 1H), 8.45 (t, J=6.0 Hz, 1H), 8.28 (s, 1H), 8.22 (s, 1H), 7.53-7.42 (m, 1H), 7.30 (s, 2H), 6.81 (d, J=2.0 Hz, 1H), 6.29 (d, J=1.6 Hz, 1H), 5.59 (s, 2H), 4.55-4.41 (m, 2H), 3.61 (dd, J=8.8, 5.6 Hz, 1H), 2.95-2.75 (m, 2H), 2.06-1.91 (m, 1H), 1.78-1.68 (m, 1H), 1.66-1.58 (m, 2H). ms (ESI+) m/z 425.1 (M+H)$^+$.

Example 117

(2S)—N-({7-[(6-amino-9H-purin-9-yl)methyl]-5-chloro-1H-indol-2-yl}methyl)-5-oxopyrrolidine-2-carboxamide Example 117 was prepared according to the procedure used for the preparation of Example 105, substituting (2S)-5-oxopyrrolidine-2-carboxylic acid for 4-methyl-pentanoic acid. $^1$H NMR (400 MHz, DMSO-d$_6$) δ 11.48 (s, 1H), 8.77 (bs, 2H), 9.24-8.51 (m, 2H), 8.44 (s, 1H), 7.85 (s, 1H), 7.50 (d, J=2.0 Hz, 1H), 6.82 (d, J=2.0 Hz, 1H), 6.37 (d, J=1.9 Hz, 1H), 5.69 (s, 2H), 4.50 (qd, J=15.8, 5.7 Hz, 2H), 4.08 (dd, J=8.5, 4.5 Hz, 1H), 2.38-2.05 (m, 3H), 2.02-1.89 (m, 1H). MS (APCI+) m/z 439.1 (M+H)$^+$.

Example 118

(2R)—N-({7-[(6-amino-9H-purin-9-yl)methyl]-5-chloro-1H-indol-2-yl}methyl)-5-oxopyrrolidine-2-carboxamide Example 118 was prepared according to the procedure used for the preparation of Example 105, substituting (R)-

5-oxo-pyrrolidine-2-carboxylic acid for 4-methyl-pentanoic acid. $^1$H NMR (400 MHz, DMSO-d$_6$) δ 11.48 (s, 1H), 8.74 (bs, 2H), 8.60-8.50 (m, 2H), 8.43 (s, 1H), 7.85 (s, 1H), 7.50 (d, J=2.0 Hz, 1H), 6.82 (d, J=2.0 Hz, 1H), 6.37 (d, J=1.8 Hz, 1H), 5.69 (s, 2H), 4.50 (qd, J=15.7, 5.7 Hz, 2H), 4.08 (dd, J=9.8, 4.7 Hz, 1H), 2.38-2.05 (m, 3H), 2.02-1.89 (m, 1H). MS (APCI+) m/z 439.1 (M+H)$^+$.

Example 119

N-({7-[(6-amino-9H-purin-9-yl)methyl]-5-chloro-1H-indol-2-yl}methyl)cyclopentanecarboxamide Example 119 was prepared according to the procedure used for the preparation of Example 232, substituting cyclopentanecarboxylic acid for 2-(pyridin-4-yl)acetic acid. $^1$H NMR (400 MHz, DMSO-d$_6$) δ 1.46-1.85 (m, 9H), 2.65 (p, J=7.6 Hz, 1H), 4.46 (d, J=5.6 Hz, 2H), 5.66 (s, 2H), 6.32 (d, J=1.9 Hz, 1H), 6.83 (d, J=2.0 Hz, 1H), 7.50 (d, J=2.0 Hz, 1H), 7.78-8.42 (m, 4H), 8.46 (s, 1H), 11.46 (d, J=2.2 Hz, 1H). MS (APCI) m/z 424.1 [M+H]$^+$.

Example 120

N-({7-[(6-amino-9H-purin-9-yl)methyl]-5-chloro-1H-indol-2-yl}methyl)-2-(pyrrolidin-1-yl)acetamide A mixture of Example 9b (50 mg, 0.153 mmol), 2-(pyrrolidin-1-yl)acetic acid (19.70 mg, 0.153 mmol), 1H-benzo[d][1,2,3]triazol-1-ol hydrate (28.0 mg, 0.183 mmol), N$^1$-((ethylimino)methylene)-N$^3$,N$^3$-dimethylpropane-1,3-diamine hydrochloride (35.1 mg, 0.183 mmol), N-ethyl-N-isopropylpropan-2-amine (80 μL, 0.458 mmol) in dimethylsulfoxide (0.5 mL) was stirred overnight at ambient temperature. The mixture was purified by reverse phase HPLC (C18, 35-70% acetonitrile/water, 0.05% ammonium hydroxide) to give the title compound (16 mg, 0.036 mmol, 23.90% yield). $^1$H NMR (400 MHz, DMSO-d$_6$) δ 11.49 (s, 1H), 8.28 (s, 1H), 8.26-8.20 (m, 2H), 7.48 (d, J=1.9 Hz, 1H), 7.29 (s, 2H), 6.84 (d, J=1.9 Hz, 1H), 6.30 (d, J=1.6 Hz, 1H), 5.58 (s, 2H), 4.50 (d, J=6.0 Hz, 2H), 3.12 (s, 2H), 2.58-2.52 (m, 4H), 1.76-1.68 (m, 4H). MS (ESI+) m/z 439.1 (M+H)$^+$.

Example 121

N-({7-[(6-amino-9H-purin-9-yl)methyl]-5-chloro-1H-indol-2-yl}methyl)-2-cyclopentylacetamide Example 121 was prepared according to the procedure used for the preparation of Example 105, substituting cyclopentylacetic acid for 4-methyl-pentanoic acid. $^1$H NMR (400 MHz, DMSO-d$_6$) δ 11.44 (d, J=2.0 Hz, 1H), 8.46 (s, 1H), 8.40-8.31 (m, 2H), 8.26 (bs, 2H), 7.50 (d, J=2.1 Hz, 1H), 6.83 (d, J=2.0 Hz, 1H), 6.32 (d, J=1.8 Hz, 1H), 5.65 (s, 2H), 4.46 (d, J=5.6 Hz, 2H), 2.25-2.12 (m, 3H), 1.71 (ddd, J=11.9, 8.1, 5.7 Hz, 2H), 1.65-1.41 (m, 4H), 1.15 (dq, J=11.5, 7.3 Hz, 2H). MS (APCI+) m/z 438.1 (M+H)$^+$.

Example 122

N-({7-[(6-amino-9H-purin-9-yl)methyl]-5-chloro-1H-indol-2-yl}methyl)-3-(pyrrolidin-1-yl)propanamide Example 122 was prepared according to the procedure used for the preparation of Example 105, substituting 3-(pyrrolidin-1-yl)propanoic acid hydrochloride for 4-methyl-pentanoic acid. $^1$H NMR (400 MHz, DMSO-d$_6$) δ 11.51 (s, 1H), 9.46 (s, 1H), 8.71 (t, J=5.6 Hz, 1H), 8.48 (s, 1H), 8.38 (s, 4H), 7.50 (d, J=2.0 Hz, 1H), 6.81 (d, J=2.1 Hz, 1H), 6.38 (d, J=1.8 Hz, 1H), 5.66 (s, 2H), 4.51 (d, J=5.6 Hz, 2H), 3.40 (s, 2H), 3.04 (s, 2H), 2.67 (t, J=7.3 Hz, 2H), 2.00 (d, J=7.2 Hz, 2H), 1.93-1.82 (m, 2H). MS (APCI+) m/z 453.1 (M+H)$^+$.

Example 123 tert-butyl (2S)-2-[({7-[(6-amino-9H-purin-9-yl)methyl]-5-chloro-1H-indol-2-yl}methyl)carbamoyl]pyrrolidine-1-carboxylate A mixture of Example 9b (100 mg, 0.305 mmol), (S)-1-(tert-butoxycarbonyl)pyrrolidine-2-carboxylic acid (65.7 mg, 0.305 mmol), 1H-benzo[d][1,2,3]triazol-1-ol hydrate (56.1 mg, 0.366 mmol), N$^1$-((ethylimino)methylene)-N$^3$,N$^3$-dimethylpropane-1,3-diamine hydrochloride (70.2 mg, 0.366 mmol), and N-ethyl-N-isopropylpropan-2-amine (160 μl, 0.915 mmol) in N,N-dimethylformamide (1.5 mL) was stirred overnight at ambient temperature. Water was added. The mixture was extracted with ethyl acetate (2×), washed sequentially with water (2×) and brine, dried over anhydrous magnesium sulfate, filtered, and concentrated to give the title compound (83 mg, 0.158 mmol, 51.8% yield). $^1$H NMR (400 MHz, DMSO-d$_6$, 90° C.) δ 11.20 (s, 1H), 8.24 (s, 1H), 8.18 (s, 1H), 8.08 (s, 1H), 7.42 (d, J=1.8 Hz, 1H), 6.94 (s, 2H), 6.89 (s, 1H), 6.33 (d, J=1.0 Hz, 1H), 5.58 (s, 2H), 4.52 (dd, J=15.6, 6.0 Hz, 1H), 4.42 (dd, J=15.6, 5.5 Hz, 1H), 4.15 (dd, J=8.4, 3.1 Hz, 1H), 3.37 (dtd, J=13.7, 10.3, 6.4 Hz, 2H), 2.11 (dt, J=18.3, 6.8 Hz, 1H), 1.92-1.72 (m, 3H), 1.33 (s, 9H). MS (ESI−) 523.2 (M−H)$^−$.

Example 124 tert-butyl (2R)-2-[({7-[(6-amino-9H-purin-9-yl)methyl]-5-chloro-1H-indol-2-yl}methyl)carbamoyl]pyrrolidine-1-carboxylate Example 124 was prepared according to the procedure used for the preparation of Example 123, substituting (R)-1-(tert-butoxycarbonyl)pyrrolidine-2-carboxylic acid for (S)-1-(tert-butoxycarbonyl)pyrrolidine-2-carboxylic acid. $^1$H NMR (400 MHz, DMSO-d$_6$, 90° C.) δ 11.24 (bs, 1H), 8.30 (s, 1H), 8.28 (s, 1H), 8.10 (bs, 1H), 7.45-7.40 (m, 1H), 6.89 (bs, 1H), 6.33 (d, J=1.8 Hz, 1H), 5.61 (s, 2H), 4.52 (dd, J=15.5, 6.0 Hz, 1H), 4.42 (dd, J=15.7, 5.6 Hz, 1H), 4.15 (dd, J=8.4, 3.3 Hz, 1H), 3.68-3.26 (m, 4H), 2.20-2.07 (m, 1H), 1.50-1.23 (m, 10H). MS (ESI−) m/z 523.2 (M−H)$^−$.

Example 125

9-({5-chloro-2-[(1,1-dioxidothiomorpholin-4-yl)methyl]-1H-indol-7-yl}methyl)-9H-purin-6-amine In a microwave vial was added Example 9b (30 mg, 0.092 mmol), THF (1 mL), N,N-diisopropylethylamine (0.064 mL, 0.366 mmol), and (vinylsulfonyl)ethene (32.4 mg, 0.275 mmol). The contents were heated at 130° C. for 20 minutes. An additional 0.5 mL DMSO was added to the mixture, filtered, and the filtrate was purified by reverse phase preparative HPLC to provide the title compound. Preparate HPLC method: Sample was purified by preparative HPLC on a Phenomenex Luna C8 (2) 5 μm 100 Å AXIA column (30 mm×150 mm). A gradient of acetonitrile (A) and 0.1% trifluoroacetic acid in water (B) was used, at a flow rate of 50 mL/min (0-0.5 minutes 10% A, 0.5-6.0 minutes linear gradient 10-100% A, 6.0-7.0 minutes 100% A, 7.0-8.0 minutes linear gradient 100-10% A). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/min. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export. $^1$H NMR (400 MHz, DMSO-d$_6$) δ 11.62 (s, 1H), 11.07-10.77 (m, 1H), 8.79 (d, J=48.0 Hz, 2H), 8.58 (s, 1H), 8.47 (s, 1H), 7.54 (d, J=1.9 Hz, 1H), 6.82 (d, J=1.9 Hz, 1H), 6.50 (d, J=1.7 Hz, 1H), 5.74 (s, 2H), 4.05 (s, 2H), 3.23 (d, J=5.0 Hz, 4H), 3.13 (dd, J=9.9, 3.1 Hz, 4H). MS (ESI) m/z: 446 (M+H)$^+$.

Example 126

N-({7-[(6-amino-9H-purin-9-yl)methyl]-5-chloro-1H-indol-2-yl}methyl)tetrahydro-2H-pyran-4-carboxamide A mixture of tetrahydro-2H-pyran-4-carboxylic acid (11.91 mg, 0.092 mmol), HATU (48.7 mg, 0.128 mmol) and N-ethyl-N-isopropylpropan-2-amine (48.0 μL, 0.275 mmol) in N,N-dimethylformamide (0.5 mL) was stirred for 10 minutes and then treated with Example 9b (30 mg, 0.092 mmol). The mixture was stirred at ambient temperature overnight. The mixture was diluted with 30 mL ethyl acetate, washed sequentially with water (2×) and brine, dried over anhydrous magnesium sulfate, and filtered. The filtrated was concentrated and the residue was purified by column chromatograph on flash silica gel (eluent: 1-10% methanol in dichloromethane) to give the title compound (22 mg, 0.050 mmol, 54.6% yield). $^1$H NMR (400 MHz, DMSO-d$_6$) δ 11.49 (s, 1H), 8.36 (t, J=5.5 Hz, 1H), 8.28 (s, 1H), 8.22 (s, 1H), 7.48 (d, J=1.9 Hz, 1H), 7.30 (s, 2H), 6.83 (d, J=1.9 Hz, 1H), 6.31 (d, J=1.6 Hz, 1H), 5.59 (s, 2H), 4.46 (d, J=5.5 Hz, 2H), 3.88 (dt, J=11.1, 3.2 Hz, 2H), 3.28-3.40 (m, 2H), 2.45 (dd, J=15.3, 7.7 Hz, 1H), 1.71-1.57 (m, 4H). MS (ESI+) m/z 440.1 (M+H)$^+$.

Example 127

N-({7-[(6-amino-9H-purin-9-yl)methyl]-5-chloro-1H-indol-2-yl}methyl)-2-(morpholin-4-yl)acetamide Example 127 was prepared according to the procedure used for the preparation of Example 105, substituting 2-morpholinoacetic acid hydrochloride for 4-methyl-pentanoic acid. $^1$H NMR (400 MHz, DMSO-d$_6$) δ 11.61 (s, 1H), 9.14 (t, J=5.6 Hz, 1H), 8.45 (s, 1H), 8.36 (s, 1H), 8.22 (bs, 2H), 7.51 (d, J=1.8 Hz, 1H), 6.82 (d, J=2.0 Hz, 1H), 6.39 (d, J=1.8 Hz, 1H), 5.65 (s, 2H), 4.57 (d, J=5.6 Hz, 2H), 4.04 (s, 2H), 3.86 (bs, 4H), 3.31 (bs, 4H). MS (APCI+) m/z 455.1 (M+H)$^+$.

Example 128

N-({7-[(6-amino-9H-purin-9-yl)methyl]-5-chloro-1H-indol-2-yl}methyl)cyclohexanecarboxamide Example 128 was prepared according to the procedure used for the preparation of Example 232, substituting cyclohexanecarboxylic acid for 2-(pyridin-4-yl)acetic acid. 1H NMR (400 MHz, DMSO-d$_6$) δ 0.79-1.46 (m, 6H), 1.57-1.79 (m, 5H), 2.20 (tt, J=11.6, 3.3 Hz, 2H), 4.44 (d, J=5.6 Hz, 2H), 5.65 (s, 2H), 6.30 (d, J=1.9 Hz, 1H), 6.82 (d, J=2.0 Hz, 1H), 7.49 (d, J=2.0 Hz, 1H), 8.06-8.41 (m, 4H), 8.45 (s, 1H), 11.43 (d, J=2.1 Hz, 1H). MS (APCI) m/z 438.2 [M+H]$^+$.

Example 129

N-({7-[(6-amino-9H-purin-9-yl)methyl]-5-chloro-1H-indol-2-yl}methyl)-1-methylcyclohexanecarboxamide Example 129 was prepared according to the procedure used for the preparation of Example 105, substituting 1-methyl-cyclohexanecarboxylic acid for 4-methyl-pentanoic acid. $^1$H NMR (400 MHz, DMSO-D$_2$O-d$_6$) δ 11.33 (s, 1H), 8.57 (s, 1H), 8.48 (s, 1H), 7.52 (d, J=1.9 Hz, 1H), 6.85 (d, J=1.9 Hz, 1H), 6.29 (s, 1H), 5.70 (s, 2H), 4.47 (s, 2H), 1.95 (dd, J=12.1, 5.5 Hz, 2H), 1.53-1.18 (m, 8H), 1.09 (s, 3H). MS (APCI+) m/z 452.1 (M+H)$^+$.

Example 130

N-({7-[(6-amino-9H-purin-9-yl)methyl]-5-chloro-1H-indol-2-yl}methyl)-4-methylcyclohexanecarboxamide Example 130 was prepared according to the procedure used for the preparation of Example 232, substituting 4-methylcyclohexanecarboxylic acid for 2-(pyridin-4-yl) acetic acid. $^1$H NMR (400 MHz, DMSO-d$_6$) δ 0.89 (dd, J=16.5, 6.7 Hz, 4H), 1.30-1.56 (m, 6H), 1.60-1.86 (m, 4H), 2.30 (dt, J=8.2, 4.0 Hz, 1H), 4.45 (t, J=5.9 Hz, 2H), 5.65 (s, 2H), 6.30 (d, J=1.8 Hz, 1H), 6.82 (d, J=2.0 Hz, 1H), 7.49 (d, J=2.0 Hz, 1H), 8.08-8.42 (m, 4H), 8.46 (s, 1H), 11.44 (dd, J=5.9, 2.0 Hz, 1H). MS (APCI) m/z 452.2 [M+H]$^+$.

Example 131

N-({7-[(6-amino-9H-purin-9-yl)methyl]-5-chloro-1H-indol-2-yl}methyl)-3-methylcyclohexanecarboxamide Example 131 was prepared according to the procedure used for the preparation of Example 105, substituting 3-methyl-cyclohexanecarboxylic acid for 4-methyl-pentanoic acid. $^1$H NMR (400 MHz, DMSO-d$_6$) δ 11.44 (s, 1H), 8.45 (s, 1H), 8.37 (s, 1H), 8.32-8.13 (m, 3H), 7.49 (d, J=1.9 Hz, 1H), 6.82 (d, J=1.9 Hz, 1H), 6.30 (s, 1H), 5.65 (s, 2H), 4.44 (dd, J=5.7, 2.9 Hz, 2H), 2.28-2.16 (m, 1H), 1.94-1.68 (m, 3H), 1.65-1.45 (m, 2H), 1.43-1.12 (m, 2H), 1.04 (q, J=12.2 Hz, 1H), 0.90 (dd, J=13.1, 6.7 Hz, 4H). MS (APCI+) m/z 452.1 (M+H)$^+$.

Example 132

N-({7-[(6-amino-9H-purin-9-yl)methyl]-5-chloro-1H-indol-2-yl}methyl)-2-methylcyclohexanecarboxamide Example 132 was prepared according to the procedure used for the preparation of Example 232, substituting 2-methylcyclohexanecarboxylic acid for 2-(pyridin-4-yl) acetic acid. $^1$H NMR (400 MHz, DMSO-d$_6$) δ 0.73-1.05 (m, 3H), 1.07-1.93 (m, 9H), 2.03 (d, J=8.6 Hz, 1H), 2.39 (dt, J=8.9, 4.2 Hz, 1H), 4.38-4.54 (m, 2H), 5.67 (s, 2H), 6.30 (d, J=1.9 Hz, 1H), 6.83 (d, J=2.0 Hz, 1H), 7.50 (d, J=2.0 Hz, 1H), 8.22 (t, J=5.8 Hz, 1H), 8.46 (d, J=31.2 Hz, 4H), 11.42 (d, J=2.2 Hz, 1H). MS (APCI) m/z 452.2 [M+H]$^+$.

Example 133

N-({7-[(6-amino-9H-purin-9-yl)methyl]-5-chloro-1H-indol-2-yl}methyl)-2-cyclohexylacetamide Example 133 was prepared according to the procedure used for the preparation of Example 232, substituting 2-cyclohexylacetic acid for 2-(pyridin-4-yl)acetic acid. $^1$H NMR (400 MHz, DMSO-d$_6$) δ 0.81-1.01 (m, 2H), 1.05-1.28 (m, 4H), 1.56-1.74 (m, 7H), 2.05 (d, J=6.8 Hz, 2H), 4.46 (d, J=5.5 Hz, 2H), 5.63 (s, 2H), 6.31 (d, J=1.9 Hz, 1H), 6.83 (d, J=2.0 Hz, 1H), 7.49 (d, J=2.0 Hz, 1H), 7.92 (s, 2H), 8.28-8.44 (m, 3H), 11.46 (d, J=2.2 Hz, 1H). MS (APCI) m/z 452.2 [M+H]$^+$.

Example 134

N-({7-[(6-amino-9H-purin-9-yl)methyl]-5-chloro-1H-indol-2-yl}methyl)-4-methoxycyclohexanecarboxamide Example 134 was prepared according to the procedure used for the preparation of Example 105, substituting 4-methoxy-cyclohexanecarboxylic acid for 4-methyl-pentanoic acid. $^1$H NMR (400 MHz, DMSO-d$_6$) δ 11.57-11.22 (m, 1H), 8.72 (bs, 2H), 8.54 (d, J=1.9 Hz, 1H), 8.44 (s, 1H), 8.37-8.24 (m, 1H), 7.50 (d, J=2.1 Hz, 1H), 6.81 (dd, J=3.4, 2.0 Hz, 1H), 6.30 (d, J=2.1 Hz, 1H), 5.69 (s, 2H), 4.44 (d, J=5.5 Hz, 2H), 3.38 (dq, J=6.8, 3.2 Hz, 1H), 3.22 (d, J=11.3 Hz, 3H), 2.30-2.11 (m, 1H), 2.09-1.80 (m, 2H), 1.81-1.62 (m, 2H), 1.55-1.00 (m, 4H). MS (APCI+) m/z 468.0 (M+H)$^+$.

Example 135

N-({7-[(6-amino-9H-purin-9-yl)methyl]-5-chloro-1H-indol-2-yl}methyl)-3-(piperidin-1-yl)propanamide Example 135 was prepared according to the procedure used for the preparation of Example 232, substituting 3-(piperidin-1-yl)propanoic acid for 2-(pyridin-4-yl)acetic acid. $^1$H NMR (400 MHz, DMSO-d$_6$) δ 1.24-1.87 (m, 7H), 2.68 (t, J=7.4 Hz, 2H), 2.84-2.99 (m, 4H), 3.03-3.34 (m, 2H), 4.50 (d, J=5.6 Hz, 2H), 5.63 (s, 2H), 6.36 (d, J=1.9 Hz, 1H), 6.78-6.88 (m, 1H), 7.49 (d, J=1.9 Hz, 1H), 7.92 (s, 2H), 8.36 (d, J=34.8 Hz, 2H), 8.71 (t, J=5.6 Hz, 1H), 9.09 (s, 1H), 11.53 (d, J=2.2 Hz, 1H). MS (APCI) m/z 467.2 [M+H]$^+$.

Example 136

N-({7-[(6-amino-9H-purin-9-yl)methyl]-5-chloro-1H-indol-2-yl}methyl)tricyclo[3.3.1.1$^{3,7}$]decane-1-carboxamide Example 136 was prepared according to the procedure used for the preparation of Example 126, substituting adamantane-1-carboxylic acid for tetrahydro-2H-pyran-4-carboxylic acid. $^1$H NMR (400 MHz, DMSO-d$_6$) δ 11.44 (s, 1H), 8.28 (s, 1H), 8.23 (s, 1H), 7.98 (t, J=5.8 Hz, 1H), 7.47 (d, J=1.7 Hz, 1H), 7.29 (s, 2H), 6.82 (d, J=1.8 Hz, 1H), 6.24 (s, 1H), 5.58 (s, 2H), 4.45 (d, J=5.7 Hz, 2H), 1.99 (s, 3H), 1.84 (d, J=2.5 Hz, 6H), 1.76-1.56 (m, 6H). MS (ESI+) m/z 490.1 (M+H)$^+$.

Example 137

N-({7-[(6-amino-9H-purin-9-yl)methyl]-5-chloro-1H-indol-2-yl}methyl)-1,2-thiazole-5-carboxamide Example 137 was prepared according to the procedure used for the preparation of Example 139, substituting isothiazole-5-carboxylic acid for isothiazole-4-carboxylic acid. $^1$H NMR (400 MHz, DMSO-d$_6$) δ 4.71 (s, 2H), 5.63 (s, 2H), 6.46 (s, 1H), 6.86 (d, J=2.0 Hz, 1H), 7.53 (d, J=2.0 Hz, 1H), 7.96 (d, J=1.8 Hz, 1H), 8.20 (s, 1H), 8.34 (s, 1H), 8.70 (d, J=1.8 Hz, 1H). MS (APCI) m/z 439.1 [M+H]$^+$.

Example 138

N-({7-[(6-amino-9H-purin-9-yl)methyl]-5-chloro-1H-indol-2-yl}methyl)-1,3-thiazole-5-carboxamide Example 138 was prepared according to the procedure used for the preparation of Example 105, substituting thiazole-5-carboxylic acid for 4-methyl-pentanoic acid. $^1$H NMR (400 MHz, DMSO-d$_6$) δ 11.53 (s, 1H), 9.30 (t, J=5.6 Hz, 1H), 9.26 (s, 1H), 8.58-8.46 (m, 4H), 8.37 (s, 1H), 7.51 (d, J=2.0 Hz, 1H), 6.82 (d, J=2.0 Hz, 1H), 6.42 (d, J=1.9 Hz, 1H), 5.69 (s, 2H), 4.68 (d, J=5.5 Hz, 2H). MS (APCI+) m/z 439.0 (M+H)$^+$.

Example 139

N-({7-[(6-amino-9H-purin-9-yl)methyl]-5-chloro-1H-indol-2-yl}methyl)-1,2-thiazole-4-carboxamide A solution of Example 9b (0.19 M in N,N-dimethylacetamide, 237 µL, 0.045 mmol), N,N-diisopropylethylamine (0.21 M in N,N-dimethylacetamide, 262 µL, 0.055 mmol), HATU (0.21 M in N,N-dimethylacetamide, 238 µL, 0.05 mmol), and isothiazole-4-carboxylic acid (0.4M in N,N-dimethylacetamide, 125 µL, 0.05 mmol) were aspirated from their respective source vials, mixed through a perfluoroalkoxy alkanes mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 µL min$^{-1}$ (10 minute residence time). Upon exiting the reactor, the reaction was loaded directly into an injection loop and purified using preparative HPLC to yield the title compound (9.95 mg, 49.50% yield). Samples were purified by preparative HPLC on a Phenomenex Luna C8 (2) 5 µm 100 Å AXIA column (50 mm×21.2 mm). A gradient of acetonitrile (A) and 0.1% trifluoroacetic acid in water (B) was used, at a flow rate of 30 mL/min (0-0.5 minutes 5% A, 0.5-6.5 minutes linear gradient 5-60% A, 6.5-7.0 minutes linear gradient 60-100% A, 7.0-8.9 minutes 100% A, 8.9-9.0 minutes linear gradient 100-5% A, 9.0-10 minutes 5% A). A sample volume of 1.0 mL was injected directly from the flow reactor stream to the HPLC system. A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0. $^1$H NMR (400 MHz, DMSO-d$_6$) δ 4.69 (d, J=3.9 Hz, 2H), 5.62 (s, 2H), 6.43 (s, 1H), 6.84 (d, J=2.0 Hz, 1H), 7.51 (d, J=2.0 Hz, 1H), 8.18 (s, 1H), 8.32 (s, 1H), 8.96 (s, 1H), 9.59 (s, 1H). MS (APCI) m/z 439.1 [M+H]$^+$.

Example 140

N-({7-[(6-amino-9H-purin-9-yl)methyl]-5-chloro-1H-indol-2-yl}methyl)-1,3-thiazole-4-carboxamide Example 140 was prepared according to the procedure used for the preparation of Example 105, substituting thiazole-4-carboxylic acid for 4-methyl-pentanoic acid. $^1$H NMR (400 MHz, DMSO-d$_6$) δ 11.46 (s, 1H), 9.22 (d, J=1.9 Hz, 1H), 9.02 (t, J=6.2 Hz, 1H), 8.49 (s, 1H), 8.42-8.34 (m, 4H), 7.49 (d, J=2.0 Hz, 1H), 6.82 (d, J=2.1 Hz, 1H), 6.35 (d, J=1.8 Hz, 1H), 5.67 (s, 2H), 4.68 (d, J=6.1 Hz, 2H). MS (APCI+) m/z 439.0 (M+H)$^+$.

Example 141

N-({7-[(6-amino-9H-purin-9-yl)methyl]-5-chloro-1H-indol-2-yl}methyl)-1,2-oxazole-4-carboxamide Example 141 was prepared according to the procedure used for the preparation of Example 139, substituting isoxazole-4-carboxylic acid for isothiazole-4-carboxylic acid. $^1$H NMR (400 MHz, DMSO-d$_6$) δ 4.66 (d, J=4.1 Hz, 2H), 5.62 (s, 2H), 6.43 (s, 1H), 6.84 (d, J=2.0 Hz, 1H), 7.45-7.55 (m, 1H), 8.20 (s, 1H), 8.33 (s, 1H), 8.98 (s, 1H), 9.43 (d, J=0.7 Hz, 1H). MS (APCI) m/z 423.1 [M+H]$^+$.

Example 142

N-({7-[(6-amino-9H-purin-9-yl)methyl]-5-chloro-1H-indol-2-yl}methyl)-1H-pyrazole-5-carboxamide Example 142 was prepared according to the procedure used for the preparation of Example 105, substituting 2H-pyrazole-3-carboxylic acid for 4-methyl-pentanoic acid. $^1$H NMR (400 MHz, DMSO-d$_6$) δ 11.47 (s, 1H), 8.71 (s, 1H), 8.45 (s, 1H), 8.33 (s, 1H), 8.15 (bs, 3H), 7.80 (s, 1H), 7.49 (d, J=2.0 Hz, 1H), 6.82 (d, J=2.0 Hz, 1H), 6.73 (d, J=2.4 Hz, 1H), 6.35 (d, J=1.8 Hz, 1H), 5.65 (s, 2H), 4.64 (d, J=6.1 Hz, 2H). MS (APCI+) m/z 422.1 (M+H)$^+$.

Example 143

N-({7-[(6-amino-9H-purin-9-yl)methyl]-5-chloro-1H-indol-2-yl}methyl)-1H-pyrazole-4-carboxamide Example 143 was prepared according to the procedure used for the preparation of Example 105, substituting 1H-pyrazole-4-carboxylic acid for 4-methyl-pentanoic acid. $^1$H NMR (400 MHz, DMSO-d$_6$) δ 11.45 (d, J=2.2 Hz, 1H), 9.49-8.25 (m, 6H), 8.10 (s, 2H), 7.50 (d, J=2.0 Hz, 1H), 6.83 (d, J=2.1 Hz, 1H), 6.38 (d, J=1.8 Hz, 1H), 5.71 (s, 2H), 4.62 (d, J=5.7 Hz, 2H). MS (APCI+) m/z 422.0 (M+H)$^+$.

Example 144

N-({7-[(6-amino-9H-purin-9-yl)methyl]-5-chloro-1H-indol-2-yl}methyl)thiophene-2-carboxamide Example 144 was prepared according to the procedure used for the preparation of Example 139, substituting thiophene-2-carboxylic acid for isothiazole-4-carboxylic acid. $^1$H NMR (400 MHz, DMSO-d$_6$) δ 4.66 (s, 2H), 5.61 (s, 2H), 6.40 (s, 1H), 6.85 (d, J=2.0 Hz, 1H), 7.19 (dd, J=5.0, 3.8 Hz, 1H), 7.50 (d, J=1.9 Hz, 1H), 7.69-7.88 (m, 2H), 8.18 (s, 1H), 8.33 (s, 1H). MS (APCI) m/z 438.1 [M+H]$^+$.

Example 145

N-({7-[(6-amino-9H-purin-9-yl)methyl]-5-chloro-1H-indol-2-yl}methyl)thiophene-3-carboxamide Example 145 was prepared according to the procedure used for the preparation of Example 139, substituting thiophene-3-carboxylic acid for isothiazole-4-carboxylic acid. $^1$H NMR (400 MHz, DMSO-d$_6$) δ 4.65 (s, 2H), 5.61 (s, 2H), 6.39 (s, 1H), 6.85 (d, J=2.0 Hz, 1H), 7.44-7.54 (m, 1H), 7.54-7.67 (m, 2H), 8.08-8.25 (m, 2H), 8.33 (s, 1H). MS (APCI) m/z 438.1 [M+H]$^+$.

Example 146

N-({7-[(6-amino-9H-purin-9-yl)methyl]-5-chloro-1H-indol-2-yl}methyl)-1H-pyrrole-2-carboxamide Example 146 was prepared according to the procedure used for the preparation of Example 105, substituting 1H-pyrrole-2-carboxylic acid for 4-methyl-pentanoic acid. $^1$H NMR (400 MHz, DMSO-d$_6$) δ 11.49 (s, 1H), 8.55 (t, J=5.8 Hz, 1H), 8.47 (s, 1H), 8.33 (s, 1H), 8.19 (bs, 3H), 7.49 (d, J=2.0 Hz, 1H), 6.93-6.88 (m, 1H), 6.88-6.84 (m, 1H), 6.83 (d, J=2.0 Hz, 1H), 6.36 (d, J=1.8 Hz, 1H), 6.15-6.08 (m, 1H), 5.66 (s, 2H), 4.64 (d, J=5.7 Hz, 2H). MS (APCI+) m/z 421.0 (M+H)$^+$.

Example 147

N-({7-[(6-amino-9H-purin-9-yl)methyl]-5-chloro-1H-indol-2-yl}methyl)-5-methyl-1,3-thiazole-4-carboxamide Example 147 was prepared according to the procedure used for the preparation of Example 139, substituting 5-methylthiazole-4-carboxylic acid for isothiazole-4-carboxylic acid. $^1$H NMR (400 MHz, DMSO-d$_6$) δ 2.80 (s, 3H), 4.67 (s, 2H), 5.62 (s, 2H), 6.39 (s, 1H), 6.85 (d, J=2.0 Hz, 1H), 7.51 (d, J=2.0 Hz, 1H), 8.20 (s, 1H), 8.34 (s, 1H), 8.93 (s, 1H). MS (APCI) m/z 452.1 [M+H]$^+$.

Example 148

N-({7-[(6-amino-9H-purin-9-yl)methyl]-5-chloro-1H-indol-2-yl}methyl)-4-methyl-1,3-thiazole-5-carboxamide Example 148 was prepared according to the procedure used for the preparation of Example 139, substituting 4-methylthiazole-5-carboxylic acid for isothiazole-4-carboxylic acid. $^1$H NMR (400 MHz, DMSO-d$_6$) δ 2.63 (s, 3H), 4.64 (s, 2H), 5.61 (s, 2H), 6.40 (s, 1H), 6.86 (d, J=1.9 Hz, 1H), 7.51 (d, J=2.0 Hz, 1H), 8.20 (s, 1H), 8.33 (s, 1H), 9.06 (s, 1H). MS (APCI) m/z 453.1 [M+H]$^+$.

Example 149

N-({7-[(6-amino-9H-purin-9-yl)methyl]-5-chloro-1H-indol-2-yl}methyl)-5-methyl-1,2-oxazole-4-carboxamide Example 149 was prepared according to the procedure used for the preparation of Example 139, substituting 5-methylisoxazole-4-carboxylic acid for isothiazole-4-carboxylic acid. ¹H NMR (400 MHz, DMSO-d₆) δ 2.68 (s, 3H), 3.18 (s, 1H), 4.64 (s, 2H), 5.61 (s, 2H), 6.42 (s, 1H), 6.85 (d, J=1.9 Hz, 1H), 7.51 (d, J=1.9 Hz, 1H), 8.19 (s, 1H), 8.32 (s, 1H), 8.90 (s, 1H). MS (APCI) m/z 437.1 [M+H]⁺.

Example 150

N-({7-[(6-amino-9H-purin-9-yl)methyl]-5-chloro-1H-indol-2-yl}methyl)-3-methyl-1,2-oxazole-4-carboxamide Example 150 was prepared according to the procedure used for the preparation of Example 139, substituting 3-methylisoxazole-4-carboxylic acid for isothiazole-4-carboxylic acid. ¹H NMR (400 MHz, DMSO-d₆) δ 2.45 (s, 4H), 3.19 (s, 2H), 4.65 (s, 2H), 5.63 (s, 2H), 6.44 (s, 1H), 6.86 (d, J=1.9 Hz, 1H), 7.52 (d, J=2.0 Hz, 1H), 8.21 (s, 1H), 8.34 (s, 1H), 9.28 (s, 1H). MS (APCI) m/z 437.1 [M+H]⁺.

Example 151

N-({7-[(6-amino-9H-purin-9-yl)methyl]-5-chloro-1H-indol-2-yl}methyl)-1-methyl-1H-pyrazole-3-carboxamide Example 151 was prepared according to the procedure used for the preparation of Example 139, substituting 1-methyl-1H-pyrazole-3-carboxylic acid for isothiazole-4-carboxylic acid. 1H NMR (400 MHz, DMSO-d₆) δ 3.93 (s, 3H), 4.63 (s, 2H), 5.60 (s, 2H), 6.36 (s, 1H), 6.70 (d, J=2.3 Hz, 1H), 6.84 (d, J=2.0 Hz, 1H), 7.49 (d, J=2.0 Hz, 1H), 7.78 (d, J=2.3 Hz, 1H), 8.20 (s, 1H), 8.33 (s, 1H). MS (APCI) m/z 436.1 [M+H]⁺.

Example 152

N-({7-[(6-amino-9H-purin-9-yl)methyl]-5-chloro-1H-indol-2-yl}methyl)-1-methyl-1H-pyrazole-5-carboxamide Example 152 was prepared according to the procedure used for the preparation of Example 139, substituting 1-methyl-1H-pyrazole-5-carboxylic acid for isothiazole-4-carboxylic acid. ¹H NMR (400 MHz, DMSO-d₆) δ 4.09 (s, 3H), 4.64 (s, 2H), 5.63 (s, 2H), 6.40 (s, 1H), 6.85 (d, J=2.0 Hz, 1H), 6.92 (d, J=2.1 Hz, 1H), 7.51 (d, J=2.0 Hz, 2H), 8.21 (s, 1H), 8.36 (s, 1H). MS (APCI) m/z 436.1 [M+H]⁺.

Example 153

N-({7-[(6-amino-9H-purin-9-yl)methyl]-5-chloro-1H-indol-2-yl}methyl)-1-methyl-1H-imidazole-5-carboxamide Example 153 was prepared according to the procedure used for the preparation of Example 139, substituting 1-methyl-1H-imidazole-5-carboxylic acid for isothiazole-4-carboxylic acid. ¹H NMR (400 MHz, DMSO-d₆) δ 3.87 (s, 3H), 4.62 (s, 2H), 5.62 (s, 2H), 6.39 (s, 1H), 6.85 (d, J=2.0 Hz, 1H), 7.50 (d, J=1.9 Hz, 1H), 8.18 (s, 1H), 8.33 (s, 1H). MS (APCI) m/z 436.1 [M+H]⁺.

Example 154

N-({7-[(6-amino-9H-purin-9-yl)methyl]-5-chloro-1H-indol-2-yl}methyl)-1-methyl-1H-imidazole-2-carboxamide Example 154 was prepared according to the procedure used for the preparation of Example 139, substituting 1-methyl-1H-imidazole-2-carboxylic acid for isothiazole-4-carboxylic acid. 1H NMR (400 MHz, DMSO-d₆) δ 3.97 (s, 3H), 4.63 (s, 2H), 5.61 (s, 2H), 6.38 (s, 1H), 6.83 (d, J=2.0 Hz, 1H), 7.04 (d, J=1.1 Hz, 1H), 7.36 (d, J=1.0 Hz, 1H), 7.50 (d, J=2.0 Hz, 1H), 8.19 (s, 1H), 8.34 (s, 1H). MS (APCI) m/z 436.1 [M+H]⁺.

Example 155

5-amino-N-({7-[(6-amino-9H-purin-9-yl)methyl]-5-chloro-1H-indol-2-yl}methyl)-3-methyl-1,2-oxazole-4-carboxamide Example 155 was prepared according to the procedure used for the preparation of Example 190, substituting 5-amino-3-methylisoxazole-4-carboxylic acid for 5-cyclopropyl-3-methylisoxazole-4-carboxylic acid. 1H NMR (400 MHz, DMSO-d₆) δ 2.33 (s, 3H), 4.59 (s, 2H), 5.61 (s, 2H), 6.37 (s, 1H), 6.84 (d, J=1.9 Hz, 1H), 7.49 (d, J=2.0 Hz, 1H), 8.19 (s, 1H), 8.32 (s, 1H). MS (APCI) m/z 452.1 [M+H]⁺.

Example 156

N-({7-[(6-amino-9H-purin-9-yl)methyl]-5-chloro-1H-indol-2-yl}methyl)-2-methylthiophene-3-carboxamide Example 156 was prepared according to the procedure used for the preparation of Example 139, substituting 2-methylthiophene-3-carboxylic acid for isothiazole-4-carboxylic acid. ¹H NMR (400 MHz, DMSO-d₆) δ 2.66 (s, 3H), 4.63 (s, 2H), 5.61 (s, 2H), 6.38 (s, 1H), 6.85 (d, J=2.0 Hz, 1H), 7.31 (d, J=5.4 Hz, 1H), 7.38 (d, J=5.4 Hz, 1H), 7.50 (d, J=2.0 Hz, 1H), 8.18 (s, 1H), 8.33 (s, 1H). MS (APCI) m/z 452.1 [M+H]⁺.

Example 157

N-({7-[(6-amino-9H-purin-9-yl)methyl]-5-chloro-1H-indol-2-yl}methyl)-3-methylthiophene-2-carboxamide Example 157 was prepared according to the procedure used for the preparation of Example 139, substituting 3-methylthiophene-2-carboxylic acid for isothiazole-4-carboxylic acid. ¹H NMR (400 MHz, DMSO-d₆) δ 2.46 (s, 3H), 4.63 (s, 2H), 5.61 (s, 2H), 6.39 (s, 1H), 6.85 (d, J=2.0 Hz, 1H), 7.01 (d, J=5.0 Hz, 1H), 7.51 (d, J=2.0 Hz, 1H), 7.60 (d, J=5.0 Hz, 1H), 8.19 (s, 1H), 8.33 (s, 1H). MS (APCI) m/z 452.1 [M+H]⁺.

Example 158

N-({7-[(6-amino-9H-purin-9-yl)methyl]-5-chloro-1H-indol-2-yl}methyl)-4-methoxythiophene-3-carboxamide Example 158 was prepared according to the procedure used for the preparation of Example 139, substituting 4-methoxythiophene-3-carboxylic acid for isothiazole-4-carboxylic acid. 1H NMR (400 MHz, DMSO-$d_6$) δ 3.92 (s, 3H), 4.69 (s, 2H), 5.62 (s, 2H), 6.39 (s, 1H), 6.83 (dd, J=19.9, 2.8 Hz, 2H), 7.52 (d, J=2.0 Hz, 1H), 8.11 (d, J=3.6 Hz, 1H), 8.20 (s, 1H), 8.34 (s, 1H). MS (APCI) m/z 468.1 [M+H]$^+$.

Example 159

N-({7-[(6-amino-9H-purin-9-yl)methyl]-5-chloro-1H-indol-2-yl}methyl)-3-methoxythiophene-2-carboxamide Example 159 was prepared according to the procedure used for the preparation of Example 139, substituting 3-methoxythiophene-2-carboxylic acid for isothiazole-4-carboxylic acid. $^1$H NMR (400 MHz, DMSO-$d_6$) δ 4.01 (s, 3H), 4.65-4.75 (m, 2H), 5.62 (s, 2H), 6.39 (s, 1H), 6.86 (d, J=2.0 Hz, 1H), 7.16 (d, J=5.6 Hz, 1H), 7.52 (d, J=2.0 Hz, 1H), 7.75 (d, J=5.5 Hz, 1H), 8.05-8.24 (m, 2H), 8.34 (s, 1H). MS (APCI) m/z 468.1 [M+H]$^+$.

Example 160

N-({7-[(6-amino-9H-purin-9-yl)methyl]-5-chloro-1H-indol-2-yl}methyl)-1-methyl-1H-pyrrole-2-carboxamide Example 160 was prepared according to the procedure used for the preparation of Example 232, substituting 1-methyl-1H-pyrrole-2-carboxylic acid for 2-(pyridin-4-yl)acetic acid. $^1$H NMR (400 MHz, DMSO-$d_6$) δ 3.88 (s, 4H), 4.59 (d, J=5.8 Hz, 2H), 5.66 (s, 2H), 6.04 (dd, J=3.9, 2.5 Hz, 1H), 6.35 (d, J=1.8 Hz, 1H), 6.79-6.98 (m, 3H), 7.49 (d, J=2.0 Hz, 1H), 8.31 (s, 3H), 8.42-8.61 (m, 2H), 11.45 (d, J=2.0 Hz, 1H). MS (APCI) m/z 435.1 [M+H]$^+$.

Example 161

N-({7-[(6-amino-9H-purin-9-yl)methyl]-5-chloro-1H-indol-2-yl}methyl)-2,4-dimethyl-1,3-thiazole-5-carboxamide Example 161 was prepared according to the procedure used for the preparation of Example 139, substituting 2,4-dimethylthiazole-5-carboxylic acid for isothiazole-4-carboxylic acid. $^1$H NMR (400 MHz, DMSO-$d_6$) δ 2.54 (d, J=1.4 Hz, 4H), 4.61 (s, 2H), 5.61 (s, 2H), 6.38 (s, 1H), 6.85 (d, J=2.0 Hz, 1H), 7.51 (d, J=1.9 Hz, 1H), 8.20 (s, 1H), 8.32 (s, 1H). MS (APCI) m/z 467.1 [M+H]$^+$.

Example 162

N-({7-[(6-amino-9H-purin-9-yl)methyl]-5-chloro-1H-indol-2-yl}methyl)-3,5-dimethyl-1,2-oxazole-4-carboxamide Example 162 was prepared according to the procedure used for the preparation of Example 105, substituting 3,5-dimethyl-isoxazole-4-carboxylic acid for 4-methyl-pentanoic acid. $^1$H NMR (400 MHz, DMSO-$D_2$O-$d_6$) δ 11.48 (s, 1H), 8.57 (s, 1H), 8.45 (s, 1H), 7.54 (d, J=2.0 Hz, 1H), 6.85 (d, J=1.9 Hz, 1H), 6.43 (s, 1H), 5.72 (s, 2H), 4.64 (s, 2H), 2.54 (s, 3H), 2.33 (s, 3H). MS (APCI+) m/z 451.0 (M+H)$^+$.

Example 163

N-({7-[(6-amino-9H-purin-9-yl)methyl]-5-(1,2,5,6-tetrahydropyridin-3-yl)-1H-indol-2-yl}methyl)-3,5-dimethyl-1,2-oxazole-4-carboxamide To a mixture of Example 162 (200 mg, 0.444 mmol), tert-butyl 3-(4,4,5,5-tetramethyl-1,3,2-dioxaborolan-2-yl)-5,6-dihydropyridine-1(2H)-carboxylate (165 mg, 0.532 mmol), potassium phosphate tribasic (0.094 g, 0.444 mmol) in 1,4-dioxane (2 mL) and water (0.111 mL) was added tris(dibenzylideneacetone)dipalladium(0) (0.0406 g, 0.044 mmol) and tricyclohexylphosphine (0.009 g, 0.032 mmol). The vessel was sealed and heated at 125° C. for 30 minutes in a microwave (Biotage, Initiator). The cooled solution was filtered through Celite® and the filtrated concentrated under reduced pressure. The crude intermediate was added to a silica gel column and was eluted with methanol/dichloromethane (0-20%). The intermediate was treated with 20% trifluoroacetic acid in dichloromethane (3 mL) for 3 days with stirring at room temperature. The mixture was concentrated to dryness and purified by preparative HPLC (Waters Sunfire C8, 15-45% acetonitrile/water; 1% TFA) to give the title compound (0.023 g, 8.48%). $^1$H NMR (400 MHz, CD$_3$OD) δ 8.43 (s, 1H), 8.23 (s, 1H), 7.55 (d, J=1.6 Hz, 1H), 7.25 (d, J=1.6 Hz, 1H), 6.47 (s, 1H), 5.71 (s, 2H), 4.68 (d, J=4.3 Hz, 2H), 4.09 (d, J=2.4 Hz, 2H), 2.58 (d, J=4.9 Hz, 2H), 2.51 (s, 3H), 2.34 (s, 3H); MS m/z: 363 [M-adinine]$^+$.

Example 164

N-({7-[(6-amino-9H-purin-9-yl)methyl]-5-phenyl-1H-indol-2-yl}methyl)-3, 5-dimethyl-1,2-oxazole-4-carboxamide Example 164 was prepared according to the procedure used for the preparation of Example 177, substituting phenylboronic acid for N-dimethyl-3-(4,4,5,5-tetramethyl-1,3,2-dioxaborolan-2-yl)benzamide. $^1$H NMR (DMSO/D$_2$O-$d_6$) δ 2.32 (s, 3H), 4.65 (s, 2H), 5.68 (s, 2H), 7.27 (t, J=7.0 Hz, 1H), 7.31-7.33 (m, 1H), 7.37-7.44 (m, 2H), 7.51-7.62 (m, 2H), 7.68-7.76 (m, 1H), 8.27 (s, 2H); (ESI) m/z 493 (M+H)$^+$.

Example 165

N-({7-[(6-amino-9H-purin-9-yl)methyl]-5-(4-fluorophenyl)-1H-indol-2-yl}methyl)-3,5-dimethyl-1,2-oxazole-4-carboxamide Example 165 was prepared according to the procedure used for the preparation of Example 177, substituting (4-fluorophenyl)boronic acid for N,N-dimethyl-3-(4,4,5,5-tetramethyl-1,3,2-dioxaborolan-2-yl)benzamide. $^1$H NMR (DMSO/D$_2$O-$d_6$) δ 2.32 (s, 3H), 4.65 (s, 2H), 5.67 (s, 2H), 7.13-7.26 (m, 2H), 7.26-7.35 (m, 1H), 7.53-7.64 (m, 2H), 7.64-7.74 (m, 1H), 8.23-8.32 (m, 2H); (ESI) m/z 511 (M+H)$^+$.

Example 166

N-({7-[(6-amino-9H-purin-9-yl)methyl]-5-(4-sulfamoylphenyl)-1H-indol-2-yl}methyl)-3,5-dimethyl-1,2-oxazole-4-carboxamide Example 166 was prepared according to the procedure used for the preparation of Example 180, substituting 4-(4, 4,5,5-tetramethyl-1,3,2-dioxaborolan-2-yl)benzenesulfonamide for (3-(morpholine-4-carbonyl)phenyl)boronic acid. $^1$H NMR (DMSO/D$_2$O-d$_6$) δ 2.33 (s, 3H), 4.66 (s, 2H), 5.67 (s, 2H), 6.50 (s, 1H), 7.41 (s, 1H), 7.70-7.77 (m, 2H), 7.79-7.82 (m, 1H), 7.83-7.92 (m, 2H), 8.24 (s, 2H) (ESI) m/z 572 (M+H)$^+$.

Example 167

N-({7-[(6-amino-9H-purin-9-yl)methyl]-5-(4-methylphenyl)-1H-indol-2-yl}methyl)-3,5-dimethyl-1,2-oxazole-4-carboxamide Example 167 was prepared according to the procedure used for the preparation of Example 177, substituting p-tolylboronic acid for N,N-dimethyl-3-(4,4,5,5-tetramethyl-1,3,2-dioxaborolan-2-yl)benzamide. $^1$H NMR (DMSO/D$_2$O-d$_6$) δ 2.30-2.33 (m, 6H), 4.64 (s, 2H), 5.66 (s, 2H), 6.45 (s, 1H), 7.16-7.26 (m, 2H), 7.26-7.34 (m, 1H), 7.42-7.47 (m, 2H), 7.67-7.69 (m, 1H), 8.23-8.26 (m, 2H). (ESI) m/z 507 (M+H)$^+$.

Example 168

N-({7-[(6-amino-9H-purin-9-yl)methyl]-5-(4-methoxyphenyl)-1H-indol-2-yl}methyl)-3,5-dimethyl-1,2-oxazole-4-carboxamide Example 168 was prepared according to the procedure used for the preparation of Example 177, substituting (4-methoxyphenyl)boronic acid for N,N-dimethyl-3-(4,4,5,5-tetramethyl-1,3,2-dioxaborolan-2-yl)benzamide. $^1$H NMR (DMSO/D$_2$O-d$_6$) δ 2.32 (s, 3H), 3.78 (s, 3H), 4.64 (s, 2H), 5.66 (s, 2H), 6.95-6.99 (m, 2H), 7.23-7.32 (m, 1H), 7.43-7.51 (m, 2H), 7.60-7.69 (m, 1H), 8.21-8.28 (m, 2H); (ESI) m/z 523 (M+H)$^+$.

Example 169

N-({7-[(6-amino-9H-purin-9-yl)methyl]-5-(3-methoxyphenyl)-1H-indol-2-yl}methyl)-3,5-dimethyl-1,2-oxazole-4-carboxamide Example 169 was prepared according to the procedure used for the preparation of Example 177, substituting (3-methoxyphenyl)boronic acid for N,N-dimethyl-3-(4,4,5,5-tetramethyl-1,3,2-dioxaborolan-2-yl)benzamide. $^1$H NMR (DMSO/D$_2$O-d$_6$) δ 2.32 (s, 3H), 3.80 (s, 3H), 4.65 (s, 2H), 5.68 (s, 2H), 6.80-6.91 (m, 1H), 7.06-7.11 (m, 1H), 7.11-7.20 (m, 1H), 7.26-7.38 (m, 2H), 7.70-7.73 (m, 1H), 8.24-8.34 (m, 2H); (ESI) m/z 523 (M+H)$^+$.

Example 170

N-({7-[(6-amino-9H-purin-9-yl)methyl]-5-[4-(methylsulfonyl)phenyl]-1H-indol-2-yl}methyl)-3,5-dimethyl-1,2-oxazole-4-carboxamide Example 170 was prepared according to the procedure used for the preparation of Example 177, substituting (4-(methylsulfonyl)phenyl)boronic acid for N,N-dimethyl-3-(4,4,5,5-tetramethyl-1,3,2-dioxaborolan-2-yl)benzamide. $^1$H NMR (DMSO/D$_2$O-d$_6$) δ 2.32 (s, 3H), 3.17 (s, 3H), 4.66 (s, 2H), 5.72 (s, 2H), 7.38-7.47 (m, 1H), 7.82-7.87 (m, 3H), 7.91-7.96 (m, 2H), 8.29-8.35 (m, 2H); (ESI) m/z 571 (M+H)$^+$.

Example 171

N-({7-[(6-amino-9H-purin-9-yl)methyl]-5-(4-cyanophenyl)-1H-indol-2-yl}methyl)-3,5-dimethyl-1,2-oxazole-4-carboxamide Example 171 was prepared according to the procedure used for the preparation of Example 177, substituting (4-cyanophenyl)boronic acid for N,N-dimethyl-3-(4,4,5,5-tetramethyl-1,3,2-dioxaborolan-2-yl)benzamide. $^1$H NMR (DMSO/D$_2$O-d$_6$) δ 2.32 (s, 3H), 4.65 (s, 2H), 5.69 (s, 2H), 6.51 (s, 1H), 7.38-7.47 (m, 1H), 7.76-7.82 (m, 4H), 7.83-7.88 (m, 1H), 8.27 (s, 2H); (ESI) m/z 518 (M+H)$^+$.

Example 172

N-({7-[(6-amino-9H-purin-9-yl)methyl]-5-(3-cyanophenyl)-H-indol-2-yl}methyl)-3,5-dimethyl-1,2-oxazole-4-carboxamide Example 172 was prepared according to the procedure used for the preparation of Example 177, substituting (3-cyanophenyl)boronic acid for N,N-dimethyl-3-(4,4,5,5-tetramethyl-1,3,2-dioxaborolan-2-yl)benzamide. $^1$H NMR (DMSO/D$_2$O-d$_6$) δ 2.32 (s, 3H), 4.65 (s, 2H), 5.67 (s, 2H), 6.50 (s, 1H), 7.41-7.44 (m, 1H), 7.58-7.70 (m, 2H), 7.77-7.86 (m, 1H), 7.89-7.96 (m, 1H), 7.96-8.02 (m, 1H), 8.21-8.30 (m, 2H); MS (ESI) m/z 518 (M+H)$^+$.

Example 173

N-({7-[(6-amino-9H-purin-9-yl)methyl]-5-(3-carbamoylphenyl)-1H-indol-2-yl}methyl)-3,5-dimethyl-1,2-oxazole-4-carboxamide Example 173 was prepared according to the procedure used for the preparation of Example 177, substituting (3-carbamoylphenyl)boronic acid for N,N-dimethyl-3-(4,4,5,5-tetramethyl-1,3,2-dioxaborolan-2-yl)benzamide. $^1$H NMR (DMSO/D$_2$O-d$_6$) δ 2.32 (s, 3H), 4.65 (s, 2H), 5.69 (s, 2H), 7.38-7.55 (m, 2H), 7.67-7.85 (m, 3H), 8.04-8.13 (m, 1H), 8.24-8.33 (m, 2H); MS (ESI) m/z 536 (M+H)$^+$.

Example 174

N-[(7-[(6-amino-9H-purin-9-yl)methyl]-5-{4-[(methylsulfonyl)amino]phenyl}-1H-indol-2-yl)methyl]-3,5-dimethyl-1,2-oxazole-4-carboxamide Example 174 was prepared according to the procedure used for the preparation of Example 177, substituting N-(4-(4,4,5,5-tetramethyl-1,3,2-dioxaborolan-2-yl)phenyl)methanesulfonamide for N,N-dimethyl-3-(4,4,5,5-tetramethyl-1,3,2-dioxaborolan-2-yl)benzamide. $^1$H NMR (DMSO/D$_2$O-d$_6$) δ 2.32 (s, 3H), 2.98 (s, 3H), 4.64 (s, 2H), 5.67 (s, 2H), 7.23-7.29 (m, 2H), 7.29-7.36 (m, 1H), 7.49-7.60 (m, 2H), 7.66-7.75 (m, 1H), 8.23-8.32 (m, 2H); MS (ESI) m/z 586 (M+H)$^+$.

Example 175

N-({7-[(6-amino-9H-purin-9-yl)methyl]-5-[4-(cyanomethyl)phenyl]-1H-indol-2-yl}methyl)-3,5-dimethyl-1,2-oxazole-4-carboxamide Example 175 was prepared according to the procedure used for the preparation of Example 177, substituting (4-

(cyanomethyl)phenyl)boronic acid for N,N-dimethyl-3-(4,4,5,5-tetramethyl-1,3,2-dioxaborolan-2-yl)benzamide. $^1$H NMR (DMSO/D$_2$O-d$_6$) δ 2.32 (s, 3H), 3.96 (s, 2H), 4.65 (s, 2H), 5.69 (s, 2H), 7.31-7.35 (m, 1H), 7.37-7.42 (m, 2H), 7.54-7.66 (m, 2H), 7.68-7.79 (m, 1H), 8.19-8.39 (m, 2H); MS (ESI) m/z 532 (M+H)$^+$.

Example 176

N-({7-[(6-amino-9H-purin-9-yl)methyl]-5-[4-(dimethylcarbamoyl)phenyl]-1H-indol-2-yl}methyl)-3,5-dimethyl-1,2-oxazole-4-carboxamide Example 176 was prepared according to the procedure used for the preparation of Example 177, substituting N,N-dimethyl-4-(4,4,5,5-tetramethyl-1,3,2-dioxaborolan-2-yl) benzamide for N,N-dimethyl-3-(4,4,5,5-tetramethyl-1,3,2-dioxaborolan-2-yl)benzamide. $^1$H NMR (DMSO/D$_2$O-d$_6$) δ 2.32 (s, 3H), 2.98 (s, 6H), 4.65 (s, 2H), 5.68 (s, 2H), 7.38-7.39 (m, 1H), 7.41-7.45 (m, 3H), 7.62-7.66 (m, 2H), 7.76-7.79 (m, 1H), 8.27 (s, 2H); MS (ESI) m/z 564 (M+H)$^+$.

Example 177

N-({7-[(6-amino-9H-purin-9-yl)methyl]-5-[3-(dimethylcarbamoyl)phenyl]-1H-indol-2-yl}methyl)-3,5-dimethyl-1,2-oxazole-4-carboxamide A microwave vial was charged with 32 mg of SiliaCat DPP-Pd (diphenylphosphine palladium (II)). Then a solution Example 162 (24 mg, 0.05 mmol) in dioxane (1.0 mL) was added, followed by the addition of N,N-dimethyl-3-(4,4,5,5-tetramethyl-1,3,2-dioxaborolan-2-yl)benzamide (0.1 mmol) in dioxane (0.4 mL) and an aqueous solution of Cs$_2$CO$_3$ (160 μL, 1M).

The resulting mixture was heated in the microwave oven (Biotage, Initiator, Power range 0-400 W from magnetron at 2.45 GHz) for 20 minutes at 120° C. The reaction was filtered, and the filtrate was purified by preparative HPLC on a Phenomenex Luna C8 (2) 5 μm 100 Å AXIA column (30 mm×150 mm). A gradient of acetonitrile (A) and 0.1% trifluoroacetic acid in water (B) was used, at a flow rate of 50 mL/min (0-0.5 minutes 10% A, 0.5-6.0 minutes linear gradient 10-100% A, 6.0-7.0 minutes 100% A, 7.0-8.0 minutes linear gradient 100-10% A). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/min. Fraction collection was automatically triggered when the extracted ion chromatogram (EIC) for the target mass exceeded the threshold specified in the method. The system was controlled using Agilent Chemstation (Rev B. 10.03), Agilent A2Prep, and Leap FractPal software, with custom Chemstation macros for data export. $^1$H NMR (DMSO/D$_2$O-d$_6$) δ 2.32 (s, 3H), 2.98 (s, 6H), 4.65 (s, 2H), 5.71 (s, 2H), 7.26-7.30 (m, 1H), 7.34-7.37 (m, 1H), 7.39-7.51 (m, 2H), 7.54-7.57 (m, 1H), 7.62-7.67 (m, 1H), 7.74-7.79 (m, 1H), 8.28-8.35 (m, 2H); MS (ESI) m/z 564 (M+H)$^+$.

Example 178

N-({7-[(6-amino-9H-purin-9-yl)methyl]-5-[3-(cyclopropylcarbamoyl)phenyl]-1H-indol-2-yl}methyl)-3,5-dimethyl-1,2-oxazole-4-carboxamide Example 178 was prepared according to the procedure used for the preparation of Example 180, substituting (3-cyclopropylcarbamoyl)phenyl)boronic acid for (3-(morpholine-4-carbonyl)phenyl)boronic acid. $^1$H NMR (DMSO/D$_2$O-d$_6$) δ 0.61 (d, J=8.0, 4.4 Hz, 2H), 0.67-0.80 (m, 2H), 2.33 (s, 3H), 2.81-2.94 (m, 1H), 4.65 (s, 2H), 5.67 (s, 2H), 6.48 (s, 1H), 7.39-7.44 (m, 1H), 7.47 (t, J=7.7 Hz, 1H), 7.64-7.74 (m, 2H), 7.74-7.83 (m, 1H), 7.96-8.04 (m, 1H), 8.18-8.28 (m, 2H); MS (ESI) m/z 576 (M+H)$^+$.

Example 179

N-({7-[(6-amino-9H-purin-9-yl)methyl]-5-[3-(morpholin-4-yl)phenyl]-1H-indol-2-yl}methyl)-3,5-dimethyl-1,2-oxazole-4-carboxamide Example 179 was prepared according to the procedure used for the preparation of Example 177, substituting (3-morpholinophenyl)boronic acid hydrochloride for N,N-dimethyl-3-(4,4,5,5-tetramethyl-1,3,2-dioxaborolan-2-yl) benzamide. $^1$H NMR (DMSO/D$_2$O-d$_6$) δ 2.32 (s, 3H), 3.12-3.16 (m, 4H), 3.75-3.80 (m, 4H), 4.65 (s, 2H), 5.70 (s, 2H), 6.80-6.91 (m, 1H), 6.97-7.08 (m, 2H), 7.20-7.33 (m, 2H), 7.66-7.75 (m, 1H), 8.26-8.36 (m, 2H); MS (ESI) m/z 578 (M+H)$^+$.

Example 180

N-({7-[(6-amino-9H-purin-9-yl)methyl]-5-[3-(morpholin-4-ylcarbonyl)phenyl]-1H-indol-2-yl}methyl)-3,5-dimethyl-1,2-oxazole-4-carboxamide A microwave vial was charged with 32 mg of SiliaCat DPP-Pd (diphenylphosphine palladium (II)). Then a solution of Example 162 (24 mg, 0.05 mmol) in dioxane (1.0 mL) was added, followed by (3-(morpholine-4-carbonyl)phenyl) boronic acid (0.1 mmol) in dioxane (0.4 mL) and an aqueous solution of Cs$_2$CO$_3$ (160 μL, 1M). The resulting mixture was heated in the microwave oven (Biotage Initiator, Power range 0-400 W from magnetron at 2.45 GHz) for 20 minutes at 120° C. The reaction was filtered, and the filtrate was purified by preparative HPLC on a Phenomenex Luna C8 (2) 5 μm 100 Å AXIA column (30 mm×150 mm). A gradient of acetonitrile (A) and 0.05% ammonium acetate in water (B) was used, at a flow rate of 50 mL/min (0-0.5 minutes 10% A, 0.5-6.0 minutes linear gradient 10-100% A, 6.0-7.0 minutes 100% A, 7.0-8.0 minutes linear gradient 100-10% A). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/min. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export. ¹H NMR (DMSO-d₆) δ 2.32 (s, 3H), 3.47-3.56 (m, 4H), 3.57-3.67 (m, 4H), 4.65 (s, 2H), 5.67 (s, 2H), 6.48 (s, 1H), 7.24-7.33 (m, 1H), 7.36 (s, 1H), 7.49 (t, J=7.7 Hz, 1H), 7.56 (s, 1H), 7.61-7.69 (m, 1H), 7.74-7.80 (m, 1H), 8.22-8.26 (m, 2H); (ESI) m/z 606 (M+H)⁺.

Example 181

N-({7-[(6-amino-9H-purin-9-yl)methyl]-5-chloro-1H-indol-2-yl}methyl)-5-ethyl-1,2-oxazole-4-carboxamide Example 181 was prepared according to the procedure used for the preparation of Example 139, substituting 5-ethylisoxazole-4-carboxylic acid for isothiazole-4-carboxylic acid. ¹H NMR (400 MHz, DMSO-d₆) δ 1.26 (t, J=7.5 Hz, 3H), 3.08-3.25 (m, 2H), 4.65 (s, 2H), 5.63 (s, 2H), 6.43 (s, 1H), 6.87 (d, J=2.0 Hz, 1H), 7.52 (d, J=2.0 Hz, 1H), 8.20 (s, 1H), 8.34 (s, 1H), 8.92 (s, 1H). MS (APCI) m/z 451.1 [M+H]⁺.

Example 182

N-({7-[(6-amino-9H-purin-9-yl)methyl]-5-chloro-1H-indol-2-yl}methyl)-1,5-dimethyl-1H-pyrazole-3-carboxamide Example 182 was prepared according to the procedure used for the preparation of Example 139, substituting 1,5-dimethyl-1H-pyrazole-3-carboxylic acid for isothiazole-4-carboxylic acid. ¹H NMR (400 MHz, DMSO-d₆) δ 2.29 (s, 3H), 3.80 (s, 3H), 4.61 (s, 2H), 5.60 (s, 2H), 6.34 (s, 1H), 6.49 (d, J=1.0 Hz, 1H), 6.83 (d, J=2.0 Hz, 1H), 7.49 (d, J=2.0 Hz, 1H), 8.21 (s, 1H), 8.33 (s, 1H). MS (APCI) m/z 450.1 [M+H]⁺.

Example 183

N-({7-[(6-amino-9H-purin-9-yl)methyl]-5-chloro-1H-indol-2-yl}methyl)-1,3-dimethyl-1H-pyrazole-5-carboxamide Example 183 was prepared according to the procedure used for the preparation of Example 139, substituting 1,3-dimethyl-1H-pyrazole-5-carboxylic acid for isothiazole-4-carboxylic acid. ¹H NMR (400 MHz, DMSO-d₆) δ 2.19 (s, 3H), 4.02 (s, 3H), 4.64 (s, 2H), 5.64 (s, 2H), 6.40 (s, 1H), 6.69 (s, 1H), 6.85 (d, J=1.9 Hz, 1H), 7.52 (d, J=2.0 Hz, 1H), 8.23 (s, 1H), 8.37 (s, 1H). MS (APCI) m/z 450.1 [M+H]⁺.

Example 184

N-({7-[(6-amino-9H-purin-9-yl)methyl]-5-chloro-1H-indol-2-yl}methyl)-1,3-dimethyl-1H-pyrazole-4-carboxamide Example 184 was prepared according to the procedure used for the preparation of Example 139, substituting 1,3-dimethyl-1H-pyrazole-4-carboxylic acid for isothiazole-4-carboxylic acid. ¹H NMR (400 MHz, DMSO-d₆) δ 2.36 (s, 3H), 3.79 (s, 3H), 4.59 (s, 2H), 5.61 (s, 2H), 6.37 (s, 1H), 6.85 (d, J=1.9 Hz, 1H), 7.49 (d, J=1.9 Hz, 1H), 8.08 (s, 1H), 8.18 (s, 1H), 8.32 (s, 1H). MS (APCI) m/z 450.1 [M+H]⁺.

Example 185

N-({7-[(6-amino-9H-purin-9-yl)methyl]-5-chloro-1H-indol-2-yl}methyl)-5-ethyl-3-methyl-1,2-oxazole-4-carboxamide Example 185 was prepared according to the procedure used for the preparation of Example 190, substituting 5-ethyl-3-methylisoxazole-4-carboxylic acid for 5-cyclopropyl-3-methylisoxazole-4-carboxylic acid. ¹H NMR (400 MHz, DMSO-d₆) δ 1.20 (t, J=7.6 Hz, 3H), 2.33 (s, 3H), 2.93 (q, J=7.6 Hz, 2H), 4.64 (s, 2H), 5.61 (s, 2H), 6.40 (s, 1H), 6.86 (d, J=2.0 Hz, 1H), 7.52 (d, J=2.0 Hz, 1H), 8.21 (s, 1H), 8.31 (s, 1H). MS (APCI) m/z 465.1 [M+H]⁺.

Example 186

N-({7-[(6-amino-9H-purin-9-yl)methyl]-5-chloro-1H-indol-2-yl}methyl)-3-ethyl-5-methyl-1,2-oxazole-4-carboxamide Example 186 was prepared according to the procedure used for the preparation of Example 139, substituting 3-ethyl-5-methylisoxazole-4-carboxylic acid for isothiazole-4-carboxylic acid. ¹H NMR (400 MHz, DMSO-d₆) δ 1.26 (t, J=7.5 Hz, 3H), 2.62 (s, 3H), 2.86 (q, J=7.5 Hz, 2H), 4.74 (s, 2H), 5.71 (s, 2H), 6.51 (s, 1H), 6.96 (d, J=1.9 Hz, 1H), 7.62 (d, J=2.0 Hz, 1H), 8.31 (s, 1H), 8.41 (s, 1H). MS (APCI) m/z 465.1 [M+H]⁺.

Example 187

N-({7-[(6-amino-9H-purin-9-yl)methyl]-5-chloro-1H-indol-2-yl}methyl)-5-(propan-2-yl)-1,2-oxazole-4-carboxamide Example 187 was prepared according to the procedure used for the preparation of Example 139, substituting 5-isopropylisoxazole-4-carboxylic acid for isothiazole-4-carboxylic acid. ¹H NMR (400 MHz, DMSO-d₆) δ 1.29 (d, J=7.0 Hz, 6H), 3.88 (p, J=7.0 Hz, 1H), 4.64 (d, J=4.1 Hz, 2H), 5.61 (s, 2H), 6.42 (s, 1H), 6.85 (d, J=2.0 Hz, 1H), 7.51 (d, J=2.0 Hz, 1H), 8.19 (s, 1H), 8.33 (s, 1H), 8.90 (s, 1H). MS (APCI) m/z 465.1 [M+H]⁺.

Example 188

N-({7-[(6-amino-9H-purin-9-yl)methyl]-5-chloro-1H-indol-2-yl}methyl)-1-ethyl-3,5-dimethyl-1H-pyrazole-4-carboxamide Example 188 was prepared according to the procedure used for the preparation of Example 139, substituting 1-ethyl-3,5-dimethyl-1H-pyrazole-4-carboxylic acid for isothiazole-4-carboxylic acid. ¹H NMR (400 MHz, DMSO-d₆) δ 1.27 (t, J=7.2 Hz, 3H), 2.28 (s, 3H), 2.37 (s, 3H), 4.00 (q, J=7.2 Hz, 2H), 4.61 (s, 2H), 5.61 (s, 2H), 6.38 (s, 1H), 6.85 (d, J=2.0 Hz, 1H), 7.50 (d, J=1.9 Hz, 1H), 8.19 (s, 1H), 8.31 (s, 1H). MS (APCI) m/z 478.1 [M+H]⁺.

Example 189

N-({7-[(6-amino-9H-purin-9-yl)methyl]-5-chloro-1H-indol-2-yl}methyl)-5-cyclopropyl-1,2-oxazole-4-carboxamide Example 189 was prepared according to the procedure used for the preparation of Example 139, substituting 5-cyclopropylisoxazole-4-carboxylic acid for isothiazole-4-carboxylic acid. $^1$H NMR (400 MHz, DMSO-$d_6$) δ 1.08-1.30 (m, 4H), 2.96 (ddd, J=8.3, 5.1, 3.3 Hz, 1H), 4.66 (s, 2H), 5.63 (s, 2H), 6.44 (s, 1H), 6.87 (d, J=1.9 Hz, 1H), 7.53 (d, J=2.0 Hz, 1H), 8.21 (s, 1H), 8.34 (s, 1H), 8.89 (s, 1H). MS (APCI) m/z 463.1 [M+H]$^+$.

Example 190

N-({7-[(6-amino-9H-purin-9-yl)methyl]-5-chloro-1H-indol-2-yl}methyl)-5-cyclopropyl-3-methyl-1,2-oxazole-4-carboxamide A solution of Example 9b (0.14 M in N,N-dimethylacetamide, 329 µL, 0.046 mmol and N,N-diisopropylethylamine (0.14 M in N,N-dimethylacetamide, 329 µL, 0.046 mmol), HATU (0.15 M in N,N-dimethylacetamide, 333 µL, 0.05 mmol), and 5-cyclopropyl-3-methylisoxazole-4-carboxylic acid (0.4M in N,N-dimethylacetamide, 125 µL, 0.05 mmol) were aspirated from their respective source vials, mixed through a perfluoroalkoxy alkanes mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 µL min$^{-1}$ (10 minute residence time). Upon exiting the reactor, the reaction was loaded directly into an injection loop and purified using preparative HPLC to yield the title compound (12.49 mg, 57.18% yield). Samples were purified by preparative HPLC on a Phenomenex Luna C8 (2) 5 µm 100 Å AXIA column (50 mm×21.2 mm). A gradient of acetonitrile (A) and 0.1% ammonium acetate in water (B) was used, at a flow rate of 30 mL/min (0-0.5 minutes 5% A, 0.5-6.5 minutes linear gradient 5-60% A, 6.5-7.0 minutes linear gradient 60-100% A, 7.0-8.9 minutes 100% A, 8.9-9.0 minutes linear gradient 100-5% A, 9.0-10 minutes 5% A). A sample volume of 1.0 mL was injected directly from the flow reactor stream to the HPLC system. A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0. $^1$H NMR (400 MHz, DMSO-$d_6$) δ 0.97-1.08 (m, 2H), 1.13 (dt, J=8.2, 3.3 Hz, 2H), 2.31 (s, 3H), 2.37-2.47 (m, 1H), 4.65 (s, 2H), 5.61 (s, 2H), 6.42 (s, 1H), 6.86 (d, J=1.9 Hz, 1H), 7.52 (d, J=2.0 Hz, 1H), 8.21 (s, 1H), 8.31 (s, 1H). MS (APCI) m/z 477.1.1 [M+H]$^+$.

Example 191

N-({7-[(6-amino-9H-purin-9-yl)methyl]-5-chloro-1H-indol-2-yl}methyl)-1-methyl-1,4,5,6-tetrahydrocyclopenta[c]pyrazole-3-carboxamide Example 191 was prepared according to the procedure used for the preparation of Example 139, substituting 1-methyl-1,4,5,6-tetrahydrocyclopenta[c]pyrazole-3-carboxylic acid for isothiazole-4-carboxylic acid. $^1$H NMR (400 MHz, DMSO-$d_6$) δ 2.44-2.52 (m, 2H), 2.71 (q, J=7.6 Hz, 5H), 3.78 (s, 3H), 4.55-4.65 (m, 2H), 5.61 (s, 2H), 6.35 (s, 1H), 6.85 (d, J=2.0 Hz, 1H), 7.50 (d, J=2.0 Hz, 1H), 8.22 (s, 1H), 8.33 (s, 1H). MS (APCI) m/z 476.1 [M+H]$^+$.

Example 192

N-({7-[(6-amino-9H-purin-9-yl)methyl]-5-chloro-1H-indol-2-yl}methyl)-4,5,6,7-tetrahydropyrazolo[1,5-a]pyridine-3-carboxamide Example 192 was prepared according to the procedure used for the preparation of Example 139, substituting 4,5,6,7-tetrahydropyrazolo[1,5-a]pyridine-3-carboxylic acid for isothiazole-4-carboxylic acid. $^1$H NMR (400 MHz, DMSO-$d_6$) δ 1.76-1.85 (m, 3H), 1.98 (tt, J=6.1, 2.9 Hz, 2H), 3.02 (t, J=6.4 Hz, 2H), 4.08 (q, J=6.0 Hz, 3H), 4.61 (s, 2H), 5.62 (s, 2H), 6.38 (s, 1H), 6.86 (d, J=2.0 Hz, 1H), 7.51 (d, J=2.1 Hz, 1H), 7.91 (d, J=33.1 Hz, 1H), 8.20 (s, 1H), 8.34 (s, 1H). MS (APCI) m/z 476.1 [M+H]$^+$.

Example 193

N-({7-[(6-amino-9H-purin-9-yl)methyl]-5-chloro-1H-indol-2-yl}methyl)pyrazine-2-carboxamide Example 193 was prepared according to the procedure used for the preparation of Example 232, substituting pyrazine-2-carboxylic acid for 2-(pyridin-4-yl)acetic acid. $^1$H NMR (400 MHz, DMSO-$d_6$) δ 4.73 (d, J=6.1 Hz, 2H), 5.63 (s, 2H), 6.37 (d, J=1.9 Hz, 1H), 6.81 (d, J=2.0 Hz, 1H), 7.48 (d, J=1.9 Hz, 1H), 7.82 (s, 2H), 8.27 (s, 1H), 8.39 (s, 1H), 8.73-8.82 (m, 1H), 9.24 (d, J=1.5 Hz, 1H), 9.46 (t, J=6.1 Hz, 1H), 11.51 (d, J=2.2 Hz, 1H). MS (APCI) m/z 434.1 [M+H]$^+$.

Example 194

9-({2-[amino(phenyl)methyl]-5-chloro-1H-indol-7-yl}methyl)-9H-purin-6-amine

Example 194 was according to the procedure used for the preparation of Example 87C, substituting phenylmagnesium bromide for methylmagnesium bromide. $^1$H NMR (400 MHz, CD$_3$OD) δ 8.27 (d, J=2.0 Hz, 1H), 8.00 (d, J=3.4 Hz, 1H), 7.61 (d, J=1.9 Hz, 1H), 7.54-7.39 (m, 5H), 7.10 (d, J=1.8 Hz, 1H), 6.69 (s, 1H), 5.87 (s, 1H), 5.73-5.55 (m, 2H), 2.65 (s, 1H). MS m/z: 387 [M−NH$_2$]$^+$.

Example 195

N-({7-[(6-amino-9H-purin-9-yl)methyl]-5-chloro-1H-indol-2-yl}methyl)pyridine-2-carboxamide Example 195 was prepared according to the procedure used for the preparation of Example 232, substituting picolinic acid for 2-(pyridin-4-yl)acetic acid. $^1$H NMR (400 MHz, DMSO-$d_6$) δ 4.72 (d, J=6.2 Hz, 2H), 5.65 (s, 2H), 6.36 (d, J=1.9 Hz, 1H), 6.81 (d, J=2.0 Hz, 1H), 7.48 (d, J=2.0 Hz, 1H), 7.58-7.70 (m, 1H), 7.91-8.18 (m, 4H), 8.31 (s, 1H), 8.44 (s, 1H), 8.64-8.74 (m, 1H), 9.31 (t, J=6.2 Hz, 1H), 11.50 (d, J=2.2 Hz, 1H). MS (APCI) m/z 433.1 [M+H]$^+$.

Example 196

N-({7-[(6-amino-9H-purin-9-yl)methyl]-5-chloro-1H-indol-2-yl}methyl)pyridine-3-carboxamide Example 196 was prepared according to the procedure used for the preparation of Example 232, substituting nicotinic acid for 2-(pyridin-4-yl)acetic acid. $^1$H NMR (400 MHz, DMSO-d$_6$) δ 2.94 (s, 1H), 4.72 (d, J=5.5 Hz, 2H), 5.71 (s, 2H), 6.43 (d, J=1.8 Hz, 1H), 6.81 (d, J=2.0 Hz, 1H), 7.46-7.64 (m, 2H), 8.31 (dt, J=8.0, 1.9 Hz, 1H), 8.42 (s, 1H), 8.66 (d, J=88.6 Hz, 3H), 9.11 (s, 1H), 9.31 (t, J=5.7 Hz, 1H), 11.53 (d, J=2.2 Hz, 1H). MS (APCI) m/z 433.1 [M+H]$^+$.

Example 197

N-({7-[(6-amino-9H-purin-9-yl)methyl]-5-chloro-1H-indol-2-yl}methyl)-6-hydroxypyridine-2-carboxamide Example 197 was prepared according to the procedure used for the preparation of Example 105, substituting 6-hydroxy-pyridine-2-carboxylic acid for 4-methyl-pentanoic acid. $^1$H NMR (400 MHz, DMSO-d$_6$) δ 11.51 (s, 1H), 8.91 (s, 1H), 8.54 (s, 1H), 8.38 (s, 1H), 7.78-7.71 (m, 1H), 7.54-7.46 (m, 1H), 7.36 (s, 2H), 6.80 (t, J=3.6 Hz, 2H), 6.40 (d, J=1.9 Hz, 1H), 5.69 (s, 2H), 4.69 (d, J=5.8 Hz, 2H). MS (APCI+) m/z 449.0 (M+H)$^+$.

Example 198

N-({7-[(6-amino-9H-purin-9-yl)methyl]-5-chloro-1H-indol-2-yl}methyl)-2-oxo-1,2-dihydropyridine-3-carboxamide Example 198 was prepared according to the procedure used for the preparation of Example 105, substituting 2-oxo-1,2-dihydro-pyridine-3-carboxylic acid. $^1$H NMR (400 MHz, DMSO-d$_6$) δ 12.54 (s, 1H), 11.56 (d, J=2.0 Hz, 1H), 10.24 (t, J=5.7 Hz, 1H), 8.57 (s, 1H), 8.46-8.34 (m, 3H), 7.74 (td, J=6.3, 2.3 Hz, 1H), 7.51 (d, J=2.1 Hz, 1H), 6.88-6.76 (m, 1H), 6.57-6.48 (m, 1H), 6.39 (d, J=1.8 Hz, 1H), 5.73-5.66 (m, 3H), 4.72 (d, J=5.8 Hz, 2H). MS (APCI+) m/z 449.0 (M+H)$^+$.

Example 199

N-({7-[(6-amino-9H-purin-9-yl)methyl]-5-chloro-1H-indol-2-yl}methyl)-3-methylpyridazine-4-carboxamide A solution of Example 9b (0.1 M in N,N-dimethylacetamide, 360 µL, 0.036 mmol), N,N-diisopropylethylamine (0.3 M in N,N-dimethylacetamide, 360 µL, 0.108 mmol), HATU (0.12 M in N,N-dimethylacetamide, 375 µL, 0.0432 mmol), and 3-methylpyridazine-4-carboxylic acid (0.4M in N,N-dimethylacetamide, 110 µL, 0.0432 mmol) were aspirated from their respective source vials, mixed through a perfluoroalkoxy alkanes mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 µL min$^{-1}$ (10 minute residence time). Upon exiting the reactor, the reaction was loaded directly into an injection loop and purified using preparative HPLC to yield the title compound (11.38 mg, 55.3% yield). Samples were purified by preparative HPLC on a Phenomenex Luna C8 (2) 5 µm 100 Å AXIA column (50 mm×21.2 mm). A gradient of acetonitrile (A) and 0.1% trifluoroacetic acid in water (B) was used, at a flow rate of 30 mL/min (0-0.5 minutes 5% A, 0.5-6.5 minutes linear gradient 5-40% A, 6.5-7.0 minutes linear gradient 40-100% A, 7.0-8.5 minutes 100% A, 8.5-9.0 minutes linear gradient 100-5% A, 9.0-10 minutes 5% A). A sample volume of 1.0 mL was injected directly from the flow reactor stream to the HPLC system. A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0. $^1$H NMR (400 MHz, DMSO-d$_6$) δ 2.69 (s, 3H), 4.70 (s, 2H), 5.73 (s, 2H), 6.49 (s, 1H), 6.84 (d, J=1.9 Hz, 1H), 7.55 (d, J=2.0 Hz, 1H), 7.69 (d, J=5.1 Hz, 1H), 8.45 (s, 1H), 8.58 (s, 1H), 9.25 (d, J=5.1 Hz, 1H). MS (APCI) m/z 448.2 [M+H]$^+$.

Example 200

N-({7-[(6-amino-9H-purin-9-yl)methyl]-5-(1,2,3,6-tetrahydropyridin-4-yl)-1H-indol-2-yl}methyl)-3-methylpyridazine-4-carboxamide Example 204 (10 mg, 0.017 mmol) in 0.6 mL dichloromethane was treated with trifluoroacetic acid (0.3 mL). The mixture was stirred at ambient temperature for 2 hours and concentrated. To the residue was added 4N HCl dioxane solution (1 mL) and concentrated again. The solid residue was triturated in 1 mL diethyl ether to afford the title compound as hydrochloric acid salt (9 mg, 0.015 mmol, 89% yield). $^1$H NMR (400 MHz, DMSO-d$_6$) δ 11.70 (s, 1H), 9.38 (t, J=5.6 Hz, 1H), 9.25 (d, J=5.0 Hz, 1H), 9.18 (s, 2H), 8.71 (s, 1H), 8.53 (d, J=21.7 Hz, 1H), 7.71 (d, J=5.1 Hz, 1H), 7.63-7.46 (m, 1H), 7.12 (s, 1H), 6.46 (s, 1H), 5.98 (s, 1H), 5.76 (s, 2H), 4.70 (d, J=5.6 Hz, 2H), 3.28 (s, 2H), 2.67 (s, 2H). MS (ESI−) m/z 493.3 (M−H)$^−$.

Example 201

N-({7-[(6-amino-9H-purin-9-yl)methyl]-5-(4,4-difluorocyclohex-1-en-1-yl)-1H-indol-2-yl}methyl)-3-methylpyridazine-4-carboxamide A mixture of Example 199 (16 mg, 0.036 mmol), 2-(4,4-difluorocyclohex-1-en-1-yl)-4,4,5,5-tetramethyl-1,3,2-dioxaborolane (13.08 mg, 0.054 mmol) and phenylallylchloro[1,3-bis(diisopropylphenyl)-2-imidazol-2-ylidene] palladium (II) (3.47 mg, 5.36 µmol), potassium phosphate (22.75 mg, 0.107 mmol) in 1 mL dioxane and 0.3 mL water was purged with nitrogen and heated at 130° C. in microwave oven (Biotage Initiator) for 1 hour. The reaction mixture was diluted with ethyl acetate, washed with brine, dried over anhydrous magnesium sulfate, and filtered. The filtrate was concentrated and the residue was first purified by column chromatography on silica gel (2-14% methanol in dichloromethane with 1% NH$_4$OH), and then triturated in diethyl ether to give the title compound. $^1$H NMR (400 MHz, DMSO-d$_6$) δ 11.40 (s, 1H), 9.27 (t, J=5.6 Hz, 1H), 9.23 (d, J=5.0 Hz, 1H), 8.27 (s, 1H), 8.21 (s, 1H), 7.64 (d, J=5.1 Hz, 1H), 7.51 (s, 1H), 7.27 (s, 2H), 7.12 (d, J=1.4 Hz, 1H), 6.44 (d, J=1.5 Hz, 1H), 5.81 (s, 1H), 5.60 (s, 2H), 4.68 (d, J=5.6 Hz, 2H), 2.71-2.61 (m, 6H), 2.22-2.08 (m, 2H), 1.26 (d, J=6.8 Hz, 1H), 1.16 (d, J=6.9 Hz, 1H). MS (ESI+) m/z 530.1 (M+H)$^+$.

Example 202

N-({7-[(6-amino-9H-purin-9-yl)methyl]-5-[1-(methylsulfonyl)-1,2,3,6-tetrahydropyridin-4-yl]-1H-indol-2-yl}methyl)-3-methylpyridazine-4-carboxamide Example 202 was prepared according to the procedure used for the preparation of Example 201, substituting 1-(methylsulfonyl)-4-(4,4,5,5-tetramethyl-1,3,2-dioxaborolan-2-yl)-1,2,3,6-tetrahydropyridine for 2-(4,4-difluorocyclohex-1-en-1-yl)-4,4,5,5-tetramethyl-1,3,2-dioxaborolane. $^1$H NMR (400 MHz, DMSO-d$_6$) δ 11.42 (s, 1H), 9.27 (dd, J=12.4, 6.9 Hz, 1H), 9.23 (d, J=5.1 Hz, 1H), 8.26 (s, 1H), 8.21 (s, 1H), 7.64 (d, J=5.1 Hz, 1H), 7.51 (s, 1H), 7.28 (s, 2H), 7.16 (d, J=1.3 Hz, 1H), 6.44 (d, J=1.5 Hz, 1H), 5.99 (s, 1H), 5.60 (s, 2H), 4.68 (d, J=5.5 Hz, 2H), 3.80 (dd, J=19.1, 4.9 Hz, 2H), 2.91 (s, 3H), 2.70 (s, 3H), 2.59 (s, 2H). MS (ESI+) m/z 573.1 (M+H)$^+$.

Example 203

N-({5-(1-acetyl-1,2,3,6-tetrahydropyridin-4-yl)-7-[(6-amino-9H-purin-9-yl)methyl]-1H-indol-2-yl}methyl)-3-methylpyridazine-4-carboxamide Example 203 was prepared according to the procedure used for the preparation of Example 201, substituting 1-(4-(4,4,5,5-tetramethyl-1,3,2-dioxaborolan-2-yl)-5,6-dihydropyridin-1(2H)-yl)ethanone (33.6 mg, 0.134 mmol) for 2-(4,4-difluorocyclohex-1-en-1-yl)-4,4,5,5-tetramethyl-1,3,2-dioxaborolane. $^1$H NMR (400 MHz, DMSO-d$_6$) δ 11.40 (s, 1H), 9.34-9.15 (m, 2H), 8.26 (s, 1H), 8.21 (s, 1H), 7.64 (d, J=5.1 Hz, 1H), 7.49 (d, J=3.1 Hz, 1H), 7.27 (s, 2H), 7.14 (s, 1H), 6.44 (s, 1H), 5.96 (d, J=11.1 Hz, 1H), 5.60 (s, 2H), 4.68 (d, J=5.5 Hz, 2H), 4.08 (d, J=21.9 Hz, 2H), 3.69-3.54 (m, 2H), 2.70 (s, 3H), 2.55-2.39 (m, 2H), 2.06 (s, 1.5H), 2.02 (s, 1.5H). MS (ESI+) m/z 537.1 (M+H)$^+$.

Example 204 tert-butyl 4-{7-[(6-amino-9H-purin-9-yl)methyl]-2-({[(3-methylpyridazin-4-yl)carbonyl]amino}methyl)-1H-indol-5-yl}-3,6-dihydropyridine-1(2H)-carboxylate Example 204 was prepared according to the procedure used for the preparation of Example 201, substituting tert-butyl 4-(4,4,5,5-tetramethyl-1,3,2-dioxaborolan-2-yl)-5,6-dihydropyridine-1(2H)-carboxylate for 2-(4,4-difluorocyclohex-1-en-1-yl)-4,4,5,5-tetramethyl-1,3,2-dioxaborolane. $^1$H NMR (400 MHz, DMSO-d$_6$) δ 11.41 (s, 1H), 9.28 (t, J=5.6 Hz, 1H), 9.23 (d, J=5.0 Hz, 1H), 8.26 (s, 1H), 8.21 (s, 1H), 7.64 (d, J=5.0 Hz, 1H), 7.49 (s, 1H), 7.27 (s, 2H), 7.14 (d, J=1.2 Hz, 1H), 6.43 (d, J=1.5 Hz, 1H), 5.94 (s, 1H), 5.59 (s, 2H), 4.68 (d, J=5.5 Hz, 2H), 3.96 (s, 2H), 3.52 (t, J=5.5 Hz, 2H), 2.70 (s, 3H), 2.45 (s, 2H), 1.42 (s, 9H). MS (ESI+) m/z 595.0 (M+H)$^+$.

Example 205

N-({7-[(6-amino-9H-purin-9-yl)methyl]-5-chloro-1H-indol-2-yl}methyl)-5-methylpyrazine-2-carboxamide Example 205 was prepared according to the procedure used for the preparation of Example 232, substituting 5-methylpyrazine-2-carboxylic acid for 2-(pyridin-4-yl)acetic acid. $^1$H NMR (400 MHz, DMSO-d$_6$) δ 2.61 (s, 3H), 4.71 (d, J=6.1 Hz, 2H), 5.66 (s, 2H), 6.36 (d, J=1.8 Hz, 1H), 6.81 (d, J=2.0 Hz, 1H), 7.48 (d, J=1.9 Hz, 1H), 8.34 (s, 3H), 8.46 (s, 1H), 8.66 (d, J=1.4 Hz, 1H), 9.10 (d, J=1.4 Hz, 1H), 9.38 (t, J=6.2 Hz, 1H), 11.49 (d, J=2.1 Hz, 1H). MS (APCI) m/z 448.1 [M+H]$^+$.

Example 206

9-{[2-(1-amino-2-phenylethyl)-5-chloro-1H-indol-7-yl]methyl}-9H-purin-6-amine

Example 206 was according to the procedure used for the preparation of Example 87C, substituting benzylmagnesium bromide for methylmagnesium bromide. $^1$H NMR (400 MHz, CD$_3$OD) δ 8.33 (s, 1H), 8.20 (d, J=1.5 Hz, 1H), 7.56 (d, J=1.9 Hz, 1H), 7.26-7.17 (m, 3H), 7.14-7.04 (m, 3H), 6.65 (s, 1H), 5.64 (s, 2H), 4.76 (t, J=7.5 Hz, 1H), 3.38 (d, J=7.5 Hz, 2H); MS m/z: 266 [M-adenine and NH$_3$]$^+$.

Example 207

9-({2-[(benzylamino)methyl]-5-chloro-1H-indol-7-yl}methyl)-9H-purin-6-amine

Example 207 was prepared according to the procedure used for the preparation of Example 97, substituting benzaldehyde for acetaldehyde. $^1$H NMR (400 MHz, CDCl$_3$ with trace dimethylsulfoxide) δ 11.64 (brs, 1H), 8.37 (s, 1H), 8.01 (s, 1H), 7.48 (s, 1H), 7.40-7.34 (m, 5H), 7.17 (s, 1H), 6.38 (s, 1H), 6.03 (brs, 1H), 5.56 (s, 2H), 4.08 (s, 2H), 3.93 (s, 2H); MS m/z: 311 [M-benzylamine]$^+$.

Example 208

9-[(2-{[(2-bromobenzyl)amino]methyl}-5-chloro-1H-indol-7-yl)methyl]-9H-purin-6-amine In a 20 mL vial, a solution of the 2-bromobenzaldehyde monomer (16 mg, 0.08 mmol) in 1:1 methanol/dichloromethane (1 mL) was added, followed by the addition of 9-((2-(aminomethyl)-5-chloro-1H-indol-7-yl)methyl)-9H-purin-6-amine amine core (25 mg, 0.08 mmol) in 1:1 methanol/dichloromethane (1.0 mL), and acetic acid (17.5 μL, 0.30 mmol). To this mixture was then added sodium cyanoborohydride resin (2.19 mmol/g loading, 140 mg) and was allowed to stir overnight at 50° C. The reaction was filtered and the filtrate was concentrated to dryness. The residue was reconstituted in 1:1 DMSO/methanol and by reverse phase HPLC on a Phenomenex Luna C8 (2) 5 μm 100 Å AXIA column (30 mm×150 mm). A gradient of acetonitrile (A) and 0.1% trifluoroacetic acid in water (B) was used, at a flow rate of 50 mL/min (0-0.5 minutes 10% A, 0.5-6.0 minutes linear gradient 10-100% A, 6.0-7.0 minutes 100% A, 7.0-8.0 minutes linear gradient 100-10% A). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/min. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export. $^1$H NMR (400 MHz, DMSO-$d_6$) δ 8.47 (s, 1H), 8.34 (s, 1H), 7.74 (dd, J=8.0, 1.2 Hz, 1H), 7.71-7.56 (m, 2H), 7.51 (td, J=7.6, 1.2 Hz, 1H), 7.41 (td, J=7.7, 1.7 Hz, 1H), 6.90 (d, J=2.0 Hz, 1H), 6.80 (s, 1H), 5.69 (s, 2H), 4.51 (s, 2H), 4.37 (s, 2H). MS (ESI+) m/z 496 (M+H)$^+$.

Example 209

9-[(5-chloro-2-{[(3-chlorobenzyl)amino]methyl}-1H-indol-7-yl)methyl]-9H-purin-6-amine Example 209 was prepared according to the procedure used for the preparation of Example 208, substituting 3-chlorobenzaldehyde for 2-bromobenzaldehyde. $^1$H NMR (400 MHz, DMSO-$d_6$) δ 8.45 (s, 1H), 8.32 (s, 1H), 7.64 (dd, J=13.2, 2.0 Hz, 2H), 7.56-7.42 (m, 3H), 6.88 (d, J=1.9 Hz, 1H), 6.74 (s, 1H), 5.67 (s, 2H), 4.41 (s, 2H), 4.28 (s, 2H). MS (ESI+) m/z 452.1 (M+H)$^+$.

Example 210

9-[(5-chloro-2-{[(2-chlorobenzyl)amino]methyl}-1H-indol-7-yl)methyl]-9H-purin-6-amine Example 210 was prepared according to the procedure used for the preparation of Example 208, substituting 2-chlorobenzaldehyde for 2-bromobenzaldehyde. $^1$H NMR (400 MHz, DMSO-$d_6$) δ 8.46 (s, 1H), 8.33 (s, 1H), 7.67 (d, J=1.9 Hz, 1H), 7.60 (ddd, J=16.7, 7.5, 1.9 Hz, 2H), 7.55-7.42 (m, 2H), 6.90 (d, J=2.0 Hz, 1H), 6.79 (s, 1H), 5.68 (s, 2H), 4.50 (s, 2H), 4.37 (s, 2H). MS (ESI+) m/z 452.1 (M+H)$^+$.

Example 211

9-[(5-chloro-2-{[(2,6-dichlorobenzyl)amino]methyl}-1H-indol-7-yl)methyl]-9H-purin-6-amine Example 211 was prepared according to the procedure used for the preparation of Example 208, substituting 2,6-dichlorobenzaldehyde for 2-bromobenzaldehyde. $^1$H NMR (400 MHz, DMSO-$d_6$) δ 8.47 (s, 1H), 8.34 (s, 1H), 7.67 (d, J=1.9 Hz, 1H), 7.63-7.46 (m, 3H), 6.92 (d, J=1.8 Hz, 1H), 6.83 (s, 1H), 5.70 (s, 2H), 4.55 (s, 2H), 4.48 (s, 2H). MS (ESI+) m/z 486 (M+H)$^+$.

Example 212

9-[(5-chloro-2-{[(3,5-dichlorobenzyl)amino]methyl}-1H-indol-7-yl)methyl]-9H-purin-6-amine Example 212 was prepared according to the procedure used for the preparation of Example 208, substituting 3,5-dichlorobenzaldehyde for 2-bromobenzaldehyde. $^1$H NMR (400 MHz, DMSO-$d_6$) δ 8.46 (s, 1H), 8.34 (s, 1H), 7.70 (t, J=1.9 Hz, 1H), 7.65 (d, J=1.9 Hz, 1H), 7.60 (d, J=1.9 Hz, 2H), 6.88 (d, J=1.9 Hz, 1H), 6.74 (s, 1H), 5.68 (s, 2H), 4.43 (s, 2H), 4.30 (s, 2H). MS (ESI+) m/z 486 (M+H)$^+$.

Example 213

9-[(5-chloro-2-{[(3,4-dichlorobenzyl)amino]methyl}-1H-indol-7-yl)methyl]-9H-purin-6-amine Example 213 was prepared according to the procedure used for the preparation of Example 208, substituting 3,4-dichlorobenzaldehyde for 2-bromobenzaldehyde. $^1$H NMR (400 MHz, DMSO-$d_6$) δ 8.45 (s, 1H), 8.33 (s, 1H), 7.80 (d, J=2.0 Hz, 1H), 7.73 (d, J=8.2 Hz, 1H), 7.65 (d, J=1.9 Hz, 1H), 7.50 (dd, J=8.4, 2.1 Hz, 1H), 6.87 (d, J=2.0 Hz, 1H), 6.73 (s, 1H), 5.67 (s, 2H), 4.41 (s, 2H), 4.28 (s, 2H). MS (ESI+) m/z 488 (M+H)$^+$.

Example 214

9-[(5-chloro-2-{[(2-fluorobenzyl)amino]methyl}-1H-indol-7-yl)methyl]-9H-purin-6-amine Example 214 was prepared according to the procedure used for the preparation of Example 208, substituting 2-fluorobenzaldehyde for 2-bromobenzaldehyde. 1H NMR (400 MHz, DMSO-$d_6$) δ 8.44 (s, 1H), 8.31 (s, 1H), 7.66 (d, J=1.9 Hz, 1H), 7.61-7.47 (m, 2H), 7.39-7.26 (m, 2H), 6.88 (d, J=2.0 Hz, 1H), 6.76 (s, 1H), 5.67 (s, 2H), 4.46 (s, 2H), 4.31 (s, 2H). MS (ESI+) m/z 436.1 (M+H)$^+$.

Example 215

9-[(5-chloro-2-{[(2-chloro-6-fluorobenzyl)amino]methyl}-1H-indol-7-yl)methyl]-9H-purin-6-amine Example 215 was prepared according to the procedure used for the preparation of Example 208, substituting 2-chloro-6-fluorobenzaldehyde for 2-bromobenzaldehyde. $^1$H NMR (400 MHz, DMSO-$d_6$) δ 8.47 (s, 1H), 8.34 (s, 1H), 7.67 (d, J=1.9 Hz, 1H), 7.57 (td, J=8.3, 6.2 Hz, 1H), 7.46 (d, J=8.1 Hz, 1H), 7.41-7.30 (m, 1H), 6.90 (d, J=1.9 Hz, 1H), 6.80 (s, 1H), 5.69 (s, 2H), 4.52 (s, 2H), 4.39 (d, J=2.0 Hz, 2H). MS (ESI+) m/z 470 (M+H)$^+$.

Example 216

9-[(5-chloro-2-{[(3-chloro-5-fluorobenzyl)amino]methyl}-1H-indol-7-yl)methyl]-9H-purin-6-amine Example 216 was prepared according to the procedure used for the preparation of Example 208, substituting 3-chloro-5-fluorobenzaldehyde for 2-bromobenzaldehyde. $^1$H NMR (400 MHz, DMSO-$d_6$) δ 8.48 (s, 1H), 8.36 (s, 1H), 7.65 (d, J=1.9 Hz, 1H), 7.52 (dt, J=8.7, 2.1 Hz, 1H), 7.49 (t, J=1.6 Hz, 1H), 7.39 (dt, J=9.3, 1.9 Hz, 1H), 6.88 (d, J=1.9 Hz, 1H), 6.74 (s, 1H), 5.69 (s, 2H), 4.43 (s, 2H), 4.30 (s, 2H). MS (ESI+) m/z 470.2 (M+H)$^+$.

Example 217

9-[(5-chloro-2-{[(2-chloro-5-fluorobenzyl)amino]methyl}-1H-indol-7-yl)methyl]-9H-purin-6-amine Example 217 was prepared according to the procedure used for the preparation of Example 208, substituting 2-chloro-5-fluorobenzaldehyde for 2-bromobenzaldehyde.

¹H NMR (400 MHz, DMSO-d$_6$) δ 8.47 (s, 1H), 8.34 (s, 1H), 7.67 (d, J=2.0 Hz, 1H), 7.63 (dd, J=8.9, 5.1 Hz, 1H), 7.52 (dd, J=9.3, 3.1 Hz, 1H), 7.37 (td, J=8.5, 3.1 Hz, 1H), 6.90 (d, J=2.0 Hz, 1H), 6.78 (s, 1H), 5.69 (s, 2H), 4.51 (s, 2H), 4.38 (s, 2H). MS (ESI+) m/z 470.1 (M+H)⁺.

Example 218

9-[(5-chloro-2-{[(3-chloro-2-fluorobenzyl)amino]methyl}-1H-indol-7-yl)methyl]-9H-purin-6-amine Example 218 was prepared according to the procedure used for the preparation of Example 208, substituting 3-chloro-2-fluorobenzaldehyde for 2-bromobenzaldehyde. 1H NMR (400 MHz, DMSO-d$_6$) δ 8.43 (s, 1H), 8.30 (s, 1H), 7.77-7.67 (m, 1H), 7.65 (d, J=1.9 Hz, 1H), 7.56 (td, J=7.3, 6.6, 1.6 Hz, 1H), 7.34 (dd, J=8.5, 7.5 Hz, 1H), 6.87 (d, J=1.9 Hz, 1H), 6.75 (s, 1H), 5.67 (s, 2H), 4.47 (s, 2H), 4.36 (s, 2H). MS (ESI+) m/z 470.1 (M+H)⁺.

Example 219

9-[(5-chloro-2-{[(2,6-difluorobenzyl)amino]methyl}-1H-indol-7-yl)methyl]-9H-purin-6-amine Example 219 was prepared according to the procedure used for the preparation of Example 208, substituting 2,6-difluorobenzaldehyde for 2-bromobenzaldehyde. ¹H NMR (400 MHz, DMSO-d$_6$) δ 8.45 (s, 1H), 8.32 (s, 1H), 7.66 (d, J=2.0 Hz, 1H), 7.60 (tt, J=8.4, 6.7 Hz, 1H), 7.23 (t, J=8.1 Hz, 2H), 6.88 (d, J=1.9 Hz, 1H), 6.77 (s, 1H), 5.68 (s, 2H), 4.49 (s, 2H), 4.32 (s, 2H). MS (ESI+) m/z 454 (M+H)⁺.

Example 220

N-({7-[(6-amino-9H-purin-9-yl)methyl]-5-chloro-1H-indol-2-yl}methyl)benzamide

To a suspension of Example 9b (0.05 g, 0.153 mmol) and triethylamine (0.021 mL, 0.153 mmol) in THF (5 mL) were added benzoyl chloride (0.018 mL, 0.153 mmol). The resulting mixture was stirred at ambient temperature for 1 hour. The mixture was concentrated. The residue was purified by reverse phase HPLC (C18, 35-70% acetonitrile/water, 0.05% ammonium hydroxide) to give the title compound (0.02 g, 0.046 mmol, 30.4% yield). MS (ESI+): m/z 432 (M+H)⁺; ¹H NMR (400 MHz, DMSO-d$_6$): δ 11.55 (s, 1H), 9.08 (brs, 1H), 8.31 (s, 1H), 8.17 (s, 1H), 7.94 (d, J=4.0 Hz, 2H), 7.58-7.48 (m, 4H), 7.32 (s, 2H), 6.84 (d, J=2.0 Hz, 1H), 6.38 (s, 1H), 5.56 (s, 2H), 4.70 (d, J=6.4 Hz, 2H).

Example 221

N-({7-[(6-amino-9H-purin-9-yl)methyl]-5-chloro-1H-indol-2-yl}methyl)-4-chlorobenzamide Example 221 was prepared according to the procedure used for the preparation of Example 232, substituting 4-chlorobenzoic acid for 2-(pyridin-4-yl)acetic acid. ¹H NMR (400 MHz, DMSO-d$_6$) δ 4.68 (d, J=5.5 Hz, 2H), 5.68 (s, 2H), 6.39 (d, J=1.9 Hz, 1H), 6.82 (d, J=2.0 Hz, 1H), 7.50 (d, J=2.0 Hz, 1H), 7.53-7.63 (m, 2H), 7.90-8.00 (m, 2H), 8.35 (s, 2H), 8.48 (s, 1H), 9.16 (t, J=5.7 Hz, 1H), 11.50 (d, J=2.1 Hz, 1H). MS (APCI) m/z 466.1 [M+H]⁺.

Example 222

N-({7-[(6-amino-9H-purin-9-yl)methyl]-5-chloro-1H-indol-2-yl}methyl)-3-chlorobenzamide Example 222 was prepared according to the procedure used for the preparation of Example 232, substituting 3-chlorobenzoic acid for 2-(pyridin-4-yl)acetic acid. ¹H NMR (400 MHz, DMSO-d$_6$) δ 4.69 (d, J=5.5 Hz, 2H), 5.65 (s, 2H), 6.40 (d, J=1.9 Hz, 1H), 6.82 (d, J=2.0 Hz, 1H), 7.45-7.59 (m, 2H), 7.60-7.94 (m, 4H), 7.98 (t, J=1.9 Hz, 1H), 8.26 (s, 1H), 8.40 (s, 1H), 9.20 (t, J=5.6 Hz, 1H), 11.53 (d, J=2.3 Hz, 1H). MS (APCI) m/z 466.1 [M+H]⁺.

Example 223

N-({7-[(6-amino-9H-purin-9-yl)methyl]-5-chloro-1H-indol-2-yl}methyl)-4-fluorobenzamide Example 223 was prepared according to the procedure used for the preparation of Example 105, substituting 4-fluorobenzoic acid for 4-methyl-pentanoic acid. ¹H NMR (400 MHz, DMSO-d$_6$) δ 11.50 (s, 1H), 9.10 (t, J=5.7 Hz, 1H), 8.42 (s, 1H), 8.29 (s, 1H), 8.16-7.83 (m, 4H), 7.49 (d, J=2.0 Hz, 1H), 7.39-7.28 (m, 2H), 6.83 (d, J=2.0 Hz, 1H), 6.39 (d, J=1.8 Hz, 1H), 5.65 (s, 2H), 4.68 (d, J=5.6 Hz, 2H). MS (APCI+) m/z 450.0 (M+H)⁺.

Example 224

N-({7-[(6-amino-9H-purin-9-yl)methyl]-5-chloro-1H-indol-2-yl}methyl)-3-fluorobenzamide Example 224 was prepared according to the procedure used for the preparation of Example 105, substituting 3-fluorobenzoic acid for 4-methyl-pentanoic acid. ¹H NMR (400 MHz, DMSO-d$_6$) δ 11.53 (s, 1H), 9.17 (t, J=5.7 Hz, 1H), 8.39 (s, 1H), 8.26 (s, 1H), 7.89-7.69 (m, 4H), 7.56 (td, J=8.0, 5.8 Hz, 1H), 7.49 (d, J=2.0 Hz, 1H), 7.42 (td, J=8.4, 2.6 Hz, 1H), 6.82 (d, J=2.0 Hz, 1H), 6.40 (d, J=1.8 Hz, 1H), 5.64 (s, 2H), 4.70 (d, J=5.6 Hz, 2H). MS (APCI+) m/z 450.0 (M+H)⁺.

Example 225

N-({7-[(6-amino-9H-purin-9-yl)methyl]-5-chloro-1H-indol-2-yl}methyl)-2-fluorobenzamide Example 225 was prepared according to the procedure used for the preparation of Example 105, substituting 2-fluorobenzoic acid for 4-methyl-pentanoic acid. ¹H NMR (400 MHz, DMSO-d$_6$) δ 11.54 (s, 1H), 8.90 (td, J=5.8, 2.2 Hz, 1H), 8.42 (s, 1H), 8.30 (s, 1H), 7.94 (s, 2H), 7.70 (td, J=7.4, 1.7 Hz, 1H), 7.61-7.48 (m, 2H), 7.37-7.27 (m, 2H), 6.82 (d, J=2.0 Hz, 1H), 6.40 (d, J=1.8 Hz, 1H), 5.65 (s, 2H), 4.68 (d, J=5.8 Hz, 2H). MS (APCI+) m/z 450.0 (M+H)⁺.

Example 226

N-({7-[(6-amino-9H-purin-9-yl)methyl]-5-chloro-1H-indol-2-yl}methyl)-2-bromo-6-fluorobenzamide Example 226 was prepared according to the procedure used for the preparation of Example 229, substituting 2-bromo-6-fluorobenzoic acid for 2-fluoro-6-hydroxybenzoic acid. $^1$H NMR (400 MHz, DMSO-$d_6$) δ 4.67 (s, 2H), 5.64 (s, 2H), 6.48 (s, 1H), 6.93 (d, J=2.0 Hz, 1H), 7.28 (t, J=8.7 Hz, 1H), 7.35-7.54 (m, 3H), 8.31 (d, J=8.6 Hz, 2H). MS (APCI) m/z 529.9 [M+H]$^+$.

Example 227

N-({7-[(6-amino-9H-purin-9-yl)methyl]-5-chloro-1H-indol-2-yl}methyl)-2-chloro-6-fluorobenzamide Example 227 was prepared according to the procedure used for the preparation of Example 229, substituting 2-chloro-6-fluorobenzoic acid for 2-fluoro-6-hydroxybenzoic acid. $^1$H NMR (400 MHz, DMSO-$d_6$) δ 4.67 (s, 2H), 5.64 (s, 2H), 6.46 (s, 1H), 6.94 (d, J=2.0 Hz, 1H), 7.24 (t, J=8.7 Hz, 1H), 7.34 (d, J=8.1 Hz, 1H), 7.40-7.54 (m, 2H), 8.31 (d, J=7.9 Hz, 2H). MS (APCI) m/z 484.1 [M+H]$^+$.

Example 228

N-({7-[(6-amino-9H-purin-9-yl)methyl]-5-chloro-1H-indol-2-yl}methyl)-2,6-difluorobenzamide Example 228 was prepared according to the procedure used for the preparation of Example 229, substituting 2,6-difluorobenzoic acid for 2-fluoro-6-hydroxybenzoic acid. $^1$H NMR (400 MHz, DMSO-$d_6$) δ 4.67 (s, 2H), 5.64 (s, 2H), 6.43 (s, 1H), 6.93 (d, J=1.9 Hz, 1H), 7.12 (t, J=8.1 Hz, 2H), 7.43-7.59 (m, 2H), 8.30 (d, J=4.0 Hz, 2H). MS (APCI) m/z 468.1 [M+H]$^+$.

Example 229

N-({7-[(6-amino-9H-purin-9-yl)methyl]-5-chloro-1H-indol-2-yl}methyl)-2-fluoro-6-hydroxybenzamide A solution of Example 9b (0.0925 M in N,N-dimethylacetamide, 329 µL, 0.03 mmol) and N,N-diisopropylethylamine (0.27 M in N,N-dimethylacetamide, 333 µL 0.09 mmol), HATU (0.12 M in N,N-dimethylacetamide, 300 µL, 0.036 mmol), and 2-fluoro-6-hydroxybenzoic acid (0.4M in N,N-dimethylacetamide, 90 µL, 0.036 mmol) were aspirated from their respective source vials, mixed through a perfluoroalkoxy alkanes mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 µL min$^{-1}$ (10 minute residence time). Upon exiting the reactor, the reaction was loaded directly into an injection loop and purified using preparative HPLC to yield the title compound (2.63 mg, 14.87% yield). Samples were purified by preparative HPLC on a Phenomenex Luna C8 (2) 5 µm 100 Å AXIA column (50 mm×21.2 mm). A gradient of acetonitrile (A) and 0.1% trifluoroacetic acid in water (B) was used, at a flow rate of 30 mL/min (0-0.5 minutes 5% A, 0.5-6.5 minutes linear gradient 5-40% A, 6.5-7.0 minutes linear gradient 40-100% A, 7.0-8.5 minutes 100% A, 8.5-9.0 minutes linear gradient 100-5% A, 9.0-10 minutes 5% A). A sample volume of 1.0 mL was injected directly from the flow reactor stream to the HPLC system. A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0. $^1$H NMR (400 MHz, DMSO-$d_6$) δ 4.71 (s, 2H), 5.60 (s, 2H), 6.43 (s, 1H), 6.65-6.83 (m, 2H), 6.91 (d, J=1.8 Hz, 1H), 7.28-7.40 (m, 1H), 7.47 (d, J=2.0 Hz, 1H), 8.22 (d, J=3.2 Hz, 2H). MS (APCI) m/z 466.0 [M+H]$^+$.

Example 230

N-({7-[(6-amino-9H-purin-9-yl)methyl]-5-chloro-1H-indol-2-yl}methyl)-2-(pyridin-2-yl)acetamide Example 230 was prepared according to the procedure used for the preparation of Example 232, substituting 2-(pyridin-2-yl)acetic acid for 2-(pyridin-4-yl)acetic acid. 1H NMR (400 MHz, DMSO-$d_6$) δ 0.73-2.40 (m, 5H), 2.63-2.83 (m, 1H), 2.87-3.58 (m, 18H), 3.86 (s, 5H), 4.51 (d, J=5.5 Hz, 2H), 5.67 (s, 2H), 6.38 (d, J=1.9 Hz, 1H), 6.82 (d, J=2.0 Hz, 1H), 7.46-7.58 (m, 2H), 7.62 (d, J=7.9 Hz, 1H), 8.06 (t, J=7.7 Hz, 1H), 8.28-8.83 (m, 6H), 11.51 (s, 1H). MS (APCI) m/z 447.1 [M+H]$^+$.

Example 231

N-({7-[(6-amino-9H-purin-9-yl)methyl]-5-chloro-1H-indol-2-yl}methyl)-2-(pyridin-3-yl)acetamide Example 231 was prepared according to the procedure used for the preparation of Example 105, substituting pyridin-3-yl-acetic acid for 4-methyl-pentanoic acid. $^1$H NMR (400 MHz, DMSO-$d_6$) δ 11.51 (d, J=2.0 Hz, 1H), 8.83-8.67 (m, 3H), 8.46 (d, J=46.1 Hz, 4H), 8.22 (dt, J=8.1, 1.8 Hz, 1H), 7.79 (dd, J=7.9, 5.3 Hz, 1H), 7.50 (d, J=2.0 Hz, 1H), 6.81 (d, J=2.0 Hz, 1H), 6.37 (d, J=1.9 Hz, 1H), 5.68 (s, 2H), 4.51 (d, J=5.5 Hz, 2H), 3.75 (s, 2H). MS (APCI+) m/z 447.1 (M+H)$^+$.

Example 232

N-({7-[(6-amino-9H-purin-9-yl)methyl]-5-chloro-1H-indol-2-yl}methyl)-2-(pyridin-4-yl)acetamide A solution of Example 9b (0.136 M in N,N-dimethylacetamide, 337 µL, 0.046 mmol), N,N-diisopropylethylamine (0.157 M in N,N-dimethylacetamide, 350 µL, 0.055 mmol), HATU (0.15 M in N,N-diemtheylacetimide, 337 µL, 0.05 mmol), and 2-(pyridin-4-yl)acetic acid (0.4 M in N,N-diemtheylacetimide, 125 µL, 0.05 mmol) were aspirated from their respective source vials, mixed through a perfluoroalkoxy alkanes mixing tube (0.2 mm inner diameter), and loaded into an injection loop. The reaction segment was injected into the flow reactor (Hastelloy coil, 0.75 mm inner diameter, 1.8 mL internal volume) set at 100° C., and passed through the reactor at 180 µL min$^{-1}$ (10 minute residence time). Upon exiting the reactor, the reaction was loaded directly into an injection loop and purified using preparative HPLC to yield the title compound (6.21 mg, 24.17% yield). Samples were purified by preparative HPLC on a Phenomenex Luna C8 (2) 5 µm 100 Å AXIA column (50 mm×21.2 mm). A gradient of acetonitrile (A) and 0.1% trifluoroacetic acid in water (B) was used, at a flow rate of 30 mL/min (0-0.5 minutes 5% A, 0.5-6.5 minutes linear gradient 5-60% A, 6.5-7.0 minutes linear gradient 60-100% A, 7.0-8.9 minutes 100% A, 8.9-9.0 minutes linear gradient 100-5% A, 9.0-10 minutes 5% A). A sample volume of 1.0 mL was injected directly from the flow reactor stream to the HPLC system. A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; Thermo MSQ Plus mass spectrometer. The system was controlled through a combination of Thermo Xcalibur 2.0.7 software and a custom application written in-house using Microsoft Visual Basic 6.0. $^1$H NMR (400 MHz, DMSO-$d_6$) δ 1.96 (s, 5H), 2.78 (s, 1H), 2.87-3.58 (m, 18H), 3.86 (s, 5H), 4.51 (d, J=5.5 Hz, 2H), 5.67 (s, 2H), 6.38 (d, J=1.9 Hz, 1H), 6.82 (d, J=2.0 Hz, 1H), 7.46-7.58 (m, 2H), 7.62 (d, J=7.9 Hz, 1H), 8.06 (t, J=7.7 Hz, 1H), 8.28-8.83 (m, 6H), 11.51 (s, 1H). MS (APCI) m/z 447.1 [M+H]$^+$.

Example 233

N-({7-[(6-amino-9H-purin-9-yl)methyl]-5-chloro-1H-indol-2-yl}methyl)-2-methylpyridine-3-carboxamide Example 233 was prepared according to the procedure used for the preparation of Example 229, substituting 2-methylnicotinic acid for 2-fluoro-6-hydroxybenzoic acid. $^1$H NMR (400 MHz, DMSO-$d_6$) δ 4.67 (s, 2H), 5.64 (s, 2H), 6.45 (s, 1H), 6.94 (s, 1H), 7.30-7.42 (m, 1H), 7.49 (d, J=2.1 Hz, 1H), 7.85 (d, J=7.5 Hz, 1H), 8.29 (s, 2H), 8.53 (dd, J=4.9, 1.8 Hz, 1H). MS (APCI) m/z 447.1 [M+H]$^+$.

Example 234

N-({7-[(6-amino-9H-purin-9-yl)methyl]-5-chloro-1H-indol-2-yl}methyl)-3,6-dimethylpyridazine-4-carboxamide Example 234 was prepared according to the procedure used for the preparation of Example 199, substituting 3,6-dimethylpyridazine-4-carboxylic acid for 3-methylpyridazine-4-carboxylic acid. $^1$H NMR (400 MHz, DMSO-$d_6$) δ 2.66 (d, J=4.1 Hz, 6H), 4.69 (s, 2H), 5.73 (s, 2H), 6.49 (s, 1H), 6.84 (d, J=1.9 Hz, 1H), 7.55 (d, J=2.0 Hz, 1H), 7.69 (s, 1H), 8.46 (s, 1H), 8.59 (s, 1H). MS (APCI) m/z 462.2 [M+H]$^+$.

Example 235

N-({7-[(6-amino-9H-purin-9-yl)methyl]-5-(1,2,3,6-tetrahydropyridin-4-yl)-1H-indol-2-yl}methyl)-3,6-dimethylpyridazine-4-carboxamide Example 235a tert-butyl 4-(7-((6-amino-9H-purin-9-yl)methyl)-2-(aminomethyl)-1H-indol-5-yl)-5,6-dihydropyridine-1(2H)-carboxylate Example 235a was prepared according to the procedure used for the preparation of Example 10, substituting tert-butyl 4-(4,4,5,5-tetramethyl-1,3,2-dioxaborolan-2-yl)-5,6-dihydropyridine-1(2H)-carboxylate [Frontier] for 4,4,5,5-tetramethyl-2-vinyl-1,3,2-dioxaborolane. MS m/z: 475 [M+H]$^+$.

Example 235b tert-butyl 4-(7-((6-amino-9H-purin-9-yl)methyl)-2-((3,6-dimethylpyridazine-4-carboxamido)methyl)-1H-indol-5-yl)-5,6-dihydropyridine-1(2H)-carboxylate Example 235b was prepared according to the procedure used for the preparation of Example 100, substituting 3,6-dimethylpyridazine-4-carboxylic acid [Enamine] for 3-methoxypropanoic acid and N,N-dimethylformamide for N,N-dimethylacetamide. MS m/z: 609 [M+H]$^+$.

Example 235c

N-({7-[(6-amino-9H-purin-9-yl)methyl]-5-(1,2,3,6-tetrahydropyridin-4-yl)-1H-indol-2-yl}methyl)-3,6-dimethylpyridazine-4-carboxamide To a flask was added Example 235b (0.074 g, 0.122 mmol), 1,4-dioxane (1 mL) and hydrogen chloride (0.365 mL, 1.459 mmol, 4 M in 1,4-dioxane). The mixture was stirred at room temperature for about 1 hour, and concentrated to dryness. The residue was suspended in methanol and sonicated. The solid was collected by filtration, washed with ether and dried to give the title compound (0.038 g, 53.8%). $^1$H NMR (400 MHz, CD$_3$OD) δ 8.53 (s, 1H), 8.38 (s, 1H), 7.99 (s, 1H), 7.65 (d, J=1.6 Hz, 1H), 7.37 (d, J=1.6 Hz, 1H), 6.54 (s, 1H), 6.09 (s, 1H), 5.78 (s, 2H), 3.85 (d, J=3.1 Hz, 2H), 3.47 (t, J=6.1 Hz, 2H), 2.86 (s, 2H), 2.77 (s, 3H), 2.75 (s, 3H); MS m/z: 509 [M+H]$^+$.

Example 236

N-({7-[(6-amino-9H-purin-9-yl)methyl]-5-(4,4-difluorocyclohex-1-en-1-yl)-1H-indol-2-yl}methyl)-3,6-dimethylpyridazine-4-carboxamide Example 236 was prepared according to the procedure used for the preparation of Example 100, substituting Example 14 for Example 9b, and substituting 3,6-dimethylpyridazine-4-carboxylic acid [Enamine] for 3-methoxypropanoic acid, and N,N-dimethylformamide for N,N-dimethylacetamide. $^1$H NMR (400 MHz, DMSO-$d_6$) δ 11.41 (s, 1H), 9.23 (t, J=5.6 Hz, 1H), 8.28 (s, 1H), 8.20 (s, 1H), 7.51 (d, J=3.9 Hz, 2H), 7.30 (s, 2H), 7.12 (d, J=1.6 Hz, 1H), 6.43 (d, J=1.8 Hz, 1H), 5.81 (s, 1H), 5.59 (s, 2H), 4.67 (d, J=5.7 Hz, 2H), 2.63 (m, 10H), 2.16 (tt, J=13.8, 6.4 Hz, 2H); MS m/z: 544 [M+H]$^+$.

Example 237

N-({5-(1-acetyl-1,2,3,6-tetrahydropyridin-4-yl)-7-[(6-amino-9H-purin-9-yl)methyl]-1H-indol-2-yl}methyl)-3,6-dimethylpyridazine-4-carboxamide Example 237 was prepared according to the procedure used for the preparation of Example 100, substituting Example 15b for Example 9b, and substituting 3,6-dimethylpyridazine-4-carboxylic acid [Enamine] for 3-methoxypropanoic acid, and N,N-dimethylformamide for N,N-dimethylacetamide. $^1$H NMR (400 MHz, DMSO-$d_6$) δ 11.42 (s, 1H), 9.24 (t, J=5.6 Hz, 1H), 8.28 (s, 1H), 8.20 (s, 1H), 7.50 (d, J=11.7 Hz, 2H), 7.30 (s, 2H), 7.15 (s, 1H), 6.44 (d, J=1.8 Hz, 1H), 5.96 (d, J=11.3 Hz, 1H), 5.60 (s, 2H), 4.67 (d, J=5.6

Hz, 2H), 4.08 (d, J=23.5 Hz, 2H), 3.62 (dt, J=11.9, 5.7 Hz, 3H), 2.64 (s, 3H), 2.63 (s, 3H), 2.10-1.98 (m, 3H); MS m/z: 551 [M+H]$^+$.

Example 238

N-({5-(1-acetyl-1,4,5,6-tetrahydropyridin-3-yl)-7-[(6-amino-9H-purin-9-yl)methyl]-1H-indol-2-yl}methyl)-3,6-dimethylpyridazine-4-carboxamide Example 238 was prepared according to the procedure used for the preparation of Example 100, substituting Example 16b for Example 9b, and substituting 3,6-dimethylpyridazine-4-carboxylic acid [Enamine] for 3-methoxypropanoic acid, and N,N-dimethylformamide for N,N-dimethylacetamide. $^1$H NMR (400 MHz, DMSO-d$_6$) δ 11.42 (s, 1H), 9.25 (t, J=5.6 Hz, 1H), 8.28 (s, 1H), 8.21 (s, 1H), 7.58-7.47 (m, 2H), 7.30 (s, 2H), 7.14 (d, J=11.2 Hz, 1H), 6.51-6.40 (m, 1H), 6.10 (d, J=14.1 Hz, 1H), 5.60 (s, 2H), 4.67 (d, J=5.5 Hz, 2H), 4.31 (s, 2H), 3.54 (dt, J=10.9, 5.7 Hz, 2H), 2.64 (s, 3H), 2.63 (s, 3H), 2.36-2.16 (m, 2H), 2.10-2.04 (m, 3H); MS m/z: 551 [M+H]$^+$.

Example 239

N-({7-[(6-amino-9H-purin-9-yl)methyl]-4-chloro-1H-indol-2-yl}methyl)-3,6-dimethylpyridazine-4-carboxamide Example 239 was prepared according to the procedure used for the preparation of Example 100, substituting Example 62j for Example 9b, and substituting 3,6-dimethylpyridazine-4-carboxylic acid [Enamine] for 3-methoxypropanoic acid, and N,N-dimethylformamide for N,N-dimethylacetamide. $^1$H NMR (400 MHz, DMSO-d$_6$) δ 11.76 (s, 1H), 9.26 (t, J=5.6 Hz, 1H), 8.42 (s, 1H), 8.36-8.09 (m, 3H), 7.55 (s, 1H), 7.01 (d, J=7.9 Hz, 1H), 6.82 (d, J=7.9 Hz, 1H), 6.49 (s, 1H), 5.67 (s, 2H), 4.70 (d, J=5.6 Hz, 2H), 2.66 (s, 3H), 2.62 (s, 3H); MS m/z: 462 [M+H]$^+$.

Example 240

N-({7-[(6-amino-9H-purin-9-yl)methyl]-5-choro-1H-indol-2-yl}methyl)-6-cyanopyridine-3-carboxamide Example 240 was prepared according to the procedure used for the preparation of Example 229, substituting 6-cyanonicotinic acid for 2-fluoro-6-hydroxybenzoic acid. $^1$H NMR (400 MHz, DMSO-d$_6$) δ 4.72 (s, 2H), 5.67 (s, 2H), 6.92 (d, J=1.9 Hz, 1H), 7.49 (d, J=2.0 Hz, 1H), 8.09 (d, J=8.0 Hz, 1H), 8.29-8.47 (m, 3H), 9.14 (d, J=2.0 Hz, 1H). MS (APCI) m/z 458.1 [M+H]$^+$.

Example 241

9-[(5-chloro-2-{[(4-methylbenzyl)amino]methyl}-1H-indol-7-yl)methyl]-9H-purin-6-amine Example 241 was prepared according to the procedure used for the preparation of Example 208, substituting 4-methylbenzaldehyde for 2-bromobenzaldehyde. $^1$H NMR (400 MHz, DMSO-d$_6$) δ 8.44 (s, 1H), 8.31 (s, 1H), 7.65 (d, J=1.9 Hz, 1H), 7.39 (d, J=8.0 Hz, 2H), 7.29 (d, J=7.9 Hz, 2H), 6.88 (d, J=1.9 Hz, 1H), 6.73 (s, 1H), 5.67 (s, 2H), 4.37 (s, 2H), 4.20 (s, 2H), 2.34 (s, 3H). MS (ESI+) m/z 432.3 (M+H)$^+$.

Example 242

9-[(5-chloro-2-{[(2-methylbenzyl)amino]methyl}-1H-indol-7-yl)methyl]-9H-purin-6-amine Example 242 was prepared according to the procedure used for the preparation of Example 208, substituting 2-methylbenzaldehyde for 2-bromobenzaldehyde. 1H NMR (400 MHz, DMSO-d$_6$) δ 8.45 (s, 1H), 8.32 (s, 1H), 7.66 (d, J=1.9 Hz, 1H), 7.49-7.39 (m, 1H), 7.38-7.25 (m, 3H), 6.90 (d, J=1.9 Hz, 1H), 6.78 (s, 1H), 5.69 (s, 2H), 4.48 (s, 2H), 4.24 (s, 2H), 2.30 (s, 3H). MS (ESI+) m/z 432.1 (M+H)$^+$.

Example 243

9-[(5-chloro-2-{[(2-chloro-6-methylbenzyl)amino]methyl})-1H-indol-7-yl)methyl]-9H-purin-6-amine Example 243 was prepared according to the procedure used for the preparation of Example 208, substituting 2-chloro-6-methylbenzaldehyde for 2-bromobenzaldehyde. 1H NMR (400 MHz, DMSO-d$_6$) δ 8.46 (s, 1H), 8.33 (s, 1H), 7.68 (d, J=1.9 Hz, 1H), 7.47-7.34 (m, 2H), 7.29 (dd, J=6.8, 2.1 Hz, 1H), 6.92 (d, J=1.9 Hz, 1H), 6.83 (s, 1H), 5.70 (s, 2H), 4.54 (s, 2H), 4.35 (s, 2H), 2.34 (s, 3H). MS (ESI+) m/z 466.1 (M+H)$^+$.

Example 244

9-[(5-chloro-2-{[(2-fluoro-6-methylbenzyl)amino]methyl}-1H-indol-7-yl)methyl]-9H-purin-6-amine Example 244 was prepared according to the procedure used for the preparation of Example 208, substituting 2-fluoro-6-methylbenzaldehyde for 2-bromobenzaldehyde. $^1$H NMR (400 MHz, DMSO-d$_6$) δ 8.46 (s, 1H), 8.33 (s, 1H), 7.67 (d, J=1.9 Hz, 1H), 7.41 (td, J=8.1, 6.2 Hz, 1H), 7.15 (t, J=8.7 Hz, 2H), 6.89 (d, J=2.0 Hz, 1H), 6.80 (s, 1H), 5.69 (s, 2H), 4.50 (s, 2H), 4.27 (d, J=1.8 Hz, 2H), 2.34 (s, 3H). MS (ESI+) m/z 450.1 (M+H)$^+$.

Example 245

9-[(5-chloro-2-{[(2-fluoro-3-methylbenzyl)amino]methyl}-1H-indol-7-yl)methyl]-9H-purin-6-amine Example 245 was prepared according to the procedure used for the preparation of Example 208, substituting 2-fluoro-3-methylbenzaldehyde for 2-bromobenzaldehyde. $^1$H NMR (400 MHz, DMSO-d$_6$) δ 8.47 (s, 1H), 8.33 (s, 1H), 7.66 (d, J=1.9 Hz, 1H), 7.39 (td, J=7.5, 7.0, 4.8 Hz, 2H), 7.20 (t, J=7.6 Hz, 1H), 6.88 (d, J=1.9 Hz, 1H), 6.76 (s, 1H), 5.68 (s, 2H), 4.45 (s, 2H), 4.29 (s, 2H), 2.27 (d, J=1.9 Hz, 3H). MS (ESI+) m/z 450.1 (M+H)$^+$.

Example 246

N-({7-[(6-amino-9H-purin-9-yl)methyl]-5-chloro-1H-indol-2-yl}methyl)-4-methylbenzamide Example 246 was prepared according to the procedure used for the preparation of Example 105, substituting 4-methylbenzoic acid for 4-methyl-pentanoic acid. $^1$H NMR (400 MHz, DMSO-d$_6$) δ 11.49 (s, 1H), 8.99 (t, J=5.8 Hz, 1H), 8.46 (s, 1H), 8.34 (s, 1H), 8.24 (s, 2H), 7.87-7.80 (m, 2H), 7.49 (d, J=2.0 Hz, 1H), 7.30 (d, J=8.0 Hz, 2H), 6.83 (d, J=2.0 Hz, 1H), 6.37 (d, J=1.8 Hz, 1H), 5.67 (s, 2H), 4.67 (d, J=5.7 Hz, 2H), 2.37 (s, 3H). MS (APCI+) m/z 446.1 (M+H)+.

Example 247

N-({7-[(6-amino-9H-purin-9-yl)methyl]-5-chloro-1H-indol-2-yl}methyl)-3-methylbenzamide Example 247 was prepared according to the procedure used for the preparation of Example 105, substituting 3-methylbenzoic acid for 4-methyl-pentanoic acid. $^1$H NMR (400 MHz, DMSO-$d_6$) δ 11.49 (s, 1H), 9.02 (t, J=5.8 Hz, 1H), 8.48 (s, 1H), 8.37-8.15 (m, 3H), 7.77-7.68 (m, 2H), 7.50 (d, J=1.9 Hz, 1H), 7.45-7.33 (m, 2H), 6.82 (d, J=2.0 Hz, 1H), 6.38 (d, J=1.8 Hz, 1H), 5.68 (s, 2H), 4.68 (d, J=5.6 Hz, 2H), 2.37 (s, 3H). MS (APCI+) m/z 446.1 (M+H)+.

Example 248

N-({7-[(6-amino-9H-purin-9-yl)methyl]-5-chloro-1H-indol-2-yl}methyl)-2-methylbenzamide Example 248 was prepared according to the procedure used for the preparation of Example 105, substituting 2-methylbenzoic acid for 4-methyl-pentanoic acid. $^1$H NMR (400 MHz, DMSO-$d_6$) δ 11.54 (s, 1H), 8.84 (t, J=5.8 Hz, 1H), 8.47 (s, 1H), 8.35 (s, 1H), 8.26 (s, 2H), 7.52 (d, J=2.1 Hz, 1H), 7.42 (dd, J=8.0, 1.6 Hz, 1H), 7.37-7.31 (m, 1H), 7.30-7.19 (m, 2H), 6.84 (d, J=2.0 Hz, 1H), 6.41 (d, J=1.8 Hz, 1H), 5.68 (s, 2H), 4.65 (d, J=5.7 Hz, 2H), 2.37 (s, 3H). MS (APCI+) m/z 446.1 (M+H)+.

Example 249

9-[(5-chloro-2-{[(3-methoxybenzyl)amino]methyl}-1H-indol-7-yl)methyl]-9H-purin-6-amine Example 249 was prepared according to the procedure used for the preparation of Example 208, substituting 3-methoxybenzaldehyde for 2-bromobenzaldehyde. $^1$H NMR (400 MHz, DMSO-$d_6$) δ 8.45 (s, 1H), 8.32 (s, 1H), 7.65 (d, J=1.9 Hz, 1H), 7.40 (t, J=7.9 Hz, 1H), 7.15-6.98 (m, 3H), 6.88 (d, J=1.9 Hz, 1H), 6.74 (s, 1H), 5.67 (s, 2H), 4.40 (s, 2H), 4.23 (s, 2H), 3.79 (s, 3H). MS (ESI+) m/z 448.2 (M+H)+.

Example 250

9-[(5-chloro-2-{[(2-methoxybenzyl)amino]methyl}-1H-indol-7-yl)methyl]-9H-purin-6-amine Example 250 was prepared according to the procedure used for the preparation of Example 208, substituting 2-methoxybenzaldehyde for 2-bromobenzaldehyde. $^1$H NMR (400 MHz, DMSO-$d_6$) δ 8.46 (s, 1H), 8.32 (s, 1H), 7.66 (d, J=1.9 Hz, 1H), 7.46 (td, J=7.9, 1.7 Hz, 1H), 7.39 (dd, J=7.6, 1.7 Hz, 1H), 7.11 (d, J=8.3 Hz, 1H), 7.02 (t, J=7.5 Hz, 1H), 6.88 (d, J=2.0 Hz, 1H), 6.76 (s, 1H), 5.68 (s, 2H), 4.40 (s, 2H), 4.18 (s, 2H), 3.82 (s, 3H). MS (ESI+) m/z 448.1 (M+H)+.

Example 251

N-({7-[(6-amino-9H-purin-9-yl)methyl]-5-chloro-1H-indol-2-yl}methyl)-2-(4-chlorophenyl)acetamide Example 251 was prepared according to the procedure used for the preparation of Example 105, substituting (4-chlorophenyl)acetic acid for 4-methyl-pentanoic acid. $^1$H NMR (400 MHz, DMSO-$d_6$) δ 11.50 (d, J=2.0 Hz, 1H), 8.64 (t, J=5.6 Hz, 1H), 8.47 (s, 1H), 8.37 (s, 3H), 7.49 (d, J=2.1 Hz, 1H), 7.42-7.19 (m, 4H), 6.82 (d, J=2.0 Hz, 1H), 6.33 (d, J=1.8 Hz, 1H), 5.66 (s, 2H), 4.47 (d, J=5.5 Hz, 2H), 3.52 (s, 2H). MS (APCI+) m/z 480.0 (M+H)+.

Example 252

N-({7-[(6-amino-9H-purin-9-yl)methyl]-5-chloro-1H-indol-2-yl}methyl)-2-(3-chlorophenyl)acetamide Example 252 was prepared according to the procedure used for the preparation of Example 232, substituting 2-(3-chlorophenyl)acetic acid for 2-(pyridin-4-yl)acetic acid. $^1$H NMR (400 MHz, DMSO-$d_6$) δ 3.54 (s, 2H), 4.48 (d, J=5.5 Hz, 2H), 5.64 (s, 2H), 6.33 (d, J=1.9 Hz, 1H), 6.82 (d, J=2.0 Hz, 1H), 7.12-7.43 (m, 5H), 7.48 (d, J=2.0 Hz, 1H), 8.07 (s, 2H), 8.33 (s, 1H), 8.43 (s, 1H), 8.66 (t, J=5.6 Hz, 1H), 11.52 (d, J=2.1 Hz, 1H). MS (APCI) m/z 480.1 [M+H]+.

Example 253

N-({7-[(6-amino-9H-purin-9-yl)methyl]-5-chloro-1H-indol-2-yl}methyl)-2-(2-chlorophenyl)acetamide Example 253 was prepared according to the procedure used for the preparation of Example 232, substituting 2-(2-chlorophenyl)acetic acid for 2-(pyridin-4-yl)acetic acid. $^1$H NMR (400 MHz, DMSO-$d_6$) δ 3.70 (s, 2H), 4.51 (d, J=5.5 Hz, 2H), 5.66 (s, 2H), 6.37 (d, J=1.9 Hz, 1H), 6.82 (d, J=2.0 Hz, 1H), 7.14-7.34 (m, 2H), 7.34-7.46 (m, 2H), 7.50 (d, J=1.9 Hz, 1H), 8.36 (s, 3H), 8.46 (s, 1H), 8.63 (t, J=5.6 Hz, 1H), 11.50 (d, J=2.1 Hz, 1H). MS (APCI) m/z 480.1 [M+H]+.

Example 254

N-({7-[(6-amino-9H-purin-9-yl)methyl]-5-chloro-1H-indol-2-yl}methyl)-2-(4-fluorophenyl)acetamide Example 254 was prepared according to the procedure used for the preparation of Example 105, substituting (4-fluorophenyl)acetic acid for 4-methyl-pentanoic acid. $^1$H NMR (400 MHz, DMSO-$d_6$) δ 11.50 (s, 1H), 8.62 (t, J=5.6 Hz, 1H), 8.46 (s, 1H), 8.36 (s, 1H), 8.29 (s, 2H), 7.49 (d, J=2.0 Hz, 1H), 7.39-7.29 (m, 2H), 7.19-7.08 (m, 2H), 6.82 (d, J=2.0 Hz, 1H), 6.33 (d, J=1.8 Hz, 1H), 5.66 (s, 2H), 4.47 (d, J=5.5 Hz, 2H), 3.51 (s, 2H). MS (APCI+) m/z 464.0 (M+H)+.

Example 255

N-({7-[(6-amino-9H-purin-9-yl)methyl]-5-chloro-1H-indol-2-yl}methyl)-2-(3-fluorophenyl)acetamide Example 255 was prepared according to the procedure used for the preparation of Example 105, substituting (3-fluorophenyl)acetic acid for 4-methyl-pentanoic acid. $^1$H NMR (400 MHz, DMSO-$d_6$) δ 11.51 (s, 1H), 8.65 (t, J=5.6 Hz, 1H), 8.46 (s, 1H), 8.36 (s, 1H), 8.26 (s, 2H), 7.49 (d, J=2.0 Hz, 1H), 7.41-7.31 (m, 1H), 7.18-7.12 (m, 2H), 7.10-7.02 (m, 1H), 6.82 (d, J=2.0 Hz, 1H), 6.33 (d, J=1.8 Hz, 1H), 5.66 (s, 2H), 4.48 (d, J=5.5 Hz, 2H), 3.55 (s, 2H). MS (APCI+) m/z 464.0 (M+H)+.

Example 256

N-({7-[(6-amino-9H-purin-9-yl)methyl]-5-chloro-1H-indol-2-yl}methyl)-2-(2-fluorophenyl)acetamide Example 256 was prepared according to the procedure used for the preparation of Example 232, substituting 2-(2-fluorophenyl)acetic acid for 2-(pyridin-4-yl)acetic acid. $^1$H NMR (400 MHz, DMSO-$d_6$) δ 3.96 (s, 2H), 4.50 (d, J=5.5 Hz, 2H), 5.66 (s, 2H), 6.36 (d, J=1.9 Hz, 1H), 6.82 (d, J=2.0 Hz, 1H), 6.85-7.24 (m, 2H), 7.24-7.44 (m, 2H), 7.50 (d, J=2.0 Hz, 1H), 8.37 (s, 3H), 8.47 (s, 1H), 8.64 (t, J=5.6 Hz, 1H), 11.51 (d, J=2.1 Hz, 1H). MS (APCI) m/z 464.1 [M+H]$^+$.

Example 257

N-({7-[(6-amino-9H-purin-9-yl)methyl]-5-chloro-1H-indol-2-yl}methyl)-2-(trifluoromethyl)benzamide Example 257 was prepared according to the procedure used for the preparation of Example 229, substituting 2-(trifluoromethyl)benzoic acid for 2-fluoro-6-hydroxybenzoic acid. $^1$H NMR (400 MHz, DMSO-$d_6$) δ 4.67 (s, 2H), 5.69 (s, 2H), 6.95 (d, J=2.0 Hz, 1H), 7.52 (d, J=1.9 Hz, 1H), 7.59 (d, J=7.5 Hz, 1H), 7.65-7.88 (m, 4H), 8.37 (d, J=2.0 Hz, 2H). MS (APCI) m/z 500.2 [M+H]$^+$.

Example 258

N-({7-[(6-amino-9H-purin-9-yl)methyl]-5-chloro-1H-indol-2-yl}methyl)-4-methoxybenzamide Example 258 was prepared according to the procedure used for the preparation of Example 232, substituting 4-methoxybenzoic acid for 2-(pyridin-4-yl)acetic acid. $^1$H NMR (400 MHz, DMSO-$d_6$) δ 3.82 (s, 3H), 4.66 (d, J=5.6 Hz, 2H), 5.67 (s, 2H), 6.37 (d, J=1.8 Hz, 1H), 6.83 (d, J=2.0 Hz, 1H), 6.97-7.08 (m, 2H), 7.49 (d, J=2.0 Hz, 1H), 7.86-7.97 (m, 2H), 8.34 (s, 3H), 8.47 (s, 1H), 8.92 (t, J=5.7 Hz, 1H), 11.43-11.51 (m, 1H). MS (APCI) m/z 462.1 [M+H]$^+$.

Example 259

N-({7-[(6-amino-9H-purin-9-yl)methyl]-5-chloro-1H-indol-2-yl}methyl)-3-methoxybenzamide Example 259 was prepared according to the procedure used for the preparation of Example 232, substituting 3-methoxybenzoic acid for 2-(pyridin-4-yl)acetic acid. $^1$H NMR (400 MHz, DMSO-$d_6$) δ 3.82 (s, 4H), 4.68 (d, J=5.6 Hz, 2H), 5.67 (s, 2H), 6.38 (d, J=1.9 Hz, 1H), 6.83 (d, J=2.0 Hz, 1H), 7.12 (ddd, J=8.2, 2.6, 1.0 Hz, 1H), 7.41 (t, J=7.9 Hz, 1H), 7.45-7.57 (m, 3H), 8.34 (s, 3H), 8.47 (s, 1H), 9.07 (t, J=5.7 Hz, 1H), 11.51 (d, J=2.1 Hz, 1H). MS (APCI) m/z 462.1 [M+H]$^+$.

Example 260

N-({7-[(6-amino-9H-purin-9-yl)methyl]-5-chloro-1H-indol-2-yl}methyl)-2-methoxybenzamide Example 260 was prepared according to the procedure used for the preparation of Example 105, substituting 2-methoxybenzoic acid for 4-methyl-pentanoic acid. $^1$H NMR (400 MHz, DMSO-$d_6$) δ 11.52 (s, 1H), 8.72 (t, J=5.8 Hz, 1H), 8.40 (s, 1H), 8.27 (s, 1H), 7.89-7.78 (m, 3H), 7.55-7.46 (m, 2H), 7.17 (d, J=8.3 Hz, 1H), 7.06 (t, J=7.4 Hz, 1H), 6.83 (d, J=2.0 Hz, 1H), 6.38 (d, J=1.8 Hz, 1H), 5.64 (s, 2H), 4.70 (d, J=5.8 Hz, 2H), 3.92 (s, 3H). MS (APCI+) m/z 462.0 (M+H)$^+$.

Example 261

N-({7-[(6-amino-9H-purin-9-yl)methyl]-5-chloro-1H-indol-2-yl}methyl)-2-(difluoromethoxy)benzamide Example 261 was prepared according to the procedure used for the preparation of Example 229, substituting 2-(difluoromethoxy)benzoic acid for 2-fluoro-6-hydroxybenzoic acid. $^1$H NMR (400 MHz, DMSO-$d_6$) δ 4.67 (s, 2H), 5.65 (s, 2H), 6.44 (s, 1H), 6.92 (d, J=1.9 Hz, 1H), 7.02 (d, J=17.3 Hz, 1H), 7.14-7.42 (m, 3H), 7.43-7.69 (m, 3H), 8.33 (d, J=2.4 Hz, 2H). MS (APCI) m/z 498.0 [M+H]$^+$.

Example 262

9-{5-chloro-2-({[3-(methylsulfonyl)benzyl]amino}methyl)-1H-indol-7-yl]methyl}-9H-purin-6-amine Example 262 was prepared according to the procedure used for the preparation of Example 208, substituting 3-(methylsulfonyl)benzaldehyde for 2-bromobenzaldehyde. $^1$H NMR (400 MHz, DMSO-$d_6$) δ 8.46 (s, 1H), 8.33 (s, 1H), 8.12 (t, J=1.8 Hz, 1H), 8.01 (dt, J=7.9, 1.4 Hz, 1H), 7.86 (dt, J=8.0, 1.4 Hz, 1H), 7.76 (t, J=7.8 Hz, 1H), 7.66 (d, J=1.9 Hz, 1H), 6.87 (d, J=2.0 Hz, 1H), 6.75 (s, 1H), 5.68 (s, 2H), 4.46 (s, 2H), 4.40 (s, 2H), 3.22 (s, 3H). MS (ESI+) m/z 496 (M+H)$^+$.

Example 263

9-{[5-chloro-2-({[4-fluoro-3-(methylsulfonyl)benzyl]amino}methyl)-1H-indol-7-yl]methyl}-9H-purin-6-amine Example 263 was prepared according to the procedure used for the preparation of Example 208, substituting 4-fluoro-3-(methylsulfonyl)benzaldehyde for 2-bromobenzaldehyde. $^1$H NMR (400 MHz, DMSO-$d_6$) δ 8.46 (s, 1H), 8.34 (s, 1H), 8.10 (dd, J=6.7, 2.4 Hz, 1H), 7.91 (ddd, J=8.6, 4.7, 2.3 Hz, 1H), 7.70-7.55 (m, 2H), 6.87 (d, J=1.9 Hz, 1H), 6.73 (s, 1H), 5.68 (s, 2H), 4.44 (s, 2H), 4.37 (s, 2H), 3.34 (s, 3H). MS (ESI+) m/z 514 (M+H)$^+$.

Example 264

9-{[5-chloro-2-({[3-fluoro-4-(methylsulfonyl)benzyl]amino}methyl)-1H-indol-7-yl]methyl}-9H-purin-6-amine Example 264 was prepared according to the procedure used for the preparation of Example 208, substituting 3-fluoro-4-(methylsulfonyl)benzaldehyde for 2-bromobenzaldehyde. $^1$H NMR (400 MHz, DMSO-$d_6$) δ 8.47 (s, 1H), 8.34 (s, 1H), 7.95 (t, J=7.7 Hz, 1H), 7.76-7.63 (m, 2H), 7.59 (dd, J=8.1, 1.6 Hz, 1H), 6.88 (d, J=2.0 Hz, 1H), 6.74 (s, 1H), 5.68 (s, 2H), 4.45 (s, 2H), 4.40 (s, 2H), 3.33 (s, 3H). MS (ESI+) m/z 514.1 (M+H)$^+$.

Example 265

N-({7-[(6-amino-9H-purin-9-yl)methyl]-5-chloro-1H-indol-2-yl}methyl)-2-(methylsulfonyl)benzamide Example 265 was prepared according to the procedure used for the preparation of Example 229, substituting 2-(methylsulfonyl)benzoic acid for 2-fluoro-6-hydroxybenzoic acid. $^1$H NMR (400 MHz, DMSO-$d_6$) δ 3.36 (s, 3H), 4.68 (s, 2H), 5.67 (s, 2H), 6.91 (d, J=1.9 Hz, 1H), 7.49 (d, J=2.0 Hz, 1H), 7.55-7.66 (m, 1H), 7.66-7.85 (m, 2H), 8.01 (d, J=7.7 Hz, 1H), 8.32 (d, J=4.2 Hz, 2H). MS (APCI) m/z 510.1 [M+H]$^+$.

Example 266

N-({7-[(6-amino-9H-purin-9-yl)methyl]-5-chloro-1H-indol-2-yl}methyl)-2-chloro-4-(methylsulfonyl)benzamide A mixture of Example 9b (30 mg, 0.092 mmol), HATU (48.7 mg, 0.128 mmol), and 2-chloro-4-(methylsulfonyl)benzoic acid (21.48 mg, 0.092 mmol) in 0.5 mL N,N-dimethylformamide was stirred at ambient temperature for 5 minutes and then treated with N-ethyl-N-isopropylpropan-2-amine (48.0 μL, 0.275 mmol). The mixture was stirred at ambient temperature overnight and then diluted with ethyl acetate, washed sequentially with water (3×) and brine, dried over magnesium sulfate, and filtered. The filtrate was concentrated and the residue was purified by column chromatography on silica gel (1-10% methanol in dichloromethane) to give the title compound (28 mg, 0.051 mmol, 56.2% yield). $^1$H NMR (400 MHz, DMSO-$d_6$) δ 11.64 (s, 1H), 9.25 (t, J=5.6 Hz, 1H), 8.30 (s, 1H), 8.21 (s, 1H), 8.07 (d, J=1.7 Hz, 1H), 7.97 (dd, J=8.0, 1.7 Hz, 1H), 7.79 (d, J=8.0 Hz, 1H), 7.51 (d, J=1.9 Hz, 1H), 7.30 (s, 2H), 6.83 (d, J=1.9 Hz, 1H), 6.46 (d, J=1.6 Hz, 1H), 5.62 (s, 2H), 4.69 (d, J=5.5 Hz, 2H), 3.33 (s, 3H); MS(ESI+) m/z 544.0 (M+H)$^+$.

Example 267

4-{[({7-[(6-amino-9H-purin-9-yl)methyl]-5-chloro-1H-indol-2-yl}methyl)amino]methyl}benzonitrile Example 267 was prepared according to the procedure used for the preparation of Example 208, substituting 4-formylbenzonitrile for 2-bromobenzaldehyde. 1H NMR (400 MHz, DMSO-$d_6$) δ 8.46 (s, 1H), 8.34 (s, 1H), 7.99-7.88 (m, 2H), 7.76-7.67 (m, 2H), 7.65 (d, J=2.0 Hz, 1H), 6.88 (d, J=2.0 Hz, 1H), 6.74 (s, 1H), 5.68 (s, 2H), 4.43 (s, 2H), 4.36 (s, 2H). MS (ESI+) m/z 443.1 (M+H)$^+$.

Example 268

3-{[({7-[(6-amino-9H-purin-9-yl)methyl]-5-chloro-1H-indol-2-yl}methyl)amino]methyl}benzonitrile Example 268 was prepared according to the procedure used for the preparation of Example 208, substituting 3-formylbenzonitrile for 2-bromobenzaldehyde. $^1$H NMR (400 MHz, DMSO-$d_6$) δ 8.47 (s, 1H), 8.34 (s, 1H), 7.97 (t, J=1.7 Hz, 1H), 7.91 (dt, J=7.7, 1.4 Hz, 1H), 7.85 (dt, J=7.9, 1.4 Hz, 1H), 7.75-7.61 (m, 2H), 6.87 (d, J=1.9 Hz, 1H), 6.74 (s, 1H), 5.68 (s, 2H), 4.43 (s, 2H), 4.34 (s, 2H). MS (ESI+) m/z 443.1 (M+H)$^+$.

Example 269

2-{[({7-[(6-amino-9H-purin-9-yl)methyl]-5-chloro-1H-indol-2-yl}methyl)amino]methyl}benzonitrile Example 269 was prepared according to the procedure used for the preparation of Example 208, substituting 2-formylbenzonitrile for 2-bromobenzaldehyde. $^1$H NMR (400 MHz, DMSO-$d_6$) δ 8.47 (s, 1H), 8.30 (d, J=11.7 Hz, 1H), 8.23 (d, J=7.8 Hz, 1H), 7.97-7.64 (m, 3H), 7.58 (dd, J=7.5, 1.9 Hz, 1H), 6.81 (dd, J=7.6, 1.9 Hz, 1H), 6.61 (d, J=3.4 Hz, 1H), 5.69 (s, 2H), 5.24 (s, 2H), 4.88 (s, 2H). MS (ESI+) m/z 443.1 (M+H)$^+$.

Example 270

3-{[({7-[(6-amino-9H-purin-9-yl)methyl]-5-chloro-1H-indol-2-yl}methyl)amino]methyl}-4-fluorobenzonitrile Example 270 was prepared according to the procedure used for the preparation of Example 208, substituting 4-fluoro-3-formylbenzonitrile for 2-bromobenzaldehyde. $^1$H NMR (400 MHz, DMSO-$d_6$) δ 8.49 (s, 1H), 8.36 (s, 1H), 8.09 (dd, J=6.7, 2.1 Hz, 1H), 8.02 (ddd, J=8.7, 4.8, 2.2 Hz, 1H), 7.66 (d, J=1.9 Hz, 1H), 7.55 (t, J=9.1 Hz, 1H), 6.87 (d, J=1.9 Hz, 1H), 6.75 (s, 1H), 5.69 (s, 2H), 4.49 (s, 2H), 4.37 (s, 2H). MS (ESI+) m/z 461.1 (M+H)$^+$.

Example 271

5-amino-N-({7-[(6-amino-9H-purin-9-yl)methyl]-5-chloro-1H-indol-2-yl}methyl)-2-methylbenzamide $N^1$-((ethylimino)methylene)-$N^3$,$N^3$-dimethylpropane-1,3-diamine hydrochloride (25.9 mg, 0.135 mmol) was added to a partial solution of Example 9b (30 mg, 0.092 mmol), HOBT (18.6 mg, 0.121 mmol), 5-amino-2-methylbenzoic acid (14 mg, 0.093 mmol), N-ethyl-N-isopropylpropan-2-amine (0.048 mL, 0.275 mmol), tetrahydrofuran (1.0 mL), and N,N-dimethylformamide (0.2 mL). The reaction mixture was stirred at room temperature overnight. Water and ethyl acetate were added to the reaction mixture. The layers were separated and the ethyl acetate layer was absorbed onto silica gel and was flash chromatographed (Biotage 10 g HP Snap Cartridge, eluting with heptanes containing a gradient with a solution of 3:1 ethyl acetate:ethanol, 35% to 100%) to provide the title compound. $^1$H NMR (400 MHz, DMSO-$d_6$) δ 11.61-11.49 (m, 1H), 8.65 (t, J=5.8 Hz, 1H), 8.31 (s, 1H), 8.21 (s, 1H), 7.49 (d, J=2.0 Hz, 1H), 7.29 (s, 2H), 6.88 (d, J=8.1 Hz, 1H), 6.84 (d, J=2.0 Hz, 1H), 6.64 (d, J=2.4 Hz, 1H), 6.54 (dd, J=8.1, 2.5 Hz, 1H), 6.37 (d, J=1.8 Hz, 1H), 5.60 (s, 2H), 5.00 (s, 2H), 4.60 (d, J=5.8 Hz, 2H), 2.18 (s, 3H). MS ESI$^+$ 461.0 (M+H)$^+$.

Example 272

N-({7-[(6-amino-9H-purin-9-yl)methyl]-5-chloro-1H-indol-2-yl}methyl)-4-cyanobenzamide Example 272 was prepared according to the procedure used for the preparation of Example 105, substituting 4-cyanobenzoic acid for 4-methyl-pentanoic acid. $^1$H NMR (400 MHz, DMSO-$d_6$) δ 11.51 (s, 1H), 9.34 (t, J=5.6 Hz, 1H), 8.48 (s, 1H), 8.34 (s, 3H), 8.11-8.04 (m, 2H), 8.00 (d, J=8.4

Hz, 2H), 7.50 (d, J=2.0 Hz, 1H), 6.82 (d, J=2.1 Hz, 1H), 6.41 (d, J=1.9 Hz, 1H), 5.68 (s, 2H), 4.71 (d, J=5.5 Hz, 2H). MS (APCI+) m/z 457.0 (M+H)$^+$.

Example 273

N-({7-[(6-amino-9H-purin-9-yl)methyl]-5-chloro-1H-indol-2-yl}methyl)-3-cyanobenzamide Example 273 was prepared according to the procedure used for the preparation of Example 232, substituting 3-cyanobenzoic acid for 2-(pyridin-4-yl)acetic acid. $^1$H NMR (400 MHz, DMSO-d$_6$) δ 4.71 (d, J=5.5 Hz, 2H), 5.68 (s, 2H), 6.43 (d, J=1.8 Hz, 1H), 6.81 (d, J=2.0 Hz, 1H), 7.50 (d, J=2.0 Hz, 1H), 7.74 (t, J=7.9 Hz, 1H), 8.04 (dt, J=7.8, 1.4 Hz, 1H), 8.13-8.40 (m, 4H), 8.46 (s, 1H), 9.29 (t, J=5.6 Hz, 1H), 11.54 (d, J=2.1 Hz, 1H). MS (APCI) m/z 457.1 [M+H]$^+$.

Example 274

N-({7-[(6-amino-9H-purin-9-yl)methyl]-5-chloro-1H-indol-2-yl}methyl)-2-cyanobenzamide Example 274 was prepared according to the procedure used for the preparation of Example 229, substituting 2-cyanobenzoic acid for 2-fluoro-6-hydroxybenzoic acid. 1H NMR (400 MHz, DMSO-d$_6$) δ 4.70 (s, 2H), 5.65 (s, 2H), 6.47 (s, 1H), 6.92 (d, J=2.0 Hz, 1H), 7.48 (d, J=2.0 Hz, 1H), 7.63-7.94 (m, 4H), 8.29 (d, J=6.2 Hz, 2H). MS (APCI) m/z 457.1 [M+H]$^+$.

Example 275

N-({7-[(6-amino-9H-purin-9-yl)methyl]-5-chloro-1H-indol-2-yl}methyl)-2-(methylamino)benzamide Example 275 was prepared according to the procedure used for the preparation of Example 229, substituting 2-(methylamino)benzoic acid for 2-fluoro-6-hydroxybenzoic acid. $^1$H NMR (400 MHz, DMSO-d$_6$) δ 2.80 (s, 3H), 4.63 (s, 2H), 5.65 (s, 2H), 6.60 (t, J=7.5 Hz, 1H), 6.69 (d, J=8.4 Hz, 1H), 6.92 (d, J=2.0 Hz, 1H), 7.26-7.38 (m, 1H), 7.47 (d, J=2.0 Hz, 1H), 7.58 (dd, J=7.7, 1.7 Hz, 1H), 8.32 (d, J=13.5 Hz, 2H). MS (APCI) m/z 461.2 [M+H]$^+$.

Example 276

N-({7-[(6-amino-9H-purin-9-yl)methyl]-5-chloro-1H-indol-2-yl}methyl)-2-chloro-4-cyanobenzamide Example 276 was prepared according to the procedure used for the preparation of Example 199, substituting 2-chloro-4-cyanobenzoic acid for 3-methylpyridazine-4-carboxylic acid. $^1$H NMR (400 MHz, DMSO-d$_6$) δ 4.64-4.73 (m, 2H), 5.65 (s, 2H), 6.48 (s, 1H), 6.84 (d, J=2.0 Hz, 1H), 7.53 (d, J=2.0 Hz, 1H), 7.69 (d, J=7.9 Hz, 1H), 7.92 (dd, J=7.9, 1.5 Hz, 1H), 8.12 (d, J=1.5 Hz, 1H), 8.29 (s, 1H), 8.40 (s, 1H), 9.28 (t, J=5.7 Hz, 1H). MS (APCI) m/z 491.1 [M+H]$^+$.

Example 277

N-({7-[(6-amino-9H-purin-9-yl)methyl]-5-(1,2,3,6-tetrahydropyridin-4-yl)-1H-indol-2-yl}methyl)-2-chloro-4-cyanobenzamide Example 277 was prepared according to the procedure used for the preparation of Example 235, substituting 2-chloro-4-cyanobenzoic acid for 3,6-dimethylpyridazine-4-carboxylic acid. $^1$H NMR (400 MHz, DMSO-d$_6$) δ 11.51 (s, 1H), 9.26 (t, J=5.6 Hz, 1H), 8.92 (s, 2H), 8.51 (s, 1H), 8.38 (s, 1H), 8.17 (d, J=1.5 Hz, 1H), 7.95 (dd, J=7.9, 1.6 Hz, 1H), 7.70 (d, J=7.9 Hz, 1H), 7.55 (s, 1H), 7.08 (s, 1H), 6.47 (s, 1H), 6.10-5.89 (m, 1H), 5.70 (s, 2H), 4.67 (d, J=5.7 Hz, 2H), 3.77-3.68 (m, 3H), 2.72-2.59 (m, 2H); MS m/z: 538 [M+H]$^+$.

Example 278

N-({7-[(6-amino-9H-purin-9-yl)methyl]-5-(4,4-difluorocyclohex-1-en-1-yl)-1H-indol-2-yl}methyl)-2-chloro-4-cyanobenzamide Example 278 was prepared according to the procedure used for the preparation of Example 100, substituting Example 14 for Example 9b, and substituting 2-chloro-4-cyanobenzoic acid for 3-methoxypropanoic acid, and N,N-dimethylformamide for N,N-dimethylacetamide. $^1$H NMR (400 MHz, DMSO-d$_6$) δ 11.41 (s, 1H), 9.23 (t, J=5.6 Hz, 1H), 8.27 (s, 1H), 8.24-8.12 (m, 2H), 7.94 (dd, J=7.9, 1.5 Hz, 1H), 7.76-7.64 (m, 1H), 7.58-7.46 (m, 1H), 7.30 (s, 2H), 7.10 (s, 1H), 6.48-6.38 (m, 1H), 5.84-5.72 (m, 1H), 5.59 (s, 2H), 4.71-4.59 (m, 2H), 2.77-2.59 (m, 4H), 2.15 (dt, J=14.2, 7.3 Hz, 2H). MS m/z: 473 [M+H]+.

Example 279

N-({5-(1-acetyl-1,2,3,6-tetrahydropyridin-4-yl)-7-[(6-amino-9H-purin-9-yl)methyl]-1H-indol-2-yl}methyl)-2-chloro-4-cyanobenzamide Example 279 was prepared according to the procedure used for the preparation of Example 100, substituting Example 15b for Example 9b, and substituting 2-chloro-4-cyanobenzoic acid for 3-methoxypropanoic acid, and N,N-dimethylformamide for N,N-dimethylacetamide. $^1$H NMR (400 MHz, DMSO-d$_6$) δ 11.40 (s, 1H), 9.23 (t, J=5.7 Hz, 1H), 8.27 (s, 1H), 8.22 (s, 1H), 8.17 (d, J=1.5 Hz, 1H), 7.94 (dd, J=7.9, 1.5 Hz, 1H), 7.70 (d, J=7.9 Hz, 1H), 7.51-7.45 (m, 1H), 7.32 (s, 2H), 7.12 (s, 1H), 6.44 (s, 1H), 6.01-5.90 (m, 1H), 5.60 (s, 2H), 4.66 (d, 2H), 4.15-4.01 (m, 2H), 3.69-3.52 (m, 2H), 2.04 (d, J=16.4 Hz, 3H); MS m/z: 480 [M+H]$^+$.

Example 280

N-({5-(1-acetyl-1,4,5,6-tetrahydropyridin-3-yl)-7-[(6-amino-9H-purin-9-yl)methyl]-1H-indol-2-yl}methyl)-2-chloro-4-cyanobenzamide Example 280 was prepared according to the procedure used for the preparation of Example 100, substituting Example 16b for Example 9b, and substituting 2-chloro-4-cyanobenzoic acid for 3-methoxypropanoic acid, and N,N-dimethylformamide for N,N-dimethylacetamide. $^1$H NMR (400 MHz, DMSO-d$_6$) δ 11.42 (s, 1H), 9.23 (t, J=5.6 Hz, 1H), 8.29-8.25 (m, 1H), 8.23-8.12 (m, 2H), 7.94 (d, J=8.0 Hz, 1H), 7.70 (d, J=8.1 Hz, 1H), 7.58-7.43 (m, 1H), 7.30 (s, 2H), 7.12 (d, J=12.2 Hz, 1H), 6.50-6.41 (m, 1H), 6.15-6.03 (m, 1H), 5.60 (s, 2H), 4.66 (d, J=5.5 Hz, 2H), 4.35-4.26 (m, 2H), 4.05 (s, 1H), 3.61-3.47 (m, 2H), 2.34-2.15 (m, 3H), 2.07 (d, J=8.3 Hz, 3H); MS m/z: 580 [M+H]$^+$.

Example 281

N-({5-(1-acetylpiperidin-4-yl)-7-[(6-amino-9H-purin-9-yl)methyl]-1H-indol-2-yl}methyl)-2-chloro-4-cyanobenzamide Example 281 was prepared according to the procedure used for the preparation of Example 100, substituting Example 17 for Example 9b, and substituting 2-chloro-4-cyanobenzoic acid for 3-methoxypropanoic acid, and N,N-dimethylformamide for N,N-dimethylacetamide. $^1$H NMR (400 MHz, CD$_3$OD) δ 8.34 (s, 1H), 8.08 (s, 1H), 7.89 (d, J=1.4 Hz, 1H), 7.75 (dd, J=7.9, 1.5 Hz, 1H), 7.59 (d, J=7.9 Hz, 1H), 7.37 (s, 1H), 7.05 (s, 1H), 6.43 (s, 1H), 5.60 (s, 2H), 4.74-4.60 (m, 3H), 4.56 (s, 2H), 4.08-3.96 (m, 1H), 3.28-3.14 (m, 1H), 2.92-2.77 (m, 1H), 2.77-2.63 (m, 1H), 2.13 (s, 3H), 1.97-1.81 (m, 2H), 1.79-1.50 (m, 2H); MS m/z: 582 [M+H]$^+$.

Example 282

N-({7-[(6-amino-9H-purin-9-yl)methyl]-4-chloro-1H-indol-2-yl}methyl)-2-chloro-4-cyanobenzamide Example 282 was prepared according to the procedure used for the preparation of Example 100, substituting Example 62j for Example 9b, and substituting 2-chloro-4-cyanobenzoic acid for 3-methoxypropanoic acid, and N,N-dimethylformamide for N,N-dimethylacetamide. $^1$H NMR (400 MHz, DMSO-d$_6$) δ 11.77 (s, 1H), 9.24 (t, i=5.6 Hz, 1H), 8.24 (s, 1H), 8.21-8.10 (m, 2H), 7.93 (dd, i=7.7, 1.5 Hz, 1H), 7.69 (d, i=7.9 Hz, 1H), 7.26 (s, 2H), 7.00 (d, i=7.7 Hz, 1H), 6.82 (d, i=7.9 Hz, 1H), 6.49 (d, J=2.1 Hz, 1H), 5.60 (s, 2H), 4.69 (d, J=5.5 Hz, 2H); MS m/z: 491 [M+H]$^+$.

Example 283

N-({7-[(6-amino-9H-purin-9-yl)methyl]-5-chloro-1H-indol-2-yl}methyl)-2,6-dichloro-4-cyanobenzamide Example 283 was prepared according to the procedure used for the preparation of Example 266, substituting 2,6-dichloro-4-cyanobenzoic acid for 2-chloro-4-(methylsulfonyl)benzoic acid. $^1$H NMR (400 MHz, DMSO-d$_6$) δ 11.65 (s, 1H), 9.41 (t, J=5.6 Hz, 1H), 8.29 (s, 1H), 8.22 (s, 1H), 8.19 (s, 2H), 7.53 (d, J=1.8 Hz, 1H), 7.30 (s, 2H), 6.85 (d, J=1.8 Hz, 1H), 6.47 (d, J=1.4 Hz, 1H), 5.60 (s, 2H), 4.70 (d, J=5.6 Hz, 2H). MS (ESI+) m/z 524.9 (M+H)$^+$.

Example 284

N-({7-[(6-amino-9H-purin-9-yl)methyl]-5-chloro-1H-indol-2-yl}methyl)-4-cyano-2-fluorobenzamide Example 284 was prepared according to the procedure used for the preparation of Example 229, substituting 4-cyano-2-fluorobenzoic acid for 2-fluoro-6-hydroxybenzoic acid. $^1$H NMR (400 MHz, DMSO-d$_6$) δ 4.71 (s, 2H), 5.64 (s, 2H), 6.45 (s, 1H), 6.96 (d, J=1.9 Hz, 1H), 7.51 (d, J=2.0 Hz, 1H), 7.76 (dd, J=7.9, 1.6 Hz, 1H), 7.80-7.91 (m, 2H), 8.26 (d, J=2.7 Hz, 2H). MS (APCI) m/z 475.1 [M+H]$^+$.

Example 285

N-({7-[(6-amino-9H-purin-9-yl)methyl]-5-(3,6-dihydro-2H-pyran-4-yl)-1H-indol-2-yl}methyl)-4-cyano-2-fluorobenzamide Using the procedure described for Example 4d and substituting Example 284 for Example 4c and substituting 2-(3,6-dihydro-2H-pyran-4-yl)-4,4,5,5-tetramethyl-1,3,2-dioxaborolane for methylboronic acid provided the title compound. $^1$H NMR (400 MHz, DMSO-d$_6$) δ 11.34 (d, J=2.2 Hz, 1H), 9.16 (q, J=6.2, 5.6 Hz, 1H), 8.26 (s, 1H), 8.20 (s, 1H), 8.04-7.96 (m, 1H), 7.86-7.79 (m, 2H), 7.49 (d, J=1.8 Hz, 1H), 7.26 (s, 2H), 7.13 (d, J=1.7 Hz, 1H), 6.43-6.38 (m, 1H), 6.02 (dq, J=3.2, 1.6 Hz, 1H), 5.59 (s, 2H), 4.67 (d, J=5.7 Hz, 2H), 4.18 (q, J=2.5 Hz, 2H), 3.80 (q, J=6.0, 5.4 Hz, 2H), 2.46-2.37 (m, 2H). MS ESI$^+$523.0 (M+H)$^+$.

Example 286

N-({7-[(6-amino-9H-purin-9-yl)methyl]-5-(1,2,3,6-tetrahydropyridin-4-yl)-1H-indol-2-yl}methyl)-4-cyano-2-fluorobenzamide

Example 286a tert-butyl 4-(7-((6-amino-9H-purin-9-yl)methyl)-2-((4-cyano-2-fluorobenzamido)methyl)-1H-indol-5-yl)-5,6-dihydropyridine-1(2H)-carboxylate Using the procedure described for Example 4d and substituting Example 284 for Example 4C and substituting tert-butyl 4-(4,4,5,5-tetramethyl-1,3,2-dioxaborolan-2-yl)-5,6-dihydropyridine-1(2H)-carboxylate for methylboronic acid provided the title compound. MS ESI$^+$ 622.0 (M+H)$^+$.

Example 286b

N-((7-((6-amino-9H-purin-9-yl)methyl)-5-(1,2,3,6-tetrahydropyridin-4-yl)-1H-indol-2-yl)methyl)-4-cyano-2-fluorobenzamide A solution of Example 286a (4.2 mg, 6.76 μmol), 2,2,2-trifluoroacetic acid (40 μL, 0.52 mmol) and dichloromethane (0.5 mL) was stirred at room temperature overnight. The reaction mixture was concentrated to dryness. Methanol (10 mL) and toluene (10 mL) were added and concentrated to dryness. The product was dried (in-vacuo) to provide the title compound. $^1$H NMR (400 MHz, DMSO-d$_6$) δ 11.51-11.25 (m, 1H), 9.18 (t, J=5.7 Hz, 1H), 8.77 (s, 2H), 8.39 (s, 1H), 8.30 (s, 1H), 8.01 (d, J=9.9 Hz, 1H), 7.94 (s, 2H), 7.82 (d, J=3.4 Hz, 2H), 7.55 (d, J=1.7 Hz, 1H), 7.06 (d, J=1.7 Hz, 1H), 6.43 (d, J=1.8 Hz, 1H), 5.96 (d, J=3.9 Hz, 1H), 5.66 (s, 2H), 4.68 (d, J=5.7 Hz, 2H), 3.73 (s, 2H), 3.31 (d, J=6.6 Hz, 2H), 2.65 (t, J=5.1 Hz, 2H). MS ESI$^+$ 522.0 (M+H)$^+$.

Example 287

N-({7-[(6-amino-9H-purin-9-yl)methyl]-5-(4,4-difluorocyclohex-1-en-1-yl)-1H-indol-2-yl}methyl)-4-cyano-2-fluorobenzamide Using the procedure described for Example 4d and substituting Example 284 for Example 4c and substituting 2-(4,4-difluorocyclohex-1-en-1-yl)-4,4,5,5-tetramethyl-1,3,2-dioxaborolane for methylboronic acid provided the title compound. $^1$H NMR (400 MHz, DMSO-d$_6$) δ 11.42-11.25

(m, 1H), 9.16 (t, J=5.8 Hz, 1H), 8.26 (s, 1H), 8.20 (s, 1H), 8.05-7.95 (m, 1H), 7.86-7.75 (m, 2H), 7.50 (d, J=1.7 Hz, 1H), 7.27 (s, 2H), 7.10 (d, J=1.8 Hz, 1H), 6.40 (d, J=1.9 Hz, 1H), 5.80 (s, 1H), 5.59 (s, 2H), 4.67 (d, J=5.6 Hz, 2H), 2.80-2.56 (m, 4H), 2.15 (tt, J=14.0, 6.6 Hz, 2H). MS ESI$^+$ 557.0 (M+H)$^+$.

Example 288

N-({5-(1-acetyl-1,2,3,6-tetrahydropyridin-4-yl)-7-[(6-amino-9H-purin-9-yl)methyl]-1H-indol-2-yl}methyl)-4-cyano-2-fluorobenzamide Using the procedure described for Example 4d and substituting Example 284 for Example 4c and substituting 1-(4-(4,4,5,5-tetramethyl-1,3,2-dioxaborolan-2-yl)-5,6-dihydropyridin-1(2H)-yl)ethanone for methylboronic acid provided the title compound. $^1$H NMR (400 MHz, DMSO-d$_6$) δ 11.35 (s, 1H), 9.15 (t, J=5.6 Hz, 1H), 8.26 (s, 1H), 8.20 (s, 1H), 8.07-7.94 (m, 1H), 7.88-7.72 (m, 2H), 7.49 (dd, J=4.3, 1.7 Hz, 1H), 7.27 (s, 2H), 7.13 (s, 1H), 6.41 (d, J=1.9 Hz, 1H), 5.96 (d, J=10.9 Hz, 1H), 5.59 (s, 2H), 4.67 (d, J=5.7 Hz, 2H), 4.16 3.98 (m, 2H), 3.62 (dt, J=11.9, 5.6 Hz, 2H), 2.43 (s, 1H), 2.03 (d, J=16.3 Hz, 3H). MS ESI$^+$ 564.1 (M+H)$^+$.

Example 289 tert-butyl 4-(7-[(6-amino-9H-purin-9-yl)methyl]-2-{[(4-cyano-2-fluorobenzoyl)amino]methyl}-1H-indol-5-yl)-3,6-dihydropyridine-1(2H)-carboxylate Example 289a tert-butyl 4-(7-((6-amino-9H-purin-9-yl)methyl)-2-(aminomethyl)-1H-indol-5-yl)-5,6-dihydropyridine-1(2H)-carboxylate Using the procedure described for Example 59, substituting Example 9b for Example 58 and substituting tert-butyl 4-(4,4,5,5-tetramethyl-1,3,2-dioxaborolan-2-yl)-5,6-dihydropyridine-1(2H)-carboxylate for 4,4,5,5-tetramethyl-2-vinyl-1,3,2-dioxaborolane provided the title compound. MS ESI$^-$ 473.2 (M–H)$^-$.

Example 289b tert-butyl 4-(7-[(6-amino-9H-purin-9-yl)methyl]-2-{[(4-cyano-2-fluorobenzoyl)amino]methyl}-1H-indol-5-yl)-3,6-dihydropyridine-1(2H)-carboxylate Using the procedure described for Example 271, substituting Example 289a for Example 9 and substituting 4-cyano-2-fluorobenzoic acid for 5-amino-2 methylbenzoic acid provided the title compound. $^1$H NMR (400 MHz, DMSO-d$_6$) δ 11.49 (s, 1H), 9.15 (t, J=5.7 Hz, 1H), 8.23 (d, J=21.4 Hz, 2H), 8.00 (d, J=10.1 Hz, 1H), 7.82 (d, J=3.9 Hz, 2H), 7.48 (d, J=1.5 Hz, 1H), 7.27 (s, 2H), 7.13 (d, J=1.7 Hz, 1H), 6.40 (d, J=1.7 Hz, 1H), 5.94 (s, 1H), 5.59 (s, 2H), 4.67 (d, J=5.7 Hz, 2H), 3.96 (s, 2H), 3.52 (t, J=5.8 Hz, 2H), 2.44 (s, 2H), 1.42 (s, 9H). MS ESI$^+$ 622.0 (M+H)$^+$.

Example 290

9-[(5-chloro-2-{[(2,6-dimethylbenzyl)amino]methyl}-1H-indol-7-yl)methyl]-9H-purin-6-amine Example 290 was prepared according to the procedure used for the preparation of Example 208, substituting 2,6-dimethylbenzaldehyde for 2-bromobenzaldehyde. $^1$H NMR (400 MHz, DMSO-d$_6$) δ 8.47 (s, 1H), 8.34 (s, 1H), 7.68 (d, J=1.9 Hz, 1H), 7.30-7.17 (m, 1H), 7.11 (d, J=7.6 Hz, 2H), 6.93 (d, J=2.0 Hz, 1H), 6.84 (s, 1H), 5.71 (s, 2H), 4.53 (s, 2H), 4.23 (s, 2H), 2.26 (s, 6H). MS (ESI+) m/z 446.1 (M+H)$^+$.

Example 291

N-({7-[(6-amino-9H-purin-9-yl)methyl]-5-chloro-1H-indol-2-yl}methyl)-3-phenylpropanamide Example 291 was prepared according to the procedure used for the preparation of Example 232, substituting 3-phenylpropanoic acid for 2-(pyridin-4-yl)acetic acid. $^1$H NMR (400 MHz, DMSO-d$_6$) δ 2.74-2.99 (m, 3H), 4.46 (d, J=5.6 Hz, 2H), 5.65 (s, 2H), 6.22 (d, J=1.9 Hz, 1H), 6.82 (d, J=2.0 Hz, 1H), 7.13-7.33 (m, 5H), 7.47 (d, J=2.0 Hz, 1H), 7.98-8.49 (m, 4H), 11.45 (d, J=2.1 Hz, 1H). MS (APCI) m/z 460.2 [M+H]$^+$.

Example 292

N-({7-[(6-amino-9H-purin-9-yl)methyl]-5-chloro-1H-indol-2-yl}methyl)-2-(4-methylphenyl)acetamide Example 292 was prepared according to the procedure used for the preparation of Example 232, substituting 2-(p-tolyl)acetic acid for 2-(pyridin-4-yl)acetic acid. $^1$H NMR (400 MHz, DMSO-d$_6$) δ 2.11 (s, 1H), 2.27 (s, 3H), 3.46 (s, 2H), 4.46 (d, J=5.6 Hz, 2H), 5.66 (s, 2H), 6.32 (d, J=1.8 Hz, 1H), 6.82 (d, J=2.0 Hz, 1H), 7.11 (d, J=7.9 Hz, 2H), 7.15-7.24 (m, 2H), 7.49 (d, J=1.9 Hz, 1H), 8.17-8.61 (m, 5H), 11.48 (d, J=2.2 Hz, 1H). MS (APCI) m/z 460.2 [M+H]$^+$.

Example 293

N-({7-[(6-amino-9H-purin-9-yl)methyl]-5-chloro-1H-indol-2-yl}methyl)-2-(3-methylphenyl)acetamide Example 293 was prepared according to the procedure used for the preparation of Example 105, substituting m-tolylacetic acid for 4-methyl-pentanoic acid. $^1$H NMR (400 MHz, DMSO-d$_6$) δ 11.50 (d, J=2.1 Hz, 1H), 8.59 (t, J=5.6 Hz, 1H), 8.46 (s, 1H), 8.36 (s, 1H), 8.27 (s, 2H), 7.49 (d, J=2.0 Hz, 1H), 7.19 (t, J=7.5 Hz, 1H), 7.14-7.01 (m, 3H), 6.82 (d, J=2.1 Hz, 1H), 6.32 (d, J=1.8 Hz, 1H), 5.66 (s, 2H), 4.47 (d, J=5.5 Hz, 2H), 3.47 (s, 2H), 2.28 (s, 3H). MS (APCI+) m/z 460.1 (M+H)$^+$.

Example 294

N-({7-[(6-amino-9H-purin-9-yl)methyl]-5-chloro-1H-indol-2-yl}methyl)-2-(2-methylphenyl)acetamide Example 294 was prepared according to the procedure used for the preparation of Example 105, substituting o-tolylacetic acid for 4-methyl-pentanoic acid. $^1$H NMR (400 MHz, DMSO-d$_6$) δ 11.70 (s, 1H), 8.75 (t, J=5.6 Hz, 1H), 8.69 (s, 2H), 8.59 (s, 2H), 7.71 (d, J=2.0 Hz, 1H), 7.43 (q, J=4.1, 3.5 Hz, 1H), 7.40-7.28 (m, 2H), 7.03 (d, J=2.0 Hz, 1H), 6.93 (s, 1H), 6.54 (d, J=1.9 Hz, 1H), 5.87 (s, 2H), 4.69 (d, J=5.6 Hz, 2H), 3.75 (s, 2H), 2.49 (s, 3H). MS (APCI+) m/z 460.1 (M+H)$^+$.

Example 295

N-({7-[(6-amino-9H-purin-9-yl)methyl]-5-chloro-1H-indol-2-yl}methyl)-2,6-dimethylbenzamide Example 295 was prepared according to the procedure used for the preparation of Example 266, substituting 2,6-dimethylbenzoic acid for 2-chloro-4-(methylsulfonyl)benzoic acid. 1H NMR (400 MHz, DMSO-d$_6$) δ 11.55 (s, 1H), 8.88 (t, J=5.8 Hz, 1H), 8.50 (s, 1H), 8.43-8.37 (m, 1H), 7.53 (d, J=1.9 Hz, 1H), 7.22-7.11 (m, 1H), 7.06 (s, 1H), 7.04 (s, 1H), 6.86 (d, J=1.9 Hz, 1H), 6.42 (d, J=1.7 Hz, 1H), 5.69 (s, 2H), 4.66 (d, J=5.8 Hz, 2H), 2.23 (s, 6H). MS (ESI+) m/z 406.1 (M+H)$^+$.

Example 296

N-({7-[(6-amino-9H-purin-9-yl)methyl]-5-chloro-1H-indol-2-yl}methyl)-2-ethylbenzamide Example 296 was prepared according to the procedure used for the preparation of Example 229, substituting 2-ethylbenzoic acid for 2-fluoro-6-hydroxybenzoic acid. $^1$H NMR (400 MHz, DMSO-d$_6$) δ 1.13 (t, J=7.5 Hz, 3H), 2.73 (q, J=7.5 Hz, 2H), 4.64 (s, 2H), 5.64 (s, 2H), 6.42 (s, 1H), 6.93 (d, J=1.9 Hz, 1H), 7.16-7.31 (m, 2H), 7.36 (d, J=7.4 Hz, 2H), 7.49 (d, J=2.0 Hz, 1H), 8.29 (d, J=2.2 Hz, 2H). MS (APCI) m/z 474.22 [M+H]$^+$.

Example 297

N-({7-[(6-amino-9H-purin-9-yl)methyl]-5-chloro-1H-indol-2-yl}methyl)-2-(4-methoxyphenyl)acetamide Example 297 was prepared according to the procedure used for the preparation of Example 232, substituting 2-(4-methoxyphenyl)acetic acid for 2-(pyridin-4-yl)acetic acid. $^1$H NMR (400 MHz, DMSO-d$_6$) δ 3.44 (s, 2H), 3.73 (s, 3H), 4.46 (d, J=5.5 Hz, 2H), 5.65 (s, 2H), 6.32 (d, J=1.9 Hz, 1H), 6.78-6.93 (m, 3H), 7.17-7.27 (m, 2H), 7.49 (d, J=2.0 Hz, 1H), 8.36 (s, 3H), 8.41-8.58 (m, 2H), 11.48 (d, J=2.2 Hz, 1H). MS (APCI) m/z 476.2 [M+H]$^+$.

Example 298

N-({7-[(6-amino-9H-purin-9-yl)methyl]-5-chloro-1H-indol-2-yl}methyl)-2-(2-methoxyphenyl)acetamide Example 298 was prepared according to the procedure used for the preparation of Example 232, substituting 2-(2-methoxyphenyl)acetic acid for 2-(pyridin-4-yl)acetic acid. $^1$H NMR (400 MHz, DMSO-d$_6$) δ 3.76 (s, 5H), 4.48 (d, J=5.7 Hz, 2H), 5.66 (s, 2H), 6.33 (d, J=1.9 Hz, 1H), 6.77-7.02 (m, 3H), 7.16-7.29 (m, 2H), 7.50 (d, J=2.0 Hz, 1H), 8.17-8.51 (m, 4H), 11.47 (d, J=2.1 Hz, 1H). MS (APCI) m/z 476.2 [M+H]$^+$.

Example 299

N-({7-[(6-amino-9H-purin-9-yl)methyl]-5-chloro-1H-indol-2-yl}methyl)-2-methoxy-6-methylbenzamide Example 299 was prepared according to the procedure used for the preparation of Example 229, substituting 2-methoxy-6-methylbenzoic acid for 2-fluoro-6-hydroxybenzoic acid. $^1$H NMR (400 MHz, DMSO-d$_6$) δ 2.19 (s, 3H), 3.76 (s, 3H), 4.63 (s, 2H), 5.62 (s, 2H), 6.45 (s, 1H), 6.76-6.96 (m, 3H), 7.24 (t, J=7.9 Hz, 1H), 7.49 (d, J=2.0 Hz, 1H), 8.28 (d, J=8.9 Hz, 2H). MS (APCI) m/z 476.2 [M+H]$^+$.

Example 300

N-({7-[(6-amino-9H-purin-9-yl)methyl]-5-chloro-1H-indol-2-yl}methyl)-3-methoxy-4-methylbenzamide Example 300 was prepared according to the procedure used for the preparation of Example 100, substituting 3-methoxy-4-methylbenzoic acid for 3-methoxypropanoic acid. $^1$H NMR (400 MHz, CD$_3$OD) δ 8.40 (s, 1H), 8.34 (s, 1H), 7.48 (d, J=1.9 Hz, 1H), 7.44-7.33 (m, 2H), 7.23 (d, J=7.7 Hz, 1H), 7.07 (d, J=1.9 Hz, 1H), 6.41 (s, 1H), 5.69 (s, 2H), 3.89 (s, 3H), 2.24 (s, 3H); MS m/z: 341 [M-adenine]$^+$.

Example 301

4-(aminomethyl)-N-({7-[(6-amino-9H-purin-9-yl)methyl]-5-(4,4-difluorocyclohexyl)-1H-indol-2-yl}methyl)-2-methylbenzamide A solution of Example 306 (9.3 mg, 0.017 mmol) in THF (4 mL) was added to 20% Pd(OH)$_2$/C (wet, 4 mg, 2.91 μmol) in a 50 mL pressure bottle and the suspension was shaken for 16 hours at room temperature under 30 psi hydrogen. The reaction mixture was filtered and was concentrated to dryness. The crude product was purified by preparative HPLC on *2-coupled C8 5 m 100 Å columns (30 mm×75 mm each) with a gradient of acetonitrile (A) and 0.1% trifluoroacetic acid in water (B) was used, at a flow rate of 50 mL/min (0-0.5 minute 5% A, 0.5-8.5 minutes linear gradient 5-100% A, 8.7-10.7 minutes 100% A, 10.7-11 minutes linear gradient 100-5% A) to provide the title compound. $^1$H NMR (500 MHz, DMSO-d$_6$) δ 11.22 (d, J=2.0 Hz, 1H), 8.86 (q, J=5.6 Hz, 1H), 8.44 (s, 1H), 8.37 (s, 1H), 8.19 (s, 4H), 7.46 (d, J=7.8 Hz, 1H), 7.41-7.29 (m, 3H), 6.84 (s, 1H), 6.35 (d, J=1.8 Hz, 1H), 5.63 (s, 2H), 4.63 (d, J=5.7 Hz, 2H), 4.04 (t, J=5.8 Hz, 2H), 2.66 (dd, J=13.6, 9.8 Hz, 1H), 2.39 (s, 3H), 2.38-2.31 (m, 1H), 2.06 (d, J=12.9 Hz, 2H), 2.02-1.85 (m, 2H), 1.81 (d, J=13.0 Hz, 2H), 1.70-1.56 (m, 2H), 1.17 (d, J=6.7 Hz, 1H), 0.82 (d, J=6.7 Hz, 1H). MS ESI$^+$ 557.3 (M+H)$^+$.

Example 302

N-({7-[(6-amino-9H-purin-9-yl)methyl]-5-chloro-1H-indol-2-yl}methyl)-4-(dimethylamino)benzamide Example 302 was prepared according to the procedure used for the preparation of Example 232, substituting 4-(dimethylamino)benzoic acid for 2-(pyridin-4-yl)acetic acid. $^1$H NMR (400 MHz, DMSO-d$_6$) δ 2.81 (s, 2H), 2.98 (s, 7H), 3.15 (s, 9H), 4.64 (d, J=5.7 Hz, 2H), 5.66 (s, 2H), 6.35 (d, J=1.9 Hz, 1H), 6.43-6.79 (m, 2H), 6.83 (d, J=2.0 Hz, 1H), 7.48 (d, J=1.9 Hz, 1H), 7.65-7.85 (m, 2H), 8.33 (s, 3H), 8.45 (s, 1H), 8.69 (t, J=5.7 Hz, 1H), 11.45 (d, J=2.2 Hz, 1H). MS (APCI) m/z 475.2 [M+H]+.

Example 303

N-({7-[(6-amino-9H-purin-9-yl)methyl]-5-chloro-1H-indol-2-yl}methyl)-4-cyano-2-methylbenzamide Example 303 was prepared according to the procedure used for the preparation of Example 199, substituting 4-cyano-2-methylbenzoic acid for 3-methylpyridazine-4-carboxylic acid. $^1$H NMR (400 MHz, DMSO-$d_6$) δ 2.38 (s, 3H), 4.67 (s, 2H), 5.70 (s, 2H), 6.45 (s, 1H), 6.85 (d, J=1.9 Hz, 1H), 7.50-7.62 (m, 2H), 7.69-7.84 (m, 2H), 8.39 (s, 1H), 8.52 (s, 1H). MS (APCI) m/z 471.2 [M+H]+.

Example 304

N-({7-[(6-amino-9H-purin-9-yl)methyl]-5-(3,6-dihydro-2H-pyran-4-yl)-1H-indol-2-yl}methyl)-4-cyano-2-methylbenzamide Using the procedure described for Example 4d, substituting Example 303 for Example 4c and substituting 2-(3,6-dihydro-2H-pyran-4-yl)-4,4,5,5-tetramethyl-1,3,2-dioxaborolane for methylboronic acid provided the title compound. $^1$H NMR (400 MHz, DMSO-$d_6$) δ 11.42 (d, J=1.9 Hz, 1H), 9.10 (t, J=5.7 Hz, 1H), 8.32 (s, 1H), 8.26 (s, 1H), 7.84 (s, 1H), 7.81 (dd, J=7.6, 1.6 Hz, 1H), 7.62 (d, J=7.8 Hz, 1H), 7.55 (d, J=1.7 Hz, 1H), 7.33 (s, 2H), 7.21 (d, J=1.7 Hz, 1H), 6.47 (d, J=1.9 Hz, 1H), 6.09 (t, J=2.8 Hz, 1H), 5.65 (s, 2H), 4.71 (d, J=5.8 Hz, 2H), 4.25 (q, J=2.7 Hz, 2H), 3.86 (t, J=5.4 Hz, 2H), 2.49 (s, 2H), 2.45 (s, 3H). MS ESI+ 519.1 (M+H)+.

Example 305

N-({7-[(6-amino-9H-purin-9-yl)methyl]-5-(1,2,3,6-tetrahydropyridin-4-yl)-1H-indol-2-yl}methyl)-4-cyano-2-methylbenzamide Using the procedure described for Example 286B and substituting Example 308 for Example 286a provided the title compound. $^1$H NMR (400 MHz, DMSO-$d_6$) δ 11.43 (s, 1H), 9.06 (t, J=5.7 Hz, 1H), 8.80 (d, J=6.3 Hz, 2H), 8.40 (s, 1H), 8.31 (s, 1H), 8.00 (s, 2H), 7.84 7.71 (m, 2H), 7.57 (d, J=8.5 Hz, 2H), 7.08 (s, 1H), 6.43 (s, 1H), 5.96 (d, J=3.5 Hz, 1H), 5.67 (s, 2H), 4.66 (d, J=5.6 Hz, 2H), 3.72 (d, J=4.5 Hz, 2H), 3.31 (d, J=6.4 Hz, 2H), 2.66 (d, J=5.8 Hz, 2H), 2.39 (s, 3H). MS ESI+ 518.0 (M+H)+.

Example 306

N-({7-[(6-amino-9H-purin-9-yl)methyl]-5-(4,4-difluorocyclohex-1-en-1-yl)-1H-indol-2-yl}methyl)-4-cyano-2-methylbenzamide Using the procedure described for Example 4d, substituting Example 303 for Example 4c and substituting 2-(4,4-difluorocyclohex-1-en-1-yl)-4,4,5,5-tetramethyl-1,3,2-dioxaborolane for methylboronic acid provided the title compound. $^1$H NMR (400 MHz, DMSO-$d_6$) δ 11.31 (d, J=2.1 Hz, 1H), 9.09 (t, J=5.8 Hz, 1H), 8.43 (s, 1H), 8.35 (s, 1H), 8.04 (s, 2H), 7.80-7.72 (m, 2H), 7.56 (d, J=7.7 Hz, 1H), 7.52 (d, J=1.7 Hz, 1H), 7.10 (d, J=1.8 Hz, 1H), 6.41 (d, J=1.9 Hz, 1H), 5.81 (s, 1H), 5.65 (s, 2H), 4.65 (d, J=5.6 Hz, 2H), 2.76-2.58 (m, 4H), 2.39 (s, 3H), 2.16 (tq, J=13.9, 7.2, 6.7 Hz, 2H), 1.17 (d, J=6.8 Hz, 1H), 0.82 (d, J=6.8 Hz, 1H). MS ESI+551.0 (M+H)+.

Example 307

N-({5-(1-acetyl-1,2,3,6-tetrahydropyridin-4-yl)-7-[(6-amino-9H-purin-9-yl)methyl]-1H-indol-2-yl}methyl)-4-cyano-2-methylbenzamide Using the procedure described for Example 4d, substituting Example 303 for Example 4c and substituting 1-(4-(4,4,5,5-tetramethyl-1,3,2-dioxaborolan-2-yl)-5,6-dihydropyridin-1(2H)-yl)ethanone for methylboronic acid provided the title compound. 1H NMR (400 MHz, DMSO-$d_6$) δ 11.37 (s, 1H), 9.04 (t, J=5.7 Hz, 1H), 8.24 (d, J=23.7 Hz, 2H), 7.83-7.72 (m, 2H), 7.56 (d, J=7.8 Hz, 1H), 7.49 (dd, J=4.4, 1.7 Hz, 1H), 7.28 (s, 2H), 7.14 (s, 1H), 6.41 (d, J=1.9 Hz, 1H), 5.96 (dt, J=10.8, 3.4 Hz, 1H), 5.59 (s, 2H), 4.65 (d, J=5.8 Hz, 2H), 4.18-3.99 (m, 2H), 3.62 (dt, J=12.0, 5.7 Hz, 2H), 2.53 (s, 1H), 2.43 (s, 1H), 2.39 (s, 3H), 2.04 (d, J=16.1 Hz, 3H). MS ESI+ 560.1 (M+H)+.

Example 308 tert-butyl 4-(7-[(6-amino-9H-purin-9-yl)methyl]-2-{[(4-cyano-2-methylbenzoyl)amino]methyl})-1H-indol-5-yl)-3,6-dihydropyridine-1(2H)-carboxylate Using the procedure described for Example 4d, substituting Example 303 for Example 4c and substituting tert-butyl 4-(4,4,5,5-tetramethyl-1,3,2-dioxaborolan-2-yl)-5,6-dihydropyridine-1(2H)-carboxylate for methylboronic acid provided the title compound. $^1$H NMR (400 MHz, DMSO-$d_6$) δ 9.04 (t, J=5.7 Hz, 1H), 8.23 (d, J=21.1 Hz, 2H), 7.91-7.69 (m, 2H), 7.56 (d, J=8.0 Hz, 1H), 7.48 (d, J=1.6 Hz, 1H), 7.27 (s, 2H), 7.15 (d, J=1.7 Hz, 1H), 6.40 (d, J=2.0 Hz, 1H), 5.94 (s, 1H), 5.59 (s, 2H), 4.65 (d, J=5.7 Hz, 2H), 4.12-3.88 (m, 2H), 3.52 (t, J=5.8 Hz, 2H), 2.45 (s, 2H), 2.39 (s, 3H), 1.90 (s, 1H), 1.42 (s, 9H). MS ESI+618.0 (M+H)+.

Example 309

N-({7-[(6-amino-9H-purin-9-yl)methyl]-5-chloro-1H-indol-2-yl}methyl)-3-(dimethylamino)benzamide Example 309 was prepared according to the procedure used for the preparation of Example 232, substituting 3-(dimethylamino)benzoic acid for 2-(pyridin-4-yl)acetic acid. $^1$H NMR (400 MHz, DMSO-$d_6$) δ 2.95 (s, 6H), 4.67 (d, J=5.6 Hz, 2H), 5.70 (s, 2H), 6.37 (d, J=1.8 Hz, 1H), 6.82 (d, J=2.0 Hz, 1H), 6.88-6.96 (m, 1H), 7.14-7.35 (m, 3H), 7.50 (d, J=1.9 Hz, 1H), 8.41 (s, 1H), 8.53 (s, 2H), 8.97 (t, J=5.7 Hz, 1H), 11.49 (d, J=2.2 Hz, 1H). MS (APCI) m/z 475.2 [M+H]+.

Example 310

N-({7-[(6-amino-9H-purin-9-yl)methyl]-5-chloro-1H-indol-2-yl}methyl)-2-(ethylamino)benzamide Example 310 was prepared according to the procedure used for the preparation of Example 229, substituting 2-(ethylamino)benzoic acid for 2-fluoro-6-hydroxybenzoic acid. $^1$H NMR (400 MHz, DMSO-$d_6$) δ 1.22 (t, J=7.1 Hz, 3H), 3.18 (q, J=7.1 Hz, 3H), 4.66 (s, 2H), 5.67 (s, 2H), 6.62 (t, J=7.8 Hz, 1H), 6.74 (d, J=8.4 Hz, 1H), 6.94 (d, J=2.0 Hz, 1H), 7.33 (ddd, J=8.6, 7.1, 1.6 Hz, 1H), 7.50 (d, J=2.0 Hz, 1H), 7.62 (dd, J=7.9, 1.5 Hz, 1H), 8.34 (d, J=11.5 Hz, 2H). MS (APCI) m/z 475.2 [M+H]⁺.

Example 311

4-{[({7-[(6-amino-9H-purin-9-yl)methyl]-5-chloro-1H-indol-2-yl}methyl)amino]methyl}-3-methoxybenzonitrile Example 311 was prepared according to the procedure used for the preparation of Example 208, substituting 4-formyl-3-methoxybenzonitrile for 2-bromobenzaldehyde. ¹H NMR (400 MHz, DMSO-d₆) δ 8.47 (s, 1H), 8.34 (s, 1H), 7.65 (d, J=1.9 Hz, 1H), 7.61-7.51 (m, 2H), 7.48 (dd, J=7.7, 1.5 Hz, 1H), 6.88 (d, J=1.9 Hz, 1H), 6.75 (s, 1H), 5.68 (s, 2H), 4.43 (s, 2H), 4.25 (s, 2H), 3.87 (s, 3H). MS (ESI+) m/z 473.1 (M+H)⁺.

Example 312

1-({7-[(6-amino-9H-purin-9-yl)methyl]-5-chloro-1H-indol-2-yl}methyl)-3-(2-methoxybenzyl)urea To a suspension of Example 9b in tetrahydrofuran (1.5 mL) was added 1-(isocyanatomethyl)-2-methoxybenzene (0.023 mL, 0.153 mmol). The reaction was stirred at room temperature for about 1 hour. The mixture was concentrated under reduced pressure and the residue purified by preparative HPLC (Waters Sunfire C8, 0-100% acetonitrile/water; 1% TFA) to give the title compound (0.066 g, 88%). ¹H NMR (400 MHz, CD₃OD) δ 8.41 (s, 1H), 8.32 (s, 1H), 7.45 (d, J=1.9 Hz, 1H), 7.28-7.01 (m, 3H), 6.90 (d, J=8.2 Hz, 1H), 6.78 (t, J=7.5 Hz, 1H), 6.33 (s, 1H), 5.65 (s, 2H), 4.48 (s, 2H), 4.34 (s, 2H), 3.79 (s, 3H); MS m/z: 356 [M-adenine]⁺.

Example 313

4-(acetylamino)-N-({7-[(6-amino-9H-purin-9-yl)methyl]-5-chloro-1H-indol-2-yl}methyl)benzamide Example 313 was prepared according to the procedure used for the preparation of Example 232, substituting 4-acetamidobenzoic acid for 2-(pyridin-4-yl)acetic acid. ¹H NMR (400 MHz, DMSO-d₆) δ 2.07 (s, 3H), 4.67 (d, J=5.6 Hz, 2H), 5.66 (s, 2H), 6.37 (d, J=1.9 Hz, 1H), 6.82 (d, J=2.0 Hz, 1H), 7.49 (d, J=2.0 Hz, 1H), 7.61-7.73 (m, 2H), 7.83-7.93 (m, 2H), 8.32 (s, 3H), 8.45 (s, 1H), 8.94 (t, J=5.7 Hz, 1H), 10.17 (s, 1H), 11.49 (d, J=2.1 Hz, 1H). MS (APCI) m/z 489.1 [M+H]⁺.

Example 314

N-({7-[(6-amino-9H-purin-9-yl)methyl]-5-chloro-1H-indol-2-yl}methyl)-2-(propan-2-yl)benzamide Example 314 was prepared according to the procedure used for the preparation of Example 229, substituting 2-isopropylbenzoic acid for 2-fluoro-6-hydroxybenzoic acid. ¹H NMR (400 MHz, DMSO-d₆) δ 1.18 (d, J=6.9 Hz, 6H), 4.64 (s, 2H), 5.66 (s, 2H), 6.93 (d, J=2.0 Hz, 1H), 7.16-7.34 (m, 2H), 7.34-7.45 (m, 2H), 7.49 (d, J=2.0 Hz, 1H), 8.34 (s, 2H). MS (APCI) m/z 474.2 [M+H]⁺.

Example 315

N-({7-[(6-amino-9H-purin-9-yl)methyl]-5-chloro-1H-indol-2-yl}methyl)-3-(4-methoxyphenyl)propanamide Example 315 was prepared according to the procedure used for the preparation of Example 105, substituting 3-(4-methoxy-phenyl)-propionic acid for 4-methyl-pentanoic acid. ¹H NMR (400 MHz, DMSO-d₆) δ 11.43 (s, 1H), 8.52-8.17 (m, 5H), 7.46 (d, J=1.9 Hz, 1H), 7.17-7.09 (m, 2H), 6.87-6.77 (m, 3H), 6.16 (d, J=1.8 Hz, 1H), 5.66 (s, 2H), 4.44 (d, J=5.6 Hz, 2H), 3.70 (s, 3H), 2.81 (dd, J=8.7, 7.0 Hz, 2H), 2.45 (dd, J=8.6, 6.9 Hz, 2H). MS (APCI+) m/z 490.0 (M+H)⁺.

Example 316

N-({7-[(6-amino-9H-purin-9-yl)methyl]-5-chloro-1H-indol-2-yl}methyl)-3-(3-methoxyphenyl)propanamide Example 316 was prepared according to the procedure used for the preparation of Example 105, substituting 3-(3-methoxy-phenyl)-propionic acid for 4-methyl-pentanoic acid. ¹H NMR (400 MHz, DMSO-d₆) δ 11.45 (s, 1H), 8.46-8.37 (m, 2H), 8.35 (s, 1H), 8.13 (s, 2H), 7.46 (d, J=2.0 Hz, 1H), 7.18 (t, J=8.0 Hz, 1H), 6.84-6.70 (m, 4H), 6.22 (d, J=1.8 Hz, 1H), 5.64 (s, 2H), 4.46 (d, J=5.5 Hz, 2H), 3.71 (s, 3H), 2.89-2.79 (m, 2H), 2.51-2.44 (m, 2H). MS (APCI+) m/z 490.0 (M+H)⁺.

Example 317

N-({7-[(6-amino-9H-purin-9-yl)methyl]-5-chloro-1H-indol-2-yl}methyl)-2-[4-(dimethylamino)phenyl]acetamide Example 317 was prepared according to the procedure used for the preparation of Example 105, substituting (4-dimethylamino-phenyl)-acetic acid for 4-methyl-pentanoic acid. ¹H NMR (400 MHz, DMSO-d₆) δ 11.46 (s, 1H), 8.57-8.47 (m, 4H), 8.43 (s, 1H), 7.49 (d, J=1.9 Hz, 1H), 7.24-7.15 (m, 2H), 6.87 (d, J=8.4 Hz, 2H), 6.82 (d, J=2.0 Hz, 1H), 6.31 (d, J=1.8 Hz, 1H), 5.68 (s, 2H), 4.46 (d, J=5.6 Hz, 2H), 3.42 (s, 2H), 2.92 (s, 6H). MS (APCI+) m/z 489.0 (M+H)⁺.

Example 318

4-{[({7-[(6-amino-9H-purin-9-yl)methyl]-5-chloro-1H-indol-2-yl}methyl)amino]methyl}-N,N-dimethylbenzamide Example 318 was prepared according to the procedure used for the preparation of Example 208, substituting 4-formyl-N,N-dimethylbenzamide for 2-bromobenzaldehyde. ¹H NMR (400 MHz, DMSO-d₆) δ 8.46 (s, 1H), 8.34 (s, 1H), 7.65 (d, J=1.8 Hz, 1H), 7.62-7.54 (m, 2H), 7.54-7.43 (m, 2H), 6.88 (d, J=1.9 Hz, 1H), 6.75 (s, 1H), 5.68 (s, 2H), 4.43 (s, 2H), 4.30 (s, 2H), 3.18 (s, 1H), 3.00 (s, 3H), 2.89 (s, 3H). MS (ESI+) m/z 450.1 (M+H)⁺.

Example 319

N-({7-[(6-amino-9H-purin-9-yl)methyl]-5-chloro-1H-indol-2-yl}methyl)-3-(2-fluorophenyl)pyrrolidine-1-carboxamide To a suspension of Example 9b (67.5 mg, 0.206 mmol) in THF (3 mL) at 0° C. was added N-ethyl-N-isopropylpropan-2-amine (39.5 µL, 0.226 mmol) and 4-nitrophenyl carbonochloridate (41.5 mg, 0.206 mmol). After the mixture was stirred at 0° C. for 40 minutes, a solution of 3-(2-fluorophenyl)pyrrolidine (34 mg, 0.206 mmol) in THF (1 mL) was added, followed by addition of Hunig's Base (43.1 µL, 0.247 mmol). The mixture was stirred at 0° C. for 30 minutes and then at ambient temperature for 2 hours. The mixture was diluted with 30 mL ethyl acetate, washed with 1N aqueous sodium hydroxide solution and brine, dried over anhydrous magnesium sulfate, filtered. The filtrate was concentrated and the residue was purified by column chromatography on silica gel (1-10% methanol in dichloromethane) to give the title compound (40 mg, 0.077 mmol, 37.5% yield). $^1$H NMR (400 MHz, DMSO-$d_6$) δ 11.41 (s, 1H), 8.30 (s, 1H), 8.21 (d, J=5.4 Hz, 1H), 7.47 (d, J=1.9 Hz, 1H), 7.38 (dd, J=10.8, 4.7 Hz, 1H), 7.34-7.26 (m, 3H), 7.23-7.14 (m, 2H), 6.85 (d, J=1.9 Hz, 1H), 6.79 (t, J=5.7 Hz, 1H), 6.32 (d, J=1.4 Hz, 1H), 5.60 (s, 2H), 4.45 (d, J=5.6 Hz, 2H), 3.82-3.73 (m, 1H), 3.58 (ddd, J=18.5, 13.3, 5.7 Hz, 2H), 3.45-3.25 (m, 2H), 2.25 (dd, J=10.6, 4.5 Hz, 1H), 2.13-1.94 (m, 1H). MS (ESI+) m/z 519.0 (M+H)$^+$.

Example 320

N-({7-[(6-amino-9H-purin-9-yl)methyl]-5-chloro-1H-indol-2-yl}methyl)-2-(pyrrolidin-1-ylcarbonyl)benzamide Example 320 was prepared according to the procedure used for the preparation of Example 229, substituting 2-(pyrrolidine-1-carbonyl)benzoic acid for 2-fluoro-6-hydroxybenzoic acid. $^1$H NMR (400 MHz, DMSO-$d_6$) δ 1.73 (d, J=6.6 Hz, 4H), 3.13 (d, J=10.2 Hz, 3H), 3.37 (s, 2H), 4.63 (s, 2H), 5.70 (s, 2H), 6.89 (d, J=2.3 Hz, 1H), 7.34 (dd, J=7.3, 1.5 Hz, 1H), 7.43-7.60 (m, 3H), 7.67 (dd, J=7.4, 1.5 Hz, 1H), 8.34 (d, J=5.1 Hz, 2H). MS (APCI) m/z 529.1 [M+H]$^+$.

Example 321

N-({7-[(6-amino-9H-purin-9-yl)methyl]-5-chloro-1H-indol-2-yl}methyl)-2-(tetrahydro-2H-pyran-4-yloxy)benzamide Example 321 was prepared according to the procedure used for the preparation of Example 229, substituting 2-((tetrahydro-2H-pyran-4-yl)oxy)benzoic acid for 2-fluoro-6-hydroxybenzoic acid. $^1$H NMR (400 MHz, DMSO-$d_6$) δ 1.55 (dtd, J=12.8, 8.4, 4.0 Hz, 2H), 1.82-2.00 (m, 2H), 3.34-3.40 (m, 1H), 3.63 (dt, J=10.5, 4.7 Hz, 2H), 4.64 (tt, J=8.1, 4.0 Hz, 1H), 4.72 (s, 2H), 5.66 (s, 2H), 6.93 (d, J=1.9 Hz, 1H), 7.08 (t, J=7.5 Hz, 1H), 7.18 (d, J=8.2 Hz, 1H), 7.40-7.54 (m, 2H), 7.82 (dd, J=7.7, 1.9 Hz, 1H), 8.33 (d, J=11.0 Hz, 2H). MS (APCI) m/z 532.2 [M+H]$^+$.

Example 322

N-({7-[(6-amino-9H-purin-9-yl)methyl]-5-chloro-1H-indol-2-yl}methyl)-2-(piperidin-1-yl)benzamide Example 322 was prepared according to the procedure used for the preparation of Example 229, substituting 2-(piperidin-1-yl)benzoic acid for 2-fluoro-6-hydroxybenzoic acid. $^1$H NMR (400 MHz, DMSO-$d_6$) δ 1.42 (dq, J=34.3, 5.8 Hz, 6H), 2.95 (t, J=5.2 Hz, 4H), 4.74 (s, 2H), 5.65 (s, 2H), 6.96 (d, J=1.9 Hz, 1H), 7.30 (t, J=7.5 Hz, 1H), 7.41 (d, J=8.2 Hz, 1H), 7.45-7.61 (m, 2H), 7.98 (dd, J=7.7, 1.7 Hz, 1H), 8.31 (d, J=10.3 Hz, 2H). MS (APCI) m/z 515.2 [M+H]$^+$.

Example 323

9-{[5-chloro-2-({[3-(piperidin-1-ylmethyl)benzyl]amino}methyl)-1H-indol-7-yl]methyl}-9H-purin-6-amine Example 323 was prepared according to the procedure used for the preparation of Example 208, substituting 3-(piperidin-1-ylmethyl)benzaldehyde for 2-bromobenzaldehyde. $^1$H NMR (400 MHz, DMSO-$d_6$) δ 8.45 (s, 1H), 8.31 (s, 1H), 7.73-7.55 (m, 4H), 7.53 (s, 1H), 6.95-6.83 (m, 1H), 6.75 (s, 1H), 5.68 (s, 2H), 4.44 (s, 2H), 4.28 (d, J=4.2 Hz, 4H), 3.33 (d, J=12.1 Hz, 2H), 2.89 (t, J=12.2 Hz, 2H), 1.83 (d, J=14.1 Hz, 2H), 1.76-1.47 (m, 3H), 1.46-1.27 (m, 1H). MS (ESI+) m/z 515.1 (M+H)$^+$.

Example 324

N-({7-[(6-amino-9H-purin-9-yl)methyl]-5-chloro-1H-indol-2-yl}methyl)-2-(piperidin-1-ylcarbonyl)benzamide Example 324 was prepared according to the procedure used for the preparation of Example 229, substituting 2-(piperidine-1-carbonyl)benzoic acid for 2-fluoro-6-hydroxybenzoic acid. $^1$H NMR (400 MHz, DMSO-$d_6$) δ 1.44 (d, J=25.2 Hz, 7H), 4.63 (s, 2H), 5.67 (s, 2H), 6.89 (d, J=1.8 Hz, 1H), 7.22-7.32 (m, 1H), 4.03-4.37 (m, −1H), 7.43-7.60 (m, 3H), 7.68 (d, J=7.6 Hz, 1H), 8.29 (d, J=1.4 Hz, 2H), MS (APCI) m/z 543.2 [M+H]$^+$.

Example 325

9-({5-chloro-2-[({3-[2-(piperidin-1-yl)ethoxy]benzyl}amino)methyl]-1H-indol-7-yl}methyl)-9H-purin-6-amine Example 325 was prepared according to the procedure used for the preparation of Example 208, substituting 3-(2-(piperidin-1-yl)ethoxy)benzaldehyde for 2-bromobenzaldehyde. $^1$H NMR (400 MHz, DMSO-$d_6$) δ 8.46 (s, 1H), 8.32 (s, 1H), 7.65 (d, J=1.9 Hz, 1H), 7.44 (t, J=7.9 Hz, 1H), 7.21-7.04 (m, 3H), 6.88 (d, J=1.9 Hz, 1H), 6.74 (s, 1H), 5.68 (s, 2H), 4.41 (s, 2H), 4.34 (t, J=4.9 Hz, 2H), 4.24 (s, 2H), 3.56-3.45 (m, 4H), 3.02 (t, J=12.0 Hz, 2H), 1.85 (d, J=13.8 Hz, 2H), 1.71 (m, 3H). MS (ESI+) m/z 545.2 (M+H)$^+$.

Example 326

N-({7-[(6-amino-9H-purin-9-yl)methyl]-5-chloro-1H-indol-2-yl}methyl)-5-methyl-3-phenyl-1,2-oxazole-4-carboxamide Example 326 was prepared according to the procedure used for the preparation of Example 232, substituting 5-methyl-3-phenylisoxazole-4-carboxylic acid for 2-(pyridin-4-yl)acetic acid. $^1$H NMR (400 MHz, DMSO-$d_6$) δ 2.55 (s, 2H), 2.69 (s, 1H), 4.64 (d, J=5.7 Hz, 2H), 5.69 (s, 2H), 6.36 (d, J=1.8 Hz, 1H), 6.85 (d, J=2.0 Hz, 1H), 7.31-7.57 (m, 4H), 7.57-7.71 (m, 2H), 8.40 (s, 1H), 8.51 (s, 2H), 8.95 (t, J=5.7 Hz, 1H), 11.56 (d, J=2.2 Hz, 1H). MS (APCI) m/z 513. [M+H]⁺.

Example 327

N-({7-[(6-amino-9H-purin-9-yl)methyl]-5-chloro-1H-indol-2-yl}methyl)-2-(1-methyl-1H-imidazol-2-yl)benzamide Example 327 was prepared according to the procedure used for the preparation of Example 229, substituting 2-(1-methyl-1H-imidazol-2-yl)benzoic acid for 2-fluoro-6-hydroxybenzoic acid. ¹H NMR (400 MHz, DMSO-d₆) δ 3.56 (s, 3H), 4.61 (s, 2H), 5.65 (s, 2H), 6.94 (d, J=2.0 Hz, 1H), 7.51 (d, J=1.9 Hz, 1H), 7.59-7.76 (m, 3H), 7.85 (dtd, J=20.1, 7.6, 1.4 Hz, 2H), 8.05 (dd, J=7.6, 1.4 Hz, 1H), 8.25-8.42 (m, 2H). MS (APCI) m/z 512.2 [M+H]⁺.

Example 328

N-({7-[(6-amino-9H-purin-9-yl)methyl]-5-chloro-1H-indol-2-yl}methyl)-2-(benzoylamino)benzamide Example 328 was prepared according to the procedure used for the preparation of Example 229, substituting 2-benzamidobenzoic acid for 2-fluoro-6-hydroxybenzoic acid. ¹H NMR (400 MHz, DMSO-d₆) δ 4.72 (s, 2H), 5.56 (s, 2H), 6.42 (s, 1H), 6.91 (d, J=1.9 Hz, 1H), 7.24 (t, J=7.8 Hz, 1H), 7.40-7.65 (m, 5H), 7.82-7.97 (m, 3H), 8.20 (s, 2H), 8.57 (d, J=8.4 Hz, 1H). MS (APCI) m/z 551.2 [M+H]⁺.

Example 329

N-({7-[(6-amino-9H-purin-9-yl)methyl]-5-chloro-1H-indol-2-yl}methyl)-1,2,3-benzothiadiazole-5-carboxamide Example 329 was prepared according to the procedure used for the preparation of Example 356 substituting benzo[d][1,2,3]thiadiazole-5-carboxylic acid for 1H-indole-6-carboxylic acid. ¹H NMR (DMSO/D₂O-d₆) δ 4.78 (s, 1H), 5.63 (s, 3H), 6.48 (s, 1H), 6.82-6.85 (m, 1H), 7.50-7.53 (m, 1H), 8.18 (s, 1H), 8.31 (dd, J=8.5, 1.5 Hz, 1H), 8.33 (s, 1H), 8.51 (d, J=8.6 Hz, 1H), 9.23-9.25 (m, 1H); MS (ESI) m/z 490 (M+H)⁺.

Example 330

N-({7-[(6-amino-9H-purin-9-yl)methyl]-5-chloro-1H-indol-2-yl}methyl)-3H-imidazo[4,5-b]pyridine-5-carboxamide Example 330 was prepared according to the procedure used for the preparation of Example 370 substituting 3H-imidazo[4,5-b]pyridine-5-carboxylic acid for 3-isopropylisoxazolo[5,4-b]pyridine-5-carboxylic acid. ¹H NMR (DMSO/D₂O-d₆) δ 4.74 (d, J=6.1 Hz, 2H), 5.66 (d, J=7.4 Hz, 1H), 5.68 (s, 2H), 6.35-6.40 (m, 1H), 6.80 (d, J=2.0 Hz, 1H), 7.49 (d, J=1.9 Hz, 1H), 8.04 (d, J=8.3 Hz, 1H), 8.18 (d, J=8.3 Hz, 1H), 8.28-8.43 (m, 3H), 8.50 (s, 1H), 8.67 (s, 1H), 9.24 (t, J=6.0 Hz, 1H), 11.45-11.59 (m, 1H); MS (ESI) m/z 473 (M+H)⁺.

Example 331

N-({7-[(6-amino-9H-purin-9-yl)methyl]-5-chloro-1H-indol-2-yl}methyl)-1H-benzotriazole-6-carboxamide Example 331 was prepared according to the procedure used for the preparation of Example 367, substituting 1H-benzo[d][1,2,3]triazole-6-carboxylic acid for 1,2-dimethyl-1H-benzo[d]imidazole-5-carboxylic acid. ¹H NMR (DMSO/D₂O-d₆) δ 4.75 (s, 2H), 5.74 (s, 2H), 6.47 (s, 1H), 6.81-6.90 (m, 1H), 7.49-7.60 (m, 1H), 7.95-8.07 (m, 2H), 8.42 (s, 1H), 8.50-8.63 (m, 2H); MS (ESI) m/e 473 (M+H)⁺.

Example 332

N-({7-[(6-amino-9H-purin-9-yl)methyl]-5-chloro-1H-indol-2-yl}methyl)-1H-benzotriazole-5-carboxamide Example 332 was prepared according to the procedure used for the preparation of Example 367, substituting 1H-benzo[d][1,2,3]triazole-5-carboxylic acid for 1,2-dimethyl-1H-benzo[d]imidazole-5-carboxylic acid. ¹H NMR (DMSO/D₂O-d₆) δ 4.75 (s, 2H), 5.74 (s, 2H), 6.47 (s, 1H), 6.81-6.87 (m, 1H), 7.48-7.61 (m, 1H), 7.96-8.09 (m, 2H), 8.43 (s, 1H), 8.52-8.58 (m, 2H); MS (ESI) m/z 473 (M+H)⁺.

Example 333

N-({7-[(6-amino-9H-purin-9-yl)methyl]-5-chloro-1H-indol-2-yl}methyl)-3H-imidazo[4,5-b]pyridine-6-carboxamide Example 333 was prepared according to the procedure used for the preparation of Example 367, substituting 1,2-dimethyl-1H-benzo[d]imidazole-5-carboxylic acid for 3H-imidazo[4,5-b]pyridine-6-carboxylic acid. ¹H NMR (DMSO/D₂O-d₆) δ 4.76 (s, 2H), 5.76 (s, 2H), 6.48 (s, 1H), 6.80-6.86 (m, 1H), 7.51-7.57 (m, 1H), 8.49 (s, 1H), 8.60-8.66 (m, 2H), 8.86 (s, 1H), 9.00-9.04 (m, 1H); MS (ESI) m/z 473 (M+H)⁺.

Example 334

N-({7-[(6-amino-9H-purin-9-yl)methyl]-5-chloro-1H-indol-2-yl}methyl)-5-fluoro-1H-benzotriazole-6-carboxamide Example 334 was prepared according to the procedure used for the preparation of Example 370, substituting 5-fluoro-1H-benzo[d][1,2,3]triazole-6-carboxylic acid for 3-isopropylisoxazolo[5,4-b]pyridine-5-carboxylic acid. ¹H NMR (DMSO/D₂O-d₆) δ 4.72 (d, J=5.6 Hz, 2H), 5.71 (s, 2H), 6.46 (d, J=1.8 Hz, 1H), 6.82 (d, J=1.9 Hz, 1H), 7.53 (d, J=1.9 Hz, 1H), 7.84 (d, J=9.7 Hz, 1H), 8.29 (s, 1H), 8.40 (s, 1H), 8.54 (s, 1H), 9.10 (t, J=5.5 Hz, 1H), 11.57 (s, 1H); MS (ESI) m/z 491 (M+H)⁺.

Example 335

N-({7-[(6-amino-9H-purin-9-yl)methyl]-5-chloro-1H-indol-2-yl}methyl)-1,3-benzothiazole-6-carboxamide Example 335 was prepared according to the procedure used for the preparation of Example 367, substituting benzo

[d]thiazole-6-carboxylic acid for 1,2-dimethyl-1H-benzo[d]imidazole-5-carboxylic acid. $^1$H NMR (DMSO/D$_2$O-d$_6$) δ 4.75 (s, 2H), 5.74 (s, 2H), 6.47 (s, 1H), 6.80-6.89 (m, 1H), 7.51-7.58 (m, 1H), 8.09 (dd, J=8.6, 1.7 Hz, 1H), 8.22 (d, J=8.6 Hz, 1H), 8.46 (s, 1H), 8.59 (s, 1H), 8.68-8.75 (m, 1H), 9.54 (s, 1H); MS (ESI) m/z 489 (M+H)$^+$.

Example 336

N-({7-[(6-amino-9H-purin-9-yl)methyl]-5-chloro-1H-indol-2-yl}methyl)-1,3-benzothiazole-5-carboxamide Example 336 was prepared according to the procedure used for the preparation of Example 367, substituting benzo[d]thiazole-5-carboxylic acid for 1,2-dimethyl-1H-benzo[d]imidazole-5-carboxylic acid. $^1$H NMR (DMSO-d$_6$) δ 4.76 (s, 2H), 5.74 (s, 2H), 6.47 (s, 1H), 6.82-6.88 (m, 1H), 7.50-7.59 (m, 1H), 8.05 (dd, J=8.4, 1.7 Hz, 1H), 8.32 (d, J=8.4 Hz, 1H), 8.45 (s, 1H), 8.59 (s, 1H), 8.61-8.70 (m, 1H), 9.50 (s, 1H); MS (ESI) m/z 489 (M+H)$^+$.

Example 337

N-({7-[(6-amino-9H-purin-9-yl)methyl]-5-chloro-1H-indol-2-yl}methyl)thieno[3,2-b]pyridine-6-carboxamide Example 337 was prepared according to the procedure used for the preparation of Example 370, substituting thieno[3,2-b]pyridine-6-carboxylic acid for 3-isopropylisoxazolo[5,4-b]pyridine-5-carboxylic acid. $^1$H NMR (DMSO/D$_2$O-d$_6$) δ 4.75 (d, J=5.4 Hz, 2H), 5.71 (s, 2H), 6.46 (d, J=1.8 Hz, 1H), 6.81 (d, J=2.0 Hz, 1H), 7.51 (d, J=1.9 Hz, 1H), 7.66 (d, J=5.4 Hz, 1H), 8.35 (d, J=5.5 Hz, 1H), 8.39 (s, 1H), 8.53 (s, 1H), 8.99 (d, J=1.7 Hz, 1H), 9.18 (d, J=2.0 Hz, 1H), 9.33 (t, J=5.6 Hz, 1H), 11.56 (s, 1H); MS (ESI) m/z 489 (M+H)$^+$.

Example 338

N-({7-[(6-amino-9H-purin-9-yl)methyl]-5-chloro-1H-indol-2-yl}methyl)-1,3-benzoxazole-6-carboxamide Example 338 was prepared according to the procedure used for the preparation of Example 367, substituting benzo[d]oxazole-6-carboxylic acid for 1,2-dimethyl-1H-benzo[d]imidazole-5-carboxylic acid. $^1$H NMR (DMSO/D$_2$O-d$_6$) δ 4.67 (s, 2H), 5.73 (s, 2H), 6.40 (s, 1H), 6.81-6.85 (m, 1H), 7.40 (dd, J=8.3, 2.0 Hz, 1H), 7.45 (d, J=2.0 Hz, 1H), 7.51-7.55 (m, 1H), 8.20 (d, J=8.4 Hz, 1H), 8.36 (s, 1H), 8.43 (s, 1H), 8.58 (s, 1H); MS (ESI) m/z 473 (M+H)$^+$ and 491 (M+NH$_4$)$^+$.

Example 339

N-({7-[(6-amino-9H-purin-9-yl)methyl]-5-chloro-1H-indol-2-yl}methyl)-1,3-benzoxazole-5-carboxamide Example 339 was prepared according to the procedure used for the preparation of Example 367, substituting benzo[d]oxazole-5-carboxylic acid for 1,2-dimethyl-1H-benzo[d]imidazole-5-carboxylic acid. $^1$H NMR (DMSO/D$_2$O-d$_6$) δ 4.63-4.67 (m, 2H), 5.71 (s, 2H), 6.39 (s, 1H), 6.80-6.89 (m, 1H), 6.97 (d, J=8.5 Hz, 1H), 7.50-7.53 (m, 1H), 7.57 (dd, J=8.5, 2.2 Hz, 1H), 8.34 (s, 1H), 8.41 (s, 1H), 8.55 (s, 1H), 8.59-8.63 (m, 1H); MS (ESI) m/z 473 (M+H)$^+$ and 491 (M+NH$_4$)$^+$.

Example 340

N-({7-[(6-amino-9H-purin-9-yl)methyl]-5-chloro-1H-indol-2-yl}methyl)furo[3,2-b]pyridine-6-carboxamide Example 340 was prepared according to the procedure used for the preparation of Example 367, substituting furo[3,2-b]pyridine-6-carboxylic acid for 1,2-dimethyl-1H-benzo[d]imidazole-5-carboxylic acid. $^1$H NMR (DMSO/D$_2$O-d$_6$) δ 4.76 (s, 2H), 5.75 (s, 2H), 6.48 (s, 1H), 6.77-6.90 (m, 1H), 7.21-7.31 (m, 1H), 7.54 (d, J=1.9 Hz, 1H), 8.45 (s, 1H), 8.47 (d, J=2.3 Hz, 1H), 8.50-8.53 (m, 1H), 8.59 (s, 1H), 9.04-9.14 (m, 1H); MS (ESI) m/z 473 (M+H)$^+$.

Example 341

N-({7-[(6-amino-9H-purin-9-yl)methyl]-5-chloro-1H-indol-2-yl)}methyl)-2-hydroxy-1,3-benzothiazole-6-carboxamide Example 341 was prepared according to the procedure used for the preparation of Example 367, substituting 2-hydroxybenzo[d]thiazole-6-carboxylic acid for 1,2-dimethyl-1H-benzo[d]imidazole-5-carboxylic acid. $^1$H NMR (DMSO/D$_2$O-d$_6$) δ 4.69 (s, 2H), 5.73 (s, 2H), 6.43 (s, 1H), 6.82-6.86 (m, 1H), 7.26 (d, J=8.4 Hz, 1H), 7.50-7.55 (m, 1H), 7.87 (dd, J=8.4, 1.8 Hz, 1H), 8.10-8.15 (m, 1H), 8.45 (s, 1H), 8.58 (s, 1H); MS (ESI) m/z 505 (M+H)$^+$.

Example 342

N-({7-[(6-amino-9H-purin-9-yl)methyl]-5-chloro-1H-indol-2-yl}methyl)-1H-indazole-6-carboxamide Example 342 was prepared according to the procedure used for the preparation of Example 367, substituting 1H-indazole-6-carboxylic acid for 1,2-dimethyl-1H-benzo[d]imidazole-5-carboxylic acid. $^1$H NMR (DMSO/D$_2$O-d$_6$) δ 4.73 (s, 2H), 5.74 (s, 2H), 6.45 (s, 1H), 6.82-6.87 (m, 1H), 7.51-7.56 (m, 1H), 7.67 (dd, J=8.4, 1.4 Hz, 1H), 7.91 (d, J=8.2 Hz, 1H), 8.15 (s, 1H), 8.21 (s, 1H), 8.45 (s, 1H), 8.60 (s, 1H); MS (ESI) m/z 472 (M+H)$^+$.

Example 343

N-({7-[(6-amino-9H-purin-9-yl)methyl]-5-chloro-1H-indol-2-yl}methyl)-1H-pyrrolo[3,2-b]pyridine-5-carboxamide Example 343 was prepared according to the procedure used for the preparation of Example 370, substituting 1H-pyrrolo[3,2-b]pyridine-5-carboxylic acid for 3-isopropylisoxazolo[5,4-b]pyridine-5-carboxylic acid. $^1$H NMR (DMSO/D$_2$O-d$_6$) δ 4.74 (d, J=6.0 Hz, 2H), 5.70 (s, 2H), 6.39 (d, J=1.7 Hz, 1H), 6.66-6.69 (m, 1H), 6.80 (d, J=2.0 Hz, 1H), 7.50 (d, J=1.9 Hz, 1H), 7.84 (t, J=3.0 Hz, 1H), 7.93 (d, J=8.5 Hz, 1H), 7.98 (d, J=8.5 Hz, 1H), 8.42 (s, 1H), 8.45-9.00 (m, 3H), 9.20 (t, J=6.2 Hz, 1H), 11.51 (s, 1H), 11.70 (s, 1H); MS (ESI) m/z 472 (M+H)$^+$.

Example 344

N-({7-[(6-amino-9H-purin-9-yl)methyl]-5-chloro-1H-indol-2-yl}methyl)-1H-benzimidazole-5-carboxamide Example 344 was prepared according to the procedure used for the preparation of Example 367, substituting 1H-benzo[d]imidazole-5-carboxylic acid for 1,2-dimethyl-1H-benzo[d]imidazole-5-carboxylic acid. $^1$H NMR (DMSO/D$_2$O-d$_6$) δ 4.74 (s, 2H), 5.72 (s, 2H), 6.44 (s, 1H), 6.83 (d, J=2.0 Hz, 1H), 7.50-7.55 (m, 1H), 7.90-7.96 (m, 1H), 8.08 (dd, J=8.6, 1.5 Hz, 1H), 8.33-8.38 (m, 1H), 8.42 (s, 1H), 8.57 (s, 1H), 9.35 (s, 1H); MS (ESI) m/z 472 (M+H)$^+$.

Example 345

N-({7-[(6-amino-9H-purin-9-yl)methyl]-5-chloro-1H-indol-2-yl}methyl)-1H-benzimidazole-6-carboxamide Example 345 was prepared according to the procedure used for the preparation of Example 370, substituting 1H-benzo[d]imidazole-6-carboxylic acid for 3-isopropylisoxazolo[5,4-b]pyridine-5-carboxylic acid. $^1$H NMR (DMSO/D$_2$O-d$_6$) δ 4.73 (d, J=5.5 Hz, 2H), 5.69 (s, 2H), 6.41 (d, J=1.8 Hz, 1H), 6.82 (d, J=1.8 Hz, 1H), 7.50 (d, J=1.9 Hz, 1H), 7.86 (d, J=8.6 Hz, 1H), 8.03 (dd, J=8.6, 1.5 Hz, 1H), 8.32-8.36 (m, 1H), 8.37 (s, 1H), 8.51 (s, 1H), 9.19 (s, 1H), 9.26 (t, J=5.6 Hz, 1H), 11.54 (s, 1H); MS (ESI) m/z 472 (M+H)$^+$.

Example 346

N-({7-[(6-amino-9H-purin-9-yl)methyl]-5-chloro-1H-indol-2-yl}methyl)-1H-indazole-5-carboxamide Example 346 was prepared according to the procedure used for the preparation of Example 367, substituting 1H-indazole-5-carboxylic acid for 1,2-dimethyl-1H-benzo[d]imidazole-5-carboxylic acid. $^1$H NMR (DMSO/D$_2$O-d$_6$) δ 4.72 (s, 2H), 5.75 (s, 2H), 6.44 (s, 1H), 6.79-6.86 (m, 1H), 7.49-7.58 (m, 1H), 7.66 (d, J=8.8 Hz, 1H), 7.94 (dd, J=8.7, 1.6 Hz, 1H), 8.25-8.29 (m, 1H), 8.39-8.44 (m, 1H), 8.47 (s, 1H), 8.61 (s, 1H); MS (ESI) m/z 472 (M+H)$^+$.

Example 347

N-({7-[(6-amino-9H-purin-9-yl)methyl]-5-chloro-1H-indol-2-yl}methyl)-1H-pyrrolo[2,3-b]pyridine-5-carboxamide Example 347 was prepared according to the procedure used for the preparation of Example 367, substituting 1H-pyrrolo[2,3-b]pyridine-5-carboxylic acid for 1,2-dimethyl-1H-benzo[d]imidazole-5-carboxylic acid. $^1$H NMR (DMSO/D$_2$O-d$_6$) δ 4.73 (s, 2H), 5.75 (s, 2H), 6.46 (s, 1H), 6.64 (d, J=3.5 Hz, 1H), 6.83-6.86 (m, 1H), 7.52-7.55 (m, 1H), 7.60 (d, J=3.5 Hz, 1H), 8.48 (s, 1H), 8.53-8.56 (m, 1H), 8.61 (s, 1H), 8.78-8.82 (m, 1H); MS (ESI) m/z 472 (M+H)$^+$.

Example 348

N-({7-[(6-amino-9H-purin-9-yl)methyl]-5-chloro-1H-indol-2-yl}methyl)-4-chloro-1H-pyrrolo[2,3-b]pyridine-5-carboxamide Example 348 was prepared according to the procedure used for the preparation of Example 370, substituting 4-chloro-1H-pyrrolo[2,3-b]pyridine-5-carboxylic acid for 3-isopropylisoxazolo[5,4-b]pyridine-5-carboxylic acid. $^1$H NMR (DMSO/D$_2$O-d$_6$) δ 4.71 (d, J=5.6 Hz, 2H), 5.68 (s, 2H), 6.48 (d, J=1.8 Hz, 1H), 6.59 (dd, J=3.5, 1.9 Hz, 1H), 6.83 (d, J=2.0 Hz, 1H), 7.53 (d, J=1.9 Hz, 1H), 7.68 (t, J=2.9 Hz, 1H), 8.12 (s, 2H), 8.36 (d, J=11.8 Hz, 2H), 8.47 (s, 1H), 9.08 (t, J=5.8 Hz, 1H), 11.59 (s, 1H), 12.19 (s, 1H); MS (ESI) m/z 506 (M+H)$^+$.

Example 349

N-({7-[(6-amino-9H-purin-9-yl)methyl]-5-chloro-1H-indol-2-yl}methyl)-5-chloro-1H-pyrrolo[2, 3-b]pyridine-6-carboxamide Example 349 was prepared according to the procedure used for the preparation of Example 370, substituting 5-chloro-1H-pyrrolo[2,3-b]pyridine-6-carboxylic acid for 3-isopropylisoxazolo[5,4-b]pyridine-5-carboxylic acid. $^1$H NMR (DMSO/D$_2$O-d$_6$) δ 4.69 (d, J=5.8 Hz, 2H), 5.64 (s, 2H), 6.45 (d, J=1.8 Hz, 1H), 6.51 (dd, J=3.5, 1.8 Hz, 1H), 6.85 (d, J=2.0 Hz, 1H), 7.52 (d, J=1.9 Hz, 1H), 7.65-7.89 (m, 3H), 8.16 (s, 1H), 8.30 (s, 1H), 8.40 (s, 1H), 9.01 (t, J=5.9 Hz, 1H), 11.60 (s, 1H), 12.02 (s, 1H); MS (ESI) m/z 506 (M+H)$^+$.

Example 350

N-({7-[(6-amino-9H-purin-9-yl)methyl]-5-chloro-1H-indol-2-yl}methyl)-4-fluoro-1H-indazole-5-carboxamide Example 350 was prepared according to the procedure used for the preparation of Example 370, substituting 4-fluoro-1H-indazole-5-carboxylic acid for 3-isopropylisoxazolo[5,4-b]pyridine-5-carboxylic acid. $^1$H NMR (DMSO/D$_2$O-d$_6$) δ 4.71 (d, J=5.7 Hz, 2H), 5.70 (s, 2H), 6.42 (d, J=1.8 Hz, 1H), 6.82 (d, J=1.9 Hz, 1H), 7.45 (d, J=8.6 Hz, 1H), 7.52 (d, J=1.9 Hz, 1H), 7.67 (dd, J=8.6, 6.6 Hz, 1H), 8.33 (s, 1H), 8.40 (s, 1H), 8.54 (s, 1H), 8.83 (td, J=5.8, 2.9 Hz, 1H), 11.51 (s, 1H); MS (ESI) m/z 490 (M+H)$^+$.

Example 351

N-({7-[(6-amino-9H-purin-9-yl)methyl]-5-chloro-1H-indol-2-yl}methyl)-3-methyl[1,2]oxazolo[5,4-b]pyridine-5-carboxamide Example 351 was prepared according to the procedure used for the preparation of Example 367, substituting 3-methylisoxazolo[5,4-b]pyridine-5-carboxylic acid for 1,2-dimethyl-1H-benzo[d]imidazole-5-carboxylic acid. $^1$H NMR (DMSO/D$_2$O-d$_6$) δ 2.65 (s, 3H), 4.77 (s, 2H), 5.75 (s, 2H), 6.50 (s, 1H), 6.79-6.89 (m, 1H), 7.50-7.58 (m, 1H), 8.46 (s, 1H), 8.60 (s, 1H), 8.89 (d, J=2.1 Hz, 1H), 9.16 (d, J=2.1 Hz, 1H); MS (ESI) m/z 488 (M+H)$^+$.

Example 352

N-({7-[(6-amino-9H-purin-9-yl)methyl]-5-chloro-1H-indol-2-yl}methyl)-1-methyl-1H-benzotriazole-5-carboxamide Example 352 was prepared according to the procedure used for the preparation of Example 367, substituting 1-methyl-1H-benzo[d][1,2,3]triazole-5-carboxylic acid for 1,2-dimethyl-1H-benzo[d]imidazole-5-carboxylic acid. $^1$H NMR (DMSO/D$_2$O-d$_6$) δ 4.36 (s, 3H), 4.75 (s, 2H), 5.72 (s, 2H), 6.47 (s, 1H), 6.77-6.94 (m, 1H), 7.47-7.61 (m, 1H), 7.96 (d, J=8.8 Hz, 1H), 8.12 (dd, J=8.8, 1.5 Hz, 1H), 8.38 (s, 1H), 8.53 (s, 1H), 8.63-8.66 (m, 1H); MS (ESI) m/z 487 (M+H)$^+$.

Example 353

N-({7-[(6-amino-9H-purin-9-yl)methyl]-5-chloro-1H-indol-2-yl}methyl)-3-methyl-1H-pyrazolo[3,4-b]pyridine-5-carboxamide Example 353 was prepared according to the procedure used for the preparation of Example 367, substituting 3-methyl-1H-pyrazolo[3,4-b]pyridine-5-carboxylic acid for 1,2-dimethyl-1H-benzo[d]imidazole-5-carboxylic acid. $^1$H NMR (DMSO/D$_2$O-d$_6$) δ 2.58 (s, 3H), 4.75 (s, 2H), 5.72 (s, 2H), 6.48 (s, 1H), 6.78-6.90 (m, 1H), 7.48-7.62 (m, 1H), 8.39 (s, 1H), 8.54 (s, 1H), 8.75-8.80 (m, 1H), 8.99-9.06 (m, 1H); MS (ESI) m/z 487 (M+H)$^+$.

Example 354

N-({7-[(6-amino-9H-purin-9-yl)methyl]-5-chloro-1H-indol-2-yl}methyl)-1-benzothiophene-5-carboxamide Example 354 was prepared according to the procedure used for the preparation of Example 367, substituting benzo[b]thiophene-5-carboxylic acid for 1,2-dimethyl-1H-benzo[d]imidazole-5-carboxylic acid. $^1$H NMR (DMSO/D$_2$O-d$_6$) δ 4.74 (s, 2H), 5.75 (s, 2H), 6.45 (s, 1H), 6.80-6.93 (m, 1H), 7.52-7.55 (m, 1H), 7.60 (d, J=5.5 Hz, 1H), 7.87 (d, J=5.5 Hz, 1H), 7.91 (dd, J=8.5, 1.8 Hz, 1H), 8.14 (d, J=8.5 Hz, 1H), 8.44-8.48 (m, 2H), 8.60 (s, 1H); MS (ESI) m/z 488 (M+H)$^+$.

Example 355

N-({7-[(6-amino-9H-purin-9-yl)methyl]-5-chloro-1H-indol-2-yl}methyl)-1-benzofuran-5-carboxamide Example 355 was prepared according to the procedure used for the preparation of Example 367, substituting benzofuran-5-carboxylic acid for 1,2-dimethyl-1H-benzo[d]imidazole-5-carboxylic acid. $^1$H NMR (DMSO/D$_2$O-d$_6$) δ 4.72 (s, 2H), 5.72 (s, 2H), 6.44 (s, 1H), 6.82-6.90 (m, 1H), 7.07-7.18 (m, 1H), 7.50-7.58 (m, 1H), 7.69-7.77 (m, 1H), 7.91 (dd, J=8.6, 1.9 Hz, 1H), 8.06-8.11 (m, 1H), 8.24-8.29 (m, 1H), 8.41 (s, 1H), 8.55 (s, 1H); MS (ESI) m/z 472 (M+H)$^+$.

Example 356

N-({7-[(6-amino-9H-purin-9-yl)methyl]-5-chloro-1H-indol-2-yl}methyl)-1H-indole-6-carboxamide To a 4 mL vial was added a solution of 1H-indole-6-carboxylic acid (0.1 mmol) in N,N-dimethylacetamide (0.35 mL), followed by a solution of HATU (52 mg, 0.14 mmol) in N,N-dimethylacetamide (0.5 mL). Then a solution of Example 9b (15 mg, 0.05 mmol) in N,N-dimethylacetamide (1.0 mL) was added followed by 30 μL of N,N-diisopropylethylamine neat. The reaction was shaken at 50° C. overnight and purified by preparative HPLC on a Phenomenex Luna C8 (2) 5 μm 100 Å AXIA column (30 mm×150 mm). A gradient of acetonitrile (A) and 0.05% ammonium acetate in water (B) was used, at a flow rate of 50 mL/min (0-0.5 minutes 10% A, 0.5-6.0 minutes linear gradient 10-100% A, 6.0-7.0 minutes 100% A, 7.0-8.0 minutes linear gradient 100-10% A). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/min. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export. $^1$H NMR (DMSO/D$_2$O-d$_6$) δ 4.71 (s, 2H), 5.62 (s, 2H), 6.40 (s, 1H), 6.49-6.56 (m, 1H), 6.81-6.91 (m, 1H), 7.48-7.50 (m, 1H), 7.52 (d, J=3.1 Hz, 1H), 7.58-7.67 (m, 2H), 8.03-8.07 (m, 1H), 8.18 (s, 1H), 8.33 (s, 1H); (ESI) m/e 471 (M+H)$^+$.

Example 357

N-({7-[(6-amino-9H-purin-9-yl)methyl]-5-chloro-1H-indol-2-yl}methyl)-1H-indole-5-carboxamide Example 357 was prepared according to the procedure used for the preparation of Example 367, substituting 1H-indole-5-carboxylic acid for 1,2-dimethyl-1H-benzo[d]imidazole-5-carboxylic acid. $^1$H NMR (DMSO/D$_2$O-d$_6$) δ 4.69 (s, 2H), 5.72 (s, 2H), 6.41 (s, 1H), 6.58 (d, J=3.3 Hz, 1H), 6.81-6.87 (m, 1H), 7.43-7.46 (m, 1H), 7.49 (d, J=8.6 Hz, 1H), 7.51-7.54 (m, 1H), 7.70 (dd, J=8.5, 1.7 Hz, 1H), 8.15-8.24 (m, 1H), 8.43 (s, 1H), 8.57 (s, 1H); MS (ESI) m/e 471 (M+H)$^+$.

Example 358

N-({7-[(6-amino-9H-purin-9-yl)methyl]-5-chloro-1H-indol-2-yl}methyl)-2-methyl-1,3-benzothiazole-6-carboxamide Example 358 was prepared according to the procedure used for the preparation of Example 356, substituting 2-methylbenzo[d]thiazole-6-carboxylic acid for 1H-indole-6-carboxylic acid. $^1$H NMR (DMSO/D$_2$O-d$_6$) δ 2.85 (s, 3H), 4.72 (s, 2H), 5.62 (s, 2H), 6.43 (s, 1H), 6.81-6.87 (m, 1H), 7.48-7.53 (m, 1H), 7.99-8.04 (m, 2H), 8.18 (s, 1H), 8.33 (s, 1H), 8.56-8.58 (m, 1H); MS ESI m/z 503 (M+H)$^+$.

Example 359

N-({7-[(6-amino-9H-purin-9-yl)methyl]-5-chloro-1H-indol-2-yl}methyl)-2-methyl-1,3-benzoxazole-6-carboxamide Example 359 was prepared according to the procedure used for the preparation of Example 367, substituting 2-methylbenzo[d]oxazole-6-carboxylic acid for 1,2-dimethyl-1H-benzo[d]imidazole-5-carboxylic acid. $^1$H NMR (DMSO/D$_2$O-d$_6$) δ 2.14 (s, 3H), 4.65 (s, 2H), 5.71 (s, 2H), 6.38 (s, 1H), 6.79-6.86 (m, 1H), 7.37 (dd, J=8.4, 2.0 Hz, 1H), 7.41-7.44 (m, 1H), 7.49-7.54 (m, 1H), 7.92 (d, J=8.4 Hz, 1H), 8.40 (s, 1H), 8.55 (s, 1H).

Example 360

N-({7-[(6-amino-9H-purin-9-yl)methyl]-5-chloro-1H-indol-2-yl}methyl)-1-methyl-1H-indazole-6-carboxamide Example 360 was prepared according to the procedure used for the preparation of Example 370, substituting 1-methyl-1H-indazole-6-carboxylic acid for 3-isopropylisoxazolo[5,4-b]pyridine-5-carboxylic acid. $^1$H NMR (DMSO/D$_2$O-d$_6$) δ 4.11 (s, 3H), 4.74 (d, J=5.6 Hz, 2H), 5.68 (s, 2H), 6.43 (d, J=1.8 Hz, 1H), 6.83 (d, J=1.9 Hz, 1H), 7.51 (d, J=1.8 Hz, 1H), 7.70 (dd, J=8.5, 1.3 Hz, 1H), 7.85 (d, J=8.3 Hz, 1H), 8.13 (s, 1H), 8.25 (s, 1H), 8.34 (s, 1H), 8.49 (s, 1H), 9.15 (t, J=5.6 Hz, 1H), 11.54 (s, 1H); MS (ESI) m/z 486 (M+H)$^+$.

Example 361

N-({7-[(6-amino-9H-purin-9-yl)methyl]-5-chloro-1H-indol-2-yl}methyl)-1-methyl-1H-benzimidazole-5-carboxamide Example 361 was prepared according to the procedure used for the preparation of Example 367, substituting 1-methyl-1H-benzo[d]imidazole-5-carboxylic acid for 1,2-dimethyl-1H-benzo[d]imidazole-5-carboxylic acid. $^1$H NMR (DMSO/D$_2$O-d$_6$) δ 4.08 (s, 3H), 4.75 (s, 2H), 5.75 (s, 2H), 6.45 (s, 1H), 6.84 (d, J=1.9 Hz, 1H), 7.52-7.55 (m, 1H), 8.02 (d, J=8.5 Hz, 1H), 8.10-8.15 (m, 1H), 8.38-8.39 (m, 1H), 8.46 (s, 1H), 8.60 (s, 1H), 9.35 (s, 1H); MS (ESI) m/z 486 (M+H)$^+$.

Example 362

N-({7-[(6-amino-9H-purin-9-yl)methyl]-5-chloro-1H-indol-2-yl}methyl)-1-methyl-1H-indazole-5-carboxamide Example 362 was prepared according to the procedure used for the preparation of Example 367, substituting 1-methyl-1H-indazole-5-carboxylic acid for 1,2-dimethyl-1H-benzo[d]imidazole-5-carboxylic acid. $^1$H NMR (DMSO/D$_2$O-d$_6$) δ 4.10 (s, 3H), 4.72 (s, 2H), 5.74 (s, 2H), 6.44 (s, 1H), 6.83-6.89 (m, 1H), 7.50-7.57 (m, 1H), 7.73 (d, J=8.9 Hz, 1H), 7.97 (dd, J=8.9, 1.6 Hz, 1H), 8.22-8.25 (m, 1H), 8.39-8.44 (m, 1H), 8.45 (s, 1H), 8.59 (s, 1H); MS (ESI) m/z 486 (M+H)$^+$.

Example 363

N-({7-[(6-amino-9H-purin-9-yl)methyl]-5-chloro-1H-indol-2-yl}methyl)-2-methyl-1H-benzimidazole-5-carboxamide Example 363 was prepared according to the procedure used for the preparation of Example 367, substituting 2-methyl-1H-benzo[d]imidazole-5-carboxylic acid for 1,2-dimethyl-1H-benzo[d]imidazole-5-carboxylic acid. $^1$H NMR (DMSO/D$_2$O-d$_6$) δ 2.84 (s, 3H), 4.75 (s, 2H), 5.73 (s, 2H), 6.45 (s, 1H), 6.80-6.87 (m, 1H), 7.48-7.59 (m, 1H), 7.88 (d, J=8.6 Hz, 1H), 8.09 (dd, J=8.6, 1.6 Hz, 1H), 8.25-8.33 (m, 1H), 8.43 (s, 1H), 8.57 (s, 1H); MS (ESI) m/z 486 (M+H)$^+$.

Example 364

N-({7-[(6-amino-9H-purin-9-yl)methyl]-5-chloro-1H-indol-2-yl}methyl)-2-methyl-1-benzofuran-5-carboxamide Example 364 was prepared according to the procedure used for the preparation of Example 367, substituting 2-methylbenzofuran-5-carboxylic acid for 1,2-dimethyl-1H-benzo[d]imidazole-5-carboxylic acid. $^1$H NMR (DMSO-d$_6$) δ 2.47-2.49 (m, 3H), 4.69 (s, 2H), 5.71 (s, 2H), 6.42 (s, 1H), 6.53 (s, 1H), 6.67-6.72 (m, 1H), 6.83-6.87 (m, 1H), 7.50-7.53 (m, 1H), 7.59 (d, J=8.7 Hz, 1H), 7.80 (dd, J=8.6, 1.9 Hz, 1H), 8.07-8.12 (m, 1H), 8.40 (s, 1H), 8.54 (s, 1H); MS (ESI) m/z 486 (M+H)$^+$.

Example 365

N-({7-[(6-amino-9H-purin-9-yl)methyl]-5-chloro-1H-indol-2-yl)}methyl)-1-methyl-1H-indole-6-carboxamide Example 365 was prepared according to the procedure used for the preparation of Example 370, substituting 1-methyl-1H-indole-6-carboxylic acid for 3-isopropylisoxazolo[5,4-b]pyridine-5-carboxylic acid. $^1$H NMR (DMSO/D$_2$O-d$_6$) δ 3.86 (s, 3H), 4.73 (s, 2H), 5.73 (s, 2H), 6.44 (s, 1H), 6.53 (d, J=3.1 Hz, 1H), 6.85 (d, J=1.9 Hz, 1H), 7.52 (dd, J=12.5, 2.5 Hz, 2H), 7.64 (d, J=1.6 Hz, 2H), 8.08 (d, J=1.2 Hz, 1H), 8.44 (s, 1H), 8.59 (s, 1H); MS (ESI) m/z 485 (M+H)$^+$.

Example 366

N-({7-[(6-amino-9H-purin-9-yl)methyl]-5-chloro-1H-indol-2-yl}methyl)-1-methyl-1H-indole-5-carboxamide Example 366 was prepared according to the procedure used for the preparation of Example 367, substituting 1-methyl-1H-indole-5-carboxylic acid for 1,2-dimethyl-1H-benzo[d]imidazole-5-carboxylic acid. $^1$H NMR (DMSO/D$_2$O-d$_6$) δ 3.83 (s, 3H), 4.70 (s, 2H), 5.72 (s, 2H), 6.42 (s, 1H), 6.58 (d, J=3.3 Hz, 1H), 6.82-6.87 (m, 1H), 7.39-7.45 (m, 1H), 7.49-7.57 (m, 2H), 7.75 (dd, J=8.6, 1.7 Hz, 1H), 8.14-8.23 (m, 1H), 8.43 (s, 1H), 8.56 (s, 1H); MS (ESI) m/z 485 (M+H)$^+$.

Example 367

N-({7-[(6-amino-9H-purin-9-yl)methyl]-5-chloro-1H-indol-2-yl}methyl)-1,2-dimethyl-1H-benzimidazole-5-carboxamide To a 4 mL vial was added a solution of 1,2-dimethyl-1H-benzo[d]imidazole-5-carboxylic acid (0.1 mmol) in N,N-dimethylacetamide (0.35 mL), followed by a solution of HATU (52 mg, 0.14 mmol) in N,N-dimethylacetamide (0.5 mL). Then a solution of Example 9b (15 mg, 0.05 mmol) in N,N-dimethylacetamide (1.0 mL) was added followed by 30 μL of N,N-diisopropylethylamine. The reaction was shaken at 50° C. temperature overnight and purified by preparative HPLC on a Phenomenex Luna C8 (2) 5 m 100 Å AXIA column (30 mm×150 mm). A gradient of acetonitrile (A) and 0.1% trifluoroacetic acid in water (B) was used, at a flow rate of 50 mL/min (0-0.5 minutes 10% A, 0.5-6.0 minutes linear gradient 10-100% A, 6.0-7.0 minutes 100% A, 7.0-8.0 minutes linear gradient 100-10% A). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/min. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export. $^1$H NMR (DMSO/D$_2$O-d$_6$) δ 2.86 (s, 3H), 3.97 (s, 3H), 4.76 (s, 2H), 5.75 (s, 2H), 6.45 (s, 1H), 6.84 (d, J=1.9 Hz, 1H), 7.50-7.57 (m, 1H), 8.00-8.05 (m, 1H), 8.12-8.18 (m, 1H), 8.29-8.32 (m, 1H), 8.46 (s, 1H), 8.60 (s, 1H); MS (ESI) m/z 500 (M+H)$^+$.

Example 368

N-({7-[(6-amino-9H-purin-9-yl)methyl]-5-chloro-1H-indol-2-yl}methyl)-2-ethyl-1H-benzimidazole-6-carboxamide Example 368 was prepared according to the procedure used for the preparation of Example 367, substituting 2-ethyl-1H-benzo[d]imidazole-6-carboxylic acid for 1,2-dimethyl-1H-benzo[d]imidazole-5-carboxylic acid. $^1$H NMR (DMSO/D$_2$O-d$_6$) δ 1.45 (t, J=7.6 Hz, 3H), 3.10-3.27 (m, 2H), 4.75 (s, 2H), 5.73 (s, 2H), 6.45 (s, 1H), 6.84 (d, J=1.9 Hz, 1H), 7.54 (d, J=1.9 Hz, 1H), 7.88 (d, J=8.6 Hz, 1H), 8.09 (dd, J=8.7, 1.6 Hz, 1H), 8.27-8.31 (m, 1H), 8.42 (s, 1H), 8.57 (s, 1H); MS (ESI) m/z 500 (M+H)$^+$.

Example 369

N-({7-[(6-amino-9H-purin-9-yl)methyl]-5-chloro-1H-indol-2-yl}methyl)-3-cyano-1H-indole-5-carboxamide Example 369 was prepared according to the procedure used for the preparation of Example 367, substituting 3-cyano-1H-indole-5-carboxylic acid for 1,2-dimethyl-1H-benzo[d]imidazole-5-carboxylic acid. $^1$H NMR (DMSO/D$_2$O-d$_6$) δ 4.73 (s, 2H), 5.73 (s, 2H), 6.45 (s, 1H), 6.81-6.86 (m, 1H), 7.52-7.56 (m, 1H), 7.69 (d, J=8.6 Hz, 1H), 7.91 (dd, J=8.6, 1.7 Hz, 1H), 8.30-8.37 (m, 2H), 8.41 (s, 1H), 8.56 (s, 1H); MS (ESI) m/z 496 (M+H)$^+$.

Example 370

N-({7-[(6-amino-9H-purin-9-yl)methyl]-5-chloro-1H-indol-2-yl}methyl)-3-(propan-2-yl)[1,2]oxazolo[5,4-b]pyridine-5-carboxamide To a 4 mL vial was added a solution of 3-isopropylisoxazolo[5,4-b]pyridine-5-carboxylic acid (0.16 mmol) in N,N-dimethylacetamide (0.5 mL), followed by a solution of HATU (80 mg, 0.2 mmol) in N,N-dimethylacetamide (0.5 mL). Then a solution of Example 9b (23 mg, 0.07 mmol) in N,N-dimethylacetamide (1.0 mL) was added followed by 50 µL of N,N-diisopropylethylamine. The reaction was shaken at 50° C. overnight and purified by preparative HPLC on a Phenomenex Luna C8 (2) 5 µm 100 Å AXIA column (30 mm×150 mm). A gradient of acetonitrile (A) and 0.1% trifluoroacetic acid in water (B) was used, at a flow rate of 50 mL/min (0-0.5 minutes 10% A, 0.5-6.0 minutes linear gradient 10-100% A, 6.0-7.0 minutes 100% A, 7.0-8.0 minutes linear gradient 100-10% A). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/min. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export. $^1$H NMR (DMSO/D$_2$O-d$_6$) δ 1.45 (d, J=7.0 Hz, 6H), 4.77 (d, J=5.3 Hz, 2H), 5.70 (s, 2H), 6.47 (d, J=1.8 Hz, 1H), 6.82 (d, J=1.9 Hz, 1H), 7.52 (d, J=1.8 Hz, 1H), 8.36 (s, 1H), 8.50 (s, 1H), 8.98 (d, J=2.1 Hz, 1H), 9.17 (d, J=2.1 Hz, 1H), 9.42 (t, J=5.5 Hz, 1H), 11.58 (s, 1H); MS (ESI) m/z 516 (M+H)$^+$.

Example 371

N-({7-[(6-amino-9H-purin-9-yl)methyl]-5-chloro-1H-indol-2-yl}methyl)-1-(propan-2-yl)-1H-benzotriazole-5-carboxamide Example 371 was prepared according to the procedure used for the preparation of Example 356, substituting 1-isopropyl-1H-benzo[d][1,2,3]triazole-5-carboxylic acid for 1H-indole-6-carboxylic acid. $^1$H NMR (DMSO/D$_2$O-d$_6$) δ 1.66 (d, J=6.7 Hz, 6H), 4.74 (s, 2H), 5.20-5.32 (m, 1H), 5.62 (s, 2H), 6.44 (s, 1H), 6.80-6.86 (m, 1H), 7.49-7.52 (m, 1H), 7.99-8.12 (m, 2H), 8.19 (s, 1H), 8.33 (s, 1H), 8.60-8.68 (m, 1H); MS (ESI) m/z 515 (M+H)$^+$.

Example 372

N-({7-[(6-amino-9H-purin-9-yl)methyl]-5-chloro-1H-indol-2-yl}methyl)-1-(propan-2-yl)-1H-pyrazolo[3,4-b]pyridine-5-carboxamide Example 372 was prepared according to the procedure used for the preparation of Example 356, substituting 1-isopropyl-1H-pyrazolo[3,4-b]pyridine-5-carboxylic acid for 1H-indole-6-carboxylic acid. $^1$H NMR (DMSO/D$_2$O-d$_6$) δ 1.53 (d, J=6.7 Hz, 6H), 4.74 (s, 2H), 5.26 (p, J=6.7 Hz, 1H), 5.62 (s, 2H), 6.45 (s, 1H), 6.80-6.84 (m, 1H), 7.48-7.52 (m, 1H), 8.20 (s, 1H), 8.33 (d, J=3.8 Hz, 2H), 8.77 (d, J=2.1 Hz, 1H), 9.06 (d, J=2.1 Hz, 1H); MS (ESI) m/z 515 (M+H)$^+$.

Example 373

N-({7-[(6-amino-9H-purin-9-yl)methyl]-5-chloro-1H-indol-2-yl}methyl)-4-methoxy-1,3-dimethyl-1H-pyrazolo[3,4-b]pyridine-5-carboxamide Example 373 was prepared according to the procedure used for the preparation of Example 367, substituting 4-methoxy-1,3-dimethyl-1H-pyrazolo[3,4-b]pyridine-5-carboxylic acid for 1,2-dimethyl-1H-benzo[d]imidazole-5-carboxylic acid. $^1$H NMR (DMSO/D$_2$O-d$_6$) δ 2.59 (s, 3H), 3.96 (s, 3H), 4.04 (s, 3H), 4.73 (s, 2H), 5.74 (s, 2H), 6.50 (s, 1H), 6.75-6.91 (m, 1H), 7.47-7.62 (m, 1H), 8.46 (s, 1H), 8.54-8.61 (m, 2H); MS (ESI) m/z 531 (M+H)$^+$.

Example 374

N-({7-[(6-amino-9H-purin-9-yl)methyl]-5-chloro-1H-indol-2-yl}methyl)-2,3-dimethyl-1H-indole-6-carboxamide Example 374 was prepared according to the procedure used for the preparation of Example 370, substituting 2,3-dimethyl-1H-indole-6-carboxylic acid for 3-isopropylisoxazolo[5,4-b]pyridine-5-carboxylic acid. $^1$H NMR (DMSO/D$_2$O-d$_6$) δ 2.18 (s, 3H), 2.35 (s, 3H), 4.69 (d, J=5.6 Hz, 2H), 5.68 (s, 2H), 6.38 (d, J=1.7 Hz, 1H), 6.83 (d, J=1.9 Hz, 1H), 7.41 (d, J=8.3 Hz, 1H), 7.49 (d, J=1.9 Hz, 1H), 7.57 (dd, J=8.3, 1.5 Hz, 1H), 7.87 (d, J=1.4 Hz, 1H), 8.35 (s, 1H), 8.49 (s, 1H), 8.89 (t, J=5.7 Hz, 1H), 10.97 (s, 1H), 11.48 (s, 1H); MS (ESI) m/z 499 (M+H)$^+$.

Example 375

N-({7-[(6-amino-9H-purin-9-yl)methyl]-5-chloro-1H-indol-2-yl}methyl)-2,3-dimethyl-1H-indole-5-carboxamide Example 375 was prepared according to the procedure used for the preparation of Example 367, substituting 2,3-dimethyl-1H-indole-5-carboxylic acid for 1,2-dimethyl-1H-benzo[d]imidazole-5-carboxylic acid. $^1$H NMR (DMSO/D$_2$O-d$_6$) δ 2.22 (s, 3H), 2.35 (s, 3H), 4.71 (s, 2H), 5.73 (s, 2H), 6.43 (s, 1H), 6.82-6.86 (m, 1H), 7.32 (d, J=8.4 Hz, 1H), 7.50-7.55 (m, 1H), 7.63 (dd, J=8.5, 1.7 Hz, 1H), 8.03-8.08 (m, 1H), 8.42 (s, 1H), 8.57 (s, 1H); MS (ESI) m/z 499 (M+H)$^+$.

Example 376

N-({7-[(6-amino-9H-purin-9-yl)methyl]-5-chloro-1H-indol-2-yl}methyl)-1-(2-hydroxyethyl)-2-methyl-1H-benzimidazole-5-carboxamide Example 376 was prepared according to the procedure used for the preparation of Example 367, substituting 1-(2-hydroxyethyl)-2-methyl-1H-benzo[d]imidazole-5-carboxylic acid for 1,2-dimethyl-1H-benzo[d]imidazole-5-carboxylic acid. $^1$H NMR (DMSO/D$_2$O-d$_6$) δ 2.90 (s, 3H), 3.86 (t, 2H), 4.55 (t, J=4.8 Hz, 2H), 4.76 (s, 2H), 5.75 (s, 2H), 6.45 (s, 1H), 6.81-6.84 (m, 1H), 7.51-7.56 (m, 1H), 8.05 (d, J=8.7 Hz, 1H), 8.13 (dd, J=8.6, 1.6 Hz, 1H), 8.29-8.33 (m, 1H), 8.46 (s, 1H), 8.60 (s, 1H); MS (ESI) m/z 530 (M+H)$^+$.

Example 377

N-({7-[(6-amino-9H-purin-9-yl)methyl]-5-chloro-1H-indol-2-yl}methyl)-6-methyl-1-(propan-2-yl)-1H-pyrazolo[3,4-b]pyridine-5-carboxamide Example 377 was prepared according to the procedure used for the preparation of Example 367, substituting 1-isopropyl-6-methyl-1H-pyrazolo[3,4-b]pyridine-5-carboxylic acid for 1,2-dimethyl-1H-benzo[d]imidazole-5-carboxylic acid. $^1$H NMR (DMSO/D$_2$O-d$_6$) δ 1.50 (d, J=6.7 Hz, 6H), 2.68 (s, 3H), 4.70 (s, 2H), 5.21 (p, J=6.7 Hz, 1H), 5.73 (s, 2H), 6.49 (s, 1H), 6.83-6.87 (m, 1H), 7.54-7.56 (m, 1H), 8.19 (s, 1H), 8.29 (s, 1H), 8.44 (s, 1H), 8.58 (s, 1H); MS (ESI) m/z 529 (M+H)$^+$.

Example 378

N-({7-[(6-amino-9H-purin-9-yl)methyl]-5-chloro-1H-indol-2-yl}methyl)-1,2,3-trimethyl-1H-indole-5-carboxamide Example 378 was prepared according to the procedure used for the preparation of Example 367, substituting 1,2,3-trimethyl-1H-indole-5-carboxylic acid for 1,2-dimethyl-1H-benzo[d]imidazole-5-carboxylic acid. $^1$H NMR (DMSO/D$_2$O-d$_6$) δ 2.25 (s, 3H), 2.36 (s, 3H), 3.69 (s, 3H), 4.71 (s, 2H), 5.71 (s, 2H), 6.43 (s, 1H), 6.78-6.90 (m, 1H), 7.43 (d, J=8.6 Hz, 1H), 7.49-7.56 (m, 1H), 7.70 (dd, J=8.6, 1.7 Hz, 1H), 8.10 (d, J=1.6 Hz, 1H), 8.38 (s, 1H), 8.53 (s, 1H); MS (ESI) m/z 513 (M+H)$^+$.

Example 379

N-({7-[(6-amino-9H-purin-9-yl)methyl]-5-chloro-1H-indol-2-yl}methyl)-2-butyl-1,3-benzoxazole-5-carboxamide Example 379 was prepared according to the procedure used for the preparation of Example 356, substituting 2-butylbenzo[d]oxazole-5-carboxylic acid for 1H-indole-6-carboxylic acid. $^1$H NMR (DMSO/D$_2$O-d$_6$) δ 0.93 (t, J=7.4 Hz, 3H), 1.40 (dq, J=14.7, 7.4 Hz, 2H), 1.80 (p, J=7.5 Hz, 2H), 2.98 (t, J=7.4 Hz, 2H), 4.71 (s, 2H), 5.62 (s, 2H), 6.42 (s, 1H), 6.81-6.86 (m, 1H), 7.49-7.51 (m, 1H), 7.78 (d, J=8.6 Hz, 1H), 7.92-7.98 (m, 1H), 8.18 (s, 1H), 8.23-8.25 (m, 1H), 8.33 (s, 1H); MS (ESI) m/z 529 (M+H)$^+$.

Determination of Biological Activity

Test compounds were dispensed by a Labcyte Echo in 384-well low volume assay plates with 3-fold serial dilutions from 50 μM to 0.00075 μM. 5 μL of SUV420H1 enzyme (Abbvie) at 90 nM was added to all wells except the no enzyme control wells, and incubated for 30 minutes at room temp before 5 μL of Histone Peptide H4(8-30)me1 (Anaspec) at 5 nM and SAM at 4 nM was added to all wells. The plates were incubated in a humidified chamber overnight at room temp and then 10 μL of the detection reagent that contained RIPA buffer (50 mM Tris-HCl, pH 8.0, 150 mM sodium chloride, 1.0% Igepal CA-630 (NP-40), 0.5% sodium deoxycholate and 0.1% sodium dodecyl sulfate) (Sigma) with 2 nM of Terbium chelate anti S-adenosyl-L-homocysteine (SAH) (Abbvie) antibody and Oregon Green labeled SAH at 4 nM was added. The plates were further incubated for 4 hours at room temperature. The plates were read in a Perkin Elmer Envision using a TR-FRET protocol with Excitation set at 335 nm and Emission at 520 and 495 nm. To generate dose response curves the data is normalized to percent inhibition by setting the average of the plus and minus enzyme control wells to 0% and 100% inhibition respectively. The $IC_{50}$ values for the compounds are generated by fitting the normalized data with Accelrys Assay Explorer 3.3 to a sigmoidal curve model using linear regression, $Y=(100*x^n)/(K^n+x^n)$, where Y is the measured response, x is the compound concentration, n is the Hill Slope and K is the $IC_{50}$ and the lower and higher asymptotes are constrained to 0 and 100 respectively.

The $IC_{50}$ of the test compounds are presented in Table 1.

TABLE 1

| Example Number | TR-FRET SAH_SUV420H1 $IC_{50}$ (μM) |
| --- | --- |
| 1 | >50 |
| 2 | 36.9 |
| 3 | 35.0 |
| 4 | 14.1 |
| 5 | 13.9 |
| 6 | 1.46 |
| 7 | 22.2 |
| 8 | 2.82 |
| 9 | 1.17 |
| 10 | 1.87 |
| 11 | 0.178 |
| 12 | 0.334 |
| 13 | 0.135 |
| 14 | 0.186 |
| 15 | 0.154 |
| 16 | 0.44 |
| 17 | 0.635 |
| 18 | 0.561 |
| 19 | ND |
| 20 | 0.866 |
| 21 | 0.78 |
| 22 | 0.458 |
| 23 | ND |
| 24 | ND |
| 25 | ND |
| 26 | 0.474 |
| 27 | 1.21 |
| 28 | 0.426 |
| 29 | 0.252 |
| 30 | 1.17 |
| 31 | 0.901 |
| 32 | 3.33 |
| 33 | 0.528 |
| 34 | 0.723 |
| 35 | 1.09 |
| 36 | 2.41 |
| 37 | 0.321 |
| 38 | 0.81 |
| 39 | 0.345 |
| 40 | 0.425 |
| 41 | 0.236 |
| 42 | 0.45 |
| 43 | ND |
| 44 | 0.56 |
| 45 | 0.356 |
| 46 | 0.541 |
| 47 | 0.354 |
| 48 | 1.33 |
| 49 | 0.193 |
| 50 | 0.223 |
| 51 | 0.294 |
| 52 | 0.244 |
| 53 | 0.59 |
| 54 | 1.18 |
| 55 | 0.293 |
| 56 | 0.24 |
| 57 | 0.457 |
| 58 | 7.88 |
| 59 | 7.51 |
| 60 | 38.4 |
| 61 | 20.3 |
| 62 | 1.12 |
| 63 | 4.03 |

TABLE 1-continued

| Example Number | TR-FRET SAH_SUV420H1 $IC_{50}$ (μM) |
| --- | --- |
| 64 | 3.08 |
| 65 | 5.08 |
| 66 | 4.29 |
| 67 | 0.20 |
| 68 | 0.972 |
| 69 | 0.663 |
| 70 | 1.0 |
| 71 | ND |
| 72 | 1.81 |
| 73 | 0.722 |
| 74 | 1.18 |
| 75 | 0.89 |
| 76 | 1.33 |
| 77 | 2.63 |
| 78 | 0.632 |
| 79 | 0.548 |
| 80 | 1.85 |
| 81 | 0.334 |
| 82 | 0.939 |
| 83 | 0.831 |
| 84 | 0.569 |
| 85 | 0.605 |
| 86 | 0.915 |
| 87 | >50 |
| 88 | 1.43 |
| 89 | 2.6 |
| 90 | 2.24 |
| 91 | 2.67 |
| 92 | >50 |
| 93 | 9.73 |
| 94 | 31.1 |
| 95 | >50 |
| 96 | 16.3 |
| 97 | 11.4 |
| 98 | 11.8 |
| 99 | 25.1 |
| 100 | 10.9 |
| 101 | >50 |
| 102 | 6.36 |
| 103 | 25.3 |
| 104 | 18.2 |
| 105 | 8.17 |
| 106 | 3.32 |
| 107 | 10.9 |
| 108 | 17.0 |
| 109 | 10.6 |
| 110 | 10.7 |
| 111 | 8.8 |
| 112 | 32.0 |
| 113 | >50 |
| 114 | 8.16 |
| 115 | 3.53 |
| 116 | 8.28 |
| 117 | 14.1 |
| 118 | 18.4 |
| 119 | 6.41 |
| 120 | 1.49 |
| 121 | 2.56 |
| 122 | 4.77 |
| 123 | 44.9 |
| 124 | 23.9 |
| 125 | 4.62 |
| 126 | 2.23 |
| 127 | 6.0 |
| 128 | 3.34 |
| 129 | 28.4 |
| 130 | 2.39 |
| 131 | 3.23 |
| 132 | 6.25 |
| 133 | 31.9 |
| 134 | 1.27 |
| 135 | 4.54 |
| 136 | 10.5 |
| 137 | 2.04 |
| 138 | 1.64 |
| 139 | 0.767 |
| 140 | 6.09 |

TABLE 1-continued

| Example Number | TR-FRET SAH_SUV420H1 IC$_{50}$ (μM) |
|---|---|
| 141 | 0.783 |
| 142 | 9.48 |
| 143 | 24.0 |
| 144 | 4.6 |
| 145 | 2.4 |
| 146 | 14.2 |
| 147 | 5.79 |
| 148 | 1.03 |
| 149 | 2.04 |
| 150 | 0.382 |
| 151 | 6.75 |
| 152 | 1.08 |
| 153 | 4.4 |
| 154 | 4.77 |
| 155 | 3.59 |
| 156 | 7.92 |
| 157 | 2.06 |
| 158 | 4.75 |
| 159 | >50 |
| 160 | 16.8 |
| 161 | 0.856 |
| 162 | 0.237 |
| 163 | 0.127 |
| 164 | 0.139 |
| 165 | 0.233 |
| 166 | 0.0889 |
| 167 | 0.225 |
| 168 | 0.333 |
| 169 | 0.0801 |
| 170 | 0.208 |
| 171 | 0.173 |
| 172 | 0.0661 |
| 173 | 0.0412 |
| 174 | 0.101 |
| 175 | 0.0828 |
| 176 | 0.0875 |
| 177 | 0.106 |
| 178 | 0.116 |
| 179 | 0.365 |
| 180 | 0.13 |
| 181 | 2.86 |
| 182 | 5.2 |
| 183 | 1.78 |
| 184 | 0.84 |
| 185 | 0.691 |
| 186 | 0.263 |
| 187 | 1.87 |
| 188 | 0.507 |
| 189 | 3.36 |
| 190 | 0.91 |
| 191 | 2.98 |
| 192 | 2.14 |
| 193 | 20.0 |
| 194 | 1.95 |
| 195 | >50 |
| 196 | 0.905 |
| 197 | 1.07 |
| 198 | 12.6 |
| 199 | 0.0939 |
| 200 | 0.10 |
| 201 | 0.0589 |
| 202 | 0.0641 |
| 203 | 0.0277 |
| 204 | 0.0532 |
| 205 | 3.43 |
| 206 | 1.05 |
| 207 | 0.943 |
| 208 | 1.89 |
| 209 | 1.92 |
| 210 | 3.34 |
| 211 | 9.33 |
| 212 | 3.64 |
| 213 | 2.76 |
| 214 | 2.84 |
| 215 | 3.91 |
| 216 | 2.47 |
| 217 | 2.43 |
| 218 | 2.33 |
| 219 | 3.13 |
| 220 | 4.05 |
| 221 | 6.24 |
| 222 | 3.54 |
| 223 | 8.25 |
| 224 | 2.77 |
| 225 | >50 |
| 226 | 0.275 |
| 227 | 0.79 |
| 228 | 2.42 |
| 229 | >50 |
| 230 | 16.7 |
| 231 | 2.48 |
| 232 | 1.98 |
| 233 | 0.236 |
| 234 | 0.0606 |
| 235 | 0.0492 |
| 236 | 0.0338 |
| 237 | 0.0288 |
| 238 | 0.0457 |
| 239 | 0.0547 |
| 240 | 0.164 |
| 241 | 3.63 |
| 242 | 2.64 |
| 243 | 5.46 |
| 244 | 1.94 |
| 245 | 2.03 |
| 246 | 7.29 |
| 247 | 9.38 |
| 248 | 0.571 |
| 249 | 3.31 |
| 250 | 4.44 |
| 251 | >50 |
| 252 | 2.14 |
| 253 | 36.1 |
| 254 | >50 |
| 255 | 15.5 |
| 256 | >50 |
| 257 | 0.493 |
| 258 | 4.58 |
| 259 | 3.53 |
| 260 | 3.55 |
| 261 | 1.99 |
| 262 | 2.75 |
| 263 | 1.75 |
| 264 | 3.23 |
| 265 | 2.14 |
| 266 | 0.911 |
| 267 | 3.43 |
| 268 | 4.64 |
| 269 | 5.6 |
| 270 | 3.75 |
| 271 | 2.98 |
| 272 | 0.378 |
| 273 | 1.5 |
| 274 | 11.3 |
| 275 | 13.2 |
| 276 | 0.039 |
| 277 | 0.0351 |
| 278 | 0.0674 |
| 279 | 0.0493 |
| 280 | 0.0419 |
| 281 | 0.141 |
| 282 | 0.0723 |
| 283 | 0.0526 |
| 284 | 0.0908 |
| 285 | 0.0579 |
| 286 | 0.0411 |
| 287 | 0.0878 |
| 288 | 0.0431 |
| 289 | 0.0613 |
| 290 | 2.8 |
| 291 | 12.9 |
| 292 | 32.2 |
| 293 | 20.5 |
| 294 | >50 |

TABLE 1-continued

| Example Number | TR-FRET SAH_SUV420H1 IC$_{50}$ (µM) |
|---|---|
| 295 | 0.607 |
| 296 | 0.623 |
| 297 | 6.04 |
| 298 | 5.98 |
| 299 | 1.84 |
| 300 | 4.15 |
| 301 | 0.75 |
| 302 | >50 |
| 303 | 0.0723 |
| 304 | 0.0491 |
| 305 | 0.0367 |
| 306 | 0.0564 |
| 307 | 0.0297 |
| 308 | 0.050 |
| 309 | 7.31 |
| 310 | 13.2 |
| 311 | 3.24 |
| 312 | >50 |
| 313 | >50 |
| 314 | 1.93 |
| 315 | 4.08 |
| 316 | 13.0 |
| 317 | 4.5 |
| 318 | 3.49 |
| 319 | 3.39 |
| 320 | 8.03 |
| 321 | 8.22 |
| 322 | 29.9 |
| 323 | 0.345 |
| 324 | 12.5 |
| 325 | 3.12 |
| 326 | 6.2 |
| 327 | 5.28 |
| 328 | ND |
| 329 | 0.41 |
| 330 | 1.06 |
| 331 | 2.58 |
| 332 | 2.02 |
| 333 | 1.7 |
| 334 | 2.04 |
| 335 | 0.401 |
| 336 | 0.431 |
| 337 | 0.0985 |
| 338 | 2.85 |
| 339 | 6.87 |
| 340 | 0.807 |
| 341 | 3.03 |
| 342 | 0.947 |
| 343 | 4.82 |
| 344 | 3.04 |
| 345 | 0.624 |
| 346 | 4.66 |
| 347 | 29.1 |
| 348 | 7.27 |
| 349 | 8.78 |
| 350 | 2.74 |
| 351 | 0.393 |
| 352 | 1.28 |
| 353 | >50 |
| 354 | 5.96 |
| 355 | 4.87 |
| 356 | 2.65 |
| 357 | 12.0 |
| 358 | 0.889 |
| 359 | 4.28 |
| 360 | 0.747 |
| 361 | 2.15 |
| 362 | 0.636 |
| 363 | 4.3 |
| 364 | 3.28 |
| 365 | 1.88 |
| 366 | 2.87 |
| 367 | 0.591 |
| 368 | 7.61 |
| 369 | >50 |
| 370 | 1.69 |
| 371 | 21.5 |
| 372 | 0.97 |
| 373 | 0.0844 |
| 374 | 0.261 |
| 375 | 12.4 |
| 376 | 2.95 |
| 377 | 2.71 |
| 378 | 6.26 |
| 379 | 0.765 |

ND = Not Determined

It is understood that the foregoing detailed description and accompanying examples are merely illustrative and are not to be taken as limitations upon the scope of the invention, which is defined solely by the appended claims and their equivalents. Various changes and modifications to the embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

We claim:

1. A compound having formula (I) or a pharmaceutically acceptable salt thereof

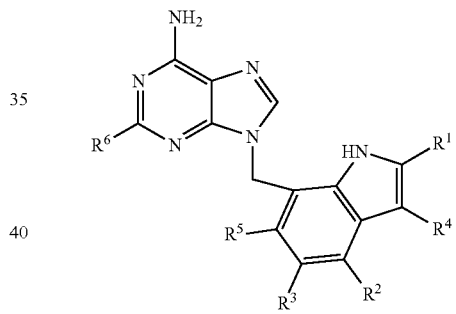

wherein

R$^1$ is hydrogen, —C(O)(C$_1$-C$_6$ alkyl), —(C$_1$-C$_6$ alkylenyl)-OH, —C(H)(benzyl)-NH$_2$, —C(H)(phenyl)-NH$_2$, —(C$_1$-C$_6$ alkylenyl)-NR$^{1A}$R$^{1B}$, or —(C$_1$-C$_6$ alkylenyl)-N(R$^j$)C(O)R$^{1C}$;

R$^{1A}$ and R$^{1B}$ are each independently hydrogen, C$_1$-C$_6$ haloalkyl, C$_1$-C$_6$ alkyl, C$_2$-C$_4$ alkenyl, —(CH$_2$)$_m$-G$^{1A}$, —(C$_1$-C$_6$ alkylenyl)-L$^{1A}$-X, or —(CH$_2$)$_n$-G$^{1A}$-L$^{1B}$-G; or R$^{1A}$ and R$^{1B}$ together with the nitrogen atom to which they are attached, form a C$_5$-C$_6$ heterocycloalkyl which is optionally substituted with 1, 2, or 3 substituents independently selected from the group consisting of C$_1$-C$_6$ haloalkyl, C$_1$-C$_6$ alkyl, and oxo;

R$^{1C}$ is C$_1$-C$_6$ haloalkyl, C$_1$-C$_6$ alkyl, C$_2$-C$_4$ alkenyl, —(CH$_2$)$_m$-G$^{1A}$, —(C$_1$-C$_6$ alkylenyl)-L$^{1A}$-X, or —(CH$_2$)$_n$-G$^{1A}$-L$^{1B}$-G;

G$^{1A}$ and G, at each occurrence, are each independently phenyl, cycloalkyl, cycloalkenyl, heteroaryl, or heterocycle; wherein each G$^{1A}$ and G are optionally substituted with 1, 2, or 3 independently selected R$^u$;

L$^{1A}$, at each occurrence, is independently O, N(H), or C(O)O;

X, at each occurrence, is independently H, $C_1$-$C_6$ alkyl, or $C_1$-$C_6$ haloalkyl;

$L^{1B}$, at each occurrence, is independently a bond, —$C_1$-$C_3$ alkylenyl, O, —O—$C_1$-$C_3$ alkylenyl-, C(O), or —N(H)C(O)—;

m is 0, 1, or 2;

n is 0, 1, or 2;

$R^2$ is hydrogen, halogen, $C_1$-$C_6$ alkyl, $C_2$-$C_4$ alkenyl, or $G^{2A}$; wherein $G^{2A}$ is $C_3$-$C_6$ cycloalkyl, $C_5$-$C_6$ cycloalkenyl, phenyl, or $C_5$-$C_6$ heteroaryl; and each $G^{2A}$ is optionally substituted with 1, 2, or 3 independently selected $R^u$ groups;

$R^3$ is hydrogen, halogen, $C_1$-$C_6$ alkyl, $C_2$-$C_4$ alkenyl, $G^{3A}$, -$G^{3A}$-$G^A$, or -$G^{3A}$-$L^3$-Y;

$G^{3A}$, at each occurrence, is independently $C_5$-$C_6$ cycloalkenyl, $C_3$-$C_6$ cycloalkyl, phenyl, $C_5$-$C_6$ heteroaryl, heterocycle; wherein each $G^{3A}$ is optionally substituted with 1, 2, or 3 independently selected $R^u$ groups;

$G^A$ is $C_3$-$C_6$ cycloalkyl or $C_5$-$C_6$ heterocycloalkyl; each of which is optionally substituted with 1, 2, or 3 independently selected $R^u$ groups;

$L^3$ is $C_1$-$C_3$ alkylenyl, C(O), or —C(O)N(H)—;

Y is —($C_1$-$C_6$ alkylenyl)-N($R^j$)$_2$, $C_3$-$C_6$ cycloalkyl, or $C_5$-$C_6$ heterocycloalkyl, wherein the $C_3$-$C_6$ cycloalkyl and the $C_5$-$C_6$ heterocycloalkyl are each optionally substituted with 1, 2, or 3 substituents independently selected from the group consisting of $C_1$-$C_3$ alkyl, halogen, and $C_1$-$C_3$ haloalkyl;

$R^4$ is hydrogen, halogen, or —($C_1$-$C_6$ alkylenyl)-C(O)N$R^{4A}R^{4B}$; wherein $R^{4A}$ and $R^{4B}$ are each independently hydrogen or $C_1$-$C_6$ alkyl;

$R^5$ is hydrogen, halogen, $C_2$-$C_4$ alkenyl, $C_1$-$C_6$ alkyl, or phenyl wherein the phenyl is optionally substituted with 1, 2, or 3 independently selected $R^u$ groups;

$R^6$ is hydrogen, halogen, $C_1$-$C_3$ alkyl, or cyclopropyl; wherein the cyclopropyl is optionally substituted with 1, 2, or 3 substituents independently selected from the group consisting of halogen, $C_1$-$C_3$ alkyl, and $C_1$-$C_3$ haloalkyl;

$R^u$, at each occurrence, is independently $C_1$-$C_6$ alkyl, $C_2$-$C_6$ alkenyl, $C_2$-$C_6$ alkynyl, halogen, $C_1$-$C_6$ haloalkyl, —CN, oxo, NO$_2$, —O$R^j$, —OC(O)$R^k$, —OC(O)N($R^j$)$_2$, —S$R^j$, —S(O)$_2R^j$, —S(O)$_2$N($R^j$)$_2$, —C(O)$R^j$, —C(O)O$R^j$, —C(O)N($R^j$)$_2$, —N($R^j$)$_2$, —N($R^j$)C(O)$R^k$, —N($R^j$)S(O)$_2R^k$, —N($R^j$)C(O)O($R^k$), —N($R^j$)C(O)N($R^j$)$_2$, —($C_1$-$C_6$ alkylenyl)-O$R^j$, —($C_1$-$C_6$ alkylenyl)-OC(O)$R^k$, —($C_1$-$C_6$ alkylenyl)-OC(O)N(W)$_2$, —($C_1$-$C_6$ alkylenyl)-S$R^j$, —($C_1$-$C_6$ alkylenyl)-S(O)$_2R^j$, —($C_1$-$C_6$ alkylenyl)-S(O)$_2$N($R^j$)$_2$, —($C_1$-$C_6$ alkylenyl)-C(O)$R^j$, —($C_1$-$C_6$ alkylenyl)-C(O)O$R^j$, —($C_1$-$C_6$ alkylenyl)-C(O)N($R^j$)$_2$, —($C_1$-$C_6$ alkylenyl)-N($R^j$)$_2$, —($C_1$-$C_6$ alkylenyl)-N($R^j$)C(O)$R^k$, —($C_1$-$C_6$ alkylenyl)-N($R^j$)S(O)$_2R^k$, —($C_1$-$C_6$ alkylenyl)-N($R^j$)C(O)O($R^k$), —($C_1$-$C_6$ alkylenyl)-N($R^j$)C(O)N($R^j$)$_2$, or —($C_1$-$C_6$ alkylenyl)-CN;

$R^j$, at each occurrence, is independently hydrogen, $C_1$-$C_6$ alkyl, or $C_1$-$C_6$ haloalkyl; and $R^k$, at each occurrence, is independently $C_1$-$C_6$ alkyl or $C_1$-$C_6$ haloalkyl.

2. The compound of claim 1 or a pharmaceutically acceptable salt thereof, wherein $R^1$ is hydrogen, —C(H)(benzyl)-NH$_2$, —C(H)(phenyl)-NH$_2$, —($C_1$-$C_6$ alkylenyl)-N$R^{1A}R^{1B}$, or —($C_1$-$C_6$ alkylenyl)-N($R^j$)C(O)$R^{1C}$.

3. The compound of claim 1 or a pharmaceutically acceptable salt thereof, wherein $R^1$ is —($C_1$-$C_6$ alkylenyl)-N$R^{1A}R^{1B}$ or —($C_1$-$C_6$ alkylenyl)-N($R^j$)C(O)$R^{1C}$.

4. The compound of claim 1 or a pharmaceutically acceptable salt thereof, wherein $R^3$ is hydrogen, halogen, $C_2$-$C_4$ alkenyl, $G^{3A}$, -$G^{3A}$-$G^A$, or -$G^{3A}$-$L^3$-Y.

5. The compound of claim 1 or a pharmaceutically acceptable salt thereof, wherein $R^3$ is halogen.

6. The compound of claim 1 or a pharmaceutically acceptable salt thereof, wherein $R^3$ is halogen; and $R^2$, $R^4$, $R^5$, and $R^6$ are hydrogen.

7. The compound of claim 1 or a pharmaceutically acceptable salt thereof, wherein $R^3$ is halogen;

$R^2$, $R^4$, $R^5$, and $R^6$ are hydrogen; and $R^1$ is —C(O)($C_1$-$C_6$ alkyl), —($C_1$-$C_6$ alkylenyl)-OH, —C(H)(benzyl)-NH$_2$, —C(H)(phenyl)-NH$_2$, —($C_1$-$C_6$ alkylenyl)-N$R^{1A}R^{1B}$, or —($C_1$-$C_6$ alkylenyl)-N($R^j$)C(O)$R^{1C}$.

8. The compound of claim 1 or a pharmaceutically acceptable salt thereof, wherein $R^3$ is $G^{3A}$.

9. The compound of claim 1 or a pharmaceutically acceptable salt thereof, wherein $R^3$ is $G^{3A}$; and $R^2$, $R^4$, $R^5$, and $R^6$ are hydrogen.

10. The compound of claim 1 or a pharmaceutically acceptable salt thereof, wherein $R^3$ is $G^{3A}$;

$R^2$, $R^4$, $R^5$, and $R^6$ are hydrogen; and $R^1$ is —($C_1$-$C_6$ alkylenyl)-N$R^{1A}R^{1B}$ or —($C_1$-$C_6$ alkylenyl)-N($R^j$)C(O)$R^{1C}$.

11. The compound of claim 1 or a pharmaceutically acceptable salt thereof, wherein $R^3$ is $G^{3A}$; wherein $G^{3A}$ is cyclohexenyl optionally substituted with 1, 2, or 3 independently selected $R^u$ groups;

$R^2$, $R^4$, $R^5$, and $R^6$ are hydrogen; and $R^1$ is —(CH$_2$)—N($R^j$)C(O)$R^{1C}$ wherein $R^{1C}$ is —(CH$_2$)$_m$-$G^{1A}$ wherein m is 0 or 1.

12. The compound of claim 1 or a pharmaceutically acceptable salt thereof, wherein $R^3$ is -$G^{3A}$-$G^A$.

13. The compound of claim 1 or a pharmaceutically acceptable salt thereof, wherein $R^3$ is -$G^{3A}$-$G^A$; and $R^2$, $R^4$, $R^5$, and $R^6$ are hydrogen.

14. The compound of claim 1 or a pharmaceutically acceptable salt thereof, wherein $R^3$ is -$G^{3A}$-$G^A$;

$R^2$, $R^4$, $R^5$, and $R^6$ are hydrogen; and $R^1$ is —($C_1$-$C_6$ alkylenyl)-N$R^{1A}R^{1B}$ or —($C_1$-$C_6$ alkylenyl)-N($R^j$)C(O)$R^{1C}$.

15. The compound of claim 14 or a pharmaceutically acceptable salt thereof, wherein $G^{3A}$ is phenyl optionally substituted with 1, 2, or 3 independently selected $R^u$ groups; and $G^A$ is $C_5$-$C_6$ heterocycloalkyl optionally substituted with 1, 2, or 3 independently selected $R^u$ groups.

16. The compound of claim 1 or a pharmaceutically acceptable salt thereof, wherein $R^3$ is -$G^{3A}$-$L^3$-Y.

17. The compound of claim 1 or a pharmaceutically acceptable salt thereof, wherein $R^3$ is -$G^{3A}$-$L^3$-Y; and $R^2$, $R^4$, $R^5$, and $R^6$ are hydrogen.

18. The compound of claim 1 or a pharmaceutically acceptable salt thereof, wherein
R$^3$ is -G$^{3,A}$-L$^3$-Y;
R$^2$, R$^4$, R$^5$, and R$^6$ are hydrogen; and
R$^1$ is —(C$_1$-C$_6$ alkylenyl)-NR$^{1A}$R$^{1B}$ or —(C$_1$-C$_6$ alkylenyl)-N(R$^J$)C(O)R$^{1C}$.

19. The compound of claim 18 or a pharmaceutically acceptable salt thereof, wherein
G$^{3,A}$ is phenyl optionally substituted with 1, 2, or 3 independently selected R$^u$ groups; and
L$^3$ is —CH$_2$—, C(O), or —C(O)N(H)—.

20. The compound of claim 1 or a pharmaceutically acceptable salt thereof, wherein
R$^2$ is hydrogen, halogen, C$_1$-C$_6$ alkyl, C$_2$-C$_4$ alkenyl, or G$^{2,A}$; wherein G$^{2,A}$ is C$_5$-C$_6$ cycloalkenyl, phenyl, or C$_5$-C$_6$ heteroaryl; and each G$^{2,A}$ is optionally substituted with 1, 2, or 3 independently selected R$^u$ groups.

21. The compound of claim 1 or a pharmaceutically acceptable salt thereof, wherein
R$^2$ is hydrogen, halogen, C$_1$-C$_6$ alkyl, C$_2$-C$_4$ alkenyl, or G$^{2,A}$; wherein G$^{2,A}$ is C$_5$-C$_6$ cycloalkenyl, phenyl, or C$_5$-C$_6$ heteroaryl; and each G$^{2,A}$ is optionally substituted 1, 2, or 3 independently selected R$^u$ groups; and
R$^3$, R$^4$, R$^5$, and R$^6$ are hydrogen.

22. The compound of claim 1 or a pharmaceutically acceptable salt thereof, wherein
R$^3$, R$^4$, R$^5$, and R$^6$ are hydrogen;
R$^2$ is hydrogen, halogen, C$_1$-C$_6$ alkyl, C$_2$-C$_4$ alkenyl, or G$^{2,A}$; wherein G$^{2,A}$ is C$_5$-C$_6$ cycloalkenyl, phenyl, or C$_5$-C$_6$ heteroaryl; and each G$^{2,A}$ is optionally substituted 1, 2, or 3 independently selected R$^u$ groups; and
R$^1$ is —(C$_1$-C$_6$ alkylenyl)-NR$^{1A}$R$^{1B}$ or —(C$_1$-C$_6$ alkylenyl)-N(R$^J$)C(O)R$^{1C}$.

23. The compound of claim 1 or a pharmaceutically acceptable salt thereof, wherein
R$^2$, R$^3$, R$^4$, and R$^6$ are hydrogen; and
R$^5$ is hydrogen, halogen, C$_2$-C$_4$ alkenyl, or phenyl wherein the phenyl is optionally substituted with 1, 2, or 3 independently selected R$^u$ groups.

24. The compound of claim 1 or a pharmaceutically acceptable salt thereof, wherein
R$^2$, R$^3$, R$^4$, and R$^6$ are hydrogen;
R$^5$ is hydrogen, halogen, C$_2$-C$_4$ alkenyl, or phenyl wherein the phenyl is optionally substituted with 1, 2, or 3 independently selected R$^u$ groups; and
R$^1$ is —(C$_1$-C$_6$ alkylenyl)-NR$^{1A}$R$^{1B}$.

25. The compound of claim 1 or a pharmaceutically acceptable salt thereof, wherein the compound is selected from the group consisting of
9-[(3-bromo-1H-indol-7-yl)methyl]-9H-purin-6-amine;
9-(1H-indol-7-ylmethyl)-2-methyl-9H-purin-6-amine;
9-(1H-indol-7-ylmethyl)-9H-purin-6-amine;
2-cyclopropyl-9-(1H-indol-7-ylmethyl)-9H-purin-6-amine;
{7-[(6-amino-9H-purin-9-yl)methyl]-5-chloro-1H-indol-2-yl}methanol;
9-{[2-(aminomethyl)-1H-indol-7-yl]methyl}-9H-purin-6-amine;
9-{[2-(aminomethyl)-5-chloro-1H-indol-7-yl]methyl}-9H-purin-6-amine;
9-{[2-(aminomethyl)-5-ethenyl-1H-indol-7-yl]methyl}-9H-purin-6-amine;
9-{[2-(aminomethyl)-5-(cyclopent-1-en-1-yl)-1H-indol-7-yl]methyl}-9H-purin-6-amine;
9-{[2-(aminomethyl)-5-(3,6-dihydro-2H-pyran-4-yl)-1H-indol-7-yl]methyl}-9H-purin-6-amine;
9-{[2-(aminomethyl)-5-(1,2,3,6-tetrahydropyridin-4-yl)-1H-indol-7-yl]methyl}-9H-purin-6-amine;
9-{[2-(aminomethyl)-5-(4,4-difluorocyclohex-1-en-1-yl)-1H-indol-7-yl]methyl}-9H-purin-6-amine;
1-[4-{2-(aminomethyl)-7-[(6-amino-9H-purin-9-yl)methyl]-1H-indol-5-yl}-3,6-dihydropyridin-1(2H)-yl]ethanone;
1-[5-{2-(aminomethyl)-7-[(6-amino-9H-purin-9-yl)methyl]-1H-indol-5-yl}-3,6-dihydropyridin-1(2H)-yl]ethanone;
1-(4-{2-(aminomethyl)-7-[(6-amino-9H-purin-9-yl)methyl]-1H-indol-5-yl}piperidin-1-yl)ethanone;
9-{[2-(aminomethyl)-5-(1-methyl-1H-pyrazol-4-yl)-1H-indol-7-yl]methyl}-9H-purin-6-amine;
9-{[2-(aminomethyl)-5-(pyrimidin-5-yl)-1H-indol-7-yl]methyl}-9H-purin-6-amine;
9-{[2-(aminomethyl)-5-(pyridin-3-yl)-1H-indol-7-yl]methyl}-9H-purin-6-amine;
9-{[2-(aminomethyl)-5-(pyridin-4-yl)-1H-indol-7-yl]methyl}-9H-purin-6-amine;
9-{[2-(aminomethyl)-5-phenyl-1H-indol-7-yl]methyl}-9H-purin-6-amine;
9-{[2-(aminomethyl)-5-(4-chlorophenyl)-1H-indol-7-yl]methyl}-9H-purin-6-amine;
9-{[2-(aminomethyl)-5-(3-chlorophenyl)-1H-indol-7-yl]methyl}-9H-purin-6-amine;
9-{[2-(aminomethyl)-5-(2-chlorophenyl)-1H-indol-7-yl]methyl}-9H-purin-6-amine;
9-{[2-(aminomethyl)-5-(4-fluorophenyl)-1H-indol-7-yl]methyl}-9H-purin-6-amine;
9-{[2-(aminomethyl)-5-(2-fluorophenyl)-1H-indol-7-yl]methyl}-9H-purin-6-amine;
9-{[2-(aminomethyl)-5-(6-methoxypyridin-3-yl)-1H-indol-7-yl]methyl}-9H-purin-6-amine;
4-{2-(aminomethyl)-7-[(6-amino-9H-purin-9-yl)methyl]-1H-indol-5-yl}benzenesulfonamide;
9-{[2-(aminomethyl)-5-(4-methylphenyl)-1H-indol-7-yl]methyl}-9H-purin-6-amine;
9-{[2-(aminomethyl)-5-(3-methylphenyl)-1H-indol-7-yl]methyl}-9H-purin-6-amine;
9-{[2-(aminomethyl)-5-(2-methylphenyl)-1H-indol-7-yl]methyl}-9H-purin-6-amine;
(4-{2-(aminomethyl)-7-[(6-amino-9H-purin-9-yl)methyl]-1H-indol-5-yl}phenyl)methanol;
9-{[2-(aminomethyl)-5-(4-methoxyphenyl)-1H-indol-7-yl]methyl}-9H-purin-6-amine;
9-{[2-(aminomethyl)-5-(3-methoxyphenyl)-1H-indol-7-yl]methyl}-9H-purin-6-amine;
9-{[2-(aminomethyl)-5-(2-methoxyphenyl)-1H-indol-7-yl]methyl}-9H-purin-6-amine;
9-({2-(aminomethyl)-5-[4-(methylsulfonyl)phenyl]-1H-indol-7-yl}methyl)-9H-purin-6-amine;
4-{2-(aminomethyl)-7-[(6-amino-9H-purin-9-yl)methyl]-1H-indol-5-yl}benzonitrile;
3-{2-(aminomethyl)-7-[(6-amino-9H-purin-9-yl)methyl]-1H-indol-5-yl}benzonitrile;
3-{2-(aminomethyl)-7-[(6-amino-9H-purin-9-yl)methyl]-1H-indol-5-yl}benzamide;
N-(4-{2-(aminomethyl)-7-[(6-amino-9H-purin-9-yl)methyl]-1H-indol-5-yl}phenyl)methanesulfonamide;
N-(3-{2-(aminomethyl)-7-[(6-amino-9H-purin-9-yl)methyl]-1H-indol-5-yl}phenyl)methanesulfonamide;
9-{[2-(aminomethyl)-5-(4-ethylphenyl)-1H-indol-7-yl]methyl}-9H-purin-6-amine;
methyl 4-{2-(aminomethyl)-7-[(6-amino-9H-purin-9-yl)methyl]-1H-indol-5-yl}benzoate;

(4-{2-(aminomethyl)-7-[(6-amino-9H-purin-9-yl)methyl]-1H-indol-5-yl}phenyl)acetonitrile;
3-{2-(aminomethyl)-7-[(6-amino-9H-purin-9-yl)methyl]-1H-indol-5-yl}-N-ethylbenzamide;
4-{2-(aminomethyl)-7-[(6-amino-9H-purin-9-yl)methyl]-1H-indol-5-yl}-N,N-dimethylbenzamide;
3-{2-(aminomethyl)-7-[(6-amino-9H-purin-9-yl)methyl]-1H-indol-5-yl}-N,N-dimethylbenzamide;
4-{2-(aminomethyl)-7-[(6-amino-9H-purin-9-yl)methyl]-1H-indol-5-yl}-N-[2-(dimethylamino)ethyl]benzamide;
4-{2-(aminomethyl)-7-[(6-amino-9H-purin-9-yl)methyl]-1H-indol-5-yl}-N-cyclopropylbenzamide;
3-{2-(aminomethyl)-7-[(6-amino-9H-purin-9-yl)methyl]-1H-indol-5-yl}-N-cyclopropylbenzamide;
9-({2-(aminomethyl)-5-[3-(morpholin-4-yl)phenyl]-1H-indol-7-yl}methyl)-9H-purin-6-amine;
(3-{2-(aminomethyl)-7-[(6-amino-9H-purin-9-yl)methyl]-1H-indol-5-yl}phenyl)(morpholin-4-yl)methanone;
9-{[2-(aminomethyl)-5-{4-[(4-methylpiperazin-1-yl)methyl]phenyl}-1H-indol-7-yl]methyl}-9H-purin-6-amine;
9-{[2-(aminomethyl)-5-{3-[(4-methylpiperazin-1-yl)methyl]phenyl}-1H-indol-7-yl]methyl}-9H-purin-6-amine;
(4-{2-(aminomethyl)-7-[(6-amino-9H-purin-9-yl)methyl]-1H-indol-5-yl}phenyl)(4-methylpiperazin-1-yl)methanone;
9-{[2-(aminomethyl)-5-(2,3-dihydro-1-benzofuran-5-yl)-1H-indol-7-yl]methyl}-9H-purin-6-amine;
9-{[2-(aminomethyl)-6-chloro-1H-indol-7-yl]methyl}-9H-purin-6-amine;
9-{[2-(aminomethyl)-6-ethenyl-1H-indol-7-yl]methyl}-9H-purin-6-amine;
9-{[2-(aminomethyl)-6-(prop-1-en-2-yl)-1H-indol-7-yl]methyl}-9H-purin-6-amine;
9-{[2-(aminomethyl)-6-phenyl-1H-indol-7-yl]methyl}-9H-purin-6-amine;
9-{[2-(aminomethyl)-4-chloro-1H-indol-7-yl]methyl}-9H-purin-6-amine;
9-{[2-(aminomethyl)-4-ethenyl-1H-indol-7-yl]methyl}-9H-purin-6-amine;
9-{[2-(aminomethyl)-4-ethyl-1H-indol-7-yl]methyl}-9H-purin-6-amine;
9-{[2-(aminomethyl)-4-(prop-1-en-2-yl)-1H-indol-7-yl]methyl}-9H-purin-6-amine;
9-{[2-(aminomethyl)-4-(propan-2-yl)-1H-indol-7-yl]methyl}-9H-purin-6-amine;
9-{[2-(aminomethyl)-4-(cyclopent-1-en-1-yl)-1H-indol-7-yl]methyl}-9H-purin-6-amine;
9-{[2-(aminomethyl)-4-(1-methyl-1H-pyrazol-4-yl)-1H-indol-7-yl]methyl}-9H-purin-6-amine;
9-{[2-(aminomethyl)-4-(pyridin-3-yl)-1H-indol-7-yl]methyl}-9H-purin-6-amine;
9-{[2-(aminomethyl)-4-phenyl-1H-indol-7-yl]methyl}-9H-purin-6-amine;
9-{[2-(aminomethyl)-4-(3-chlorophenyl)-1H-indol-7-yl]methyl}-9H-purin-6-amine;
9-{[2-(aminomethyl)-4-(2-chlorophenyl)-1H-indol-7-yl]methyl}-9H-purin-6-amine;
9-{[2-(aminomethyl)-4-(4-fluorophenyl)-1H-indol-7-yl]methyl}-9H-purin-6-amine;
9-{[2-(aminomethyl)-4-(2-fluorophenyl)-1H-indol-7-yl]methyl}-9H-purin-6-amine;
9-{[2-(aminomethyl)-4-(4-methylphenyl)-1H-indol-7-yl]methyl}-9H-purin-6-amine;
9-{[2-(aminomethyl)-4-(3-methylphenyl)-1H-indol-7-yl]methyl}-9H-purin-6-amine;
9-{[2-(aminomethyl)-4-(2-methylphenyl)-1H-indol-7-yl]methyl}-9H-purin-6-amine;
9-{[2-(aminomethyl)-4-(4-methoxyphenyl)-1H-indol-7-yl]methyl}-9H-purin-6-amine;
9-{[2-(aminomethyl)-4-(3-methoxyphenyl)-1H-indol-7-yl]methyl}-9H-purin-6-amine;
9-{[2-(aminomethyl)-4-(2-methoxyphenyl)-1H-indol-7-yl]methyl}-9H-purin-6-amine;
9-({2-(aminomethyl)-4-[4-(methylsulfonyl)phenyl]-1H-indol-7-yl}methyl)-9H-purin-6-amine;
4-{2-(aminomethyl)-7-[(6-amino-9H-purin-9-yl)methyl]-1H-indol-4-yl}benzonitrile;
3-{2-(aminomethyl)-7-[(6-amino-9H-purin-9-yl)methyl]-1H-indol-4-yl}benzonitrile;
3-{2-(aminomethyl)-7-[(6-amino-9H-purin-9-yl)methyl]-1H-indol-4-yl}benzamide;
N-(4-{2-(aminomethyl)-7-[(6-amino-9H-purin-9-yl)methyl]-1H-indol-4-yl}phenyl)methanesulfonamide;
4-{2-(aminomethyl)-7-[(6-amino-9H-purin-9-yl)methyl]-1H-indol-4-yl}-N,N-dimethylbenzamide;
1-{7-[(6-amino-9H-purin-9-yl)methyl]-5-chloro-1H-indol-2-yl}ethanone;
9-{[2-(1-aminoethyl)-5-chloro-1H-indol-7-yl]methyl}-9H-purin-6-amine;
9-({5-chloro-2-[(methylamino)methyl]-1H-indol-7-yl}methyl)-9H-purin-6-amine;
1-{7-[(6-amino-9H-purin-9-yl)methyl]-5-chloro-1H-indol-2-yl}propan-1-one;
9-{[2-(1-aminopropyl)-5-chloro-1H-indol-7-yl]methyl}-9H-purin-6-amine;
N-({7-[(6-amino-9H-purin-9-yl)methyl]-5-chloro-1H-indol-2-yl}methyl)acetamide;
N-({7-[(6-amino-9H-purin-9-yl)methyl]-5-chloro-1H-indol-2-yl}methyl)prop-2-enamide;
N-({7-[(6-amino-9H-purin-9-yl)methyl]-5-chloro-1H-indol-2-yl}methyl)propanamide;
N-({7-[(6-amino-9H-purin-9-yl)methyl]-5-chloro-1H-indol-2-yl}methyl)-2-methoxyacetamide;
3-[({7-[(6-amino-9H-purin-9-yl)methyl]-5-chloro-1H-indol-2-yl}methyl)amino]propanoic acid;
9-({5-chloro-2-[(diethyl amino)methyl]-1H-indol-7-yl}methyl)-9H-purin-6-amine;
N-({7-[(6-amino-9H-purin-9-yl)methyl]-5-chloro-1H-indol-2-yl}methyl)butanamide;
N-({7-[(6-amino-9H-purin-9-yl)methyl]-5-chloro-1H-indol-2-yl}methyl)-2-methylpropanamide;
N-({7-[(6-amino-9H-purin-9-yl)methyl]-5-chloro-1H-indol-2-yl}methyl)-3-methoxypropanamide;
2,2'-[({7-[(6-amino-9H-purin-9-yl)methyl]-5-chloro-1H-indol-2-yl}methyl)imino]diacetic acid;
N-({7-[(6-amino-9H-purin-9-yl)methyl]-5-chloro-1H-indol-2-yl}methyl)-3-methylbutanamide;
N-({7-[(6-amino-9H-purin-9-yl)methyl]-5-chloro-1H-indol-2-yl}methyl)-3-hydroxy-3-methylbutanamide;
N-({7-[(6-amino-9H-purin-9-yl)methyl]-5-chloro-1H-indol-2-yl}methyl)-3,3-dimethylbutanamide;
N-({7-[(6-amino-9H-purin-9-yl)methyl]-5-chloro-1H-indol-2-yl}methyl)-4-methylpentanamide;
tert-butyl[({7-[(6-amino-9H-purin-9-yl)methyl]-5-chloro-1H-indol-2-yl}methyl)amino]acetate;
N-({7-[(6-amino-9H-purin-9-yl)methyl]-5-chloro-1H-indol-2-yl}methyl)cyclopropanecarboxamide;
N-({7-[(6-amino-9H-purin-9-yl)methyl]-5-chloro-1H-indol-2-yl}methyl)-1-methylcyclopropanecarboxamide;

N-({7-[(6-amino-9H-purin-9-yl)methyl]-5-chloro-1H-indol-2-yl}methyl)-2-methylcyclopropanecarboxamide;
N-({7-[(6-amino-9H-purin-9-yl)methyl]-5-chloro-1H-indol-2-yl}methyl)-2-cyclopropylacetamide;
N-({7-[(6-amino-9H-purin-9-yl)methyl]-5-chloro-1H-indol-2-yl}methyl)cyclobutanecarboxamide;
N-({7-[(6-amino-9H-purin-9-yl)methyl]-5-chloro-1H-indol-2-yl}methyl)-1-hydroxycyclobutanecarboxamide;
N-({7-[(6-amino-9H-purin-9-yl)methyl]-5-chloro-1H-indol-2-yl}methyl)tetrahydrofuran-2-carboxamide;
N-({7-[(6-amino-9H-purin-9-yl)methyl]-5-chloro-1H-indol-2-yl}methyl)tetrahydrofuran-3-carboxamide;
(2S)—N-({7-[(6-amino-9H-purin-9-yl)methyl]-5-chloro-1H-indol-2-yl}methyl)pyrrolidine-2-carboxamide;
(2R)—N-({7-[(6-amino-9H-purin-9-yl)methyl]-5-chloro-1H-indol-2-yl}methyl)pyrrolidine-2-carboxamide;
(2S)—N-({7-[(6-amino-9H-purin-9-yl)methyl]-5-chloro-1H-indol-2-yl}methyl)-5-oxopyrrolidine-2-carboxamide;
(2R)—N-({7-[(6-amino-9H-purin-9-yl)methyl]-5-chloro-1H-indol-2-yl}methyl)-5-oxopyrrolidine-2-carboxamide;
N-({7-[(6-amino-9H-purin-9-yl)methyl]-5-chloro-1H-indol-2-yl}methyl)cyclopentanecarboxamide;
N-({7-[(6-amino-9H-purin-9-yl)methyl]-5-chloro-1H-indol-2-yl}methyl)-2-(pyrrolidin-1-yl)acetamide;
N-({7-[(6-amino-9H-purin-9-yl)methyl]-5-chloro-1H-indol-2-yl}methyl)-2-cyclopentylacetamide;
N-({7-[(6-amino-9H-purin-9-yl)methyl]-5-chloro-1H-indol-2-yl}methyl)-3-(pyrrolidin-1-yl)propanamide;
tert-butyl (2S)-2-[({7-[(6-amino-9H-purin-9-yl)methyl]-5-chloro-1H-indol-2-yl}methyl)carbamoyl]pyrrolidine-1-carboxylate;
tert-butyl (2R)-2-[({7-[(6-amino-9H-purin-9-yl)methyl]-5-chloro-1H-indol-2-yl}methyl)carbamoyl]pyrrolidine-1-carboxylate;
9-({5-chloro-2-[(1,1-dioxidothiomorpholin-4-yl)methyl]-1H-indol-7-yl}methyl)-9H-purin-6-amine;
N-({7-[(6-amino-9H-purin-9-yl)methyl]-5-chloro-1H-indol-2-yl}methyl)tetrahydro-2H-pyran-4-carboxamide;
N-({7-[(6-amino-9H-purin-9-yl)methyl]-5-chloro-1H-indol-2-yl}methyl)-2-(morpholin-4-yl)acetamide;
N-({7-[(6-amino-9H-purin-9-yl)methyl]-5-chloro-1H-indol-2-yl}methyl)cyclohexanecarboxamide;
N-({7-[(6-amino-9H-purin-9-yl)methyl]-5-chloro-1H-indol-2-yl}methyl)-1-methylcyclohexanecarboxamide;
N-({7-[(6-amino-9H-purin-9-yl)methyl]-5-chloro-1H-indol-2-yl}methyl)-4-methylcyclohexanecarboxamide;
N-({7-[(6-amino-9H-purin-9-yl)methyl]-5-chloro-1H-indol-2-yl}methyl)-3-methylcyclohexanecarboxamide;
N-({7-[(6-amino-9H-purin-9-yl)methyl]-5-chloro-1H-indol-2-yl}methyl)-2-methylcyclohexanecarboxamide;
N-({7-[(6-amino-9H-purin-9-yl)methyl]-5-chloro-1H-indol-2-yl}methyl)-2-cyclohexylacetamide;
N-({7-[(6-amino-9H-purin-9-yl)methyl]-5-chloro-1H-indol-2-yl}methyl)-4-methoxycyclohexanecarboxamide;
N-({7-[(6-amino-9H-purin-9-yl)methyl]-5-chloro-1H-indol-2-yl}methyl)-3-(piperidin-1-yl)propanamide;
N-({7-[(6-amino-9H-purin-9-yl)methyl]-5-chloro-1H-indol-2-yl}methyl)tricyclo[3.3.1.1$^{3,7}$]decane-1-carboxamide;
N-({7-[(6-amino-9H-purin-9-yl)methyl]-5-chloro-1H-indol-2-yl}methyl)-1,2-thiazole-5-carboxamide;
N-({7-[(6-amino-9H-purin-9-yl)methyl]-5-chloro-1H-indol-2-yl}methyl)-1,3-thiazole-5-carboxamide;
N-({7-[(6-amino-9H-purin-9-yl)methyl]-5-chloro-1H-indol-2-yl}methyl)-1,2-thiazole-4-carboxamide;
N-({7-[(6-amino-9H-purin-9-yl)methyl]-5-chloro-1H-indol-2-yl}methyl)-1,3-thiazole-4-carboxamide;
N-({7-[(6-amino-9H-purin-9-yl)methyl]-5-chloro-1H-indol-2-yl}methyl)-1,2-oxazole-4-carboxamide;
N-({7-[(6-amino-9H-purin-9-yl)methyl]-5-chloro-1H-indol-2-yl}methyl)-1H-pyrazole-5-carboxamide;
N-({7-[(6-amino-9H-purin-9-yl)methyl]-5-chloro-1H-indol-2-yl}methyl)-1H-pyrazole-4-carboxamide;
N-({7-[(6-amino-9H-purin-9-yl)methyl]-5-chloro-1H-indol-2-yl}methyl)thiophene-2-carboxamide;
N-({7-[(6-amino-9H-purin-9-yl)methyl]-5-chloro-1H-indol-2-yl}methyl)thiophene-3-carboxamide;
N-({7-[(6-amino-9H-purin-9-yl)methyl]-5-chloro-1H-indol-2-yl}methyl)-1H-pyrrole-2-carboxamide;
N-({7-[(6-amino-9H-purin-9-yl)methyl]-5-chloro-1H-indol-2-yl}methyl)-5-methyl-1,3-thiazole-4-carboxamide;
N-({7-[(6-amino-9H-purin-9-yl)methyl]-5-chloro-1H-indol-2-yl}methyl)-4-methyl-1,3-thiazole-5-carboxamide;
N-({7-[(6-amino-9H-purin-9-yl)methyl]-5-chloro-1H-indol-2-yl}methyl)-5-methyl-1,2-oxazole-4-carboxamide;
N-({7-[(6-amino-9H-purin-9-yl)methyl]-5-chloro-1H-indol-2-yl}methyl)-3-methyl-1,2-oxazole-4-carboxamide;
N-({7-[(6-amino-9H-purin-9-yl)methyl]-5-chloro-1H-indol-2-yl}methyl)-1-methyl-1H-pyrazole-3-carboxamide;
N-({7-[(6-amino-9H-purin-9-yl)methyl]-5-chloro-1H-indol-2-yl}methyl)-1-methyl-1H-pyrazole-5-carboxamide;
N-({7-[(6-amino-9H-purin-9-yl)methyl]-5-chloro-1H-indol-2-yl}methyl)-1-methyl-1H-imidazole-5-carboxamide;
N-({7-[(6-amino-9H-purin-9-yl)methyl]-5-chloro-1H-indol-2-yl}methyl)-1-methyl-1H-imidazole-2-carboxamide;
5-amino-N-({7-[(6-amino-9H-purin-9-yl)methyl]-5-chloro-1H-indol-2-yl}methyl)-3-methyl-1,2-oxazole-4-carboxamide;
N-({7-[(6-amino-9H-purin-9-yl)methyl]-5-chloro-1H-indol-2-yl}methyl)-2-methylthiophene-3-carboxamide;
N-({7-[(6-amino-9H-purin-9-yl)methyl]-5-chloro-1H-indol-2-yl}methyl)-3-methylthiophene-2-carboxamide;
N-({7-[(6-amino-9H-purin-9-yl)methyl]-5-chloro-1H-indol-2-yl}methyl)-4-methoxythiophene-3-carboxamide;
N-({7-[(6-amino-9H-purin-9-yl)methyl]-5-chloro-1H-indol-2-yl}methyl)-3-methoxythiophene-2-carboxamide;
N-({7-[(6-amino-9H-purin-9-yl)methyl]-5-chloro-1H-indol-2-yl}methyl)-1-methyl-1H-pyrrole-2-carboxamide;
N-({7-[(6-amino-9H-purin-9-yl)methyl]-5-chloro-1H-indol-2-yl}methyl)-2,4-dimethyl-1,3-thiazole-5-carboxamide;
N-({7-[(6-amino-9H-purin-9-yl)methyl]-5-chloro-1H-indol-2-yl}methyl)-3,5-dimethyl-1,2-oxazole-4-carboxamide;
N-({7-[(6-amino-9H-purin-9-yl)methyl]-5-(1,2,5,6-tetrahydropyridin-3-yl)-1H-indol-2-yl}methyl)-3,5-dimethyl-1,2-oxazole-4-carboxamide;

N-({7-[(6-amino-9H-purin-9-yl)methyl]-5-phenyl-1H-indol-2-yl}methyl)-3,5-dimethyl-1,2-oxazole-4-carboxamide;
N-({7-[(6-amino-9H-purin-9-yl)methyl]-5-(4-fluorophenyl)-1H-indol-2-yl}methyl)-3,5-dimethyl-1,2-oxazole-4-carboxamide;
N-({7-[(6-amino-9H-purin-9-yl)methyl]-5-(4-sulfamoylphenyl)-1H-indol-2-yl}methyl)-3,5-dimethyl-1,2-oxazole-4-carboxamide;
N-({7-[(6-amino-9H-purin-9-yl)methyl]-5-(4-methylphenyl)-1H-indol-2-yl}methyl)-3,5-dimethyl-1,2-oxazole-4-carboxamide;
N-({7-[(6-amino-9H-purin-9-yl)methyl]-5-(4-methoxyphenyl)-1H-indol-2-yl}methyl)-3,5-dimethyl-1,2-oxazole-4-carboxamide;
N-({7-[(6-amino-9H-purin-9-yl)methyl]-5-(3-methoxyphenyl)-1H-indol-2-yl}methyl)-3,5-dimethyl-1,2-oxazole-4-carboxamide;
N-({7-[(6-amino-9H-purin-9-yl)methyl]-5-[4-(methylsulfonyl)phenyl]-1H-indol-2-yl}methyl)-3,5-dimethyl-1,2-oxazole-4-carboxamide;
N-({7-[(6-amino-9H-purin-9-yl)methyl]-5-(4-cyanophenyl)-1H-indol-2-yl}methyl)-3,5-dimethyl-1,2-oxazole-4-carboxamide;
N-({7-[(6-amino-9H-purin-9-yl)methyl]-5-(3-cyanophenyl)-1H-indol-2-yl}methyl)-3,5-dimethyl-1,2-oxazole-4-carboxamide;
N-({7-[(6-amino-9H-purin-9-yl)methyl]-5-(3-carbamoylphenyl)-1H-indol-2-yl}methyl)-3,5-dimethyl-1,2-oxazole-4-carboxamide;
N-[(7-[(6-amino-9H-purin-9-yl)methyl]-5-{4-[(methylsulfonyl)amino]phenyl}-1H-indol-2-yl)methyl]-3,5-dimethyl-1,2-oxazole-4-carboxamide;
N-({7-[(6-amino-9H-purin-9-yl)methyl]-5-[4-(cyanomethyl)phenyl]-1H-indol-2-yl}methyl)-3,5-dimethyl-1,2-oxazole-4-carboxamide;
N-({7-[(6-amino-9H-purin-9-yl)methyl]-5-[4-(dimethylcarbamoyl)phenyl]-1H-indol-2-yl}methyl)-3,5-dimethyl-1,2-oxazole-4-carboxamide;
N-({7-[(6-amino-9H-purin-9-yl)methyl]-5-[3-(dimethylcarbamoyl)phenyl]-1H-indol-2-yl}methyl)-3,5-dimethyl-1,2-oxazole-4-carboxamide;
N-({7-[(6-amino-9H-purin-9-yl)methyl]-5-[3-(cyclopropylcarbamoyl)phenyl]-1H-indol-2-yl}methyl)-3,5-dimethyl-1,2-oxazole-4-carboxamide;
N-({7-[(6-amino-9H-purin-9-yl)methyl]-5-[3-(morpholin-4-yl)phenyl]-1H-indol-2-yl}methyl)-3,5-dimethyl-1,2-oxazole-4-carboxamide;
N-({7-[(6-amino-9H-purin-9-yl)methyl]-5-[3-(morpholin-4-ylcarbonyl)phenyl]-1H-indol-2-yl}methyl)-3,5-dimethyl-1,2-oxazole-4-carboxamide;
N-({7-[(6-amino-9H-purin-9-yl)methyl]-5-chloro-1H-indol-2-yl}methyl)-5-ethyl-1,2-oxazole-4-carboxamide;
N-({7-[(6-amino-9H-purin-9-yl)methyl]-5-chloro-1H-indol-2-yl}methyl)-1,5-dimethyl-1H-pyrazole-3-carboxamide;
N-({7-[(6-amino-9H-purin-9-yl)methyl]-5-chloro-1H-indol-2-yl}methyl)-1,3-dimethyl-1H-pyrazole-5-carboxamide;
N-({7-[(6-amino-9H-purin-9-yl)methyl]-5-chloro-1H-indol-2-yl}methyl)-1,3-dimethyl-1H-pyrazole-4-carboxamide;
N-({7-[(6-amino-9H-purin-9-yl)methyl]-5-chloro-1H-indol-2-yl}methyl)-5-ethyl-3-methyl-1,2-oxazole-4-carboxamide;
N-({7-[(6-amino-9H-purin-9-yl)methyl]-5-chloro-1H-indol-2-yl}methyl)-3-ethyl-5-methyl-1,2-oxazole-4-carboxamide;
N-({7-[(6-amino-9H-purin-9-yl)methyl]-5-chloro-1H-indol-2-yl}methyl)-5-(propan-2-yl)-1,2-oxazole-4-carboxamide;
N-({7-[(6-amino-9H-purin-9-yl)methyl]-5-chloro-1H-indol-2-yl}methyl)-1-ethyl-3,5-dimethyl-1H-pyrazole-4-carboxamide;
N-({7-[(6-amino-9H-purin-9-yl)methyl]-5-chloro-1H-indol-2-yl}methyl)-5-cyclopropyl-1,2-oxazole-4-carboxamide;
N-({7-[(6-amino-9H-purin-9-yl)methyl]-5-chloro-1H-indol-2-yl}methyl)-5-cyclopropyl-3-methyl-1,2-oxazole-4-carboxamide;
N-({7-[(6-amino-9H-purin-9-yl)methyl)methyl]-5-chloro-1H-indol-2-yl}methyl)-1-methyl-1,4,5,6-tetrahydrocyclopenta[c]pyrazole-3-carboxamide;
N-({7-[(6-amino-9H-purin-9-yl)methyl]-5-chloro-1H-indol-2-yl}methyl)-4,5,6,7-tetrahydropyrazolo[1,5-a]pyridine-3-carboxamide;
N-({7-[(6-amino-9H-purin-9-yl)methyl]-5-chloro-1H-indol-2-yl}methyl)pyrazine-2-carboxamide;
9-({2-[amino(phenyl)methyl]-5-chloro-1H-indol-7-yl}methyl)-9H-purin-6-amine;
N-({7-[(6-amino-9H-purin-9-yl)methyl]-5-chloro-1H-indol-2-yl}methyl)pyridine-2-carboxamide;
N-({7-[(6-amino-9H-purin-9-yl)methyl]-5-chloro-1H-indol-2-yl}methyl)pyridine-3-carboxamide;
N-({7-[(6-amino-9H-purin-9-yl)methyl]-5-chloro-1H-indol-2-yl}methyl)-6-hydroxypyridine-2-carboxamide;
N-({7-[(6-amino-9H-purin-9-yl)methyl]-5-chloro-1H-indol-2-yl}methyl)-2-oxo-1,2-dihydropyridine-3-carboxamide;
N-({7-[(6-amino-9H-purin-9-yl)methyl]-5-chloro-1H-indol-2-yl}methyl)-3-methylpyridazine-4-carboxamide;
N-({7-[(6-amino-9H-purin-9-yl)methyl]-5-(1,2,3,6-tetrahydropyridin-4-yl)-1H-indol-2-yl}methyl)-3-methylpyridazine-4-carboxamide;
N-({7-[(6-amino-9H-purin-9-yl)methyl]-5-(4,4-difluorocyclohex-1-en-1-yl)-1H-indol-2-yl}methyl)-3-methylpyridazine-4-carboxamide;
N-({7-[(6-amino-9H-purin-9-yl)methyl]-5-[1-(methylsulfonyl)-1,2,3,6-tetrahydropyridin-4-yl]-1H-indol-2-yl}methyl)-3-methylpyridazine-4-carboxamide;
N-({5-(1-acetyl-1,2,3,6-tetrahydropyridin-4-yl)-7-[(6-amino-9H-purin-9-yl)methyl]-1H-indol-2-yl}methyl)-3-methylpyridazine-4-carboxamide;
tert-butyl 4-{7-[(6-amino-9H-purin-9-yl)methyl]-2-({[(3-methylpyridazin-4-yl)carbonyl]amino}methyl)-1H-indol-5-yl}-3,6-dihydropyridine-1(2H)-carboxylate;
N-({7-[(6-amino-9H-purin-9-yl)methyl]-5-chloro-1H-indol-2-yl}methyl)-5-methylpyrazine-2-carboxamide;
9-{[2-(1-amino-2-phenylethyl)-5-chloro-1H-indol-7-yl]methyl}-9H-purin-6-amine;
9-({2-[(benzylamino)methyl]-5-chloro-1H-indol-7-yl}methyl)-9H-purin-6-amine;
9-[(2-{[(2-bromobenzyl)amino]methyl}-5-chloro-1H-indol-7-yl)methyl]-9H-purin-6-amine;
9-[(5-chloro-2-{[(3-chlorobenzyl)amino]methyl}-1H-indol-7-yl)methyl]-9H-purin-6-amine;
9-[(5-chloro-2-{[(2-chlorobenzyl)amino]methyl}-1H-indol-7-yl)methyl]-9H-purin-6-amine;
9-[(5-chloro-2-{[(2,6-dichlorobenzyl)amino]methyl}-1H-indol-7-yl)methyl]-9H-purin-6-amine;
9-[(5-chloro-2-{[(3,5-dichlorobenzyl)amino]methyl}-1H-indol-7-yl)methyl]-9H-purin-6-amine;

9-[(5-chloro-2-{[(3,4-dichlorobenzyl)amino]methyl}-1H-indol-7-yl)methyl]-9H-purin-6-amine;
9-[(5-chloro-2-{[(2-fluorobenzyl)amino]methyl}-1H-indol-7-yl)methyl]-9H-purin-6-amine;
9-[(5-chloro-2-{[(2-chloro-6-fluorobenzyl)amino]methyl}-1H-indol-7-yl)methyl]-9H-purin-6-amine;
9-[(5-chloro-2-{[(3-chloro-5-fluorobenzyl)amino]methyl}-1H-indol-7-yl)methyl]-9H-purin-6-amine;
9-[(5-chloro-2-{[(2-chloro-5-fluorobenzyl)amino]methyl}-1H-indol-7-yl)methyl]-9H-purin-6-amine;
9-[(5-chloro-2-{[(3-chloro-2-fluorobenzyl)amino]methyl}-1H-indol-7-yl)methyl]-9H-purin-6-amine;
9-[(5-chloro-2-{[(2,6-difluorobenzyl)amino]methyl}-1H-indol-7-yl)methyl]-9H-purin-6-amine;
N-({7-[(6-amino-9H-purin-9-yl)methyl]-5-chloro-1H-indol-2-yl}methyl)benzamide;
N-({7-[(6-amino-9H-purin-9-yl)methyl]-5-chloro-1H-indol-2-yl}methyl)-4-chlorobenzamide;
N-({7-[(6-amino-9H-purin-9-yl)methyl]-5-chloro-1H-indol-2-yl}methyl)-3-chlorobenzamide;
N-({7-[(6-amino-9H-purin-9-yl)methyl]-5-chloro-1H-indol-2-yl}methyl)-4-fluorobenzamide;
N-({7-[(6-amino-9H-purin-9-yl)methyl]-5-chloro-1H-indol-2-yl}methyl)-3-fluorobenzamide;
N-({7-[(6-amino-9H-purin-9-yl)methyl]-5-chloro-1H-indol-2-yl}methyl)-2-fluorobenzamide;
N-({7-[(6-amino-9H-purin-9-yl)methyl]-5-chloro-1H-indol-2-yl}methyl)-2-bromo-6-fluorobenzamide;
N-({7-[(6-amino-9H-purin-9-yl)methyl]-5-chloro-1H-indol-2-yl}methyl)-2-chloro-6-fluorobenzamide;
N-({7-[(6-amino-9H-purin-9-yl)methyl]-5-chloro-1H-indol-2-yl}methyl)-2,6-difluorobenzamide;
N-({7-[(6-amino-9H-purin-9-yl)methyl]-5-chloro-1H-indol-2-yl}methyl)-2-fluoro-6-hydroxybenzamide;
N-({7-[(6-amino-9H-purin-9-yl)methyl]-5-chloro-1H-indol-2-yl}methyl)-2-(pyridin-2-yl)acetamide;
N-({7-[(6-amino-9H-purin-9-yl)methyl)methyl]-5-chloro-1H-indol-2-yl}methyl)-2-(pyridin-3-yl)acetamide;
N-({7-[(6-amino-9H-purin-9-yl)methyl]-5-chloro-1H-indol-2-yl}methyl)-2-(pyridin-4-yl)acetamide;
N-({7-[(6-amino-9H-purin-9-yl)methyl]-5-chloro-1H-indol-2-yl}methyl)-2-methylpyridine-3-carboxamide;
N-({7-[(6-amino-9H-purin-9-yl)methyl]-5-chloro-1H-indol-2-yl}methyl)-3,6-dimethylpyridazine-4-carboxamide;
N-({7-[(6-amino-9H-purin-9-yl)methyl]-5-(1,2,3,6-tetrahydropyridin-4-yl)-1H-indol-2-yl}methyl)-3,6-dimethylpyridazine-4-carboxamide;
N-({7-[(6-amino-9H-purin-9-yl)methyl]-5-(4,4-difluorocyclohex-1-en-1-yl)-1H-indol-2-yl}methyl)-3,6-dimethylpyridazine-4-carboxamide;
N-({5-(1-acetyl-1,2,3,6-tetrahydropyridin-4-yl)-7-[(6-amino-9H-purin-9-yl)methyl]-1H-indol-2-yl}methyl)-3,6-dimethylpyridazine-4-carboxamide;
N-({5-(1-acetyl-1,4,5,6-tetrahydropyridin-3-yl)-7-[(6-amino-9H-purin-9-yl)methyl]-1H-indol-2-yl}methyl)-3,6-dimethylpyridazine-4-carboxamide;
N-({7-[(6-amino-9H-purin-9-yl)methyl]-4-chloro-1H-indol-2-yl}methyl)-3,6-dimethylpyridazine-4-carboxamide;
N-({7-[(6-amino-9H-purin-9-yl)methyl]-5-chloro-1H-indol-2-yl}methyl)-6-cyanopyridine-3-carboxamide;
9-[(5-chloro-2-{[(4-methylbenzyl)amino]methyl}-1H-indol-7-yl)methyl]-9H-purin-6-amine;
9-[(5-chloro-2-{[(2-methylbenzyl)amino]methyl}-1H-indol-7-yl)methyl]-9H-purin-6-amine;
9-[(5-chloro-2-{[(2-chloro-6-methylbenzyl)amino]methyl}-1H-indol-7-yl)methyl]-9H-purin-6-amine;
9-[(5-chloro-2-{[(2-fluoro-6-methylbenzyl)amino]methyl}-1H-indol-7-yl)methyl]-9H-purin-6-amine;
9-[(5-chloro-2-{[(2-fluoro-3-methylbenzyl)amino]methyl}-1H-indol-7-yl)methyl]-9H-purin-6-amine;
N-({7-[(6-amino-9H-purin-9-yl)methyl]-5-chloro-1H-indol-2-yl}methyl)-4-methylbenzamide;
N-({7-[(6-amino-9H-purin-9-yl)methyl]-5-chloro-1H-indol-2-yl}methyl)-3-methylbenzamide;
N-({7-[(6-amino-9H-purin-9-yl)methyl]-5-chloro-1H-indol-2-yl}methyl)-2-methylbenzamide;
9-[(5-chloro-2-{[(3-methoxybenzyl)amino]methyl}-1H-indol-7-yl)methyl]-9H-purin-6-amine;
9-[(5-chloro-2-{[(2-methoxybenzyl)amino]methyl}-1H-indol-7-yl)methyl]-9H-purin-6-amine;
N-({7-[(6-amino-9H-purin-9-yl)methyl]-5-chloro-1H-indol-2-yl}methyl)-2-(4-chlorophenyl)acetamide;
N-({7-[(6-amino-9H-purin-9-yl)methyl]-5-chloro-1H-indol-2-yl}methyl)-2-(3-chlorophenyl)acetamide;
N-({7-[(6-amino-9H-purin-9-yl)methyl]-5-chloro-1H-indol-2-yl}methyl)-2-(2-chlorophenyl)acetamide;
N-({7-[(6-amino-9H-purin-9-yl)methyl]-5-chloro-1H-indol-2-yl}methyl)-2-(4-fluorophenyl)acetamide;
N-({7-[(6-amino-9H-purin-9-yl)methyl]-5-chloro-1H-indol-2-yl}methyl)-2-(3-fluorophenyl)acetamide;
N-({7-[(6-amino-9H-purin-9-yl)methyl]-5-chloro-1H-indol-2-yl}methyl)-2-(2-fluorophenyl)acetamide;
N-({7-[(6-amino-9H-purin-9-yl)methyl]-5-chloro-1H-indol-2-yl}methyl)-2-(trifluoromethyl)benzamide;
N-({7-[(6-amino-9H-purin-9-yl)methyl]-5-chloro-1H-indol-2-yl}methyl)-4-methoxybenzamide;
N-({7-[(6-amino-9H-purin-9-yl)methyl]-5-chloro-1H-indol-2-yl}methyl)-3-methoxybenzamide;
N-({7-[(6-amino-9H-purin-9-yl)methyl]-5-chloro-1H-indol-2-yl}methyl)-2-methoxybenzamide;
N-({7-[(6-amino-9H-purin-9-yl)methyl]-5-chloro-1H-indol-2-yl}methyl)-2-(difluoromethoxy)benzamide;
9-{[5-chloro-2-({[3-(methylsulfonyl)benzyl]amino}methyl)-1H-indol-7-yl]methyl}-9H-purin-6-amine;
9-{[5-chloro-2-({[4-fluoro-3-(methylsulfonyl)benzyl]amino}methyl)-1H-indol-7-yl]methyl}-9H-purin-6-amine;
9-{[5-chloro-2-({[3-fluoro-4-(methylsulfonyl)benzyl]amino}methyl)-1H-indol-7-yl]methyl}-9H-purin-6-amine;
N-({7-[(6-amino-9H-purin-9-yl)methyl]-5-chloro-1H-indol-2-yl}methyl)-2-(methylsulfonyl)benzamide;
N-({7-[(6-amino-9H-purin-9-yl)methyl]-5-chloro-1H-indol-2-yl}methyl)-2-chloro-4-(methylsulfonyl)benzamide;
4-{[({7-[(6-amino-9H-purin-9-yl)methyl]-5-chloro-1H-indol-2-yl}methyl)amino]methyl}benzonitrile;
3-{[({7-[(6-amino-9H-purin-9-yl)methyl]-5-chloro-1H-indol-2-yl}methyl)amino]methyl}benzonitrile;
2-{[({7-[(6-amino-9H-purin-9-yl)methyl]-5-chloro-1H-indol-2-yl}methyl)amino]methyl}benzonitrile;
3-{[({7-[(6-amino-9H-purin-9-yl)methyl]-5-chloro-1H-indol-2-yl}methyl)amino]methyl}-4-fluorobenzonitrile;
5-amino-N-({7-[(6-amino-9H-purin-9-yl)methyl]-5-chloro-1H-indol-2-yl}methyl)-2-methylbenzamide;
N-({7-[(6-amino-9H-purin-9-yl)methyl]-5-chloro-1H-indol-2-yl}methyl)-4-cyanobenzamide;
N-({7-[(6-amino-9H-purin-9-yl)methyl]-5-chloro-1H-indol-2-yl}methyl)-3-cyanobenzamide;

N-({7-[(6-amino-9H-purin-9-yl)methyl]-5-chloro-1H-indol-2-yl}methyl)-2-cyanobenzamide;
N-({7-[(6-amino-9H-purin-9-yl)methyl]-5-chloro-1H-indol-2-yl}methyl)-2-(methylamino)benzamide;
N-({7-[(6-amino-9H-purin-9-yl)methyl]-5-chloro-1H-indol-2-yl}methyl)-2-chloro-4-cyanobenzamide;
N-({7-[(6-amino-9H-purin-9-yl)methyl]-5-(1,2,3,6-tetrahydropyridin-4-yl)-1H-indol-2-yl}methyl)-2-chloro-4-cyanobenzamide;
N-({7-[(6-amino-9H-purin-9-yl)methyl]-5-(4,4-difluorocyclohex-1-en-1-yl)-1H-indol-2-yl}methyl)-2-chloro-4-cyanobenzamide;
N-({5-(1-acetyl-1,2,3,6-tetrahydropyridin-4-yl)-7-[(6-amino-9H-purin-9-yl)methyl]-1H-indol-2-yl}methyl)-2-chloro-4-cyanobenzamide;
N-({5-(1-acetyl-1,4,5,6-tetrahydropyridin-3-yl)-7-[(6-amino-9H-purin-9-yl)methyl]-1H-indol-2-yl}methyl)-2-chloro-4-cyanobenzamide;
N-({5-(1-acetylpiperidin-4-yl)-7-[(6-amino-9H-purin-9-yl)methyl]-1H-indol-2-yl}methyl)-2-chloro-4-cyanobenzamide;
N-({7-[(6-amino-9H-purin-9-yl)methyl]-4-chloro-1H-indol-2-yl}methyl)-2-chloro-4-cyanobenzamide;
N-({7-[(6-amino-9H-purin-9-yl)methyl]-5-chloro-1H-indol-2-yl}methyl)-2,6-dichloro-4-cyanobenzamide;
N-({7-[(6-amino-9H-purin-9-yl)methyl]-5-chloro-1H-indol-2-yl}methyl)-4-cyano-2-fluorobenzamide;
N-({7-[(6-amino-9H-purin-9-yl)methyl]-5-(3,6-dihydro-2H-pyran-4-yl)-1H-indol-2-yl}methyl)-4-cyano-2-fluorobenzamide;
N-({7-[(6-amino-9H-purin-9-yl)methyl]-5-(1,2,3,6-tetrahydropyridin-4-yl)-1H-indol-2-yl}methyl)-4-cyano-2-fluorobenzamide;
N-({7-[(6-amino-9H-purin-9-yl)methyl]-5-(4,4-difluorocyclohex-1-en-1-yl)-1H-indol-2-yl}methyl)-4-cyano-2-fluorobenzamide;
N-({5-(1-acetyl-1,2,3,6-tetrahydropyridin-4-yl)-7-[(6-amino-9H-purin-9-yl)methyl]-1H-indol-2-yl}methyl)-4-cyano-2-fluorobenzamide;
tert-butyl 4-(7-[(6-amino-9H-purin-9-yl)methyl]-2-{[(4-cyano-2-fluorobenzoyl)amino]methyl}-1H-indol-5-yl)-3,6-dihydropyridine-1(2H)-carboxylate;
9-[(5-chloro-2-{[(2,6-dimethylbenzyl)amino]methyl}-1H-indol-7-yl)methyl]-9H-purin-6-amine;
N-({7-[(6-amino-9H-purin-9-yl)methyl]-5-chloro-1H-indol-2-yl}methyl)-3-phenylpropanamide;
N-({7-[(6-amino-9H-purin-9-yl)methyl]-5-chloro-1H-indol-2-yl}methyl)-2-(4-methylphenyl)acetamide;
N-({7-[(6-amino-9H-purin-9-yl)methyl]-5-chloro-1H-indol-2-yl}methyl)-2-(3-methylphenyl)acetamide;
N-({7-[(6-amino-9H-purin-9-yl)methyl]-5-chloro-1H-indol-2-yl}methyl)-2-(2-methylphenyl)acetamide;
N-({7-[(6-amino-9H-purin-9-yl)methyl]-5-chloro-1H-indol-2-yl}methyl)-2,6-dimethylbenzamide;
N-({7-[(6-amino-9H-purin-9-yl)methyl]-5-chloro-1H-indol-2-yl}methyl)-2-ethylbenzamide;
N-({7-[(6-amino-9H-purin-9-yl)methyl]-5-chloro-1H-indol-2-yl}methyl)-2-(4-methoxyphenyl)acetamide;
N-({7-[(6-amino-9H-purin-9-yl)methyl]-5-chloro-1H-indol-2-yl}methyl)-2-(2-methoxyphenyl)acetamide;
N-({7-[(6-amino-9H-purin-9-yl)methyl]-5-chloro-1H-indol-2-yl}methyl)-2-methoxy-6-methylbenzamide;
N-({7-[(6-amino-9H-purin-9-yl)methyl]-5-chloro-1H-indol-2-yl}methyl)-3-methoxy-4-methylbenzamide;
4-(aminomethyl)-N-({7-[(6-amino-9H-purin-9-yl)methyl]-5-(4,4-difluorocyclohexyl)-1H-indol-2-yl}methyl)-2-methylbenzamide;
N-({7-[(6-amino-9H-purin-9-yl)methyl]-5-chloro-1H-indol-2-yl}methyl)-4-(dimethylamino)benzamide;
N-({7-[(6-amino-9H-purin-9-yl)methyl]-5-chloro-1H-indol-2-yl}methyl)-4-cyano-2-methylbenzamide;
N-({7-[(6-amino-9H-purin-9-yl)methyl]-5-(3,6-dihydro-2H-pyran-4-yl)-1H-indol-2-yl}methyl)-4-cyano-2-methylbenzamide;
N-({7-[(6-amino-9H-purin-9-yl)methyl]-5-(1,2,3,6-tetrahydropyridin-4-yl)-1H-indol-2-yl}methyl)-4-cyano-2-methylbenzamide;
N-({7-[(6-amino-9H-purin-9-yl)methyl]-5-(4,4-difluorocyclohex-1-en-1-yl)-1H-indol-2-yl}methyl)-4-cyano-2-methylbenzamide;
N-({5-(1-acetyl-1,2,3,6-tetrahydropyridin-4-yl)-7-[(6-amino-9H-purin-9-yl)methyl]-1H-indol-2-yl}methyl)-4-cyano-2-methylbenzamide;
tert-butyl 4-(7-[(6-amino-9H-purin-9-yl)methyl]-2-{[(4-cyano-2-methylbenzoyl)amino]methyl}-1H-indol-5-yl)-3,6-dihydropyridine-1(2H)-carboxylate;
N-({7-[(6-amino-9H-purin-9-yl)methyl]-5-chloro-1H-indol-2-yl}methyl)-3-(dimethylamino)benzamide;
N-({7-[(6-amino-9H-purin-9-yl)methyl]-5-chloro-1H-indol-2-yl}methyl)-2-(ethylamino)benzamide;
4-{[({7-[(6-amino-9H-purin-9-yl)methyl]-5-chloro-1H-indol-2-yl}methyl)amino]methyl}-3-methoxybenzonitrile;
4-(acetylamino)-N-({7-[(6-amino-9H-purin-9-yl)methyl]-5-chloro-1H-indol-2-yl}methyl)benzamide;
N-({7-[(6-amino-9H-purin-9-yl)methyl]-5-chloro-1H-indol-2-yl}methyl)-2-(propan-2-yl)benzamide;
N-({7-[(6-amino-9H-purin-9-yl)methyl]-5-chloro-1H-indol-2-yl}methyl)-3-(4-methoxyphenyl)propanamide;
N-({7-[(6-amino-9H-purin-9-yl)methyl]-5-chloro-1H-indol-2-yl}methyl)-3-(3-methoxyphenyl)propanamide;
N-({7-[(6-amino-9H-purin-9-yl)methyl]-5-chloro-1H-indol-2-yl}methyl)-2-[4-(dimethylamino)phenyl]acetamide;
4-{[({7-[(6-amino-9H-purin-9-yl)methyl]-5-chloro-1H-indol-2-yl}methyl)amino]methyl}-N,N-dimethylbenzamide;
N-({7-[(6-amino-9H-purin-9-yl)methyl]-5-chloro-1H-indol-2-yl}methyl)-3-(2-fluorophenyl)pyrrolidine-1-carboxamide;
N-({7-[(6-amino-9H-purin-9-yl)methyl]-5-chloro-1H-indol-2-yl}methyl)-2-(pyrrolidin-1-ylcarbonyl)benzamide;
N-({7-[(6-amino-9H-purin-9-yl)methyl]-5-chloro-1H-indol-2-yl}methyl)-2-(tetrahydro-2H-pyran-4-yloxy)benzamide;
N-({7-[(6-amino-9H-purin-9-yl)methyl]-5-chloro-1H-indol-2-yl}methyl)-2-(piperidin-1-yl)benzamide;
9-{[5-chloro-2-({[3-(piperidin-1-ylmethyl)benzyl]amino}methyl)-1H-indol-7-yl]methyl}-9H-purin-6-amine;
N-({7-[(6-amino-9H-purin-9-yl)methyl]-5-chloro-1H-indol-2-yl}methyl)-2-(piperidin-1-ylcarbonyl)benzamide;
9-({5-chloro-2-[({3-[2-(piperidin-1-yl)ethoxy]benzyl}amino)methyl]-1H-indol-7-yl}methyl)-9H-purin-6-amine;
N-({7-[(6-amino-9H-purin-9-yl)methyl]-5-chloro-1H-indol-2-yl}methyl)-5-methyl-3-phenyl-1,2-oxazole-4-carboxamide;
N-({7-[(6-amino-9H-purin-9-yl)methyl]-5-chloro-1H-indol-2-yl}methyl)-2-(1-methyl-1H-imidazol-2-yl)benzamide;

N-({7-[(6-amino-9H-purin-9-yl)methyl]-5-chloro-1H-indol-2-yl}methyl)-2-(benzoylamino)benzamide;
N-({7-[(6-amino-9H-purin-9-yl)methyl]-5-chloro-1H-indol-2-yl}methyl)-1,2,3-benzothiadiazole-5-carboxamide;
N-({7-[(6-amino-9H-purin-9-yl)methyl]-5-chloro-1H-indol-2-yl}methyl)-3H-imidazo[4,5-b]pyridine-5-carboxamide;
N-({7-[(6-amino-9H-purin-9-yl)methyl]-5-chloro-1H-indol-2-yl}methyl)-1H-benzotriazole-6-carboxamide;
N-({7-[(6-amino-9H-purin-9-yl)methyl]-5-chloro-1H-indol-2-yl}methyl)-1H-benzotriazole-5-carboxamide;
N-({7-[(6-amino-9H-purin-9-yl)methyl]-5-chloro-1H-indol-2-yl}methyl)-3H-imidazo[4,5-b]pyridine-6-carboxamide;
N-({7-[(6-amino-9H-purin-9-yl)methyl]-5-chloro-1H-indol-2-yl}methyl)-5-fluoro-1H-benzotriazole-6-carboxamide;
N-({7-[(6-amino-9H-purin-9-yl)methyl]-5-chloro-1H-indol-2-yl}methyl)-1,3-benzothiazole-6-carboxamide;
N-({7-[(6-amino-9H-purin-9-yl)methyl]-5-chloro-1H-indol-2-yl}methyl)-1,3-benzothiazole-5-carboxamide;
N-({7-[(6-amino-9H-purin-9-yl)methyl]-5-chloro-1H-indol-2-yl}methyl)thieno[3,2-b]pyridine-6-carboxamide;
N-({7-[(6-amino-9H-purin-9-yl)methyl]-5-chloro-1H-indol-2-yl}methyl)-1,3-benzoxazole-6-carboxamide;
N-({7-[(6-amino-9H-purin-9-yl)methyl]-5-chloro-1H-indol-2-yl}methyl)-1,3-benzoxazole-5-carboxamide;
N-({7-[(6-amino-9H-purin-9-yl)methyl]-5-chloro-1H-indol-2-yl}methyl)furo[3,2-b]pyridine-6-carboxamide;
N-({7-[(6-amino-9H-purin-9-yl)methyl]-5-chloro-1H-indol-2-yl}methyl)-2-hydroxy-1,3-benzothiazole-6-carboxamide;
N-({7-[(6-amino-9H-purin-9-yl)methyl]-5-chloro-1H-indol-2-yl}methyl)-1H-indazole-6-carboxamide;
N-({7-[(6-amino-9H-purin-9-yl)methyl]-5-chloro-1H-indol-2-yl}methyl)-1H-pyrrolo[3,2-b]pyridine-5-carboxamide;
N-({7-[(6-amino-9H-purin-9-yl)methyl]-5-chloro-1H-indol-2-yl}methyl)-1H-benzimidazole-5-carboxamide;
N-({7-[(6-amino-9H-purin-9-yl)methyl]-5-chloro-1H-indol-2-yl}methyl)-1H-benzimidazole-6-carboxamide;
N-({7-[(6-amino-9H-purin-9-yl)methyl]-5-chloro-1H-indol-2-yl}methyl)-1H-indazole-5-carboxamide;
N-({7-[(6-amino-9H-purin-9-yl)methyl]-5-chloro-1H-indol-2-yl}methyl)-1H-pyrrolo[2,3-b]pyridine-5-carboxamide;
N-({7-[(6-amino-9H-purin-9-yl)methyl]-5-chloro-1H-indol-2-yl}methyl)-4-chloro-1H-pyrrolo[2,3-b]pyridine-5-carboxamide;
N-({7-[(6-amino-9H-purin-9-yl)methyl]-5-chloro-1H-indol-2-yl}methyl)-5-chloro-1H-pyrrolo[2,3-b]pyridine-6-carboxamide;
N-({7-[(6-amino-9H-purin-9-yl)methyl]-5-chloro-1H-indol-2-yl}methyl)-4-fluoro-1H-indazole-5-carboxamide;
N-({7-[(6-amino-9H-purin-9-yl)methyl]-5-chloro-1H-indol-2-yl}methyl)-3-methyl[1,2]oxazolo[5,4-b]pyridine-5-carboxamide;
N-({7-[(6-amino-9H-purin-9-yl)methyl]-5-chloro-1H-indol-2-yl}methyl)-1-methyl-1H-benzotriazole-5-carboxamide;
N-({7-[(6-amino-9H-purin-9-yl)methyl]-5-chloro-1H-indol-2-yl}methyl)-3-methyl-1H-pyrazolo[3,4-b]pyridine-5-carboxamide;
N-({7-[(6-amino-9H-purin-9-yl)methyl]-5-chloro-1H-indol-2-yl}methyl)-1-benzothiophene-5-carboxamide;
N-({7-[(6-amino-9H-purin-9-yl)methyl]-5-chloro-1H-indol-2-yl}methyl)-1-benzofuran-5-carboxamide;
N-({7-[(6-amino-9H-purin-9-yl)methyl]-5-chloro-1H-indol-2-yl}methyl)-1H-indole-6-carboxamide;
N-({7-[(6-amino-9H-purin-9-yl)methyl]-5-chloro-1H-indol-2-yl}methyl)-1H-indole-5-carboxamide;
N-({7-[(6-amino-9H-purin-9-yl)methyl)methyl]-5-chloro-1H-indol-2-yl}methyl)-2-methyl-1,3-benzothiazole-6-carboxamide;
N-({7-[(6-amino-9H-purin-9-yl)methyl]-5-chloro-1H-indol-2-yl}methyl)-2-methyl-1,3-benzoxazole-6-carboxamide;
N-({7-[(6-amino-9H-purin-9-yl)methyl]-5-chloro-1H-indol-2-yl}methyl)-1-methyl-1H-indazole-6-carboxamide;
N-({7-[(6-amino-9H-purin-9-yl)methyl]-5-chloro-1H-indol-2-yl}methyl)-1-methyl-1H-benzimidazole-5-carboxamide;
N-({7-[(6-amino-9H-purin-9-yl)methyl]-5-chloro-1H-indol-2-yl}methyl)-1-methyl-1H-indazole-5-carboxamide;
N-({7-[(6-amino-9H-purin-9-yl)methyl]-5-chloro-1H-indol-2-yl}methyl)-2-methyl-1H-benzimidazole-5-carboxamide;
N-({7-[(6-amino-9H-purin-9-yl)methyl]-5-chloro-1H-indol-2-yl}methyl)-2-methyl-1-benzofuran-5-carboxamide;
N-({7-[(6-amino-9H-purin-9-yl)methyl]-5-chloro-1H-indol-2-yl}methyl)-1-methyl-1H-indole-6-carboxamide;
N-({7-[(6-amino-9H-purin-9-yl)methyl]-5-chloro-1H-indol-2-yl}methyl)-1-methyl-1H-indole-5-carboxamide;
N-({7-[(6-amino-9H-purin-9-yl)methyl]-5-chloro-1H-indol-2-yl}methyl)-1,2-dimethyl-1H-benzimidazole-5-carboxamide;
N-({7-[(6-amino-9H-purin-9-yl)methyl]-5-chloro-1H-indol-2-yl}methyl)-2-ethyl-1H-benzimidazole-6-carboxamide;
N-({7-[(6-amino-9H-purin-9-yl)methyl]-5-chloro-1H-indol-2-yl}methyl)-3-cyano-1H-indole-5-carboxamide;
N-({7-[(6-amino-9H-purin-9-yl)methyl]-5-chloro-1H-indol-2-yl}methyl)-3-(propan-2-yl)[1,2]oxazolo[5,4-b]pyridine-5-carboxamide;
N-({7-[(6-amino-9H-purin-9-yl)methyl]-5-chloro-1H-indol-2-yl}methyl)-1-(propan-2-yl)-1H-benzotriazole-5-carboxamide;
N-({7-[(6-amino-9H-purin-9-yl)methyl]-5-chloro-1H-indol-2-yl}methyl)-1-(propan-2-yl)-1H-pyrazolo[3,4-b]pyridine-5-carboxamide;
N-({7-[(6-amino-9H-purin-9-yl)methyl]-5-chloro-1H-indol-2-yl}methyl)-4-methoxy-1,3-dimethyl-1H-pyrazolo[3,4-b]pyridine-5-carboxamide;
N-({7-[(6-amino-9H-purin-9-yl)methyl]-5-chloro-1H-indol-2-yl}methyl)-2,3-dimethyl-1H-indole-6-carboxamide;
N-({7-[(6-amino-9H-purin-9-yl)methyl]-5-chloro-1H-indol-2-yl}methyl)-2,3-dimethyl-1H-indole-5-carboxamide;
N-({7-[(6-amino-9H-purin-9-yl)methyl]-5-chloro-1H-indol-2-yl}methyl)-1-(2-hydroxyethyl)-2-methyl-1H-benzimidazole-5-carboxamide;
N-({7-[(6-amino-9H-purin-9-yl)methyl]-5-chloro-1H-indol-2-yl}methyl)-6-methyl-1-(propan-2-yl)-1H-pyrazolo[3,4-b]pyridine-5-carboxamide;
N-({7-[(6-amino-9H-purin-9-yl)methyl]-5-chloro-1H-indol-2-yl}methyl)-1,2,3-trimethyl-1H-indole-5-carboxamide; and N-({7-[(6-amino-9H-purin-9-yl)methyl]-5-chloro-1H-indol-2-yl}methyl)-2-butyl-1,3-benzoxazole-5-carboxamide.

26. A pharmaceutical composition comprising a therapeutically effective amount of a compound of formula (I) according to claim 1, or a pharmaceutically acceptable salt thereof, in combination with a pharmaceutically acceptable carrier.

27. A kit for use in measuring the activity of SUV420H1 or a fragment thereof in a biological sample in vitro or in vivo, comprising
- (i) a first composition comprising a compound of formula (I) according to claim 1; and
- (ii) instructions for:
  - (a) contacting the composition with the biological sample; and
  - (b) measuring activity of said SUV420H1 or a fragment thereof.

* * * * *